(12) United States Patent
Farrow et al.

(10) Patent No.: US 8,637,550 B2
(45) Date of Patent: Jan. 28, 2014

(54) HETEROARYL DIAMIDE COMPOUNDS USEFUL AS MMP-13 INHIBITORS

(75) Inventors: Neil Alexander Farrow, Ridgefield, CT (US); Donghong Amy Gao, Hopewell Junction, NY (US); Alexander Heim-Riether, Biberach an der Riss (DE); Sabine Schlyer, New Milford, CT (US); Lana Louise Smith Keenan, Poughquag, NY (US); Steven John Taylor, Southbury, CT (US); Bernd Wellenzohn, Langenargen (DE); Dieter Wiedenmayer, Biberach (DE); Zhaoming Xiong, Brookfield, CT (US); Qiang Zhang, Woodbury, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 132 days.

(21) Appl. No.: 13/127,256

(22) PCT Filed: Nov. 5, 2009

(86) PCT No.: PCT/US2009/063343
§ 371 (c)(1),
(2), (4) Date: Jun. 9, 2011

(87) PCT Pub. No.: WO2010/056585
PCT Pub. Date: May 20, 2010

(65) Prior Publication Data
US 2011/0275625 A1 Nov. 10, 2011

Related U.S. Application Data

(60) Provisional application No. 61/115,216, filed on Nov. 17, 2008.

(51) Int. Cl.
*A61K 31/443* (2006.01)
*C07D 405/12* (2006.01)
*C07D 405/10* (2006.01)

(52) U.S. Cl.
USPC ............... 514/336; 546/284.4; 546/284.7

(58) Field of Classification Search
USPC ............... 546/284.4, 284.7; 514/336
See application file for complete search history.

(56) References Cited

U.S. PATENT DOCUMENTS

| | | |
|---|---|---|
| 6,849,660 B1 | 2/2005 | Jefferson et al. |
| 2004/0198780 A1 | 10/2004 | Liu et al. |
| 2011/0269668 A1 | 11/2011 | Heim-Riether et al. |
| 2011/0275625 A1 | 11/2011 | Farrow et al. |
| 2011/0275631 A1 | 11/2011 | Abeywardane et al. |

FOREIGN PATENT DOCUMENTS

| | | |
|---|---|---|
| EP | 1493739 A1 | 1/2005 |
| WO | 03097617 A1 | 11/2003 |
| WO | 2004052921 A1 | 6/2004 |
| WO | 2004084843 A2 | 10/2004 |
| WO | 2005003115 A1 | 1/2005 |
| WO | 2010045188 A1 | 4/2010 |
| WO | 2010045190 A1 | 4/2010 |
| WO | 2010056585 A2 | 5/2010 |

OTHER PUBLICATIONS

Aventis Res. and Tech.: WO2004060874 and WO2004060883, MMP-13 Inhibitors, Patent Evaluation, Expert Opinion on Therapeutic Patents, vol. 15, No. 2, Jun. 1, 2005, p. 237-241.

Heim-Riether, A., et al "Improving potency and selectivity of a new class of non-Zn-chelating MMP-13 inhibitors". biorganic and Medicinal Chemistry Letters, Pergamon, Elsevier Science, GB, vol. 19, No. 18, Sep. 15, 2009, p. 5321-5324.

International Search Report and Written Opinion for PCT/US2009/063343 mailed Oct. 13, 2010.

Xu, Yang et al., "Synthesis and biological activity of N-[[5-(2-chlorophenyl)-2-furanyl]carbonyl]alaninamide derivatives". Youji Huaxue / Chinese Journal of Organic Chemistry, Science Press, Beijing, CH, vol. 28, No. 11, Jan. 1, 2008, p. 1998-2000.

*Primary Examiner* — Patricia L Morris
(74) *Attorney, Agent, or Firm* — Michael P. Morris; Anthony P. Bottino

(57) ABSTRACT

Disclosed are compounds and compositions of the formula (I) as described herein which are inhibitors of MMP-13. Also disclosed are methods of using and making compounds of the formula (I).

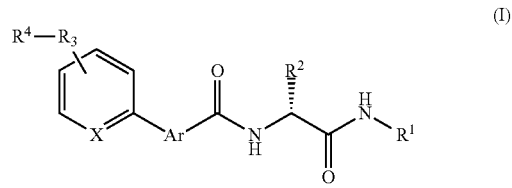

(I)

9 Claims, No Drawings

HETEROARYL DIAMIDE COMPOUNDS USEFUL AS MMP-13 INHIBITORS

APPLICATION DATA

This application claims benefit to U.S. provisional application Ser. No. 61/115,216 filed Nov. 17, 2008.

BACKGROUND OF THE INVENTION

1. Technical Field

The invention relates to MMP-13 metalloprotease inhibiting compounds.

2. Background Information

Matrix metalloproteinases (MMPs) are zinc-dependent endopeptidases. MMPs function to degrade extracellular matrix proteins and are involved in the cleavage of cell surface receptors, growth factors, cell-adhesion molecules, cytokines and chemokines, as well as other MMPs and unrelated proteases. MMPs are also thought to play a major role on cellular processes such as proliferation, migration (adhesion/dispersion), differentiation, angiogenesis, apoptosis and host defense. (Hu J. et al. Nat. Rev. Drug Discov. 2007 6:480-498; Ramnath N. and Creaven P. J. Curr. Oncol. Rep. 2004 6:96-102). MMPs are therefore targets for therapeutic diseases including rheumatoid arthritis, osteoarthritis, osteoporosis, peridontitis, atherosclerosis, congestive heart failure, multiple sclerosis and tumor metastasis.

The mammalian MMP family includes more than 20 members that share common structural attributes: a propeptide domain, a catalytic domain and a C-terminal hemopexin-like domain (except for MMP-7 and MMP-26). The function of MMPs in health and disease is regulated in multiple ways. MMPs are secreted as inactive proproteins which are activated when the propepetide domain is cleaved by extracellular proteinases or destabilized by protein-protein interactions. The activity of MMPs is also regulated by tissue inhibitors of metalloproteinases (TIMPs) which bind to the catalytic site of MMPs. The production of MMPs is also regulated at the level of transcription by specific signals that are temporally limited and spatially confined. (Parks W. C. et al 2004, Nat. Rev. Immunol. 2004 4:617-629).

The collagenase subset of the matrix metalloproteinase family, comprising MMP-1 (collagenase 1), MMP-8 (collagenase 2), MMP-13 (collagenase 3) and more recently MMP-14, catalyzes the initial cleavage of collagen types I, II, III, V and X (Parks W. C. et al Nat. Rev. Immunol. 2004 4:617-629). MMP-13 cleaves type II collagen more efficiently than types I and III and is capable of cleaving multiple extracellular matrix proteins in addition to fibrillar collagens (Leeman M. F. et al Crit. Rev. Biochem. Mol. Biol. 2003 37:149-166). MMP-13 is the most proficient catalyst of collagen type II degradation, the committed step in articular cartilage degradation and progressive joint damage associated with RA and osteoarthritis (OA). In the case of collagen type II (90-95% of articular cartilage), the triple helix is cleaved at position G775/L776 at least an order of magnitude faster by MMP-13 than by MMP-1 and MMP-8 (Billinghurst, R. C. et al. J. Clin. Invest. 1997 99:1534-1545). Cleavage of collagen type II triple helix at position G775/L776 by MMP-13 triggers the initial unfolding of the molecule, rendering it susceptible to catalytic degradation by additional members of the MMP family. The superior catalytic efficiency of MMP-13 for collagen type II degradation, coupled with induced expression of MMP-13 in synovial fibroblasts and chondrocytes associated with rheumatoid arthritis (RA) and osteoarthritis (OA) pathology, is consistent with MMP-13 being responsible for catalyzing the committed step in cartilage degradation associated with RA and OA (Mitchell, P. G. et al. 1996 J. Clin. Invest. 1996 97:761-768; Moore, B. A. et al, Biochim Biophys. Acta 2000 1502:307-318).

Furthermore, transient adenoviral expression of MMP-13 in mouse knee chondrocytes and synoviocytes induces a transient arthritic condition, including recruitment of inflammatory cells, and up-regulation of inflammatory cytokine mRNA (Oronen, K. et al. 2004. Ann. Rheum. Dis. 63, 656-664). Transgenic mice with a constitutively active form of human MMP-13 in cartilage exhibit augmented cleavage of type II collagen and leading to an osteoarthritic-like phenotype with marked cartilage degradation and synovial hyperplasia (Neuhold, L. A. et al 2001 J. Clin. Invest. 107, 35-44). These in vivo validation studies further support the role of MMP-13 in RA and OA pathogenesis.

BRIEF SUMMARY OF THE INVENTION

It has been found that compounds of the present invention are inhibitors of MMP-13.

It is therefore an object of the invention to provide compounds and compositions of the formula I as described herein below which are inhibitors of MMP-13.

It is a further object of the invention to provide methods of using and making compounds of the formula I which are inhibitors of MMP-13.

DETAILED DESCRIPTION OF THE INVENTION

In the broadest generic embodiment 1, there is provided a compound of the formula (I):

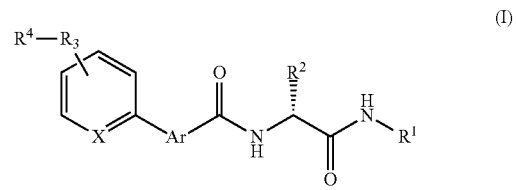

(I)

wherein:

$R^1$ is $C_1$-$C_5$ alkyl optionally substituted with 1-3 substituents chosen from hydroxyl, $C_1$-$C_5$ alkoxy which is optionally substituted with a carboxamido group, $C_3$-$C_6$ carbocyclyl, heterocyclyl, amino, alkylamino, dialkylamino, aryl and heteroaryl;

$R^2$ is $C_1$-$C_5$ alkyl, carbocycle, heterocycle, aryl or heteroaryl, each optionally independently substituted with 1-2 substituents chosen from amino, hydroxyl, $C_1$-$C_5$ alkoxy, oxo, aryl, $C_3$-$C_6$ carbocyclyl and carboxyl;

$R^3$ is a bond, hydrogen, $CH_2$, —C(O)—NH—, —NH—C(O)—, —CHR$_a$—O—, —O—CH$_2$—, —C(O)—NH—CH$_2$—, —CH$_2$—NH—C(O), S(O)$_{0-2}$—, SO$_2$—NH— or —NH—SO$_2$—; wherein R$_a$ is $C_1$-$C_5$ alkyl;

$R^4$ is $C_1$-$C_5$ alkyl, $C_2$-$C_4$ alkenyl, amino, alkylamino, dialkylamino, arylamino, cyano, hydroxyl, halogen, nitro, $C_1$-$C_5$ thioalkyl wherein the sulfur atom may be oxidized, $C_1$-$C_5$ alkoxyl, —O-alkoxyl, O—CH$_2$-aryl, aryloxy, O—CH$_2$-heteroaryl, —NH—SO$_2$—, carbocyclyl, heterocyclyl, aryl or heteroaryl, each optionally independently substituted with 1-3 substituents chosen from $C_1$-$C_5$ alkyl, acyl, amino, aryl, halogen, hydroxyl, oxo, trihaloalkyl, carboxamide and $C_1$-$C_5$ alkoxy;

X is N or CH and

Ar is a heteroaryl ring chosen from furanyl, thiazolyl, pyrazolyl, imidazolyl, pyrrolyl, thienyl, pyridinyl, pyrimidinyl, pyridazinyl, oxazolyl and quinolinyl, wherein each ring may be optionally substituted with 1-2 substituents chosen from $C_1$-$C_5$ alkyl, halogen, amino and oxo;

or a pharmaceutically acceptable salt thereof.

In another embodiment 2, there is provided a compound of the formula (I) according the embodiment described immediately above, and wherein $R^1$ is $C_1$-$C_5$ alkyl optionally substituted with 1-3 substituents chosen from hydroxyl, $C_1$-$C_5$ alkoxy which is optionally substituted with a carboxamido group, $C_3$-$C_6$ carbocyclyl, amino, alkylamino and dialkylamino;

$R^2$ is $C_1$-$C_5$ alkyl, cyclopropyl, cyclobutyl, cyclopentyl, cyclohexyl, cycloheptyl, tetrahydrofuranyl, tetrahydropyranyl, piperidinyl, phenyl, naphthyl, benzothienyl, benzofuranyl, indolyl, thienyl, furanyl or pyrrolyl, each optionally independently substituted with 1-2 substituents chosen from hydroxyl, $C_1$-$C_5$ alkoxy, $C_3$-$C_6$ carbocyclyl, phenyl and carboxyl;

$R^3$ is a bond, hydrogen, —C(O)—NH—, —NH—C(O)—, —CHR$_a$—O—, —O—CH$_2$—, —C(O)—NH—CH$_2$—, —CH$_2$—NH—C(O), SO$_2$—NH— or —NH—SO$_2$—;

$R^4$ is $C_1$-$C_5$ alkyl, $C_2$-$C_4$ alkenyl, amino, alkylamino, dialkylamino, arylamino, cyano, hydroxyl, halogen, nitro, $C_1$-$C_5$ thioalkyl wherein the sulfur atom may be oxidized, $C_1$-$C_5$ alkoxyl, —O-alkoxyl, O—CH$_2$-aryl, O—CH$_2$-heteroaryl, aryloxy, —NH—SO$_2$—, cyclopropyl, cyclobutyl, cyclopentyl, cyclohexyl, phenyl, furanyl, thienyl, pyrrolyl, pyrazolyl, imidazolyl, pyridinyl, pyrimidinyl, pyrazinyl, imidazopyridinyl, benzofuranyl, benzothienyl, or indolyl, each optionally independently substituted with 1-3 substituents chosen from $C_1$-$C_5$ alkyl, $C_1$-$C_5$ acyl, amino, phenyl, halogen, hydroxyl, oxo, trifluoromethyl, carboxamide and $C_1$-$C_5$ alkoxy;

and

Ar is a heteroaryl ring chosen from furanyl, thiazolyl, pyrazolyl, imidazolyl, pyrrolyl, thienyl, pyridinyl, pyrimidinyl, pyridazinyl, oxazolyl and quinolinyl, wherein each ring may be optionally substituted with 1-2 substituents chosen from $C_1$-$C_5$ alkyl, halogen, amino and oxo.

In another embodiment 3, there is provided a compound of the formula (I) according the embodiment described immediately above, and wherein $R^1$ is $C_1$-$C_5$ alkyl optionally substituted with 1-3 substituents chosen from hydroxyl, $C_1$-$C_5$ alkoxy optionally substituted with a carboxamido group and $C_3$-$C_6$ cycloalkyl;

$R^2$ is $C_1$-$C_5$ alkyl, cyclopropyl, cyclopentyl, cyclohexyl, tetrahydropyranyl or piperidinyl, each optionally independently substituted with 1-2 substituents chosen from hydroxyl, $C_1$-$C_5$ alkoxy and phenyl;

$R^3$ is a bond, —C(O)—NH—, —NH—C(O)—, —CHR$_a$—O—, —O—CH$_2$—, —C(O)—NH—CH$_2$—, —CH$_2$—NH—C(O), SO$_2$—NH— or —NH—SO$_2$—;

$R^4$ is $C_1$-$C_5$ alkyl, $C_1$-$C_5$ alkylamino, amino, $C_1$-$C_5$ dialkylamino, phenylamino, cyano, halogen, nitro, $C_1$-$C_5$ thioalkyl wherein the sulfur atom may be oxidized, $C_1$-$C_5$ alkoxyl, —O-alkoxyl, —NH—SO$_2$—, —OCH$_2$-phenyl, cyclopropyl, phenyl, furanyl, thienyl, pyrazolyl, imidazolyl, pyridinyl, pyrimidinyl, imidazopyridinyl or benzofuranyl, each optionally independently substituted with 1-3 substituents chosen from $C_1$-$C_5$ alkyl, amino, halogen, trifluoromethyl and $C_1$-$C_5$ alkoxy;

and

Ar is furanyl or thiazolyl.

In another embodiment 4, there is provided a compound of the formula (I) according the embodiment described immediately above, and wherein $R^1$ is $C_1$-$C_5$ alkyl optionally substituted with 1-2 substituents chosen from hydroxyl and methoxy;

$R^2$ is $C_1$-$C_3$ alkyl, cyclohexyl or tetrahydropyranyl, wherein the alkyl group is optionally substituted with a hydroxyl;

$R^3$ is a bond, —C(O)—NH—, —NH—C(O)—, —CHR$_a$—O—, —O—CH$_2$—, —C(O)—NH—CH$_2$—, or —CH$_2$—NH—C(O);

$R^4$ is $C_1$-$C_5$ alkyl, phenyl, furanyl, thienyl, pyrazolyl, imidazolyl, pyridinyl, pyrimidinyl, imidazopyridinyl or benzofuranyl, each optionally independently substituted with 1-3 substituents chosen from $C_1$-$C_3$ alkyl and trifluoromethyl;

and

Ar is furanyl.

In another embodiment 5, there is provided a compound of the formula (I) according to embodiment 4, wherein $R^1$ is methyl;

$R^3$ is —O—CH$_2$—.

In another embodiment 6, there is provided a compound of the formula (I) according to embodiment 4, wherein $R^1$ is methyl;

$R^3$ is —NH—C(O)—.

In another embodiment 7, there is provided a compound of the formula (I) according to embodiment 4, wherein $R^1$ is methyl;

$R^3$ is —CH$_2$—NH—C(O)—.

In another embodiment 8, the invention provides compounds in Table I which can be made in view of the general schemes, examples and methods known in the art.

TABLE I

| Name | Structure |
|---|---|
| N-[(1S)-1-cyclohexyl-2-(methylamino)-2-oxoethyl]-5-[4-(1-methyl-1H-pyrazol-4-yl)phenyl]furan-2-carboxamide | 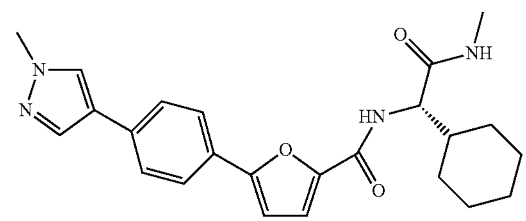 [SMILES: CNC(=O)[C@@H](NC(=O)c1ccc(-c2ccc(-c3cnn(C)c3)cc2)o1)C1CCCCC1] |

TABLE I-continued

| Name | Structure |
|---|---|
| N-[(1S)-1-cyclohexyl-2-(methylamino)-2-oxoethyl]-5-(5-ethoxypyridin-2-yl)furan-2-carboxamide | 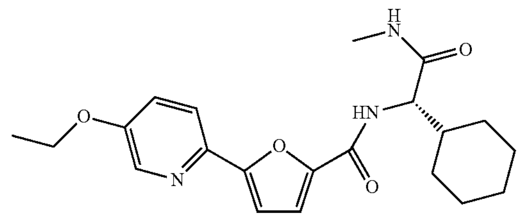 [SMILES: CCOc1ccc(-c2ccc(C(=O)N[C@H](C(=O)NC)C3CCCCC3)o2)nc1] |
| N-[(1S)-1-cyclohexyl-2-(methylamino)-2-oxoethyl]-5-(5-nitropyridin-2-yl)furan-2-carboxamide | |
| 5-(4-cyanophenyl)-N-{(1S)-1-cyclohexyl-2-[(2-methoxyethyl)amino]-2-oxoethyl}furan-2-carboxamide | 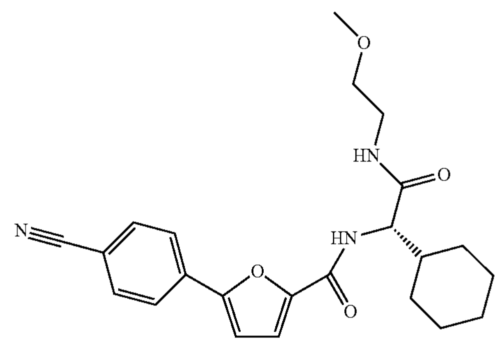 [SMILES: COCCNC(=O)[C@@H](NC(=O)c1ccc(-c2ccc(C#N)cc2)o1)C1CCCCC1] |
| 5-(4-cyanophenyl)-N-[(1S)-2-(methylamino)-2-oxo-1-(tetrahydro-2H-pyran-4-yl)ethyl]furan-2-carboxamide | 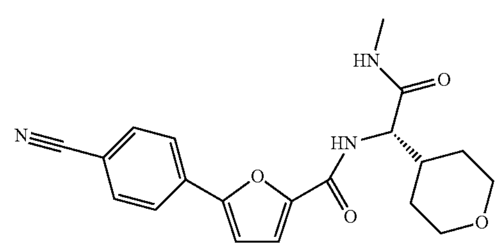 [SMILES: CNC(=O)[C@@H](NC(=O)c1ccc(-c2ccc(C#N)cc2)o1)C1CCOCC1] |
| 5-(4-cyanophenyl)-N-{(1S)-1-cyclohexyl-2-[(2-hydroxyethyl)amino]-2-oxoethyl}furan-2-carboxamide | 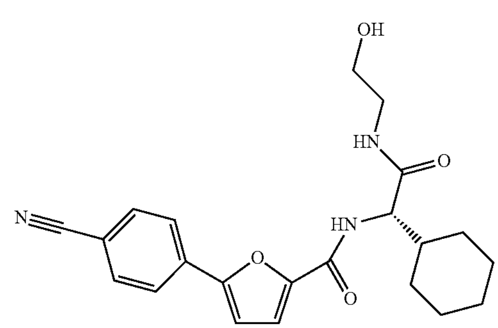 [SMILES: N#Cc1ccc(-c2ccc(C(=O)N[C@H](C(=O)NCCO)C3CCCCC3)o2)cc1] |

TABLE I-continued

| Name | Structure |
|---|---|
| 5-(4-cyanophenyl)-N-{(1S)-1-cyclohexyl-2-[(2-hydroxypropyl)amino]-2-oxoethyl}furan-2-carboxamide | 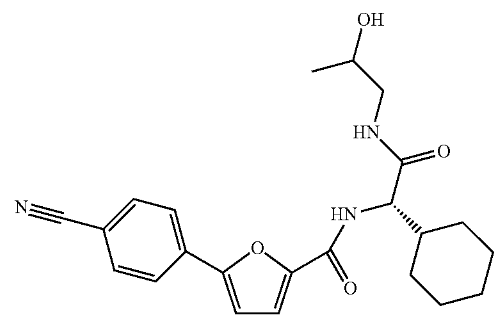 [SMILES: CC(O)CNC(=O)[C@@H](NC(=O)c1ccc(-c2ccc(C#N)cc2)o1)C1CCCCC1] |
| N-[(1S)-1-cyclohexyl-2-(methylamino)-2-oxoethyl]-5-[4-(methylsulfanyl)phenyl]furan-2-carboxamide | 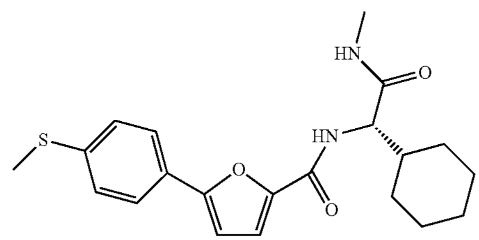 [SMILES: CNC(=O)[C@@H](NC(=O)c1ccc(-c2ccc(SC)cc2)o1)C1CCCCC1] |
| 5-(4-cyanophenyl)-N-[(1S)-1-cyclohexyl-2-(methylamino)-2-oxoethyl]furan-2-carboxamide | 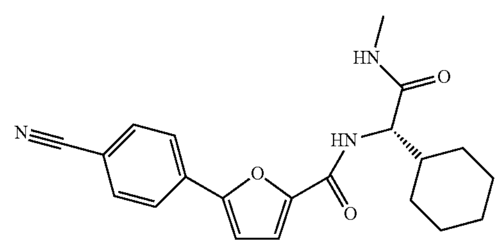 [SMILES: CNC(=O)[C@@H](NC(=O)c1ccc(-c2ccc(C#N)cc2)o1)C1CCCCC1] |
| 5-(4-cyanophenyl)-N-[(1S)-1-cyclohexyl-2-{[(2S)-1-hydroxypropan-2-yl]amino}-2-oxoethyl]furan-2-carboxamide | 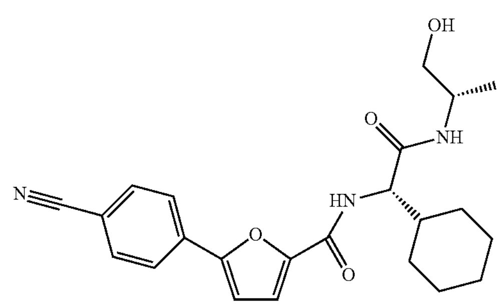 [SMILES: C[C@@H](CO)NC(=O)[C@@H](NC(=O)c1ccc(-c2ccc(C#N)cc2)o1)C1CCCCC1] |
| 5-(4-cyanophenyl)-N-[(1S)-1-cyclohexyl-2-{[(2S)-1-methoxypropan-2-yl]amino}-2-oxoethyl]furan-2-carboxamide | 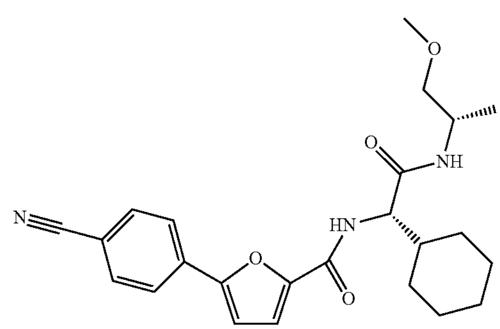 [SMILES: COC[C@H](C)NC(=O)[C@@H](NC(=O)c1ccc(-c2ccc(C#N)cc2)o1)C1CCCCC1] |

TABLE I-continued

| Name | Structure |
|---|---|
| N-[(1S)-1-cyclohexyl-2-(methylamino)-2-oxoethyl]-5-(4-methoxyphenyl)furan-2-carboxamide | 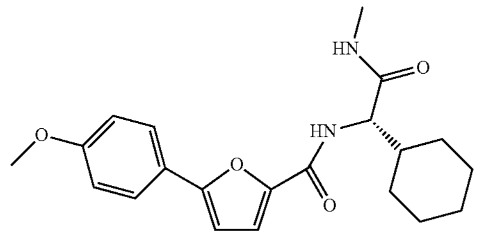 |
| Methyl [4-(5-{[(1S)-1-cyclohexyl-2-(methylamino)-2-oxoethyl]carbamoyl}furan-2-yl)phenyl]carbamate | 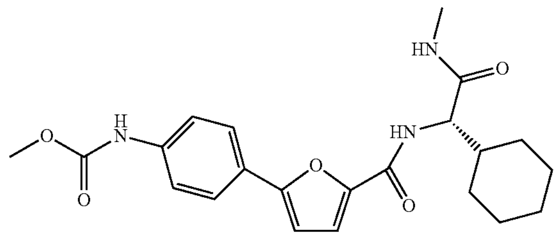 [SMILES: CNC(=O)[C@@H](NC(=O)c1ccc(-c2ccc(NC(=O)OC)cc2)o1)C1CCCCC1] |
| 5-(5-Chloropyridin-2-yl)-N-[(1S)-1-cyclohexyl-2-(methylamino)-2-oxoethyl]furan-2-carboxamide | 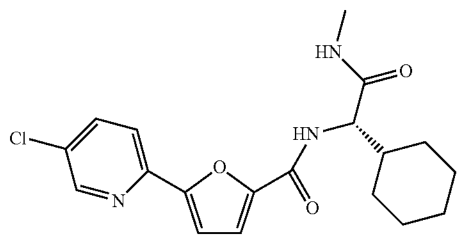 [SMILES: CNC(=O)[C@@H](NC(=O)c1ccc(-c2ccc(Cl)cn2)o1)C1CCCCC1] |
| N-[(1S)-1-cyclohexyl-2-(methylamino)-2-oxoethyl]-5-(4-ethoxyphenyl)furan-2-carboxamide | 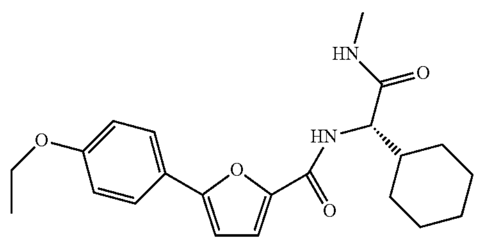 [SMILES: CCOc1ccc(-c2ccc(C(=O)N[C@H](C(=O)NC)C3CCCCC3)o2)cc1] |
| N-[(1S)-1-cyclohexyl-2-(methylamino)-2-oxoethyl]-5-(4-methylphenyl)furan-2-carboxamide | 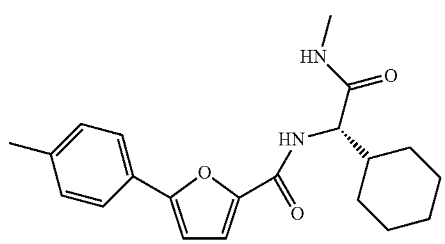 [SMILES: CNC(=O)[C@@H](NC(=O)c1ccc(-c2ccc(C)cc2)o1)C1CCCCC1] |
| 5-(4-cyanophenyl)-N-[(1S)-1-cyclohexyl-2-(ethylamino)-2-oxoethyl]furan-2-carboxamide | 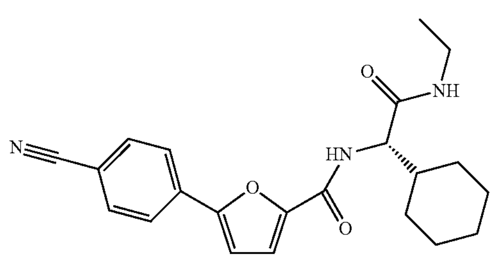 [SMILES: CCNC(=O)[C@@H](NC(=O)c1ccc(-c2ccc(C#N)cc2)o1)C1CCCCC1] |

TABLE I-continued

| Name | Structure |
|---|---|
| 5-(4-Chloro-phenyl)-furan-2-carboxylic acid ((1S,2S)-2-methyl-1-methylcarbamoyl-butyl)-amide | 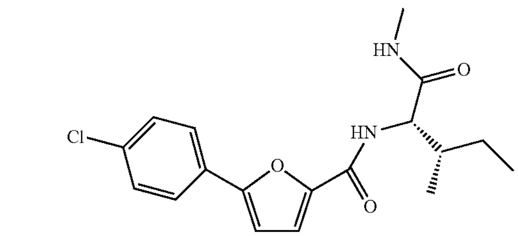 [SMILES: CC[C@H](C)[C@H](NC(=O)c1ccc(-c2ccc(Cl)cc2)o1)C(=O)NC] |
| N-[(1S)-1-cyclohexyl-2-(methylamino)-2-oxoethyl]-5-(4-ethylphenyl)furan-2-carboxamide | 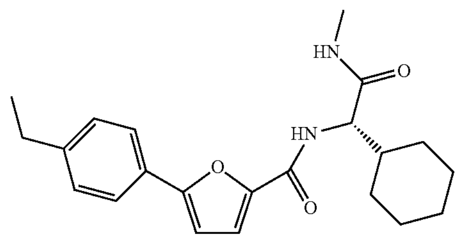 [SMILES: CCc1ccc(-c2ccc(C(=O)N[C@H](C(=O)NC)C3CCCCC3)o2)cc1] |
| N-[(1S)-2-{[2-(2-amino-2-oxoethoxy)ethyl]amino}-1-cyclohexyl-2-oxoethyl]-5-(4-chlorophenyl)furan-2-carboxamide | 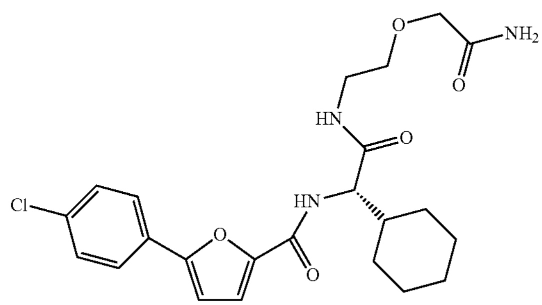 [SMILES: NC(=O)COCCNC(=O)[C@@H](NC(=O)c1ccc(-c2ccc(Cl)cc2)o1)C1CCCCC1] |
| 2-(4-Methylphenyl)-thiazole-4-carboxylic acid ((1S,2R)-2-methyl-1-methylcarbamoyl-butyl)-amide | 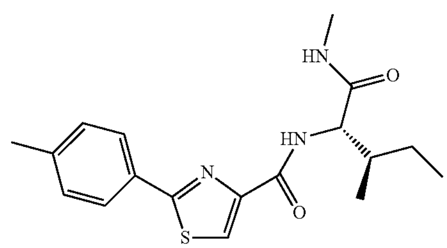 [SMILES: CC[C@@H](C)[C@H](NC(=O)c1csc(-c2ccc(C)cc2)n1)C(=O)NC] |
| 5-(4-Bromophenyl)-N-[(1S)-1-cyclohexyl-2-(methylamino)-2-oxoethyl]furan-2-carboxamide | 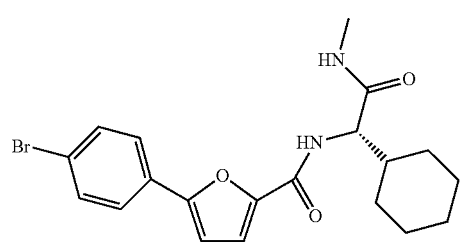 |
| 5-(4-Chlorophenyl)-N-[(1S)-2-(methylamino)-2-oxo-1-(piperidin-4-yl)ethyl]furan-2-carboxamide | 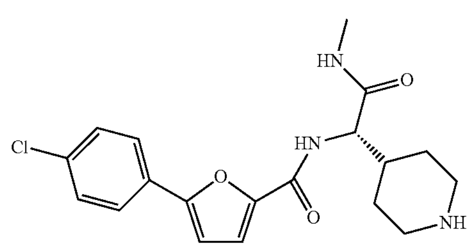 [SMILES: CNC(=O)[C@@H](NC(=O)c1ccc(-c2ccc(Cl)cc2)o1)C1CCNCC1] |

TABLE I-continued

| Name | Structure |
|---|---|
| N-[(1S)-1-cyclohexyl-2-(methylamino)-2-oxoethyl]-5-{4-[(methylsulfonyl)amino]phenyl}furan-2-carboxamide | 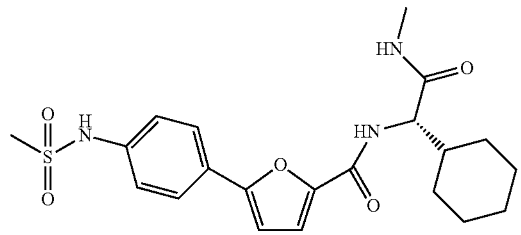 [SMILES: CNC(=O)[C@@H](NC(=O)c1ccc(-c2ccc(NS(C)(=O)=O)cc2)o1)C1CCCCC1] |
| 5-(4-Chlorophenyl)-N-[(1S)-1-cyclopentyl-2-(methylamino)-2-oxoethyl]furan-2-carboxamide | 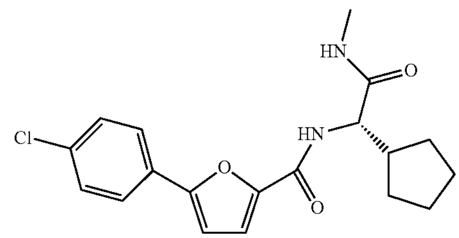 [SMILES: CNC(=O)[C@@H](NC(=O)c1ccc(-c2ccc(Cl)cc2)o1)C1CCCC1] |
| N-[(1S)-1-cyclohexyl-2-(methylamino)-2-oxoethyl]-5-(4-nitrophenyl)furan-2-carboxamide | |
| 2-(4-Chlorophenyl)-N-[(1S)-1-cyclohexyl-2-(methylamino)-2-oxoethyl]-1,3-thiazole-4-carboxamide | 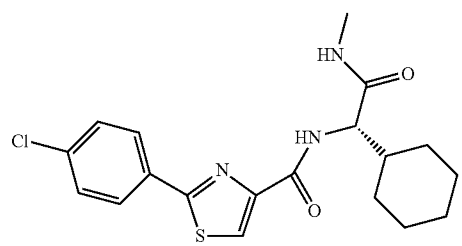 [SMILES: CNC(=O)[C@@H](NC(=O)c1csc(-c2ccc(Cl)cc2)n1)C1CCCCC1] |
| 5-(4-chlorophenyl)-N-[(1S)-1-cyclohexyl-2-(methylamino)-2-oxoethyl]furan-2-carboxamide | 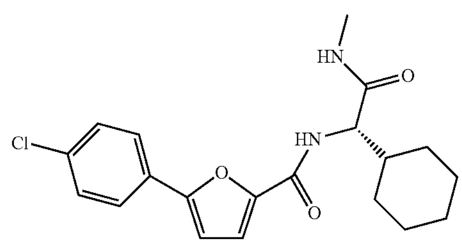 [SMILES: CNC(=O)[C@@H](NC(=O)c1ccc(-c2ccc(Cl)cc2)o1)C1CCCCC1] |
| N-[(1S)-1-cyclohexyl-2-(methylamino)-2-oxoethyl]-5-[4-(methylsulfamoyl)phenyl]furan-2-carboxamide | 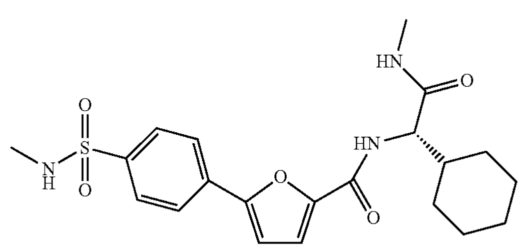 [SMILES: CNC(=O)[C@@H](NC(=O)c1ccc(-c2ccc(S(=O)(=O)NC)cc2)o1)C1CCCCC1] |

TABLE I-continued

| Name | Structure |
|---|---|
| 5-(4-Chloro-phenyl)-furan-2-carboxylic acid ((S)-1-methylcarbamoyl-2-phenyl-ethyl)-amide | 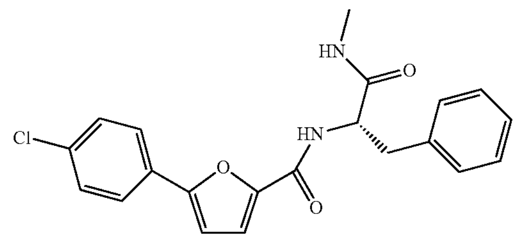 [SMILES: CNC(=O)[C@H](Cc1ccccc1)NC(=O)c1ccc(-c2ccc(Cl)cc2)o1] |
| 5-(4-Chloro-phenyl)-furan-2-carboxylic acid ((S)-2-methyl-1-methylcarbamoyl-propyl)-amide | 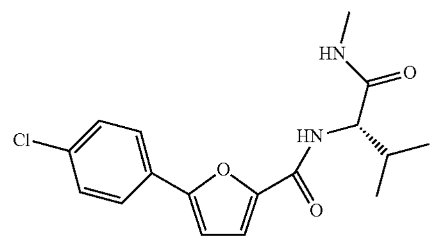 [SMILES: CNC(=O)[C@@H](NC(=O)c1ccc(-c2ccc(Cl)cc2)o1)C(C)C] |
| 5-(4-Cyanophenyl)-N-{(1S)-1-cyclohexyl-2-[(1-methoxypropan-2-yl)amino]-2-oxoethyl}furan-2-carboxamide | 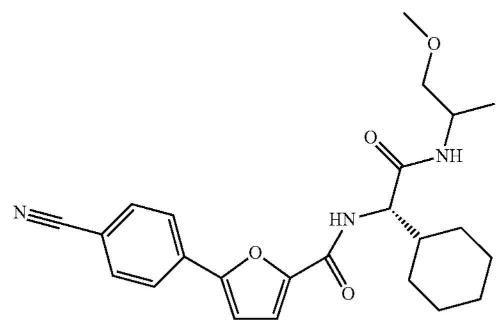 |
| 5-(4-Cyano-phenyl)-furan-2-carboxylic acid ((S)-2-hydroxy-2-methyl-1-methylcarbamoyl-propyl)-amide | 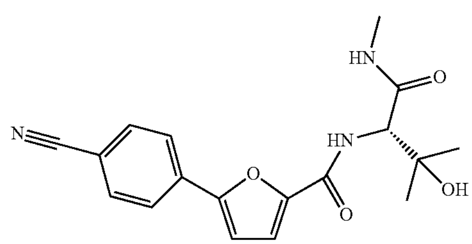 [SMILES: CNC(=O)[C@@H](NC(=O)c1ccc(-c2ccc(C#N)cc2)o1)C(C)(C)O] |
| 5-(4-Chloro-phenyl)-furan-2-carboxylic acid ((1S,2R)-2-methyl-1-methylcarbamoyl-butyl)-amide | 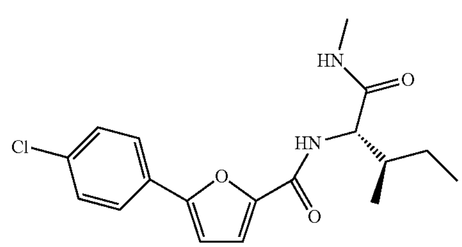 [SMILES: CC[C@@H](C)[C@H](NC(=O)c1ccc(-c2ccc(Cl)cc2)o1)C(=O)NC] |
| N-[(2S)-1-(methylamino)-4-(methylsulfonyl)-1-oxobutan-2-yl]-2-(4-methylphenyl)-1,3-thiazole-4-carboxamide | 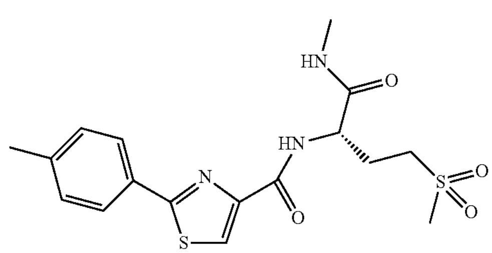 [SMILES: CNC(=O)[C@H](CCS(C)(=O)=O)NC(=O)c1csc(-c2ccc(C)cc2)n1] |

TABLE I-continued

| Name | Structure |
|---|---|
| 5-(5-Chloro-pyridin-2-yl)-furan-2-carboxylic acid ((1S,2R)-2-methyl-1-methylcarbamoyl-butyl)-amide | 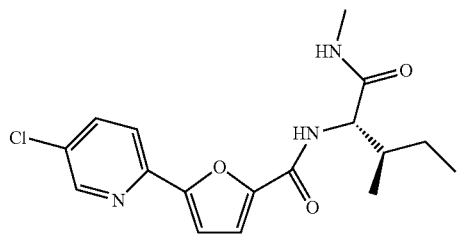 [SMILES: CC[C@@H](C)[C@H](NC(=O)c1ccc(-c2ccc(Cl)cn2)o1)C(=O)NC] |
| 5-(4-Cyanophenyl)-N-{(1S)-1-cyclohexyl-2-[(2-methylbutan-2-yl)amino]-2-oxoethyl}furan-2-carboxamide | 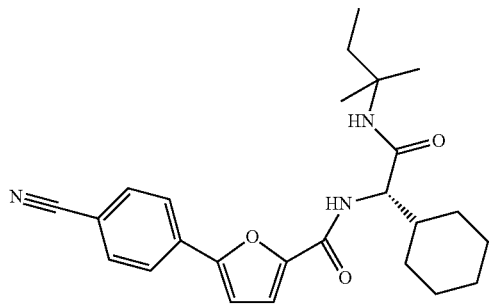 [SMILES: CCC(C)(C)NC(=O)[C@@H](NC(=O)c1ccc(-c2ccc(C#N)cc2)o1)C1CCCCC1] |
| 2-(4-Chloro-phenyl)-thiazole-4-carboxylic acid ((1S,2S)-2-methyl-1-methylcarbamoyl-butyl)-amide | 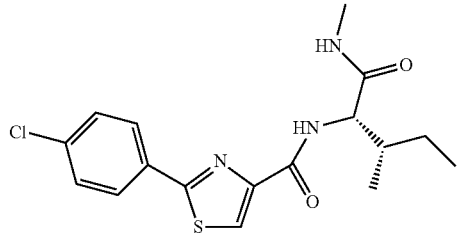 [SMILES: CC[C@H](C)[C@H](NC(=O)c1csc(-c2ccc(Cl)cc2)n1)C(=O)NC] |
| 2-(4-Chloro-phenyl)-thiazole-4-carboxylic acid ((1S,2R)-2-methyl-1-methylcarbamoyl-butyl)-amide | 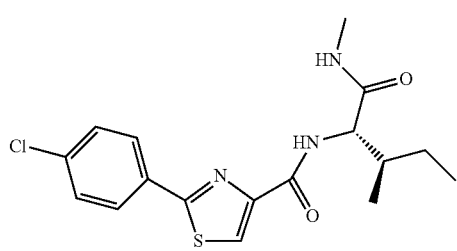 [SMILES: CC[C@@H](C)[C@H](NC(=O)c1csc(-c2ccc(Cl)cc2)n1)C(=O)NC] |
| 5-(4-Cyanophenyl)-N-[(1S)-1-cyclohexyl-2-{[(2R)-1-hydroxypropan-2-yl]amino}-2-oxoethyl]furan-2-carboxamide | 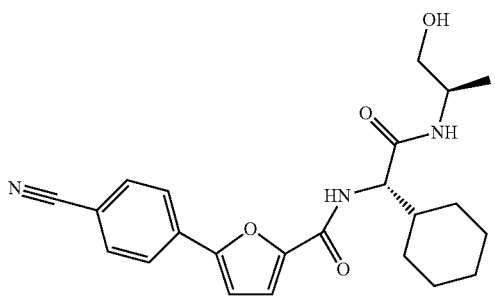 [SMILES: C[C@H](CO)NC(=O)[C@@H](NC(=O)c1ccc(-c2ccc(C#N)cc2)o1)C1CCCCC1] |
| 4-(4-Bromophenyl)-N-[(1S)-1-cyclohexyl-2-(methylamino)-2-oxoethyl]-1,3-thiazole-2-carboxamide | 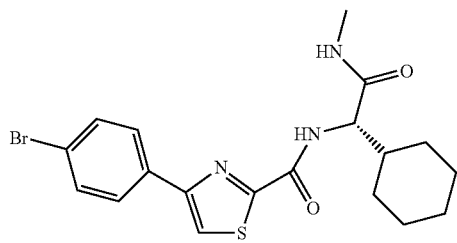 [SMILES: CNC(=O)[C@@H](NC(=O)c1nc(-c2ccc(Br)cc2)cs1)C1CCCCC1] |

TABLE I-continued

| Name | Structure |
|---|---|
| N-[(1S)-1-cyclohexyl-2-(methylamino)-2-oxoethyl]-5-(5-hydroxypyridin-2-yl)furan-2-carboxamide | 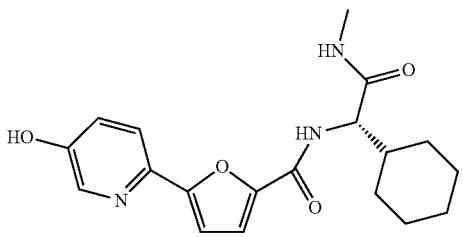 [SMILES: CNC(=O)[C@@H](NC(=O)c1ccc(-c2ccc(O)cn2)o1)C1CCCCC1] |
| 2-(4-Chloro-phenyl)-thiazole-4-carboxylic acid ((S)-1-methylcarbamoyl-pentyl)-amide | 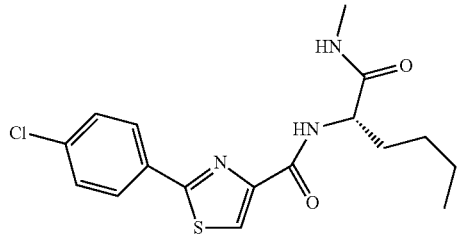 [SMILES: CCCC[C@H](NC(=O)c1csc(-c2ccc(Cl)cc2)n1)C(=O)NC] |
| 2-(4-Chloro-phenyl)-thiazole-4-carboxylic acid ((S)-2-methyl-1-methylcarbamoyl-propyl)-amide | 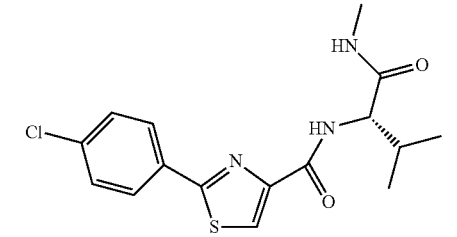 [SMILES: CNC(=O)[C@@H](NC(=O)c1csc(-c2ccc(Cl)cc2)n1)C(C)C] |
| 5-(4-Cyanophenyl)-N-[(1S)-1-cyclohexyl-2-{[1-(dimethylamino)propan-2-yl]amino}-2-oxoethyl]furan-2-carboxamide | 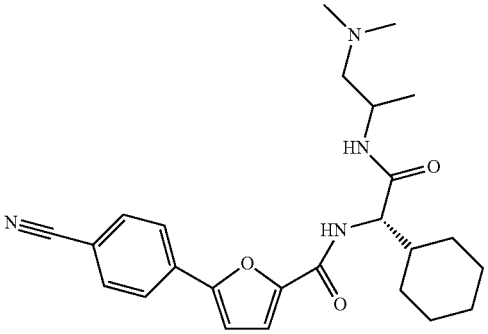 [SMILES: CC(CN(C)C)NC(=O)[C@@H](NC(=O)c1ccc(-c2ccc(C#N)cc2)o1)C1CCCCC1] |
| N-[(1S)-1-cyclohexyl-2-(methylamino)-2-oxoethyl]-2-phenyl-1,3-thiazole-4-carboxamide | 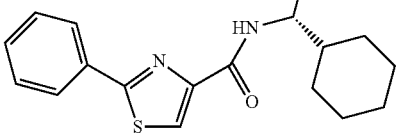 |
| N-[(1S)-2-(butan-2-ylamino)-1-cyclohexyl-2-oxoethyl]-5-(4-cyanophenyl)furan-2-carboxamide | 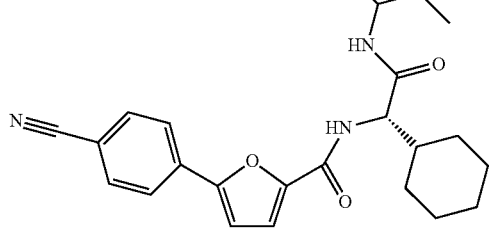 |

TABLE I-continued

| Name | Structure |
|---|---|
| N-[(1S)-1-cyclohexyl-2-(methylamino)-2-oxoethyl]-1-(4-nitrophenyl)-1H-pyrazole-3-carboxamide | 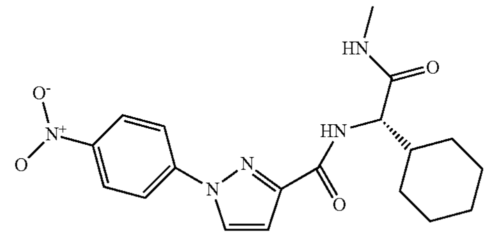 [SMILES: CNC(=O)[C@@H](NC(=O)c1ccn(-c2ccc([NH+]([O-])O)cc2)n1)C1CCCCC1] |
| 2-(4-Chloro-phenyl)-thiazole-4-carboxylic acid ((S)-1-methylcarbamoyl-butyl)-amide | 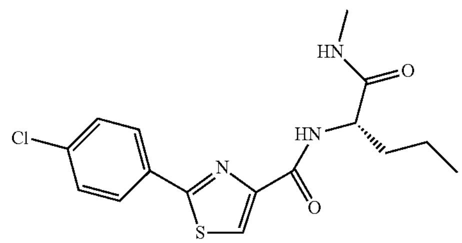 [SMILES: CCC[C@H](NC(=O)c1csc(-c2ccc(Cl)cc2)n1)C(=O)NC] |
| 5-[4-(Acetylamino)phenyl]-N-[(1S)-1-cyclohexyl-2-(methylamino)-2-oxoethyl]furan-2-carboxamide | 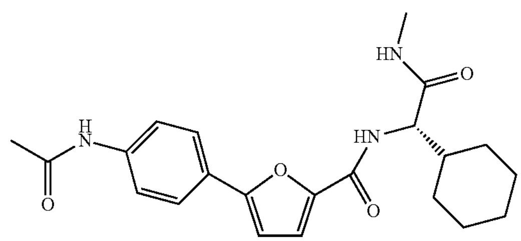 [SMILES: CNC(=O)[C@@H](NC(=O)c1ccc(-c2ccc(NC(C)=O)cc2)o1)C1CCCCC1] |
| 5-(4-Cyanophenyl)-N-[(1S)-1-cyclohexyl-2-oxo-2-(propan-2-ylamino)ethyl]furan-2-carboxamide | 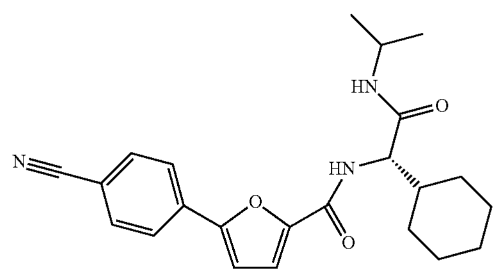 [SMILES: CC(C)NC(=O)[C@@H](NC(=O)c1ccc(-c2ccc(C#N)cc2)o1)C1CCCCC1] |
| N-[(2S)-3-(1-benzothiophen-3-yl)-1-(methylamino)-1-oxopropan-2-yl]-2-(4-chlorophenyl)-1,3-thiazole-4-carboxamide | 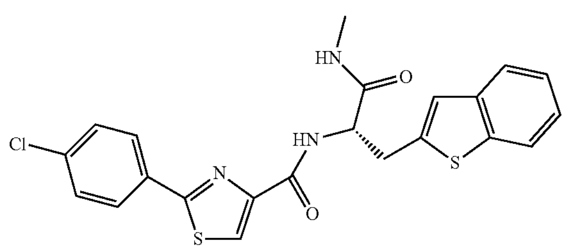 [SMILES: CNC(=O)[C@H](Cc1cc2ccccc2s1)NC(=O)c1csc(-c2ccc(Cl)cc2)n1] |
| N-[(1S)-1-cyclohexyl-2-(methylamino)-2-oxoethyl]-5-{4-[(methylcarbamoyl)amino]phenyl}furan-2-carboxamide | 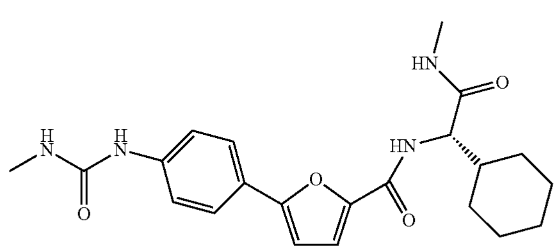 [SMILES: CNC(=O)Nc1ccc(-c2ccc(C(=O)N[C@H](C(=O)NC)C3CCCCC3)o2)cc1] |

TABLE I-continued

| Name | Structure |
|---|---|
| N-[(1S)-1-cyclohexyl-2-(methylamino)-2-oxoethyl]-5-(4-{[(2E)-3-(2,4-difluorophenyl)prop-2-enoyl]amino}phenyl)furan-2-carboxamide | 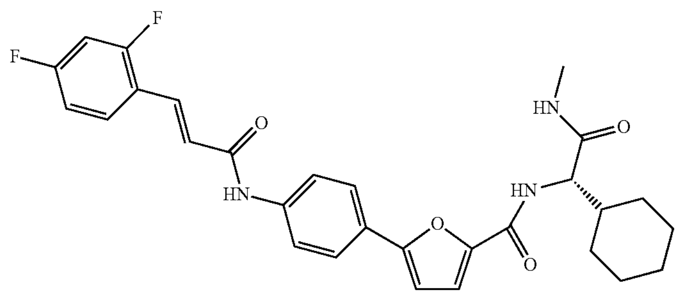 [SMILES: CNC(=O)[C@@H](NC(=O)c1ccc(-c2ccc(NC(=O)/C=C/c3ccc(F)cc3F)cc2)o1)C1CCCCC1] |
| 5-(4-Chlorophenyl)-N-[(1S)-1-cyclopropyl-2-(methylamino)-2-oxoethyl]furan-2-carboxamide | 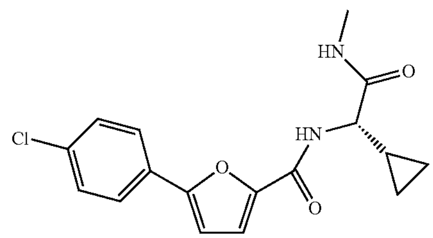 [SMILES: CNC(=O)[C@@H](NC(=O)c1ccc(-c2ccc(Cl)cc2)o1)C1CC1] |
| 5-(4-Aminophenyl)-N-[(1S)-1-cyclohexyl-2-(methylamino)-2-oxoethyl]furan-2-carboxamide | 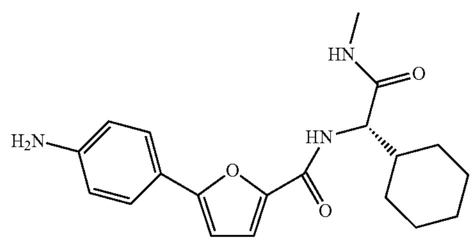 [SMILES: CNC(=O)[C@@H](NC(=O)c1ccc(-c2ccc(N)cc2)o1)C1CCCCC1] |
| N-[(2S)-3-cyclohexyl-1-(methylamino)-1-oxopropan-2-yl]-5-(4-nitrophenyl)furan-2-carboxamide | 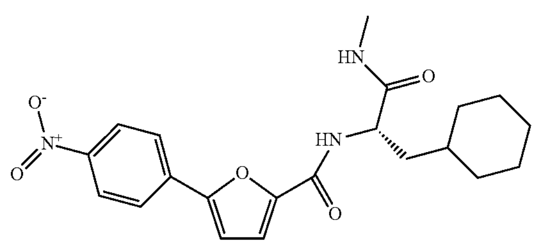 [SMILES: CNC(=O)[C@H](CC1CCCCC1)NC(=O)c1ccc(-c2ccc([N+](=O)[O-])cc2)o1] |
| 5-(4-Chlorophenyl)-N-[(1S)-2-(methylamino)-2-oxo-1-phenylethyl]furan-2-carboxamide | 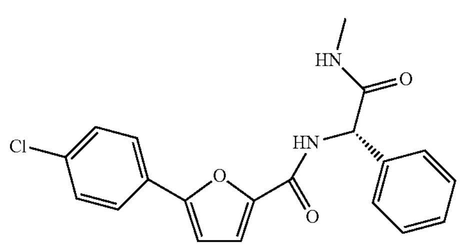 [SMILES: CNC(=O)[C@@H](NC(=O)c1ccc(-c2ccc(Cl)cc2)o1)c1ccccc1] |
| N-[(1S)-1-cyclohexyl-2-(methylamino)-2-oxoethyl]-5-[4-(1H-pyrazol-5-yl)phenyl]furan-2-carboxamide | 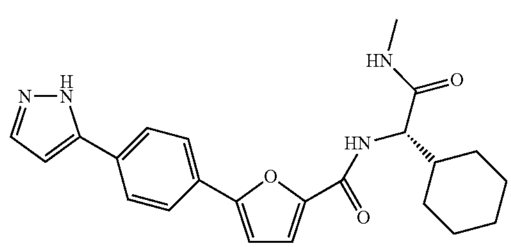 [SMILES: CNC(=O)[C@@H](NC(=O)c1ccc(-c2ccc(-c3ccn[nH]3)cc2)o1)C1CCCCC1] |

TABLE I-continued

| Name | Structure |
|---|---|
| 2-(4-Chlorophenyl)-N-[(2S)-1-(methylamino)-1-oxobutan-2-yl]-1,3-thiazole-4-carboxamide | 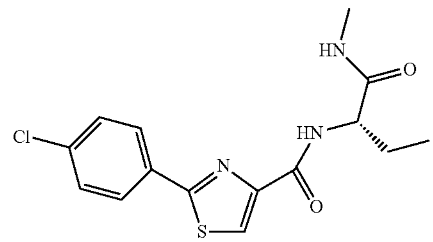 [SMILES: CC[C@H](NC(=O)c1csc(-c2ccc(Cl)cc2)n1)C(=O)NC] |
| 2-(4-Cyanophenyl)-N-[(1S)-1-cyclohexyl-2-(methylamino)-2-oxoethyl]-1,3-oxazole-4-carboxamide | 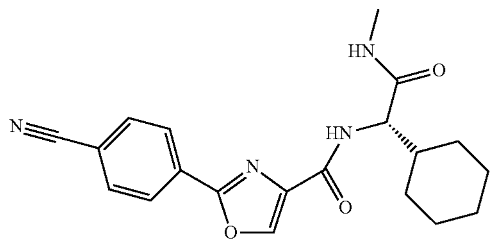 [SMILES: CNC(=O)[C@@H](NC(=O)c1coc(-c2ccc(C#N)cc2)n1)C1CCCCC1] |
| N-[(2S)-3-(1-benzothiophen-3-yl)-1-(methylamino)-1-oxopropan-2-yl]-5-(4-chlorophenyl)furan-2-carboxamide | 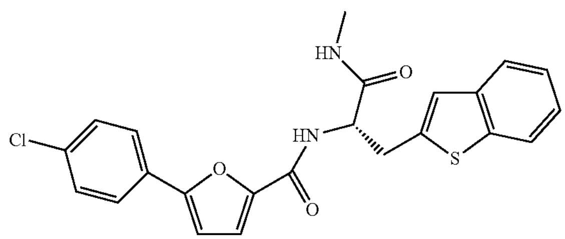 [SMILES: CNC(=O)[C@H](Cc1cc2ccccc2s1)NC(=O)c1ccc(-c2ccc(Cl)cc2)o1] |
| N-[(1S)-1-cyclohexyl-2-(methylamino)-2-oxoethyl]-5-[4-(methylsulfinyl)phenyl]furan-2-carboxamide | |
| 5-(4-Cyanophenyl)-N-[(1S)-1-cyclopropyl-2-(methylamino)-2-oxoethyl]furan-2-carboxamide | 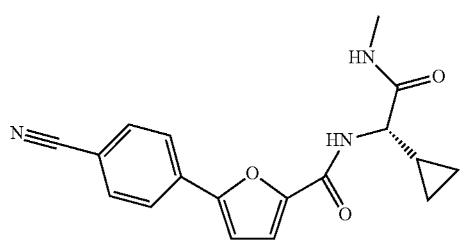 [SMILES: CNC(=O)[C@@H](NC(=O)c1ccc(-c2ccc(C#N)cc2)o1)C1CC1] |
| N-[(1S)-1-cyclohexyl-2-(methylamino)-2-oxoethyl]-4-(4-methoxyphenyl)thiophene-2-carboxamide | 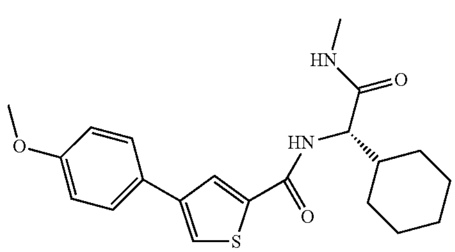 [SMILES: CNC(=O)[C@@H](NC(=O)c1cc(-c2ccc(OC)cc2)cs1)C1CCCCC1] |

TABLE I-continued

| Name | Structure |
|---|---|
| (S)-4-Methylcarbamoyl-4-[(2-p-tolyl-thiazole-4-carbonyl)-amino]-butyric acid | 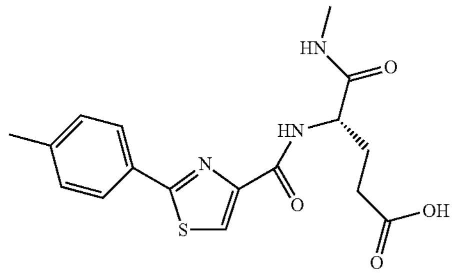 [SMILES: CNC(=O)[C@H](CCC(=O)O)NC(=O)c1csc(-c2ccc(C)cc2)n1] |
| 5-(4-Cyanophenyl)-N-{(1S)-1-cyclohexyl-2-[(cyclopropylmethyl)amino]-2-oxoethyl}furan-2-carboxamide | 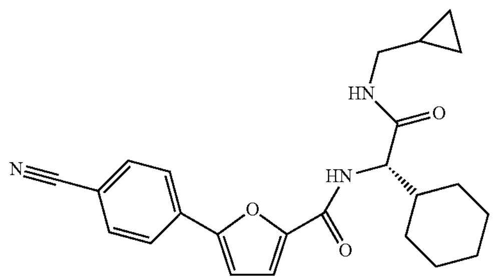 [SMILES: N#Cc1ccc(-c2ccc(C(=O)N[C@H](C(=O)NCC3CC3)C3CCCCC3)o2)cc1] |
| 5-(5-Aminopyridin-2-yl)-N-[(1S)-1-cyclohexyl-2-(methylamino)-2-oxoethyl]furan-2-carboxamide | 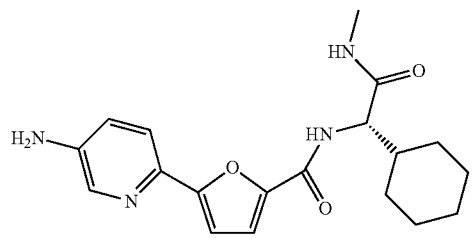 [SMILES: CNC(=O)[C@@H](NC(=O)c1ccc(-c2ccc(N)cn2)o1)C1CCCCC1] |
| N-[(2S)-1-(methylamino)-3-(naphthalen-1-yl)-1-oxopropan-2-yl]-5-oxo-1-phenyl-4,5-dihydro-1H-pyrazole-3-carboxamide | 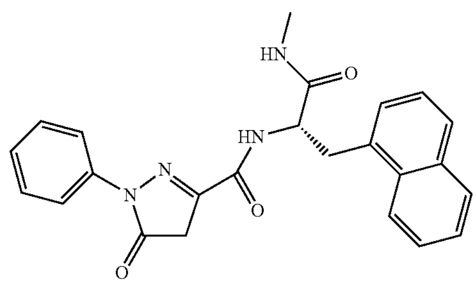 [SMILES: CNC(=O)[C@H](Cc1cccc2ccccc12)NC(=O)C1=NN(c2ccccc2)C(=O)C1] |
| 4-(4-Chlorophenyl)-N-[(1S)-1-cyclohexyl-2-(methylamino)-2-oxoethyl]thiophene-2-carboxamide | 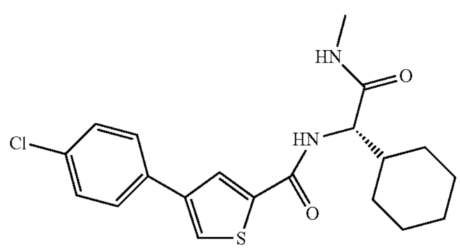 [SMILES: CNC(=O)[C@@H](NC(=O)c1cc(-c2ccc(Cl)cc2)cs1)C1CCCCC1] |
| Methyl (2S)-{[(5-{4-[(tert-butoxycarbonyl)amino]phenyl}furan-2-yl)carbonyl]amino}(cyclohexyl)ethanoate | 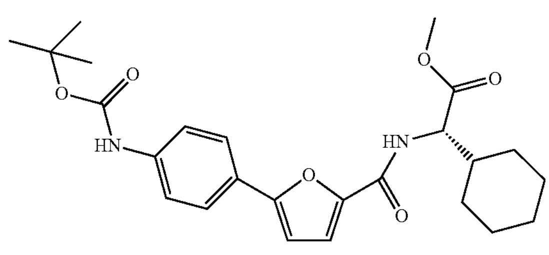 [SMILES: COC(=O)[C@@H](NC(=O)c1ccc(-c2ccc(NC(=O)OC(C)(C)C)cc2)o1)C1CCCCC1] |

TABLE I-continued

| Name | Structure |
|---|---|
| 5-(4-Amino-3-nitrophenyl)-N-[(1S)-1-cyclohexyl-2-(methylamino)-2-oxoethyl]furan-2-carboxamide | 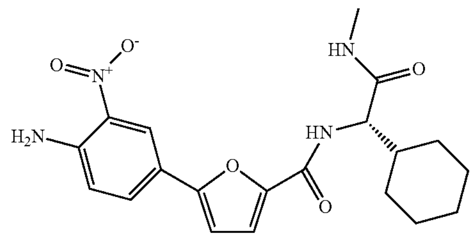 [SMILES: CNC(=O)[C@@H](NC(=O)c1ccc(-c2ccc(N)c([N+](=O)[O-])c2)o1)C1CCCCC1] |
| 4-(5-Cyanopyridin-2-yl)-N-[(1S)-1-cyclohexyl-2-(methylamino)-2-oxoethyl]-1-methyl-1H-pyrrole-2-carboxamide | 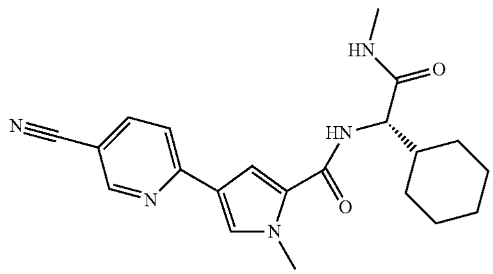 [SMILES: CNC(=O)[C@@H](NC(=O)c1cc(-c2ccc(C#N)cn2)cn1C)C1CCCCC1] |
| N-[(1S)-1-cyclohexyl-2-(methylamino)-2-oxoethyl]-5-(3,4-diaminophenyl)furan-2-carboxamide | 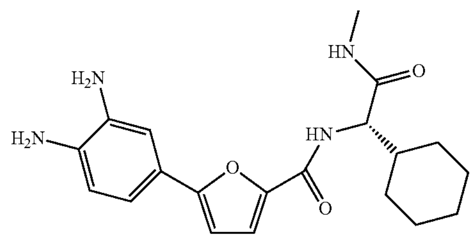 [SMILES: CNC(=O)[C@@H](NC(=O)c1ccc(-c2ccc(N)c(N)c2)o1)C1CCCCC1] |
| N-[(1S)-1-cyclopropyl-2-(methylamino)-2-oxoethyl]-5-[4-(6-methylimidazo[1,2-a]pyridin-2-yl)phenyl]furan-2-carboxamide | 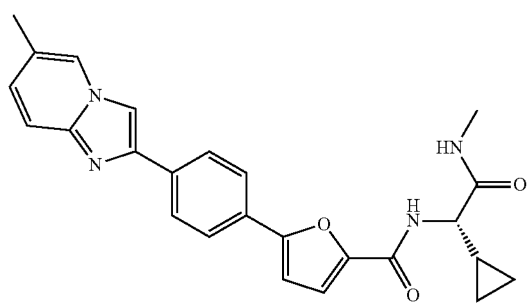 [SMILES: CNC(=O)[C@@H](NC(=O)c1ccc(-c2ccc(-c3cn4cc(C)ccc4n3)cc2)o1)C1CC1] |
| 5-[4-(6-Methyl-imidazo[1,2-a]pyridin-2-yl)-phenyl]-furan-2-carboxylic acid ((S)-2-methyl-1-methylcarbamoyl-propyl)-amide | 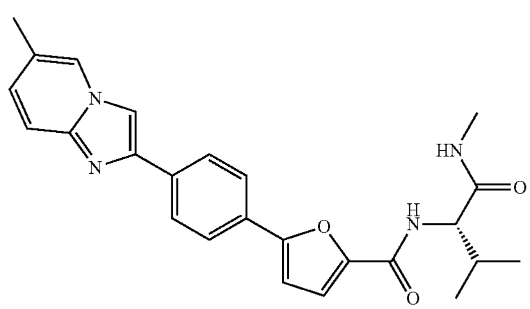 [SMILES: CNC(=O)[C@@H](NC(=O)c1ccc(-c2ccc(-c3cn4cc(C)ccc4n3)cc2)o1)C(C)C] |

TABLE I-continued

| Name | Structure |
|---|---|
| N-[(1S)-1-cyclohexyl-2-(methylamino)-2-oxoethyl]-5-[4-(6-methylimidazo[1,2-a]pyridin-2-yl)phenyl]furan-2-carboxamide | 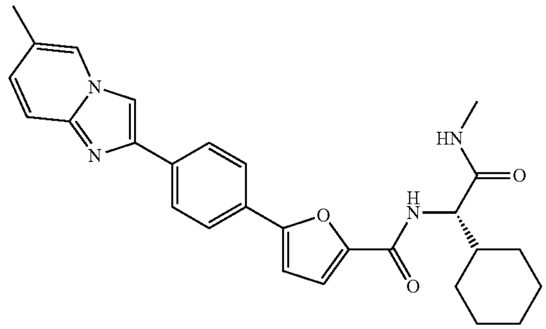 [SMILES: CNC(=O)[C@@H](NC(=O)c1ccc(-c2ccc(-c3cn4cc(C)ccc4n3)cc2)o1)C1CCCCC1] |
| N-[(1S)-1-cyclohexyl-2-(methylamino)-2-oxoethyl]-2-(5-hydroxypyridin-2-yl)-1,3-thiazole-4-carboxamide | 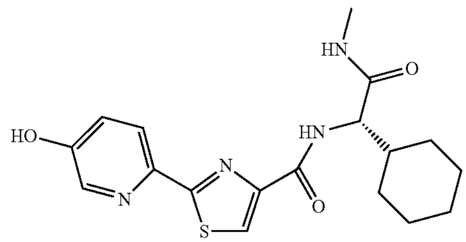 [SMILES: CNC(=O)[C@@H](NC(=O)c1csc(-c2ccc(O)cn2)n1)C1CCCCC1] |
| 5-(5-Benzyloxy-pyridin-2-yl)-furan-2-carboxylic acid ((S)-2-hydroxy-2-methyl-1-methylcarbamoyl-propyl)-amide | 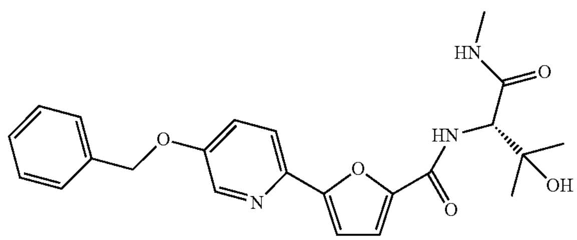 [SMILES: CNC(=O)[C@@H](NC(=O)c1ccc(-c2ccc(OCc3ccccc3)cn2)o1)C(C)(C)O] |
| 5-[5-(Benzyloxy)pyridin-2-yl]-N-[(1S)-2-(methylamino)-2-oxo-1-(tetrahydro-2H-pyran-4-yl)ethyl]furan-2-carboxamide | 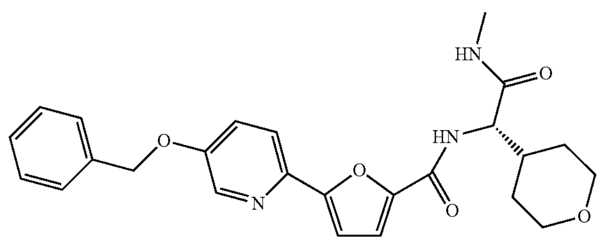 |
| 5-[5-(Pyridin-3-ylmethoxy)-pyridin-2-yl]-furan-2-carboxylic acid ((S)-cyclohexyl-methylcarbamoyl-methyl)-amide | 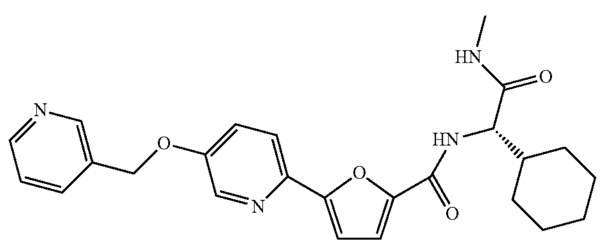 [SMILES: CNC(=O)[C@@H](NC(=O)c1ccc(-c2ccc(OCc3cccnc3)cn2)o1)C1CCCCC1] |
| 5-[5-(Benzyloxy)pyridin-2-yl]-N-[(1S)-1-cyclohexyl-2-(methylamino)-2-oxoethyl]furan-2-carboxamide | 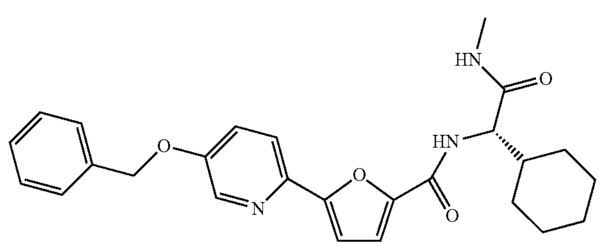 |

TABLE I-continued

| Name | Structure |
|---|---|
| N-[(1S)-1-cyclohexyl-2-(methylamino)-2-oxoethyl]-5-[5-(pyridin-2-ylmethoxy)pyridin-2-yl]furan-2-carboxamide | 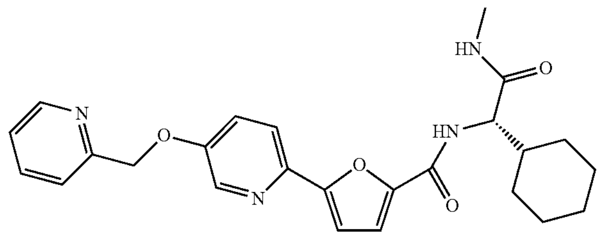 [SMILES: CNC(=O)[C@@H](NC(=O)c1ccc(-c2ccc(OCc3ccccn3)cn2)o1)C1CCCCC1] |
| 5-[5-(1-Benzofuran-2-ylmethoxy)pyridin-2-yl]-N-[(1S)-1-cyclohexyl-2-(methylamino)-2-oxoethyl]furan-2-carboxamide | 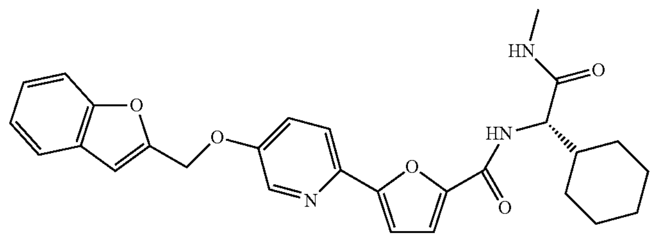 [SMILES: CNC(=O)[C@@H](NC(=O)c1ccc(-c2ccc(OCc3cc4ccccc4o3)cn2)o1)C1CCCCC1] |
| N-[(1S)-1-cyclohexyl-2-(methylamino)-2-oxoethyl]-5-[5-(pyridin-4-ylmethoxy)pyridin-2-yl]furan-2-carboxamide | 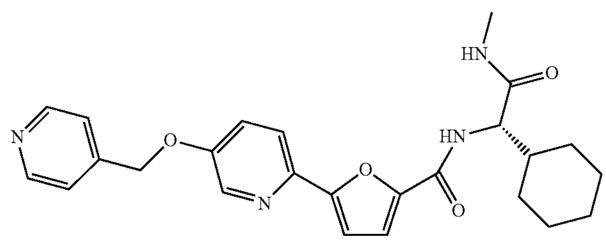 [SMILES: CNC(=O)[C@@H](NC(=O)c1ccc(-c2ccc(OCc3ccncc3)cn2)o1)C1CCCCC1] |
| N-[(1S)-1-cyclohexyl-2-(methylamino)-2-oxoethyl]-5-{5-[(1-methyl-1H-imidazol-4-yl)methoxy]pyridin-2-yl}furan-2-carboxamide | 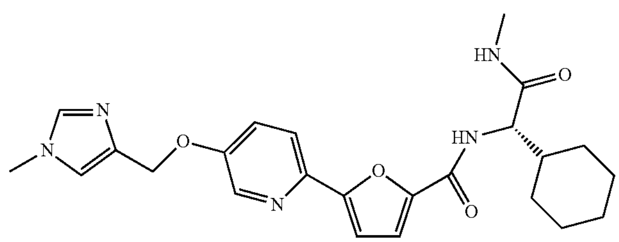 [SMILES: CNC(=O)[C@@H](NC(=O)c1ccc(-c2ccc(OCc3cn(C)cn3)cn2)o1)C1CCCCC1] |
| N-[(1S)-1-cyclohexyl-2-(methylamino)-2-oxoethyl]-5-{5-[(6-methylpyridin-2-yl)methoxy]pyridin-2-yl}furan-2-carboxamide | 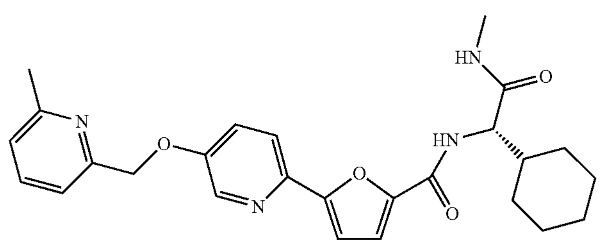 [SMILES: CNC(=O)[C@@H](NC(=O)c1ccc(-c2ccc(OCc3cccc(C)n3)cn2)o1)C1CCCCC1] |
| N-[(1S)-1-cyclohexyl-2-(methylamino)-2-oxoethyl]-5-{5-[(1-methyl-1H-imidazol-5-yl)methoxy]pyridin-2-yl}furan-2-carboxamide | 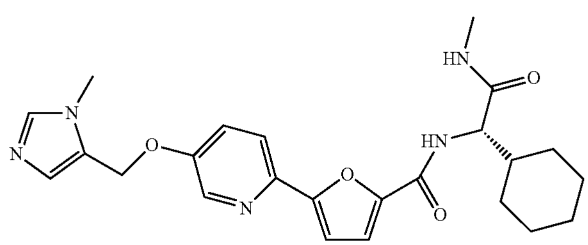 [SMILES: CNC(=O)[C@@H](NC(=O)c1ccc(-c2ccc(OCc3cncn3C)cn2)o1)C1CCCCC1] |

| Name | Structure |
|---|---|
| N-[(1S)-1-cyclohexyl-2-(methylamino)-2-oxoethyl]-5-{5-[(1,5-dimethyl-1H-pyrazol-3-yl)methoxy]pyridin-2-yl}furan-2-carboxamide | 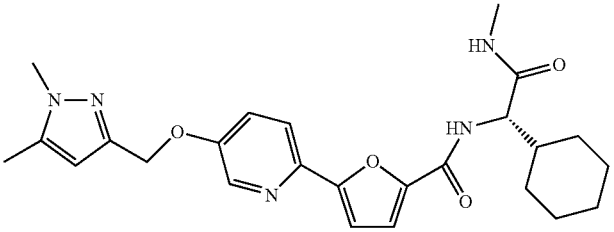 [SMILES: CNC(=O)[C@@H](NC(=O)c1ccc(-c2ccc(OCc3cc(C)n(C)n3)cn2)o1)C1CCCCC1] |
| 5-(5-Benzyloxy-pyridin-2-yl)-furan-2-carboxylic acid ((S)-cyclohexyl-methylcarbamoyl-methyl)-amide | 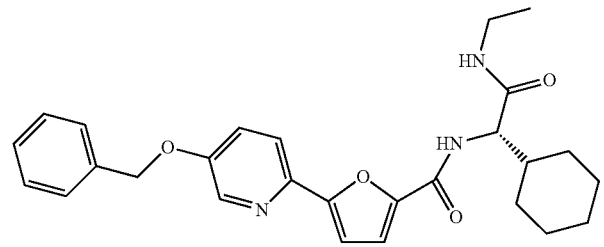 [SMILES: CCNC(=O)[C@@H](NC(=O)c1ccc(-c2ccc(OCc3ccccc3)cn2)o1)C1CCCCC1] |
| N-[(1S)-1-cyclohexyl-2-(methylamino)-2-oxoethyl]-5-{5-[(1-methyl-1H-pyrazol-3-yl)methoxy]pyridin-2-yl}furan-2-carboxamide | 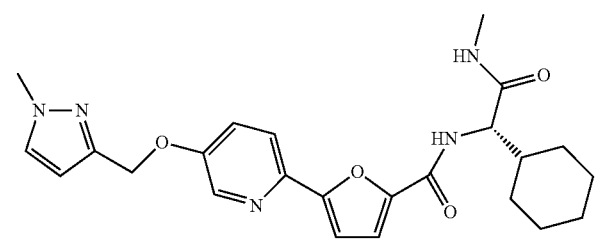 [SMILES: CNC(=O)[C@@H](NC(=O)c1ccc(-c2ccc(OCc3ccn(C)n3)cn2)o1)C1CCCCC1] |
| N-[(1S)-1-cyclohexyl-2-(methylamino)-2-oxoethyl]-5-{5-[(3-methylbenzyl)oxy]pyridin-2-yl}furan-2-carboxamide | 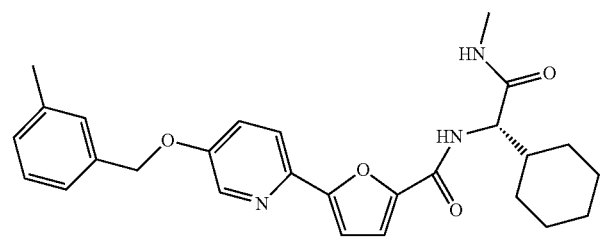 [SMILES: CNC(=O)[C@@H](NC(=O)c1ccc(-c2ccc(OCc3cccc(C)c3)cn2)o1)C1CCCCC1] |
| N-[(1S)-1-cyclohexyl-2-(methylamino)-2-oxoethyl]-5-{5-[(3,5-dimethylbenzyl)oxy]pyridin-2-yl}furan-2-carboxamide | 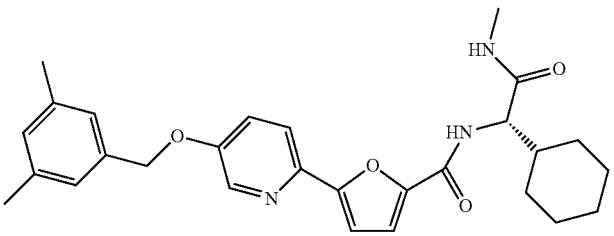 [SMILES: CNC(=O)[C@@H](NC(=O)c1ccc(-c2ccc(OCc3cc(C)cc(C)c3)cn2)o1)C1CCCCC1] |
| N-[(1S)-1-cyclohexyl-2-(methylamino)-2-oxoethyl]-5-{5-[(1S)-1-phenylethoxy]pyridin-2-yl}furan-2-carboxamide | 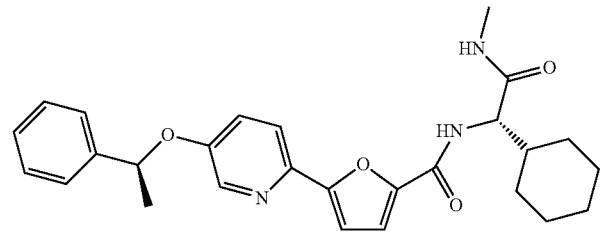 |

TABLE I-continued

| Name | Structure |
|---|---|
| N-[(1S)-1-cyclohexyl-2-(methylamino)-2-oxoethyl]-5-{5-[(1R)-1-phenylethoxy]pyridin-2-yl}furan-2-carboxamide | 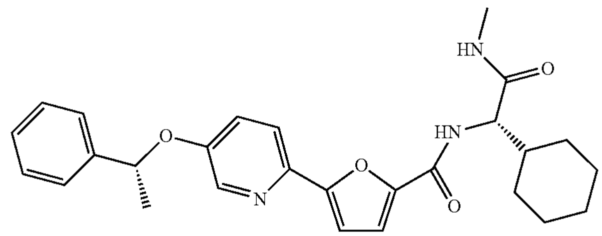 [SMILES: CNC(=O)[C@@H](NC(=O)c1ccc(-c2ccc(O[C@H](C)c3ccccc3)cn2)o1)C1CCCCC1] |
| N-[(1S)-1-cyclohexyl-2-(methylamino)-2-oxoethyl]-5-{5-[(1-methyl-1H-imidazol-2-yl)methoxy]pyridin-2-yl}furan-2-carboxamide | 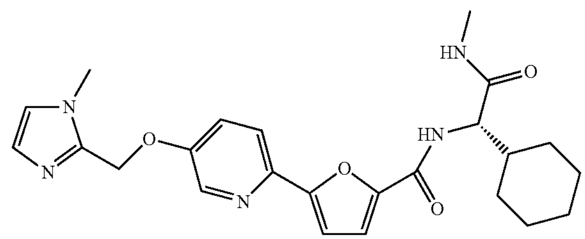 [SMILES: CNC(=O)[C@@H](NC(=O)c1ccc(-c2ccc(OCc3nccn3C)cn2)o1)C1CCCCC1] |
| N-[(1S)-1-cyclohexyl-2-(methylamino)-2-oxoethyl]-5-{5-[(4-methylpyridin-2-yl)methoxy]pyridin-2-yl}furan-2-carboxamide | 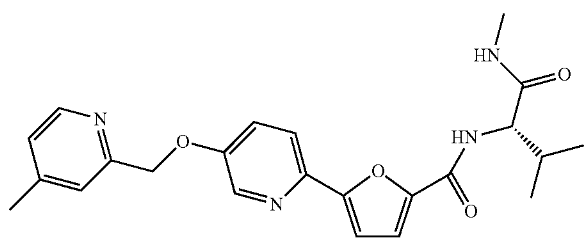 [SMILES: CNC(=O)[C@@H](NC(=O)c1ccc(-c2ccc(OCc3cc(C)ccn3)cn2)o1)C(C)C] |
| N-[(1S)-1-cyclohexyl-2-(methylamino)-2-oxoethyl]-5-[5-(1H-pyrazol-5-ylmethoxy)pyridin-2-yl]furan-2-carboxamide | 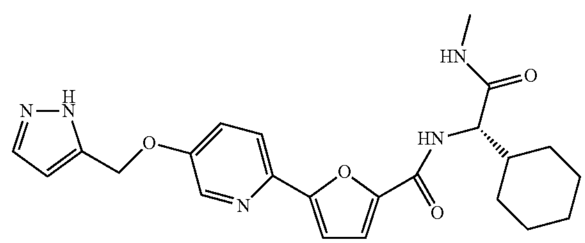 [SMILES: CNC(=O)[C@@H](NC(=O)c1ccc(-c2ccc(OCc3ccn[nH]3)cn2)o1)C1CCCCC1] |
| 5-(5-Benzyloxy-pyridin-2-yl)-furan-2-carboxylic acid ((S)-2-methyl-1-methylcarbamoyl-propyl)-amide | 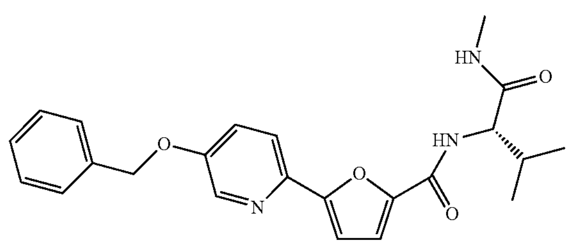 [SMILES: CNC(=O)[C@@H](NC(=O)c1ccc(-c2ccc(OCc3ccccc3)cn2)o1)C(C)C] |
| N-[(1S)-1-cyclohexyl-2-(methylamino)-2-oxoethyl]-5-{5-[(3-methyl-1H-pyrazol-5-yl)methoxy]pyridin-2-yl}furan-2-carboxamide | 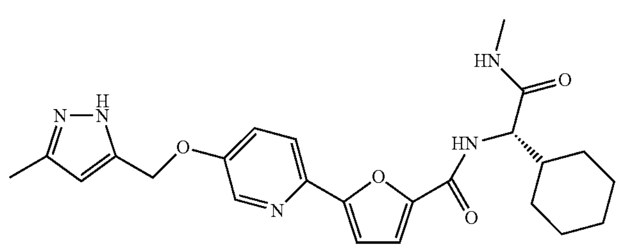 [SMILES: CNC(=O)[C@@H](NC(=O)c1ccc(-c2ccc(OCc3cc(C)n[nH]3)cn2)o1)C1CCCCC1] |

TABLE I-continued

| Name | Structure |
|---|---|
| N-[(1S)-1-cyclohexyl-2-(methylamino)-2-oxoethyl]-5-[5-(pyridin-3-ylmethoxy)pyridin-2-yl]furan-2-carboxamide | 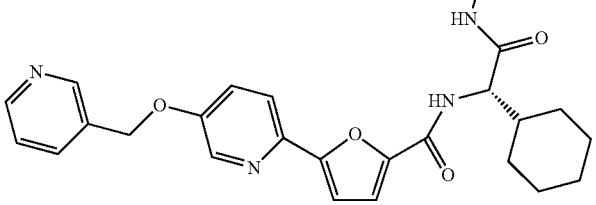 |
| 5-[5-(5-Methyl-3H-imidazol-4-ylmethoxy)-pyridin-2-yl]-furan-2-carboxylic acid ((S)-2-methyl-1-methylcarbamoyl-propyl)-amide | 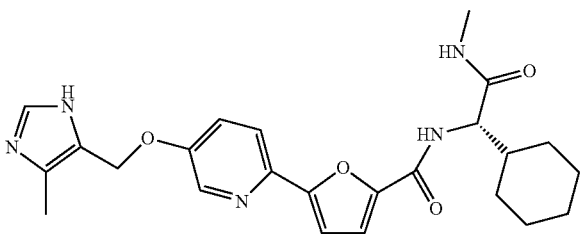 [SMILES: CNC(=O)[C@@H](NC(=O)c1ccc(-c2ccc(OCc3[nH]cnc3C)cn2)o1)C1CCCCC1] |
| 5-[5-(2,5-Dimethyl-2H-pyrazol-3-ylmethoxy)-pyridin-2-yl]-furan-2-carboxylic acid ((S)-cyclohexyl-methylcarbamoyl-methyl)-amide | 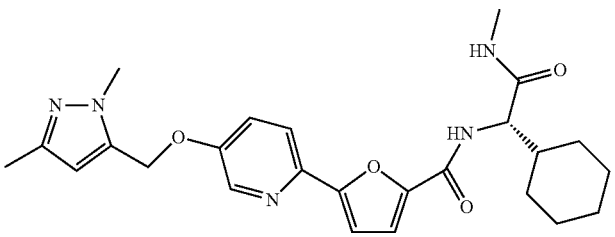 [SMILES: CNC(=O)[C@@H](NC(=O)c1ccc(-c2ccc(OCc3cc(C)nn3C)cn2)o1)C1CCCCC1] |
| 5-[4-(2,5-Dimethyl-2H-pyrazol-3-ylmethoxy)-phenyl]-furan-2-carboxylic acid ((S)-cyclohexyl-methylcarbamoyl-methyl)-amide | 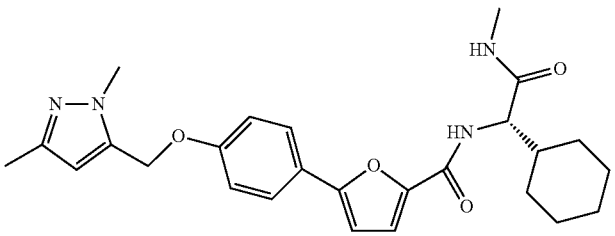 [SMILES: CNC(=O)[C@@H](NC(=O)c1ccc(-c2ccc(OCc3cc(C)nn3C)cc2)o1)C1CCCCC1] |
| N-[(1S)-1-cyclohexyl-2-(methylamino)-2-oxoethyl]-5-{5-[(1-methyl-1H-pyrazol-5-yl)methoxy]pyridin-2-yl}furan-2-carboxamide | 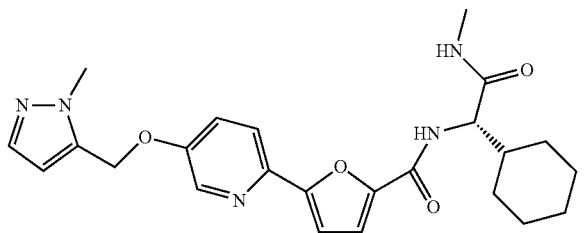 [SMILES: CNC(=O)[C@@H](NC(=O)c1ccc(-c2ccc(OCc3ccnn3C)cn2)o1)C1CCCCC1] |
| N-[(1S)-1-cyclohexyl-2-(methylamino)-2-oxoethyl]-5-{5-[(2-methylpyridin-4-yl)methoxy]pyridin-2-yl}furan-2-carboxamide | 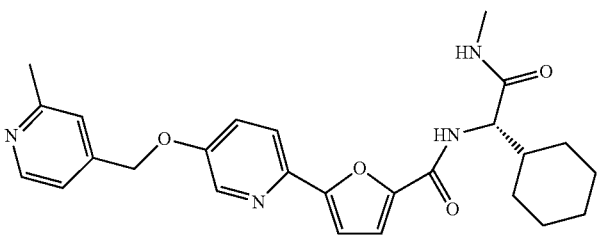 [SMILES: CNC(=O)[C@@H](NC(=O)c1ccc(-c2ccc(OCc3ccnc(C)c3)cn2)o1)C1CCCCC1] |

TABLE I-continued

| Name | Structure |
|---|---|
| N-[(1S)-1-cyclohexyl-2-(methylamino)-2-oxoethyl]-5-{5-[(3-methylpyridin-4-yl)methoxy]pyridin-2-yl}furan-2-carboxamide | 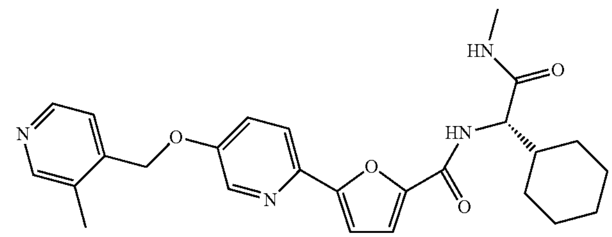 [SMILES: CNC(=O)[C@@H](NC(=O)c1ccc(-c2ccc(OCc3ccncc3C)cn2)o1)C1CCCCC1] |
| 5-[5-(1,5-Dimethyl-1H-pyrazol-3-ylmethoxy)-pyridin-2-yl]-furan-2-carboxylic acid ((S)-2-methyl-1-methylcarbamoyl-propyl)-amide | 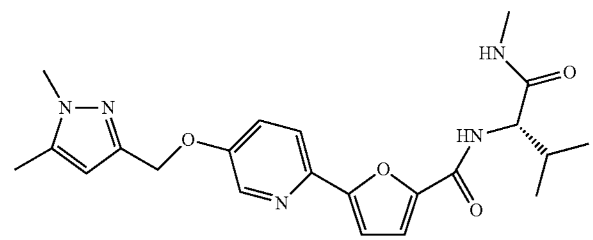 [SMILES: CNC(=O)[C@@H](NC(=O)c1ccc(-c2ccc(OCc3cc(C)n(C)n3)cn2)o1)C(C)C] |
| N-[(1S)-1-cyclohexyl-2-(methylamino)-2-oxoethyl]-5-{5-[(2,6-dimethylpyridin-4-yl)methoxy]pyridin-2-yl}furan-2-carboxamide | 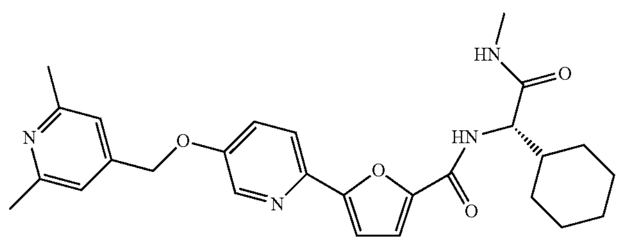 [SMILES: CNC(=O)[C@@H](NC(=O)c1ccc(-c2ccc(OCc3cc(C)nc(C)c3)cn2)o1)C1CCCCC1] |
| N-[(1S)-1-cyclohexyl-2-(methylamino)-2-oxoethyl]-5-{5-(1H-imidazol-5-ylmethoxy)pyridin-2-yl]furan-2-carboxamide | 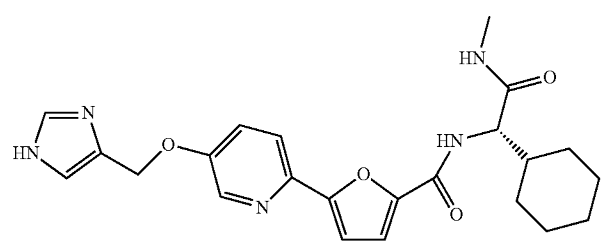 [SMILES: CNC(=O)[C@@H](NC(=O)c1ccc(-c2ccc(OCc3c[nH]cn3)cn2)o1)C1CCCCC1] |
| N-[(1S)-2-(methylamino)-2-oxo-1-(piperidin-4-yl)ethyl]-5-{5-[(1-methyl-1H-imidazol-4-yl)methoxy]pyridin-2-yl}furan-2-carboxamide | 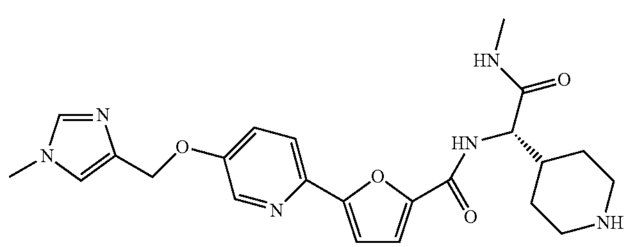 [SMILES: CNC(=O)[C@@H](NC(=O)c1ccc(-c2ccc(OCc3cn(C)cn3)cn2)o1)C1CCNCC1] |
| N-[(1S)-1-cyclohexyl-2-(methylamino)-2-oxoethyl]-5-{5-[(1R)-1-(pyridin-4-yl)ethoxy]pyridin-2-yl}furan-2-carboxamide | 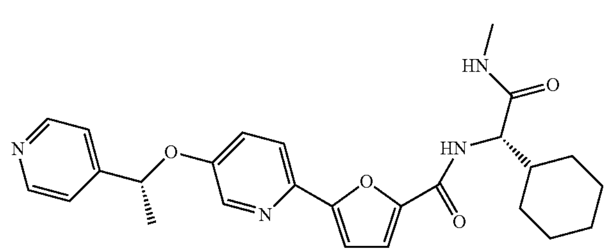 [SMILES: CNC(=O)[C@@H](NC(=O)c1ccc(-c2ccc(O[C@H](C)c3ccncc3)cn2)o1)C1CCCCC1] |

TABLE I-continued

| Name | Structure |
|---|---|
| 5-[5-((R)-1-Phenyl-ethoxy)-pyridin-2-yl]-furan-2-carboxylic acid ((S)-2-methyl-1-methylcarbamoyl-propyl)-amide | 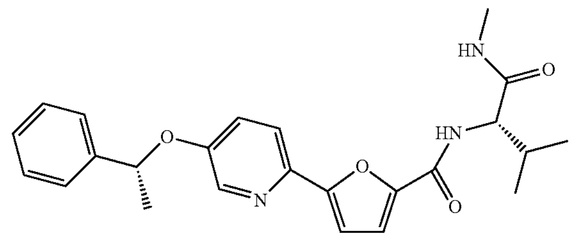 [SMILES: CNC(=O)[C@@H](NC(=O)c1ccc(-c2ccc(O[C@H](C)c3ccccc3)cn2)o1)C(C)C] |
| N-[(1S)-1-cyclohexyl-2-(methylamino)-2-oxoethyl]-5-{5-[(1S)-1-(pyridin-2-yl)ethoxy]pyridin-2-yl}furan-2-carboxamide | 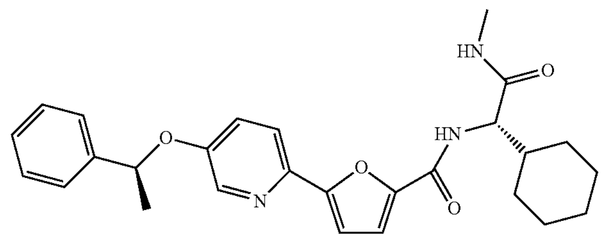 [SMILES: CNC(=O)[C@@H](NC(=O)c1ccc(-c2ccc(O[C@@H](C)c3ccccc3)cn2)o1)C1CCCCC1] |
| 5-[5-((S)-1-Phenyl-ethoxy)-pyridin-2-yl]-furan-2-carboxylic acid ((S)-2-methyl-1-methylcarbamoyl-propyl)-amide | 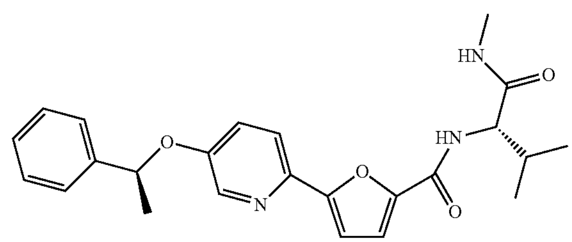 [SMILES: CNC(=O)[C@@H](NC(=O)c1ccc(-c2ccc(O[C@@H](C)c3ccccc3)cn2)o1)C(C)C] |
| N-[(1S)-1-cyclohexyl-2-(methylamino)-2-oxoethyl]-5-{5-[(1S)-1-(pyridin-4-yl)ethoxy]pyridin-2-yl}furan-2-carboxamide | 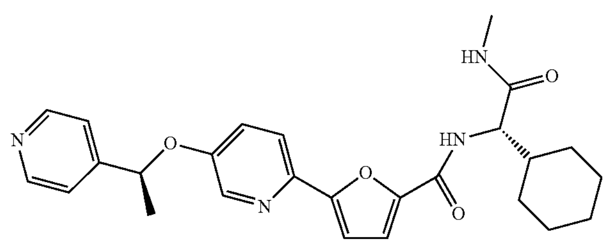 [SMILES: CNC(=O)[C@@H](NC(=O)c1ccc(-c2ccc(O[C@@H](C)c3ccncc3)cn2)o1)C1CCCCC1] |
| N-[(1S)-1-cyclohexyl-2-(methylamino)-2-oxoethyl]-5-{5-[(1R)-1-(pyridin-2-yl)ethoxy]pyridin-2-yl}furan-2-carboxamide | 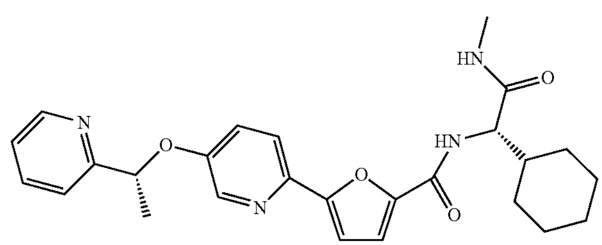 [SMILES: CNC(=O)[C@@H](NC(=O)c1ccc(-c2ccc(O[C@H](C)c3ccccn3)cn2)o1)C1CCCCC1] |
| N-[(1S)-1-cyclohexyl-2-(methylamino)-2-oxoethyl]-5-{5-[1-(pyridin-3-yl)ethoxy]pyridin-2-yl}furan-2-carboxamide | 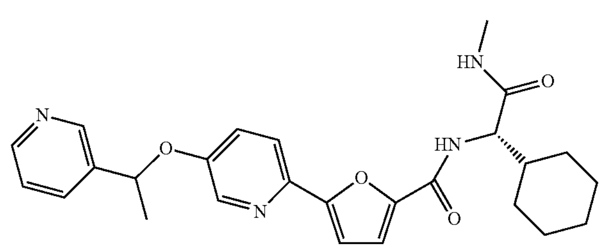 [SMILES: CNC(=O)[C@@H](NC(=O)c1ccc(-c2ccc(OC(C)c3cccnc3)cn2)o1)C1CCCCC1] |

TABLE I-continued

| Name | Structure |
|---|---|
| 5-[5-(5-Methyl-3H-imidazol-4-ylmethoxy)-pyridin-2-yl]-furan-2-carboxylic acid ((S)-2-methyl-1-methylcarbamoyl-propyl)-amide | 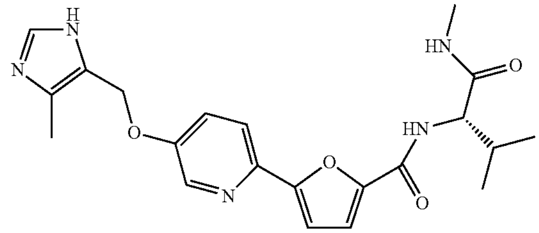 [SMILES: CNC(=O)[C@@H](NC(=O)c1ccc(-c2ccc(OCc3[nH]cnc3C)cn2)o1)C(C)C] |
| 5-[5-(5-Methyl-3H-imidazol-4-ylmethoxy)-pyridin-2-yl]-furan-2-carboxylic acid [(S)-methylcarbamoyl-(tetrahydro-pyran-4-yl)-methyl]-amide | 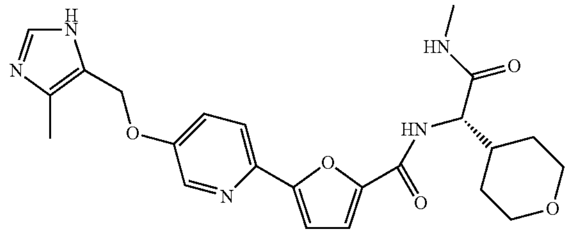 [SMILES: CNC(=O)[C@@H](NC(=O)c1ccc(-c2ccc(OCc3[nH]cnc3C)cn2)o1)C1CCOCC1] |
| 5-[4-(5-Methyl-3H-imidazol-4-ylmethoxy)-phenyl]-furan-2-carboxylic acid [(S)-methylcarbamoyl-(tetrahydro-pyran-4-yl)-methyl]-amide | 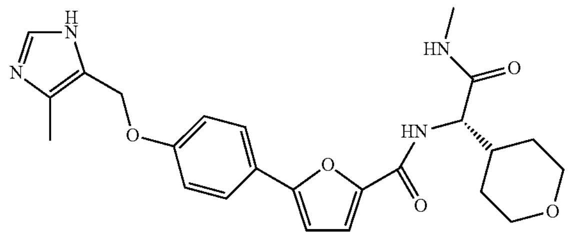 [SMILES: CNC(=O)[C@@H](NC(=O)c1ccc(-c2ccc(OCc3[nH]cnc3C)cc2)o1)C1CCOCC1] |
| N-{4-[5-({(1S)-1-cyclohexyl-2-[(1-methoxypropan-2-yl)amino]-2-oxoethyl}carbamoyl)furan-2-yl]phenyl}-1-benzofuran-2-carboxamide | 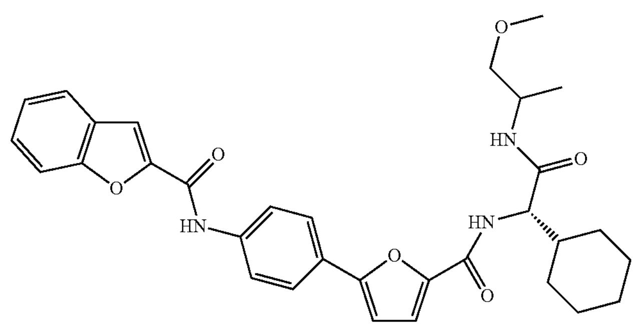 [SMILES: COCC(C)NC(=O)[C@@H](NC(=O)c1ccc(-c2ccc(NC(=O)c3cc4ccccc4o3)cc2)o1)C1CCCCC1] |
| N-[4-(5-{[(1S)-1-cyclohexyl-2-(methylamino)-2-oxoethyl]carbamoyl}furan-2-yl)phenyl]-5-methylfuran-2-carboxamide | 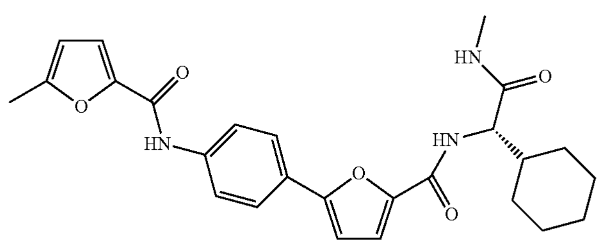 [SMILES: CNC(=O)[C@@H](NC(=O)c1ccc(-c2ccc(NC(=O)c3ccc(C)o3)cc2)o1)C1CCCCC1] |
| N-[4-(5-{[(1S)-1-cyclopropyl-2-(methylamino)-2-oxoethyl]carbamoyl}furan-2-yl)phenyl]-6-methylpyridine-2-carboxamide | 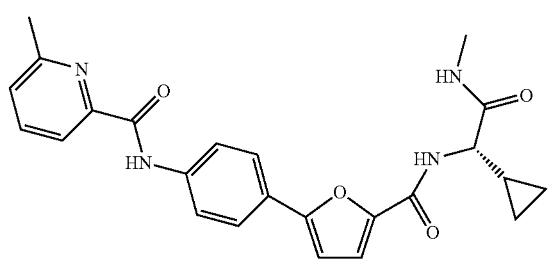 [SMILES: CNC(=O)[C@@H](NC(=O)c1ccc(-c2ccc(NC(=O)c3cccc(C)n3)cc2)o1)C1CC1] |

TABLE I-continued

| Name | Structure |
|---|---|
| 6-Methyl-N-[4-(5-{[(2S)-3-methyl-1-(methylamino)-1-oxobutan-2-yl]carbamoyl}furan-2-yl)phenyl]pyridine-2-carboxamide | 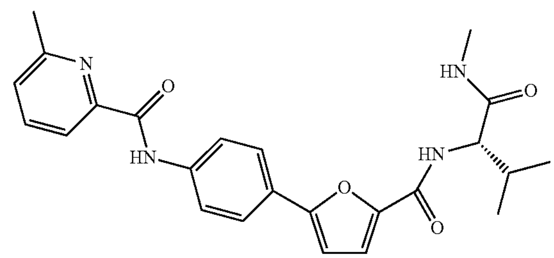 [SMILES: CNC(=O)[C@@H](NC(=O)c1ccc(-c2ccc(NC(=O)c3cccc(C)n3)cc2)o1)C(C)C] |
| N-[4-(5-{[(1S)-1-cyclohexyl-2-{[(2S)-1-methoxypropan-2-yl]amino}-2-oxoethyl]carbamoyl}furan-2-yl)phenyl]-6-methylpyridine-2-carboxamide | 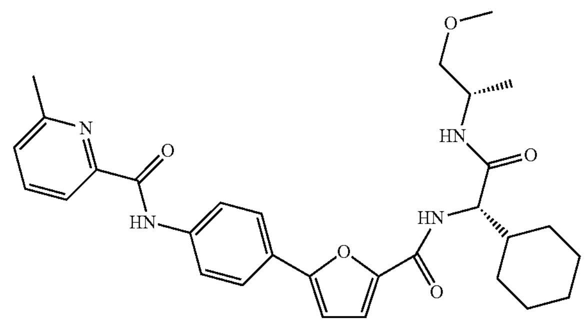 [SMILES: COC[C@H](C)NC(=O)[C@@H](NC(=O)c1ccc(-c2ccc(NC(=O)c3cccc(C)n3)cc2)o1)C1CCCCC1] |
| N-[4-(5-{[(1S)-1-cyclohexyl-2-{[(2S)-2-hydroxypropyl]amino}-2-oxoethyl]carbamoyl}furan-2-yl)phenyl]-6-methylpyridine-2-carboxamide | 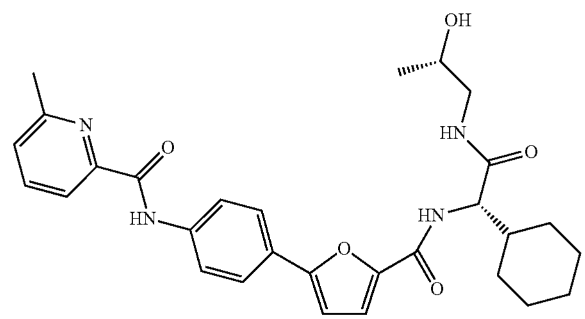 [SMILES: Cc1cccc(C(=O)Nc2ccc(-c3ccc(C(=O)N[C@H](C(=O)NC[C@H](C)O)C4CCCCC4)o3)cc2)n1] |
| N-[4-(5-{[(1S)-1-cyclohexyl-2-{[(2R)-2-hydroxypropyl]amino}-2-oxoethyl]carbamoyl}furan-2-yl)phenyl]-6-methylpyridine-2-carboxamide | 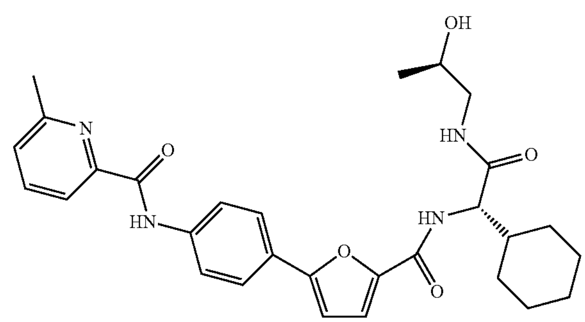 [SMILES: Cc1cccc(C(=O)Nc2ccc(-c3ccc(C(=O)N[C@H](C(=O)NC[C@@H](C)O)C4CCCCC4)o3)cc2)n1] |
| N-[6-(5-{[(1S)-1-cyclohexyl-2-(methylamino)-2-oxoethyl]carbamoyl}furan-2-yl)pyridin-3-yl]-1-benzofuran-2-carboxamide | 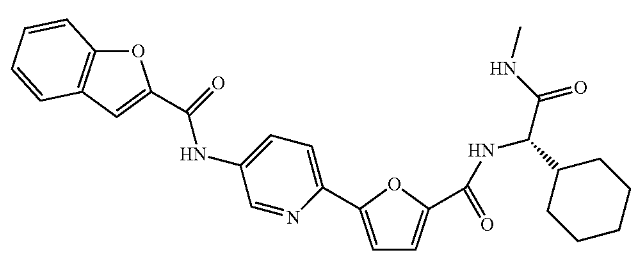 [SMILES: CNC(=O)[C@@H](NC(=O)c1ccc(-c2ccc(NC(=O)c3cc4ccccc4o3)cn2)o1)C1CCCCC1] |

TABLE I-continued

| Name | Structure |
|---|---|
| N-[6-(5-{[(1S)-1-cyclohexyl-2-(methylamino)-2-oxoethyl]carbamoyl}furan-2-yl)pyridin-3-yl]-6-methylpyridine-2-carboxamide | 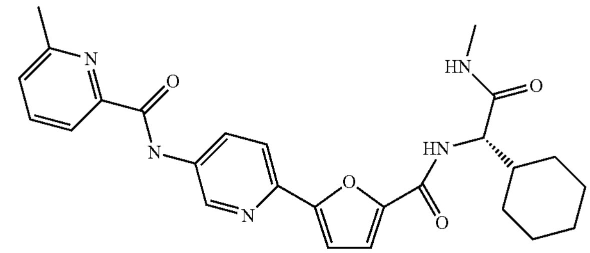 [SMILES: CNC(=O)[C@@H](NC(=O)c1ccc(-c2ccc(NC(=O)c3cccc(C)n3)cn2)o1)C1CCCCC1] |
| N-[4-(5-{[(1S)-1-cyclohexyl-2-(methylamino)-2-oxoethyl]carbamoyl}furan-2-yl)phenyl]-4,5-dimethylfuran-2-carboxamide | 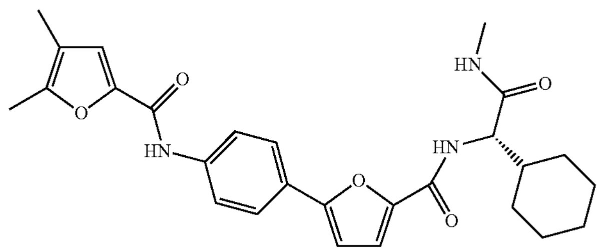 [SMILES: CNC(=O)[C@@H](NC(=O)c1ccc(-c2ccc(NC(=O)c3cc(C)c(C)o3)cc2)o1)C1CCCCC1] |
| N-[4-(5-{[(1S)-1-cyclohexyl-2-(methylamino)-2-oxoethyl]carbamoyl}furan-2-yl)phenyl]-1-methyl-1H-imidazole-4-carboxamide | 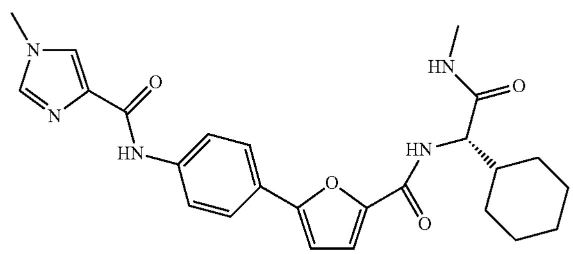 [SMILES: CNC(=O)[C@@H](NC(=O)c1ccc(-c2ccc(NC(=O)c3cn(C)cn3)cc2)o1)C1CCCCC1] |
| N-[4-(5-{[(1S)-1-cyclohexyl-2-(methylamino)-2-oxoethyl]carbamoyl}furan-2-yl)phenyl]-1-methyl-1H-imidazole-5-carboxamide | 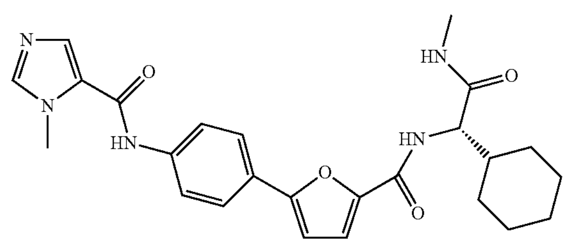 [SMILES: CNC(=O)[C@@H](NC(=O)c1ccc(-c2ccc(NC(=O)c3cncn3C)cc2)o1)C1CCCCC1] |
| N-[4-(5-{[(1S)-1-cyclohexyl-2-(methylamino)-2-oxoethyl]carbamoyl}furan-2-yl)phenyl]-6-methylpyridine-2-carboxamide | 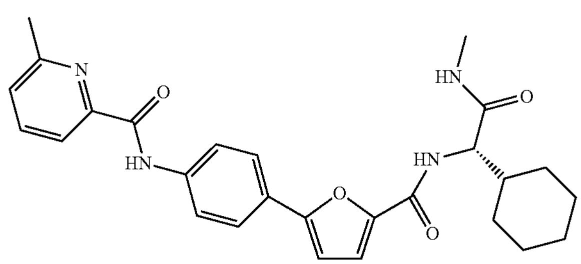 [SMILES: CNC(=O)[C@@H](NC(=O)c1ccc(-c2ccc(NC(=O)c3cccc(C)n3)cc2)o1)C1CCCCC1] |
| N-[4-(5-{[(1S)-1-cyclohexyl-2-(methylamino)-2-oxoethyl]carbamoyl}furan-2-yl)phenyl]-5-methylpyridine-3-carboxamide | 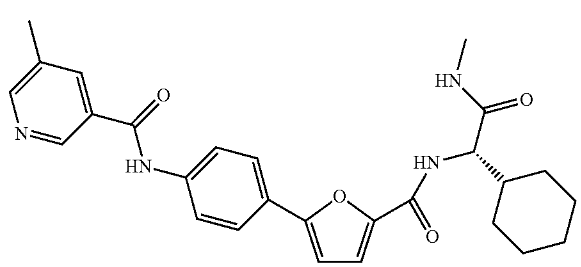 [SMILES: CNC(=O)[C@@H](NC(=O)c1ccc(-c2ccc(NC(=O)c3cncc(C)c3)cc2)o1)C1CCCCC1] |

TABLE I-continued

| Name | Structure |
|---|---|
| N-[4-(5-{[(1S)-1-cyclohexyl-2-(methylamino)-2-oxoethyl]carbamoyl}furan-2-yl)phenyl]-1-methyl-1H-pyrazole-5-carboxamide | 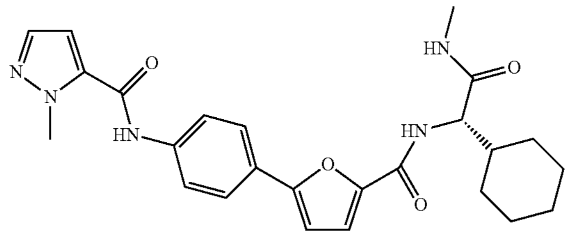 [SMILES: CNC(=O)[C@@H](NC(=O)c1ccc(-c2ccc(NC(=O)c3ccnn3C)cc2)o1)C1CCCCC1] |
| N-[4-(5-{[(1S)-1-cyclohexyl-2-(methylamino)-2-oxoethyl]carbamoyl}furan-2-yl)phenyl]-3-methylfuran-2-carboxamide | 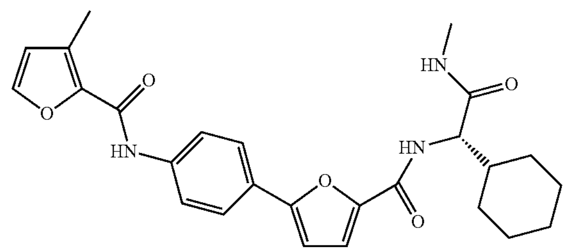 [SMILES: CNC(=O)[C@@H](NC(=O)c1ccc(-c2ccc(NC(=O)c3occc3C)cc2)o1)C1CCCCC1] |
| N-[(1S)-1-cyclohexyl-2-(methylamino)-2-oxoethyl]-5-(4-{[(2-methylfuran-3-yl)carbonyl]amino}phenyl)furan-2-carboxamide | |
| N-[4-(5-{[(1S)-1-cyclohexyl-2-(methylamino)-2-oxoethyl]carbamoyl}furan-2-yl)phenyl]-5-methylfuran-2-carboxamide | 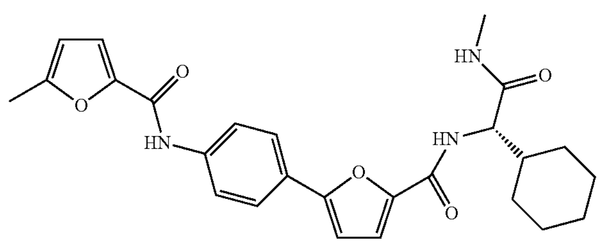 [SMILES: CNC(=O)[C@@H](NC(=O)c1ccc(-c2ccc(NC(=O)c3ccc(C)o3)cc2)o1)C1CCCCC1] |
| N-[4-(5-{[(1S)-1-cyclohexyl-2-(methylamino)-2-oxoethyl]carbamoyl}furan-2-yl)phenyl]-5-methyl-1H-pyrazole-3-carboxamide | 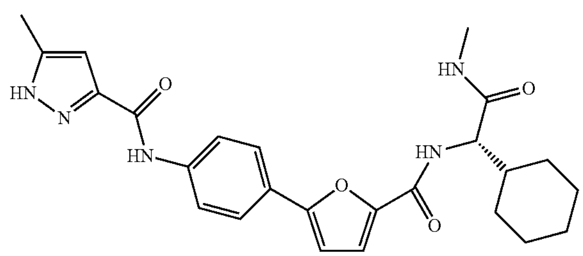 [SMILES: CNC(=O)[C@@H](NC(=O)c1ccc(-c2ccc(NC(=O)c3cc(C)[nH]n3)cc2)o1)C1CCCCC1] |
| N-[4-(5-{[(1S)-1-cyclohexyl-2-(methylamino)-2-oxoethyl]carbamoyl}furan-2-yl)phenyl]-1-methyl-1H-pyrazole-3-carboxamide | 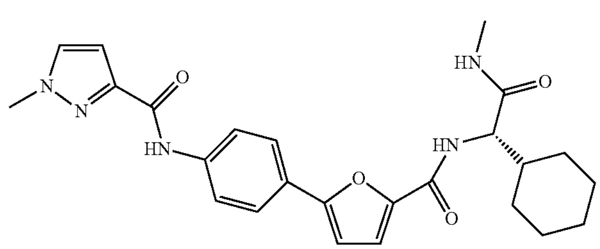 [SMILES: CNC(=O)[C@@H](NC(=O)c1ccc(-c2ccc(NC(=O)c3ccn(C)n3)cc2)o1)C1CCCCC1] |

TABLE I-continued

| Name | Structure |
|---|---|
| N-[4-(5-{[(1S)-1-cyclohexyl-2-(methylamino)-2-oxoethyl]carbamoyl}furan-2-yl)phenyl]-1-methyl-1H-pyrazole-4-carboxamide | 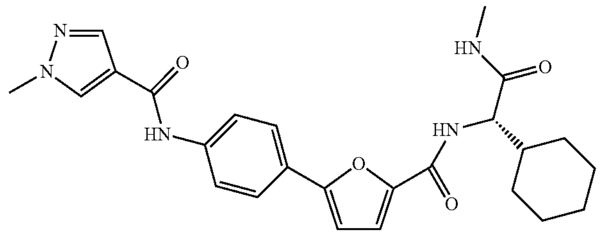 [SMILES: CNC(=O)[C@@H](NC(=O)c1ccc(-c2ccc(NC(=O)c3cnn(C)c3)cc2)o1)C1CCCCC1] |
| N-[4-(5-{[(1S)-1-cyclohexyl-2-(methylamino)-2-oxoethyl]carbamoyl}furan-2-yl)phenyl]imidazo[1,2-a]pyridine-2-carboxamide | 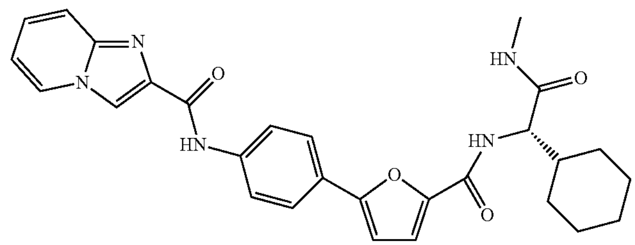 [SMILES: CNC(=O)[C@@H](NC(=O)c1ccc(-c2ccc(NC(=O)c3cn4ccccc4n3)cc2)o1)C1CCCCC1] |
| N-[4-(5-{[(1S)-1-cyclohexyl-2-(methylamino)-2-oxoethyl]carbamoyl}furan-2-yl)phenyl]-8-methylimidazo[1,2-a]pyridine-2-carboxamide | 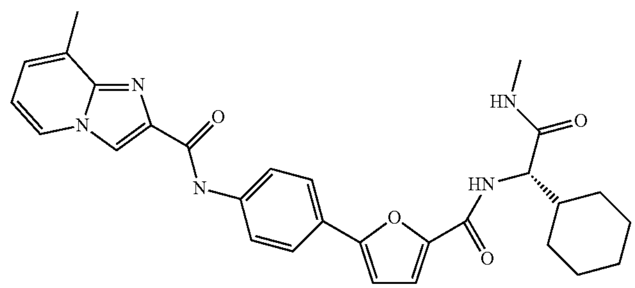 [SMILES: CNC(=O)[C@@H](NC(=O)c1ccc(-c2ccc(NC(=O)c3cn4cccc(C)c4n3)cc2)o1)C1CCCCC1] |
| N-[4-(5-{[(1S)-1-cyclohexyl-2-(methylamino)-2-oxoethyl]carbamoyl}furan-2-yl)phenyl]-7-methylimidazo[1,2-a]pyridine-2-carboxamide | 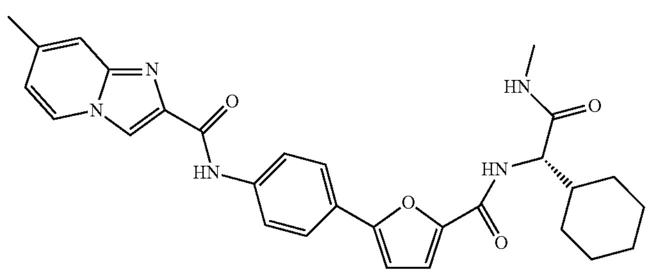 [SMILES: CNC(=O)[C@@H](NC(=O)c1ccc(-c2ccc(NC(=O)c3cn4ccc(C)cc4n3)cc2)o1)C1CCCCC1] |
| N-[4-(5-{[(1S)-1-cyclohexyl-2-(methylamino)-2-oxoethyl]carbamoyl}furan-2-yl)phenyl]-5-methylimidazo[1,2-a]pyridine-2-carboxamide | 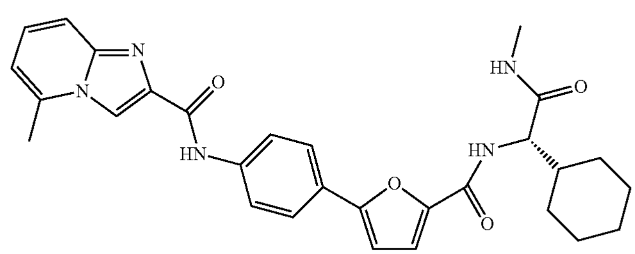 [SMILES: CNC(=O)[C@@H](NC(=O)c1ccc(-c2ccc(NC(=O)c3cn4c(C)cccc4n3)cc2)o1)C1CCCCC1] |
| 5-Cyano-N-[4-(5-{[(1S)-1-cyclohexyl-2-(methylamino)-2-oxoethyl]carbamoyl}furan-2-yl)phenyl]imidazo[1,2-a]pyridine-2-carboxamide | 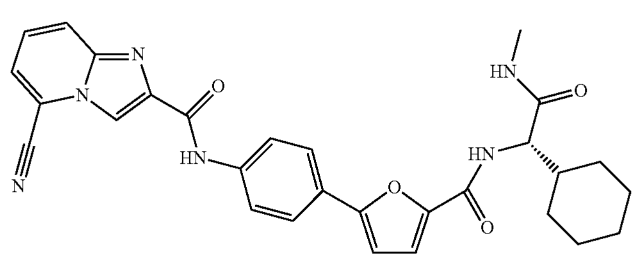 [SMILES: CNC(=O)[C@@H](NC(=O)c1ccc(-c2ccc(NC(=O)c3cn4c(C#N)cccc4n3)cc2)o1)C1CCCCC1] |

TABLE I-continued

| Name | Structure |
|---|---|
| Imidazo[1,2-a]pyridine-2,6-dicarboxylic acid 6-amide 2-[(4-{5-[((S)-cyclohexyl-methylcarbamoyl-methyl)-carbamoyl]-furan-2-yl}-phenyl)-amide] | |
| N-[4-(5-{[(1S)-1-cyclohexyl-2-(methylamino)-2-oxoethyl]carbamoyl}furan-2-yl)phenyl]-1-benzofuran-2-carboxamide | 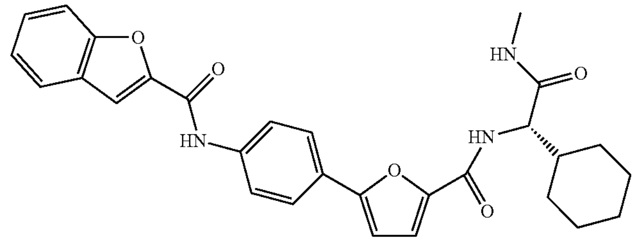 [SMILES: CNC(=O)[C@@H](NC(=O)c1ccc(-c2ccc(NC(=O)c3cc4ccccc4o3)cc2)o1)C1CCCCC1] |
| 5-{4-[(Acetylamino)methyl]phenyl}-N-[(1S)-1-cyclohexyl-2-(methylamino)-2-oxoethyl]furan-2-carboxamide | 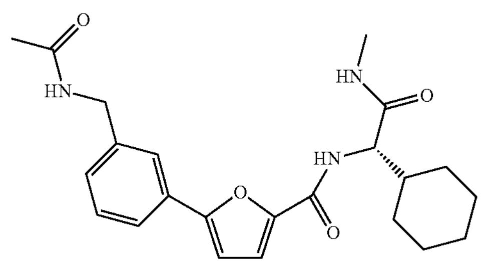 [SMILES: CNC(=O)[C@@H](NC(=O)c1ccc(-c2cccc(CNC(C)=O)c2)o1)C1CCCCC1] |
| N-(3-{5-[((S)-Cyclohexyl-methylcarbamoyl-methyl)-carbamoyl]-furan-2-yl}-benzyl)-2-fluoro-isonicotinamide | 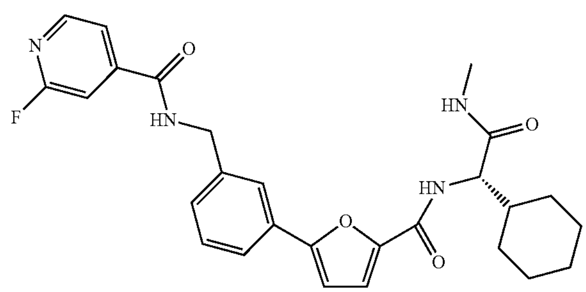 [SMILES: CNC(=O)[C@@H](NC(=O)c1ccc(-c2cccc(CNC(=O)c3ccnc(F)c3)c2)o1)C1CCCCC1] |
| N-[3-(5-{[(1S)-1-cyclohexyl-2-(methylamino)-2-oxoethyl]carbamoyl}furan-2-yl)benzyl]-1-benzofuran-2-carboxamide | 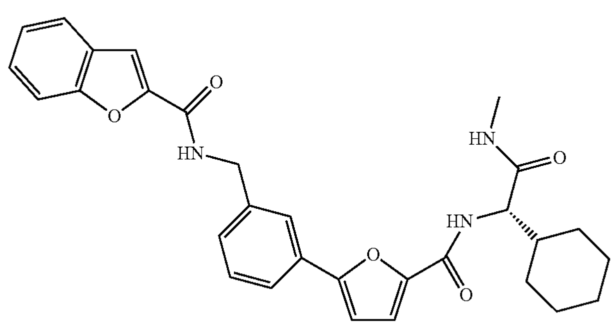 [SMILES: CNC(=O)[C@@H](NC(=O)c1ccc(-c2cccc(CNC(=O)c3cc4ccccc4o3)c2)o1)C1CCCCC1] |

TABLE I-continued

| Name | Structure |
|---|---|
| N-[3-(5-{[(1S)-1-cyclohexyl-2-(methylamino)-2-oxoethyl]carbamoyl}furan-2-yl)benzyl]imidazo[1,2-a]pyridine-2-carboxamide | 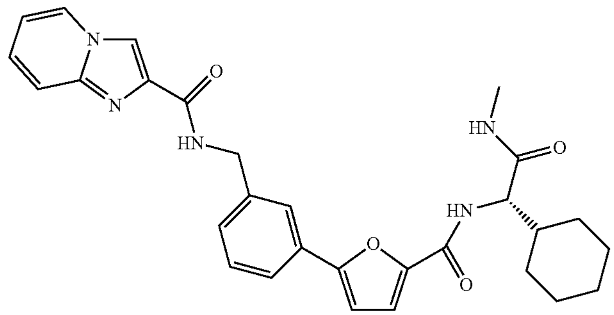 [SMILES: CNC(=O)[C@@H](NC(=O)c1ccc(-c2cccc(CNC(=O)c3cn4ccccc4n3)c2)o1)C1CCCCC1] |
| N-{[2-(5-{[(2S)-3-methyl-1-(methylamino)-1-oxobutan-2-yl]carbamoyl}furan-2-yl)pyridin-4-yl]methyl}-2-(trifluoromethyl)pyrimidine-4-carboxamide | 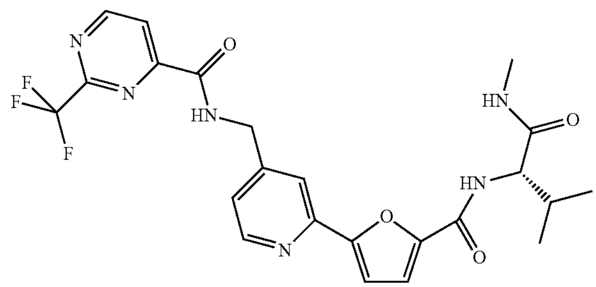 [SMILES: CNC(=O)[C@@H](NC(=O)c1ccc(-c2cc(CNC(=O)c3ccnc(C(F)(F)F)n3)ccn2)o1)C(C)C] |
| N-{[2-(5-{[(1S)-1-cyclohexyl-2-(methylamino)-2-oxoethyl]carbamoyl}furan-2-yl)pyridin-4-yl]methyl}-6-methylpyridine-2-carboxamide | 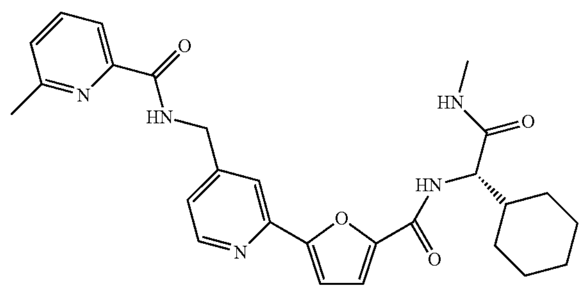 [SMILES: CNC(=O)[C@@H](NC(=O)c1ccc(-c2cc(CNC(=O)c3cccc(C)n3)ccn2)o1)C1CCCCC1] |
| N-{[2-(5-{[(1S)-1-cyclohexyl-2-(methylamino)-2-oxoethyl]carbamoyl}furan-2-yl)pyridin-4-yl]methyl}pyridine-2-carboxamide | 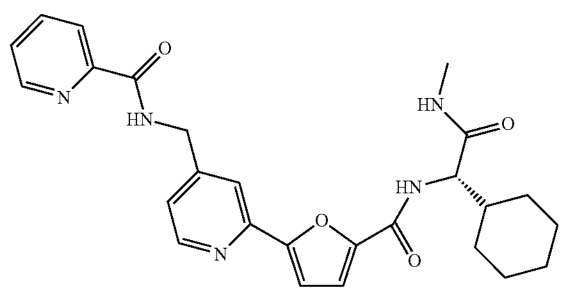 [SMILES: CNC(=O)[C@@H](NC(=O)c1ccc(-c2cc(CNC(=O)c3ccccn3)ccn2)o1)C1CCCCC1] |
| N-{[2-(5-{[(1S)-1-cyclohexyl-2-(methylamino)-2-oxoethyl]carbamoyl}furan-2-yl)pyridin-4-yl]methyl}-6-fluoropyridine-2-carboxamide | 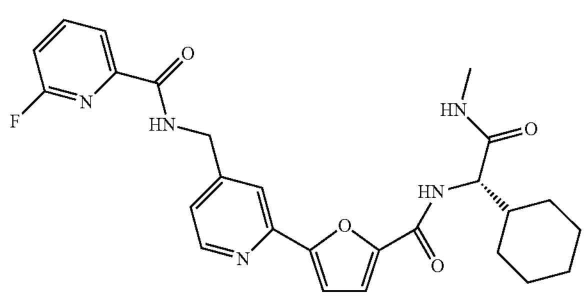 [SMILES: CNC(=O)[C@@H](NC(=O)c1ccc(-c2cc(CNC(=O)c3cccc(F)n3)ccn2)o1)C1CCCCC1] |

TABLE I-continued

| Name | Structure |
|---|---|
| N-{[2-(5-{[(1S)-1-cyclohexyl-2-(methylamino)-2-oxoethyl]carbamoyl}furan-2-yl)pyridin-4-yl]methyl}-1,5-dimethyl-1H-pyrazole-3-carboxamide | 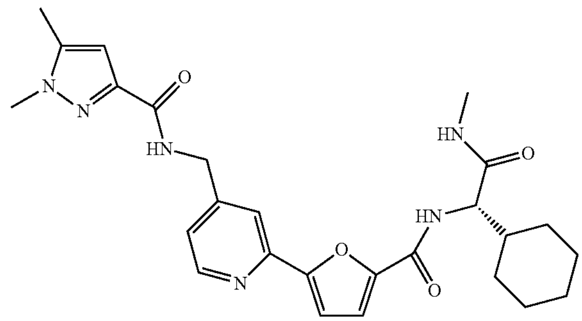 [SMILES: CNC(=O)[C@@H](NC(=O)c1ccc(-c2cc(CNC(=O)c3cc(C)n(C)n3)ccn2)o1)C1CCCCC1] |
| N-{[2-(5-{[(1S)-1-cyclohexyl-2-(methylamino)-2-oxoethyl]carbamoyl}furan-2-yl)pyridin-4-yl]methyl}-5-methylpyridine-3-carboxamide | 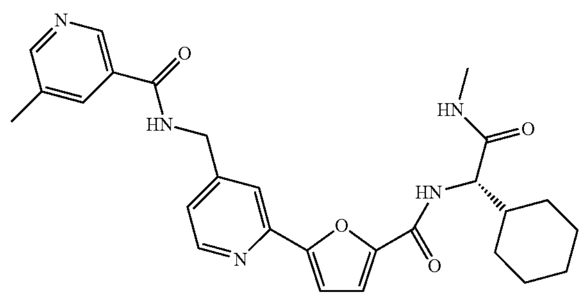 [SMILES: CNC(=O)[C@@H](NC(=O)c1ccc(-c2cc(CNC(=O)c3cncc(C)c3)ccn2)o1)C1CCCCC1] |
| N-{[2-(5-{[(1S)-1-cyclohexyl-2-(methylamino)-2-oxoethyl]carbamoyl}furan-2-yl)pyridin-4-yl]methyl}-4,5-dimethylfuran-2-carboxamide | |
| N-{[2-(5-{[(1S)-1-cyclohexyl-2-(methylamino)-2-oxoethyl]carbamoyl}furan-2-yl)pyridin-4-yl]methyl}-5-ethylfuran-2-carboxamide | 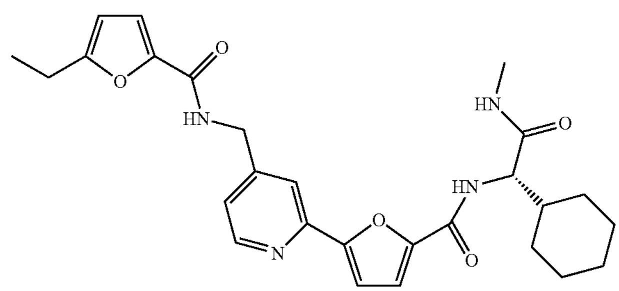 [SMILES: CCc1ccc(C(=O)NCc2ccnc(-c3ccc(C(=O)N[C@H](C(=O)NC)C4CCCCC4)o3)c2)o1] |
| N-{[2-(5-{[(1S)-1-cyclohexyl-2-(methylamino)-2-oxoethyl]carbamoyl}furan-2-yl)pyridin-4-yl]methyl}-1-benzofuran-2-carboxamide | 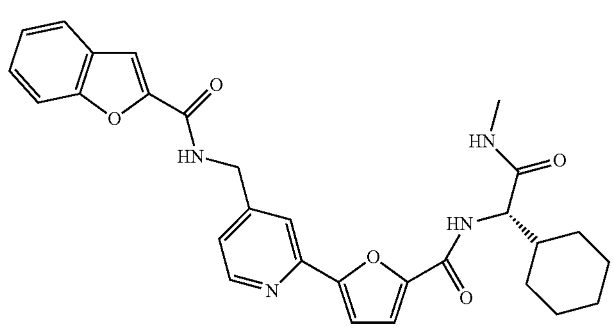 |

TABLE I-continued

| Name | Structure |
|---|---|
| 6-Methyl-N-{[2-(5-{[(2S)-3-methyl-1-(methylamino)-1-oxobutan-2-yl]carbamoyl}furan-2-yl)pyridin-4-yl]methyl}pyridine-2-carboxamide | 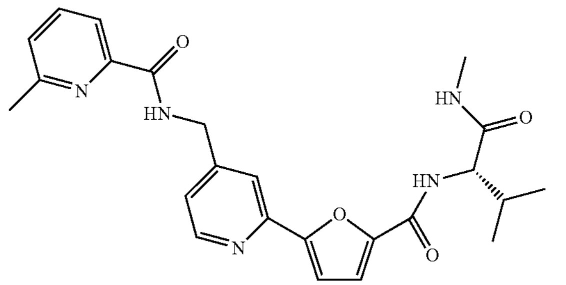 [SMILES: CNC(=O)[C@@H](NC(=O)c1ccc(-c2cc(CNC(=O)c3cccc(C)n3)ccn2)o1)C(C)C] |
| N-{[2-(5-{[(2S)-3-methyl-1-(methylamino)-1-oxobutan-2-yl]carbamoyl}furan-2-yl)pyridin-4-yl]methyl}pyridine-2-carboxamide | 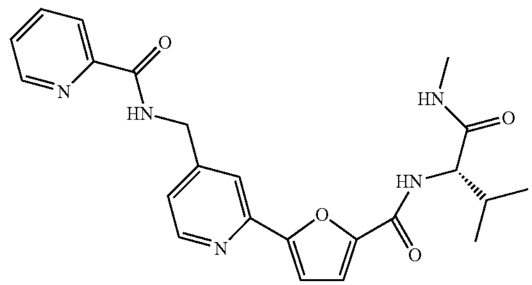 [SMILES: CNC(=O)[C@@H](NC(=O)c1ccc(-c2cc(CNC(=O)c3ccccn3)ccn2)o1)C(C)C] |
| 6-Fluoro-N-{[2-(5-{[(2S)-3-methyl-1-(methylamino)-1-oxobutan-2-yl]carbamoyl}furan-2-yl)pyridin-4-yl]methyl}pyridine-2-carboxamide | 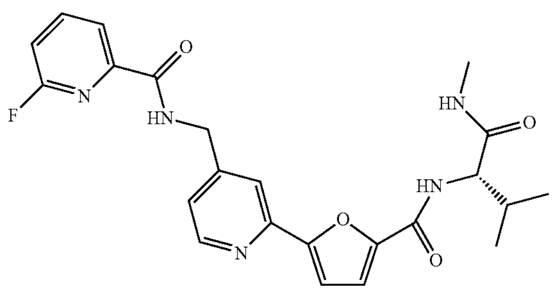 [SMILES: CNC(=O)[C@@H](NC(=O)c1ccc(-c2cc(CNC(=O)c3cccc(F)n3)ccn2)o1)C(C)C] |
| 5-Methyl-N-{[2-(5-{[(2S)-3-methyl-1-(methylamino)-1-oxobutan-2-yl]carbamoyl}furan-2-yl)pyridin-4-yl]methyl}pyridine-3-carboxamide | 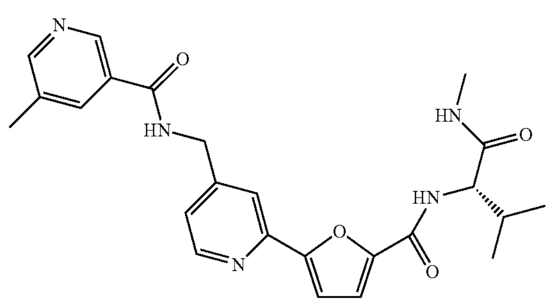 [SMILES: CNC(=O)[C@@H](NC(=O)c1ccc(-c2cc(CNC(=O)c3cncc(C)c3)ccn2)o1)C(C)C] |
| N-{[2-(5-{[(1S)-1-cyclohexyl-2-(methylamino)-2-oxoethyl]carbamoyl}furan-2-yl)pyridin-4-yl]methyl}-2-(trifluoromethyl)pyrimidine-4-carboxamide | 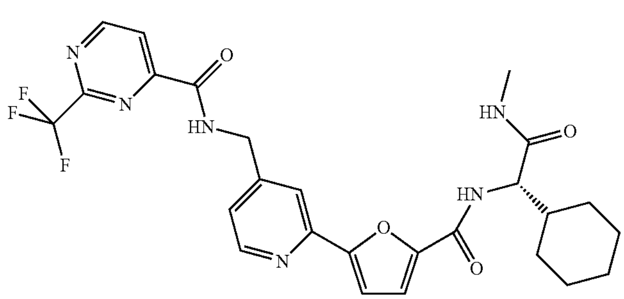 |

TABLE I-continued

| Name | Structure |
|---|---|
| 1,5-Dimethyl-1H-pyrazole-3-carboxylic acid {2-[5-((S)-2-methyl-1-methylcarbamoyl-propylcarbamoyl)-furan-2-yl]-pyridin-4-ylmethyl}-amide | 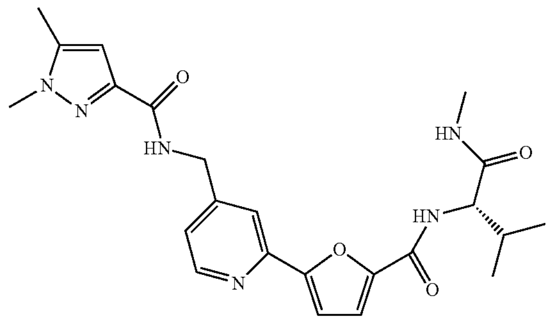 [SMILES: CNC(=O)[C@@H](NC(=O)c1ccc(-c2cc(CNC(=O)c3cc(C)n(C)n3)ccn2)o1)C(C)C] |
| 4,5-Dimethyl-furan-2-carboxylic acid {2-[5-((S)-2-methyl-1-methylcarbamoyl-propylcarbamoyl)-furan-2-yl]-pyridin-4-ylmethyl}-amide | 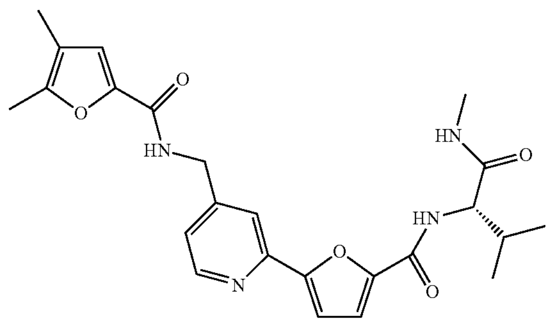 [SMILES: CNC(=O)[C@@H](NC(=O)c1ccc(-c2cc(CNC(=O)c3cc(C)c(C)o3)ccn2)o1)C(C)C] |
| 5-Ethyl-furan-2-carboxylic acid {2-[5-((S)-2-methyl-1-methylcarbamoyl-propylcarbamoyl)-furan-2-yl]-pyridin-4-ylmethyl}-amide | 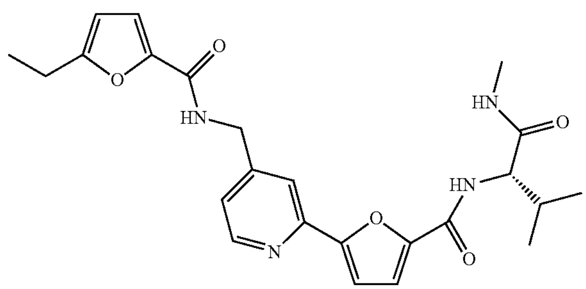 [SMILES: CCc1ccc(C(=O)NCc2ccnc(-c3ccc(C(=O)N[C@H](C(=O)NC)C(C)C)o3)c2)o1] |
| N-[3-(5-{[(1S)-1-cyclohexyl-2-(methylamino)-2-oxoethyl]carbamoyl}furan-2-yl)benzyl]pyrimidine-4-carboxamide | 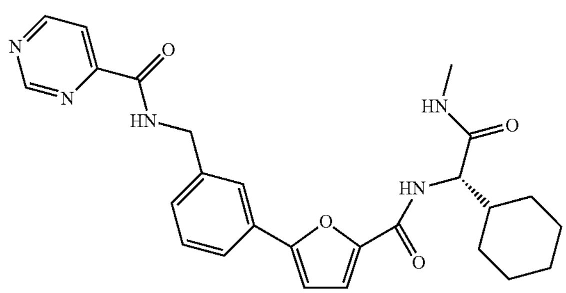 [SMILES: CNC(=O)[C@@H](NC(=O)c1ccc(-c2cccc(CNC(=O)c3ccncn3)c2)o1)C1CCCCC1] |
| N-{[2-(5-{[(1S)-2-(methylamino)-2-oxo-1-(tetrahydro-2H-pyran-4-yl)ethyl]carbamoyl}furan-2-yl)pyridin-4-yl]methyl}-2-(trifluoromethyl)pyrimidine-4-carboxamide | 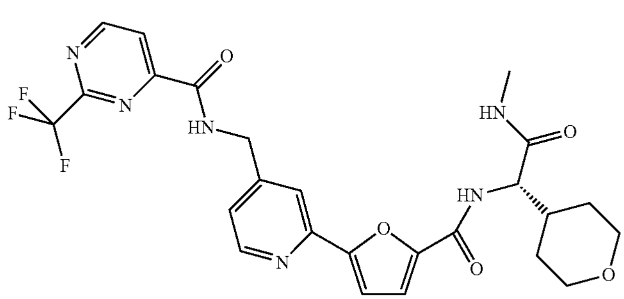 [SMILES: CNC(=O)[C@@H](NC(=O)c1ccc(-c2cc(CNC(=O)c3ccnc(C(F)(F)F)n3)ccn2)o1)C1CCOCC1] |

TABLE I-continued

| Name | Structure |
|---|---|
| N-{[2-(5-{[(1S)-1-cyclohexyl-2-(methylamino)-2-oxoethyl]carbamoyl}furan-2-yl)pyridin-4-yl]methyl}-6-(trifluoromethyl)pyridine-2-carboxamide | 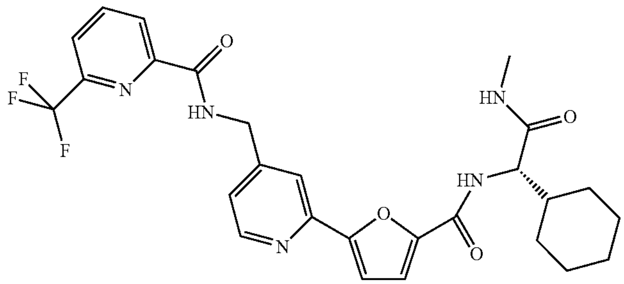 |
| N-{[2-(5-{[(2S)-3-methyl-1-(methylamino)-1-oxobutan-2-yl]carbamoyl}furan-2-yl)pyridin-4-yl]methyl}-6-(trifluoromethyl)pyridine-2-carboxamide | 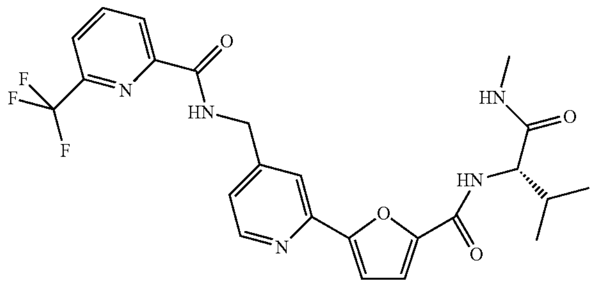 [SMILES: CNC(=O)[C@@H](NC(=O)c1ccc(-c2cc(CNC(=O)c3cccc(C(F)(F)F)n3)ccn2)o1)C(C)C] |
| N-[3-(5-{[(1S)-1-cyclohexyl-2-(methylamino)-2-oxoethyl]carbamoyl}furan-2-yl)benzyl]-6-(trifluoromethyl)pyridine-2-carboxamide | |
| 2-Chloro-N-[3-(5-{[(1S)-1-cyclohexyl-2-(methylamino)-2-oxoethyl]carbamoyl}furan-2-yl)benzyl]pyrimidine-4-carboxamide | 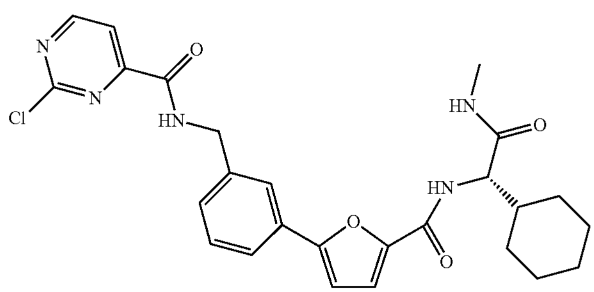 [SMILES: CNC(=O)[C@@H](NC(=O)c1ccc(-c2cccc(CNC(=O)c3ccnc(Cl)n3)c2)o1)C1CCCCC1] |
| 2-Chloro-N-[3-(5-{[(1S)-1-cyclohexyl-2-(methylamino)-2-oxoethyl]carbamoyl}furan-2-yl)benzyl]pyridine-4-carboxamide | 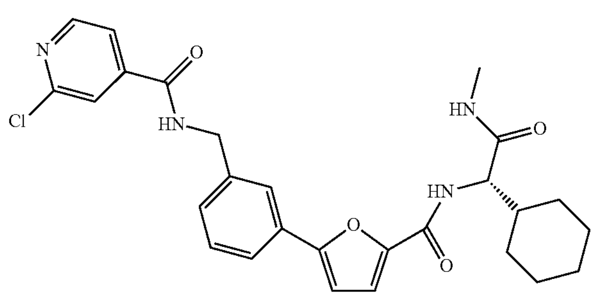 |

TABLE I-continued

| Name | Structure |
|---|---|
| N-[(1S)-1-cyclohexyl-2-(methylamino)-2-oxoethyl]-5-(3-{[(propan-2-ylcarbamoyl)amino]methyl}phenyl)furan-2-carboxamide | 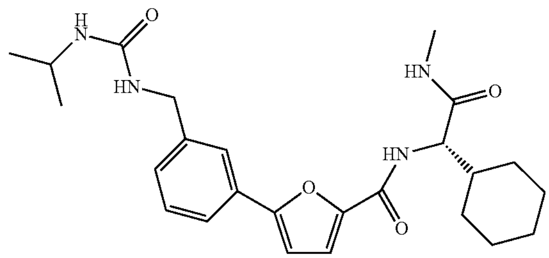 [SMILES: CNC(=O)[C@@H](NC(=O)c1ccc(-c2cccc(CNC(=O)NC(C)C)c2)o1)C1CCCCC1] |
| 5-(3-{[(tert-Butylcarbamoyl)amino]methyl}phenyl)-N-[(1S)-1-cyclohexyl-2-(methylamino)-2-oxoethyl]furan-2-carboxamide | 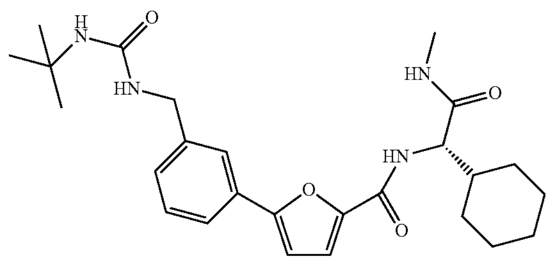 [SMILES: CNC(=O)[C@@H](NC(=O)c1ccc(-c2cccc(CNC(=O)NC(C)(C)C)c2)o1)C1CCCCC1] |
| N-[(1S)-1-cyclohexyl-2-(methylamino)-2-oxoethyl]-5-{4-[(pyridin-4-ylmethyl)carbamoyl]phenyl}furan-2-carboxamide | 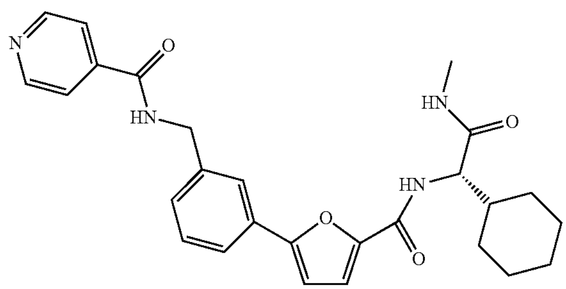 [SMILES: CNC(=O)[C@@H](NC(=O)c1ccc(-c2cccc(CNC(=O)c3ccncc3)c2)o1)C1CCCCC1] |
| N-[3-(5-{[(1S)-1-cyclohexyl-2-(methylamino)-2-oxoethyl]carbamoyl}furan-2-yl)benzyl]-N'-methylpyrimidine-4,6-dicarboxamide | 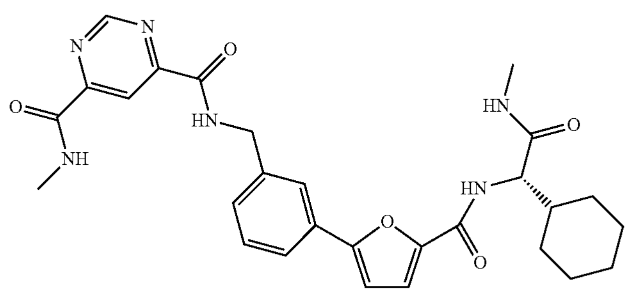 [SMILES: CNC(=O)c1cc(C(=O)NCc2cccc(-c3ccc(C(=O)N[C@H](C(=O)NC)C4CCCCC4)o3)c2)ncn1] |
| N-[3-(5-{[(1S)-1-cyclohexyl-2-(methylamino)-2-oxoethyl]carbamoyl}furan-2-yl)benzyl]-1-methyl-1H-imidazole-5-carboxamide | 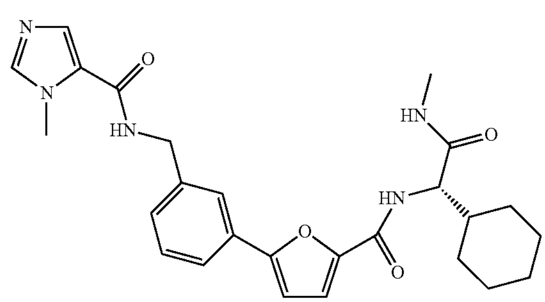 [SMILES: CNC(=O)[C@@H](NC(=O)c1ccc(-c2cccc(CNC(=O)c3cncn3C)c2)o1)C1CCCCC1] |

TABLE I-continued

| Name | Structure |
|---|---|
| N-[3-(5-{[(1S)-1-cyclohexyl-2-(methylamino)-2-oxoethyl]carbamoyl}furan-2-yl)benzyl]-6-methylpyridine-2-carboxamide | 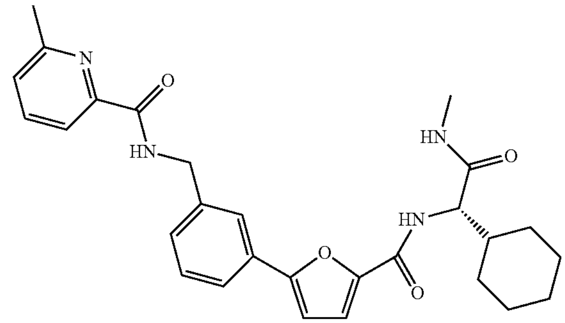 [SMILES: CNC(=O)[C@@H](NC(=O)c1ccc(-c2cccc(CNC(=O)c3cccc(C)n3)c2)o1)C1CCCCC1] |
| N-[3-(5-{[(1S)-1-cyclohexyl-2-(methylamino)-2-oxoethyl]carbamoyl}furan-2-yl)benzyl]-5-methylpyridine-3-carboxamide | 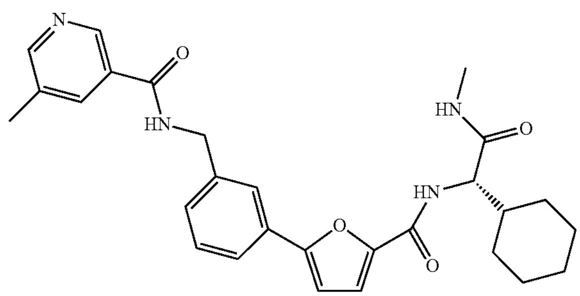 [SMILES: CNC(=O)[C@@H](NC(=O)c1ccc(-c2cccc(CNC(=O)c3cncc(C)c3)c2)o1)C1CCCCC1] |
| N-[3-(5-{[(1S)-1-cyclohexyl-2-(methylamino)-2-oxoethyl]carbamoyl}furan-2-yl)benzyl]-1-methyl-1H-pyrazole-5-carboxamide | 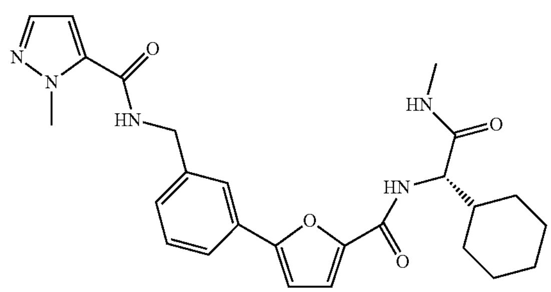 [SMILES: CNC(=O)[C@@H](NC(=O)c1ccc(-c2cccc(CNC(=O)c3ccnn3C)c2)o1)C1CCCCC1] |
| N-[3-(5-{[(1S)-1-cyclohexyl-2-(methylamino)-2-oxoethyl]carbamoyl}furan-2-yl)benzyl]-3-methylfuran-2-carboxamide | 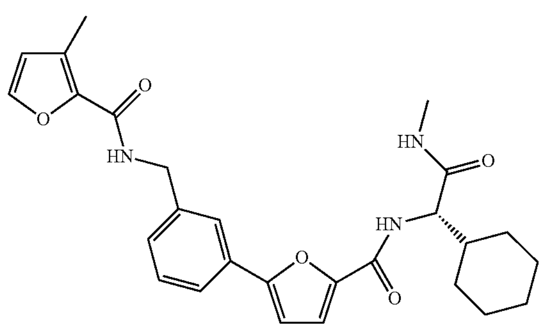 [SMILES: CNC(=O)[C@@H](NC(=O)c1ccc(-c2cccc(CNC(=O)c3occc3C)c2)o1)C1CCCCC1] |
| N-[(1S)-1-cyclohexyl-2-(methylamino)-2-oxoethyl]-5-[3-({[(2-methylfuran-3-yl)carbonyl]amino}methyl)phenyl]furan-2-carboxamide | 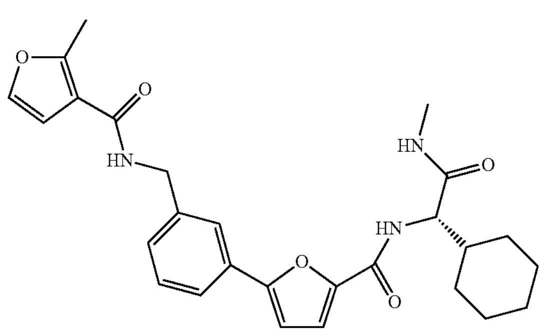 [SMILES: CNC(=O)[C@@H](NC(=O)c1ccc(-c2cccc(CNC(=O)c3ccoc3C)c2)o1)C1CCCCC1] |

TABLE I-continued

| Name | Structure |
|---|---|
| N-[3-(5-{[(1S)-1-cyclohexyl-2-(methylamino)-2-oxoethyl]carbamoyl}furan-2-yl)benzyl]-5-methylfuran-2-carboxamide | 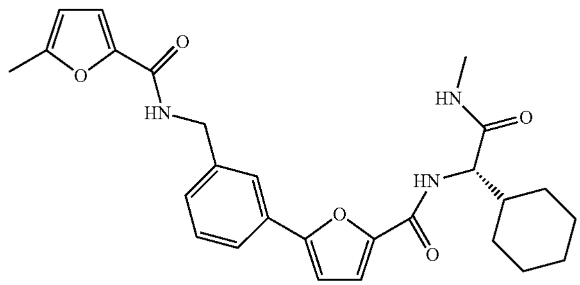 [SMILES: CNC(=O)[C@@H](NC(=O)c1ccc(-c2cccc(CNC(=O)c3ccc(C)o3)c2)o1)C1CCCCC1] |
| N-[3-(5-{[(1S)-1-cyclohexyl-2-(methylamino)-2-oxoethyl]carbamoyl}furan-2-yl)benzyl]-3-methyl-1H-pyrazole-5-carboxamide | 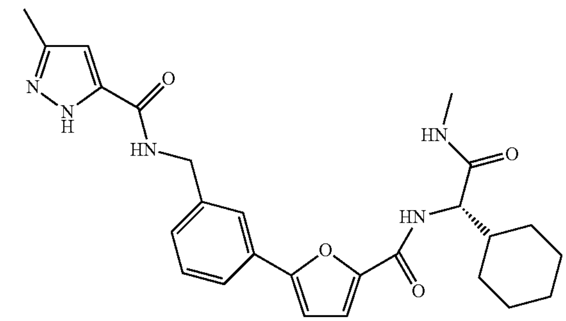 [SMILES: CNC(=O)[C@@H](NC(=O)c1ccc(-c2cccc(CNC(=O)c3cc(C)n[nH]3)c2)o1)C1CCCCC1] |
| N-[3-(5-{[(1S)-1-cyclohexyl-2-(methylamino)-2-oxoethyl]carbamoyl}furan-2-yl)benzyl]-1-methyl-1H-pyrazole-3-carboxamide | 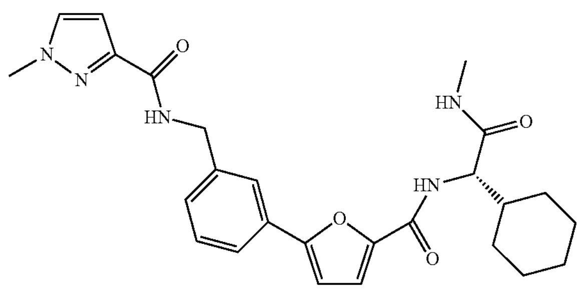 [SMILES: CNC(=O)[C@@H](NC(=O)c1ccc(-c2cccc(CNC(=O)c3ccn(C)n3)c2)o1)C1CCCCC1] |
| N-[3-(5-{[(1S)-1-cyclohexyl-2-(methylamino)-2-oxoethyl]carbamoyl}furan-2-yl)benzyl]-1-methyl-1H-pyrazole-4-carboxamide | 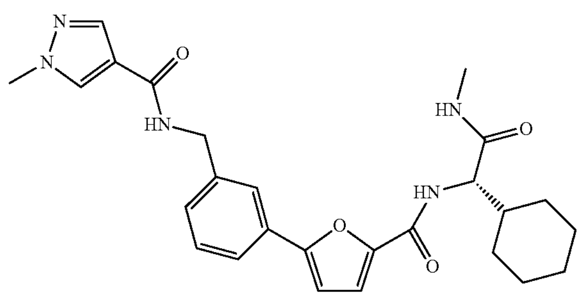 [SMILES: CNC(=O)[C@@H](NC(=O)c1ccc(-c2cccc(CNC(=O)c3cnn(C)c3)c2)o1)C1CCCCC1] |
| N-[(1S)-1-cyclohexyl-2-(methylamino)-2-oxoethyl]-5-{3-[(propanoylamino)methyl]phenyl}furan-2-carboxamide | 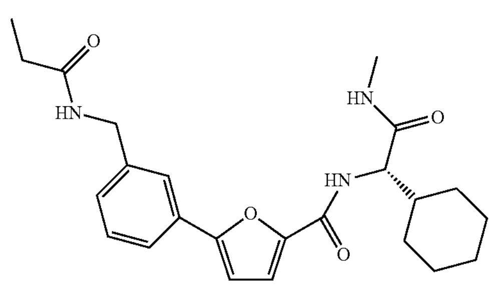 [SMILES: CCC(=O)NCc1cccc(-c2ccc(C(=O)N[C@H](C(=O)NC)C3CCCCC3)o2)c1] |

TABLE I-continued

| Name | Structure |
|---|---|
| N-[(1S)-1-cyclohexyl-2-(methylamino)-2-oxoethyl]-5-(3-{[(2-methylpropanoyl)amino]methyl}phenyl)furan-2-carboxamide | 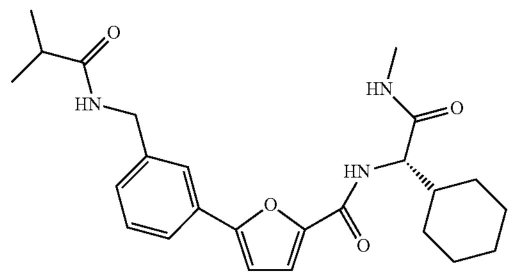 [SMILES: CNC(=O)[C@@H](NC(=O)c1ccc(-c2cccc(CNC(=O)C(C)C)c2)o1)C1CCCCC1] |
| N-[(1S)-1-cyclohexyl-2-(methylamino)-2-oxoethyl]-5-(3-{[(cyclopropylcarbonyl)amino]methyl}phenyl)furan-2-carboxamide | 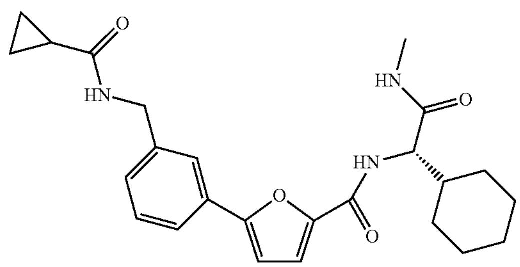 [SMILES: CNC(=O)[C@@H](NC(=O)c1ccc(-c2cccc(CNC(=O)C3CC3)c2)o1)C1CCCCC1] |
| N-[3-(5-{[(1S)-1-cyclohexyl-2-(methylamino)-2-oxoethyl]carbamoyl}furan-2-yl)benzyl]pyridine-2-carboxamide | 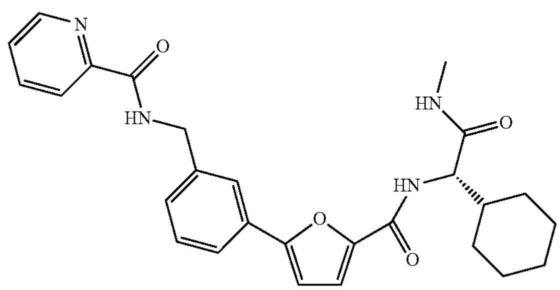 [SMILES: CNC(=O)[C@@H](NC(=O)c1ccc(-c2cccc(CNC(=O)c3ccccn3)c2)o1)C1CCCCC1] |
| N-[3-(5-{[(1S)-1-cyclohexyl-2-(methylamino)-2-oxoethyl]carbamoyl}furan-2-yl)benzyl]-3-methylpyridine-2-carboxamide | 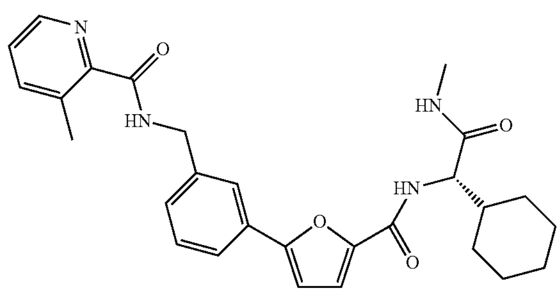 [SMILES: CNC(=O)[C@@H](NC(=O)c1ccc(-c2cccc(CNC(=O)c3ncccc3C)c2)o1)C1CCCCC1] |
| N-[3-(5-{[(1S)-1-cyclohexyl-2-(methylamino)-2-oxoethyl]carbamoyl}furan-2-yl)benzyl]-4-ethylpyridine-2-carboxamide | 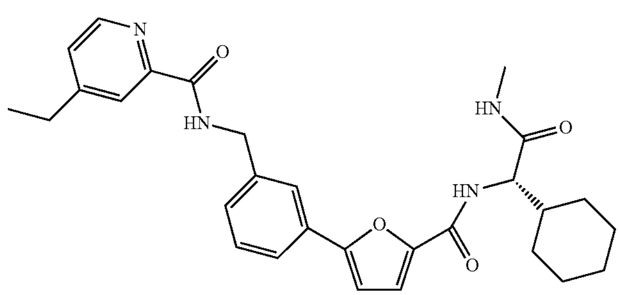 [SMILES: CCc1ccnc(C(=O)NCc2cccc(-c3ccc(C(=O)N[C@H](C(=O)NC)C4CCCCC4)o3)c2)c1] |

TABLE I-continued

| Name | Structure |
|---|---|
| N-[(1S)-1-cyclohexyl-2-(methylamino)-2-oxoethyl]-5-(3-{[(furan-2-ylcarbonyl)amino]methyl}phenyl)furan-2-carboxamide | 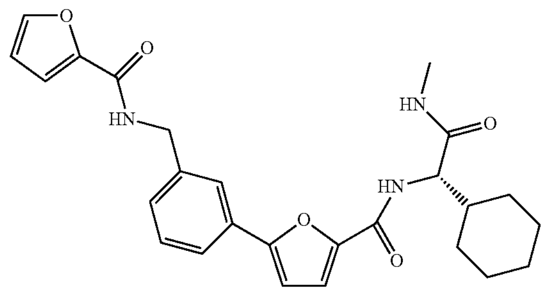 [SMILES: CNC(=O)[C@@H](NC(=O)c1ccc(-c2cccc(CNC(=O)c3ccco3)c2)o1)C1CCCCC1] |
| N-[3-(5-{[(1S)-1-cyclohexyl-2-(methylamino)-2-oxoethyl]carbamoyl}furan-2-yl)benzyl]-1-methyl-1H-imidazole-2-carboxamide | 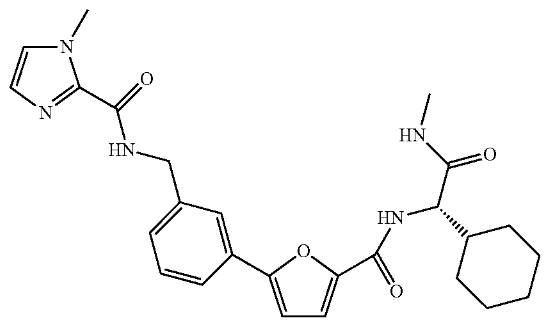 [SMILES: CNC(=O)[C@@H](NC(=O)c1ccc(-c2cccc(CNC(=O)c3nccn3C)c2)o1)C1CCCCC1] |
| N-[3-(5-{[(1S)-1-cyclohexyl-2-(methylamino)-2-oxoethyl]carbamoyl}furan-2-yl)benzyl]-2-(trifluoromethyl)pyrimidine-4-carboxamide | 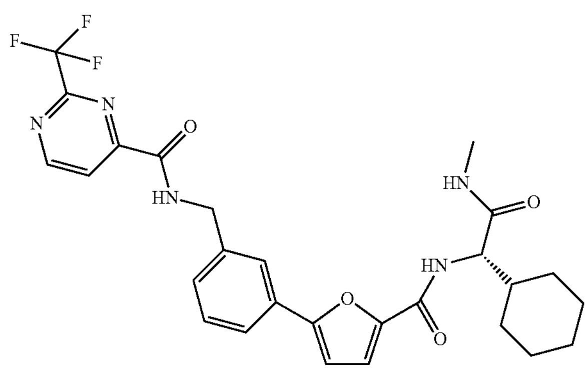 [SMILES: CNC(=O)[C@@H](NC(=O)c1ccc(-c2cccc(CNC(=O)c3ccnc(C(F)(F)F)n3)c2)o1)C1CCCCC1] |
| N-[3-(5-{[(1S)-1-cyclohexyl-2-(methylamino)-2-oxoethyl]carbamoyl}furan-2-yl)benzyl]-7-methylimidazo[1,2-a]pyridine-2-carboxamide | 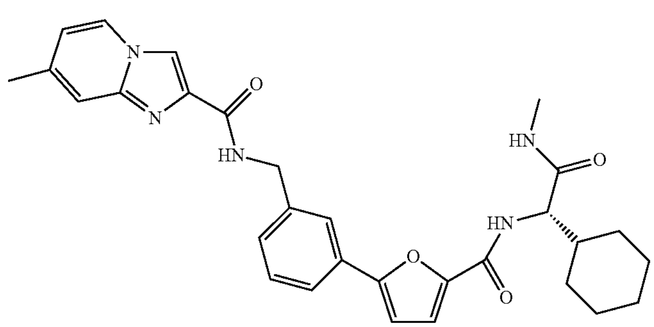 [SMILES: CNC(=O)[C@@H](NC(=O)c1ccc(-c2cccc(CNC(=O)c3cn4ccc(C)cc4n3)c2)o1)C1CCCCC1] |

TABLE I-continued

| Name | Structure |
|---|---|
| N-[3-(5-{[(1S)-1-cyclohexyl-2-(methylamino)-2-oxoethyl]carbamoyl}furan-2-yl)benzyl]-5-methylimidazo[1,2-a]pyridine-2-carboxamide | 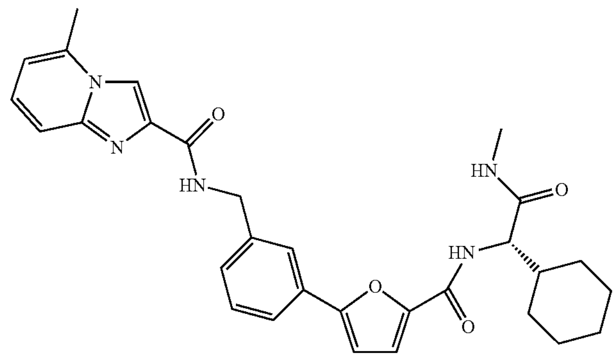 [SMILES: CNC(=O)[C@@H](NC(=O)c1ccc(-c2cccc(CNC(=O)c3cn4c(C)cccc4n3)c2)o1)C1CCCCC1] |
| N-[(1S)-1-cyclohexyl-2-(methylamino)-2-oxoethyl]-5-[3-({[(4,5-dimethylthiophen-2-yl)carbonyl]amino}methyl)phenyl]furan-2-carboxamide | 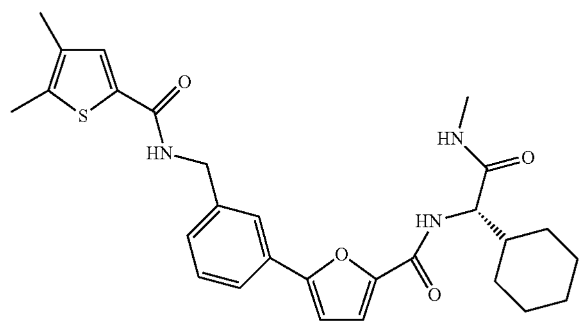 [SMILES: CNC(=O)[C@@H](NC(=O)c1ccc(-c2cccc(CNC(=O)c3cc(C)c(C)s3)c2)o1)C1CCCCC1] |
| N-[3-(5-{[(1S)-1-cyclohexyl-2-(methylamino)-2-oxoethyl]carbamoyl}furan-2-yl)benzyl]-1,5-dimethyl-1H-pyrazole-3-carboxamide | 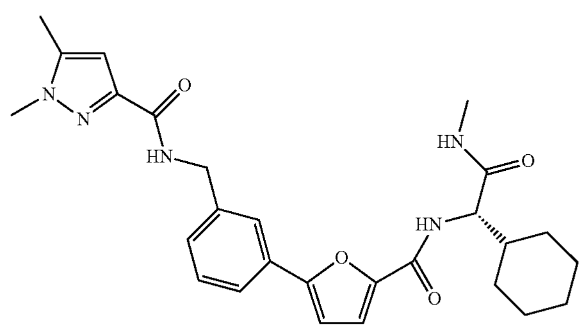 [SMILES: CNC(=O)[C@@H](NC(=O)c1ccc(-c2cccc(CNC(=O)c3cc(C)n(C)n3)c2)o1)C1CCCCC1] |
| 2-Methoxyethyl [3-(5-{[(1S)-1-cyclohexyl-2-(methylamino)-2-oxoethyl}carbamoyl}furan-2-yl)benzyl]carbamate (again should we cover carbamates?) | 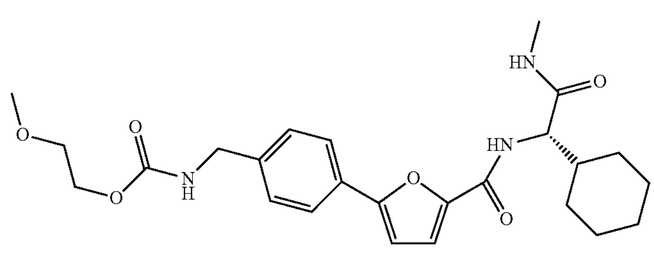 [SMILES: CNC(=O)[C@@H](NC(=O)c1ccc(-c2ccc(CNC(=O)OCCOC)cc2)o1)C1CCCCC1] |
| 2-Methylpropyl [3-(5-{[(1S)-1-cyclohexyl-2-(methylamino)-2-oxoethyl]carbamoyl}furan-2-yl)benzyl]carbamate | 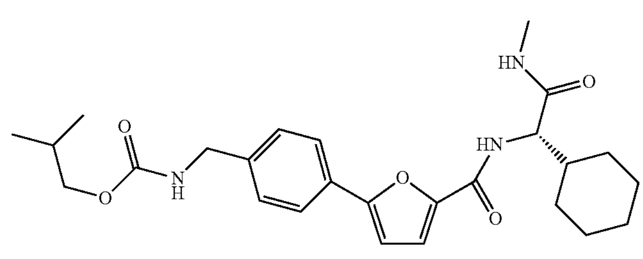 [SMILES: CNC(=O)[C@@H](NC(=O)c1ccc(-c2ccc(CNC(=O)OCC(C)C)cc2)o1)C1CCCCC1] |

TABLE I-continued

| Name | Structure |
|---|---|
| Benzyl [3-(5-{[(1S)-1-cyclohexyl-2-(methylamino)-2-oxoethyl]carbamoyl}furan-2-yl)benzyl]carbamate | 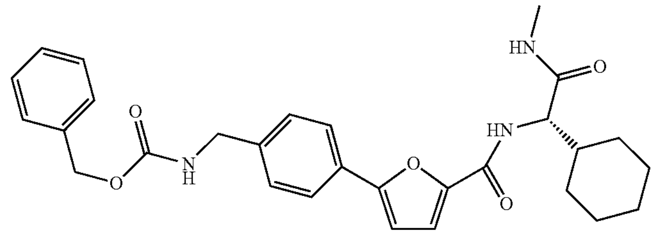 [SMILES: CNC(=O)[C@@H](NC(=O)c1ccc(-c2ccc(CNC(=O)OCc3ccccc3)cc2)o1)C1CCCCC1] |
| N-[4-(5-{[(1S)-1-cyclohexyl-2-(methylamino)-2-oxoethyl]carbamoyl}furan-2-yl)benzyl]-4,5-dimethylfuran-2-carboxamide | 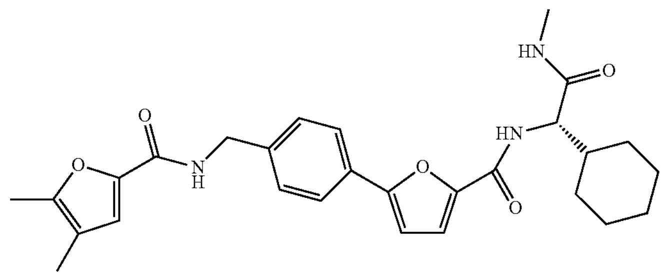 [SMILES: CNC(=O)[C@@H](NC(=O)c1ccc(-c2ccc(CNC(=O)c3cc(C)c(C)o3)cc2)o1)C1CCCCC1] |
| N-[4-(5-{[(1S)-1-cyclohexyl-2-(methylamino)-2-oxoethyl]carbamoyl}furan-2-yl)benzyl]-1-methyl-1H-imidazole-5-carboxamide | 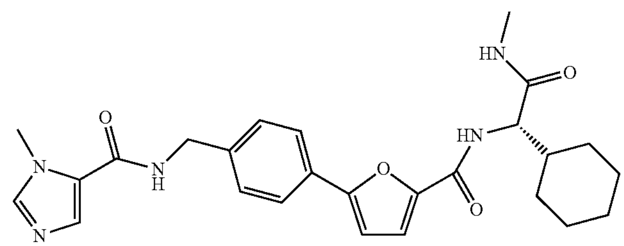 [SMILES: CNC(=O)[C@@H](NC(=O)c1ccc(-c2ccc(CNC(=O)c3cncn3C)cc2)o1)C1CCCCC1] |
| N-[4-(5-{[(1S)-1-cyclohexyl-2-(methylamino)-2-oxoethyl]carbamoyl}furan-2-yl)benzyl]-6-methylpyridine-2-carboxamide | 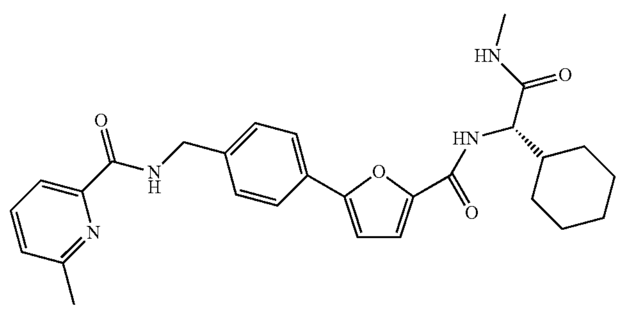 [SMILES: CNC(=O)[C@@H](NC(=O)c1ccc(-c2ccc(CNC(=O)c3cccc(C)n3)cc2)o1)C1CCCCC1] |
| N-[4-(5-{[(1S)-1-cyclohexyl-2-(methylamino)-2-oxoethyl]carbamoyl}furan-2-yl)benzyl]-5-methylpyridine-3-carboxamide | 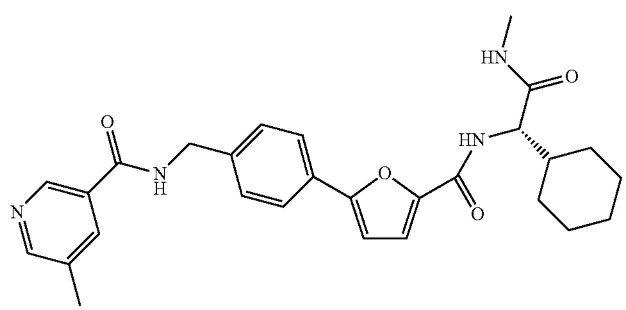 [SMILES: CNC(=O)[C@@H](NC(=O)c1ccc(-c2ccc(CNC(=O)c3cncc(C)c3)cc2)o1)C1CCCCC1] |

TABLE I-continued

| Name | Structure |
|---|---|
| N-[4-(5-{[(1S)-1-cyclohexyl-2-(methylamino)-2-oxoethyl]carbamoyl}furan-2-yl)benzyl]-1-methyl-1H-pyrazole-5-carboxamide | 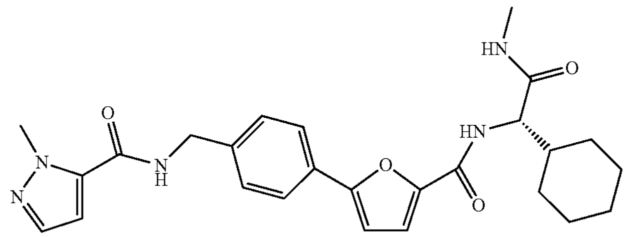 [SMILES: CNC(=O)[C@@H](NC(=O)c1ccc(-c2ccc(CNC(=O)c3ccnn3C)cc2)o1)C1CCCCC1] |
| N-[4-(5-{[(1S)-1-cyclohexyl-2-(methylamino)-2-oxoethyl]carbamoyl}furan-2-yl)benzyl]-3-methylfuran-2-carboxamide | 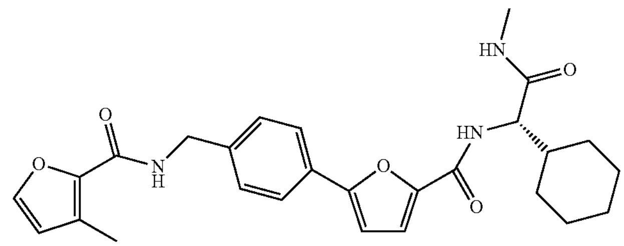 [SMILES: CNC(=O)[C@@H](NC(=O)c1ccc(-c2ccc(CNC(=O)c3occc3C)cc2)o1)C1CCCCC1] |
| N-[(1S)-1-cyclohexyl-2-(methylamino)-2-oxoethyl]-5-[4-({[(2-methylfuran-3-yl)carbonyl]amino}methyl)phenyl]furan-2-carboxamide | 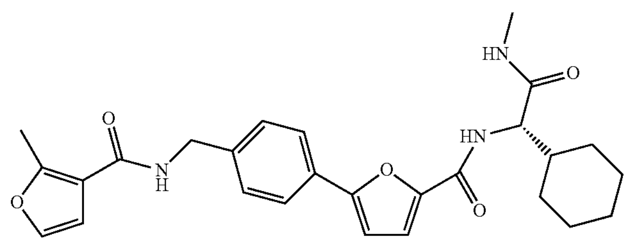 [SMILES: CNC(=O)[C@@H](NC(=O)c1ccc(-c2ccc(CNC(=O)c3ccoc3C)cc2)o1)C1CCCCC1] |
| N-[4-(5-{[(1S)-1-cyclohexyl-2-(methylamino)-2-oxoethyl]carbamoyl}furan-2-yl)benzyl]-5-methylfuran-2-carboxamide | 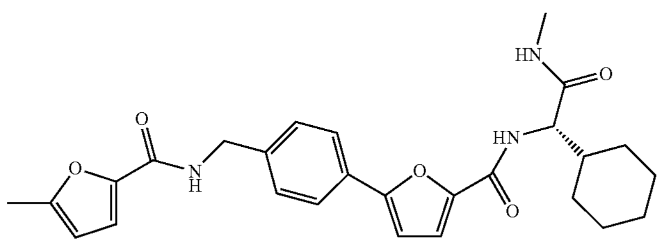 [SMILES: CNC(=O)[C@@H](NC(=O)c1ccc(-c2ccc(CNC(=O)c3ccc(C)o3)cc2)o1)C1CCCCC1] |
| N-[4-(5-{[(1S)-1-cyclohexyl-2-(methylamino)-2-oxoethyl]carbamoyl}furan-2-yl)benzyl]-1-methyl-1H-pyrazol-3-carboxamide | 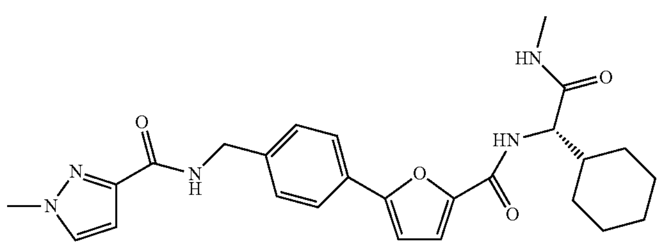 [SMILES: CNC(=O)[C@@H](NC(=O)c1ccc(-c2ccc(CNC(=O)c3ccn(C)n3)cc2)o1)C1CCCCC1] |
| N-[4-(5-{[(1S)-1-cyclohexyl-2-(methylamino)-2-oxoethyl]carbamoyl}furan-2-yl)benzyl]-1-methyl-1H-pyrazole-4-carboxamide | 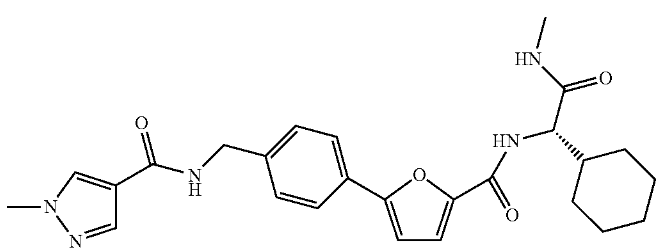 [SMILES: CNC(=O)[C@@H](NC(=O)c1ccc(-c2ccc(CNC(=O)c3cnn(C)c3)cc2)o1)C1CCCCC1] |

TABLE I-continued

| Name | Structure |
|---|---|
| N-[(1S)-1-cyclohexyl-2-(methylamino)-2-oxoethyl]-5-{4-[(propanoylamino)methyl]phenyl}furan-2-carboxamide | 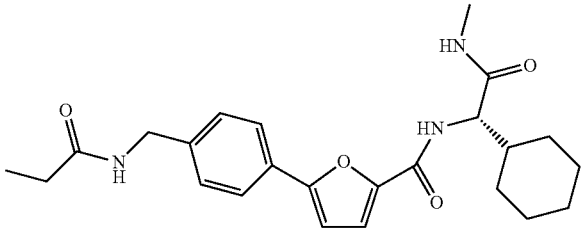 [SMILES: CCC(=O)NCc1ccc(-c2ccc(C(=O)N[C@H](C(=O)NC)C3CCCCC3)o2)cc1] |
| N-[(1S)-1-cyclohexyl-2-(methylamino)-2-oxoethyl]-5-(4-{[(2-methylpropanoyl)amino]methyl}phenyl)furan-2-carboxamide | 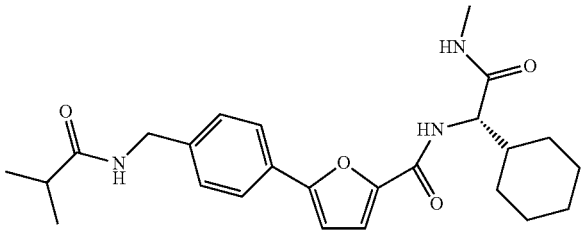 [SMILES: CNC(=O)[C@@H](NC(=O)c1ccc(-c2ccc(CNC(=O)C(C)C)cc2)o1)C1CCCCC1] |
| N-[(1S)-1-cyclohexyl-2-(methylamino)-2-oxoethyl]-5-(4-{[(cyclopropylcarbonyl)amino]methyl}phenyl)furan-2-carboxamide | 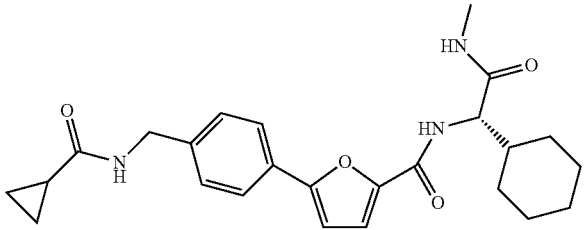 [SMILES: CNC(=O)[C@@H](NC(=O)c1ccc(-c2ccc(CNC(=O)C3CC3)cc2)o1)C1CCCCC1] |
| N-[4-(5-{[(1S)-1-cyclohexyl-2-(methylamino)-2-oxoethyl]carbamoyl}furan-2-yl)benzyl]pyridine-2-carboxamide | 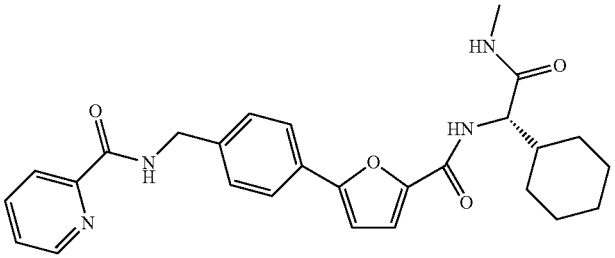 [SMILES: CNC(=O)[C@@H](NC(=O)c1ccc(-c2ccc(CNC(=O)c3ccccn3)cc2)o1)C1CCCCC1] |
| N-[4-(5-{[(1S)-1-cyclohexyl-2-(methylamino)-2-oxoethyl]carbamoyl}furan-2-yl)benzyl]-3-methylpyridine-carboxamide | 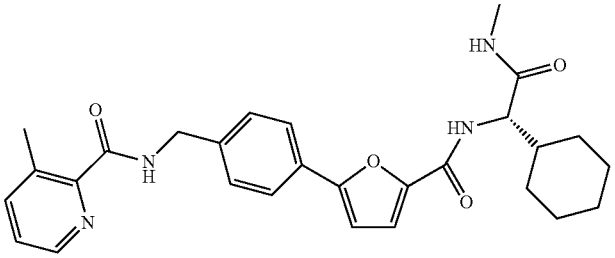 [SMILES: CNC(=O)[C@@H](NC(=O)c1ccc(-c2ccc(CNC(=O)c3ncccc3C)cc2)o1)C1CCCCC1] |
| N-[4-(5-{[(1S)-1-cyclohexyl-2-(methylamino)-2-oxoethyl]carbamoyl}furan-2-yl)benzyl]-4-ethylpyridine-2-carboxamide | 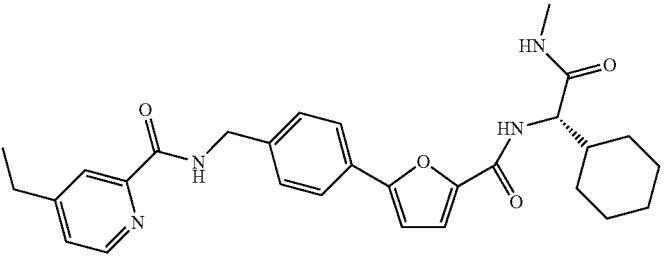 [SMILES: CCc1ccnc(C(=O)NCc2ccc(-c3ccc(C(=O)N[C@H](C(=O)NC)C4CCCCC4)o3)cc2)c1] |

TABLE I-continued

| Name | Structure |
| --- | --- |
| N-[(1S)-1-cyclohexyl-2-(methylamino)-2-oxoethyl]-5-(4-{[(furan-2-ylcarbonyl)amino]methyl}phenyl)furan-2-carboxamide | 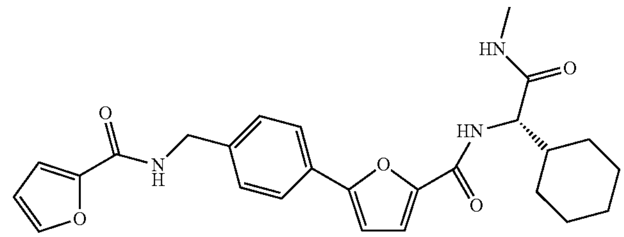 [SMILES: CNC(=O)[C@@H](NC(=O)c1ccc(-c2ccc(CNC(=O)c3ccco3)cc2)o1)C1CCCCC1] |
| N-[4-(5-{[(1S)-1-cyclohexyl-2-(methylamino)-2-oxoethyl]carbamoyl}furan-2-yl)benzyl]-2-(trifluoromethyl)pyrimidine-4-carboxamide | 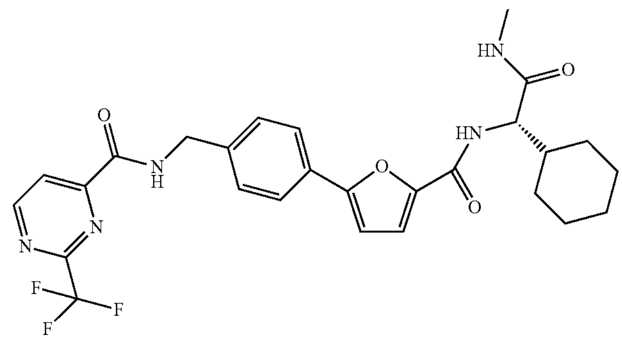 [SMILES: CNC(=O)[C@@H](NC(=O)c1ccc(-c2ccc(CNC(=O)c3ccnc(C(F)(F)F)n3)cc2)o1)C1CCCCC1] |
| N-[4-(5-{[(1S)-1-cyclohexyl-2-(methylamino)-2-oxoethyl]carbamoyl}furan-2-yl)benzyl]-1-methyl-1H-imidazole-4-carboxamide | 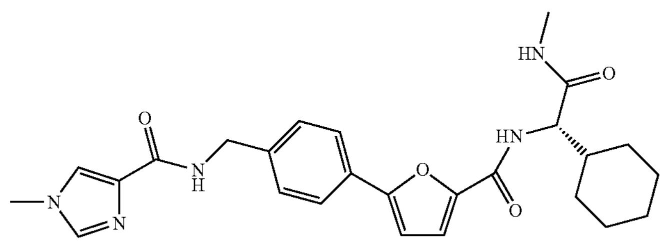 [SMILES: CNC(=O)[C@@H](NC(=O)c1ccc(-c2ccc(CNC(=O)c3cn(C)cn3)cc2)o1)C1CCCCC1] |
| N-[4-(5-{[(1S)-1-cyclohexyl-2-(methylamino)-2-oxoethyl]carbamoyl}furan-2-yl)benzyl]-1-benzofuran-2-carboxamide | 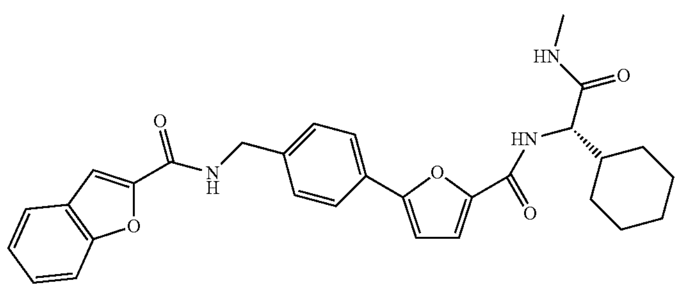 [SMILES: CNC(=O)[C@@H](NC(=O)c1ccc(-c2ccc(CNC(=O)c3cc4ccccc4o3)cc2)o1)C1CCCCC1] |
| N-[3-(5-{[(1S)-2-(methylamino)-2-oxo-1-(tetrahydro-2H-pyran-4-yl)ethyl]carbamoyl}-2-furyl)benzyl]-6-(trifluoromethyl)pyridine-2-carboxamide | 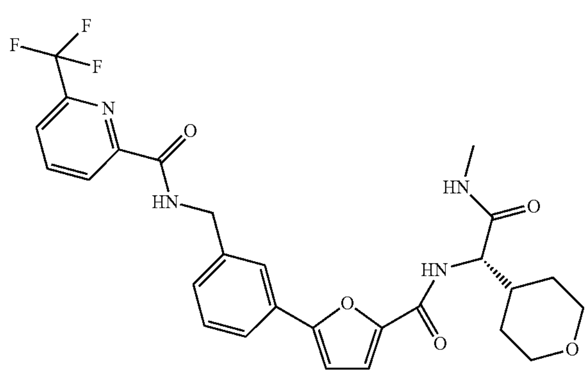 [SMILES: CNC(=O)[C@@H](NC(=O)c1ccc(-c2cccc(CNC(=O)c3cccc(C(F)(F)F)n3)c2)o1)C1CCOCC1] |

TABLE I-continued

| Name | Structure |
|---|---|
| N-[3-(5-{[(1S)-2-(methylamino)-2-oxo-1-(tetrahydro-2H-pyran-4-yl)ethyl]carbamoyl}-2-furyl)benzyl]-2-(trifluoromethyl)pyrimidine-4-carboxamide | 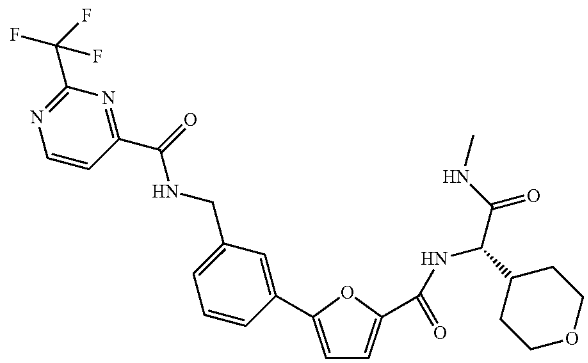 |
| 6-Chloro-N-[3-(5-{[(1S)-2-methyl-1-(methylcarbamoyl)propyl]carbamoyl}-2-furyl)benzyl]pyridine-2-carboxamide | 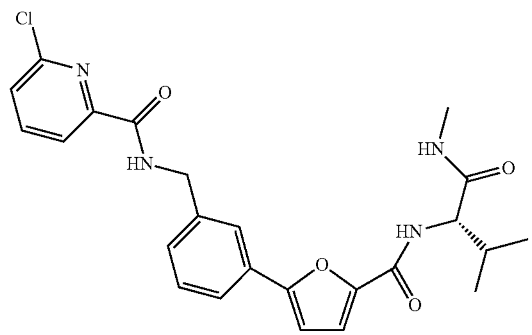 |
| 6-Fluoro-N-[3-(5-{[(1S)-2-methyl-1-(methylcarbamoyl)propyl]carbamoyl}-2-furyl)benzyl]pyridine-2-carboxamide | 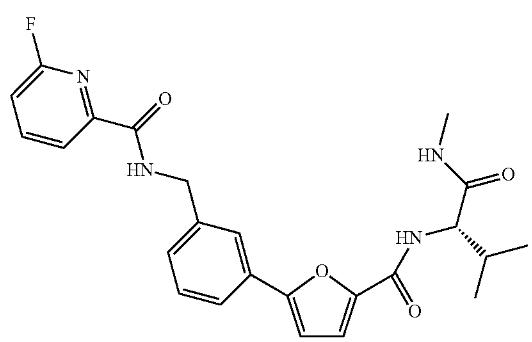 [SMILES: CNC(=O)[C@@H](NC(=O)c1ccc(-c2cccc(CNC(=O)c3cccc(F)n3)c2)o1)C(C)C] |
| N-[3-(5-{[(1S)-2-hydroxy-2-methyl-1-(methylcarbamoyl)propyl]carbamoyl}-2-furyl)benzyl]-2-(trifluoromethyl)pyrimidine-4-carboxamide | 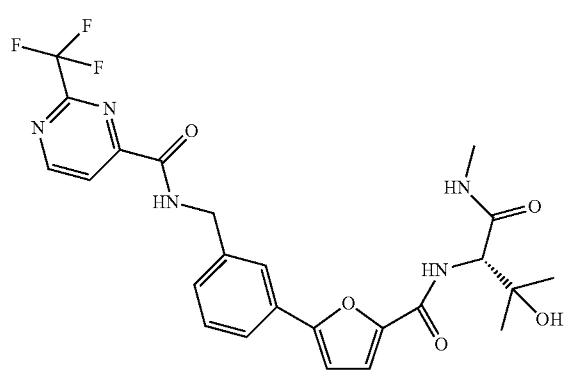 [SMILES: CNC(=O)[C@@H](NC(=O)c1ccc(-c2cccc(CNC(=O)c3ccnc(C(F)(F)F)n3)c2)o1)C(C)(C)O] |

TABLE I-continued

| Name | Structure |
|---|---|
| 4-Trifluoromethyl-thiazole-2-carboxylic acid 3-[5-((S)-2-methyl-1-methylcarbamoyl-propylcarbamoyl)-furan-2-yl]-benzylamide | 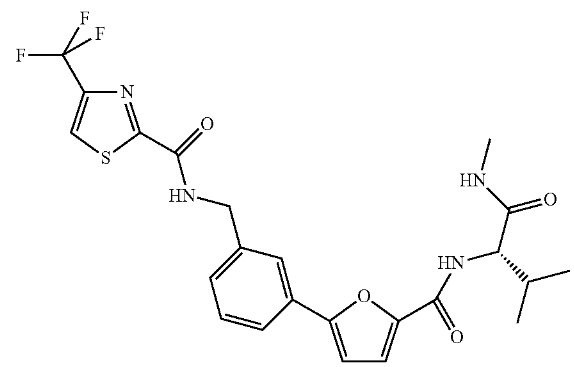 [SMILES: CNC(=O)[C@@H](NC(=O)c1ccc(-c2cccc(CNC(=O)c3nc(C(F)(F)F)cs3)c2)o1)C(C)C] |
| N-[3-(5-{[(1S)-2-methyl-1-(methylcarbamoyl)propyl]carbamoyl}-2-furyl)benzyl]-1-benzofuran-2-carboxamide | 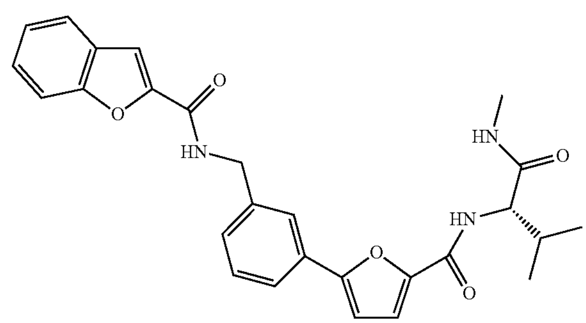 [SMILES: CNC(=O)[C@@H](NC(=O)c1ccc(-c2cccc(CNC(=O)c3cc4ccccc4o3)c2)o1)C(C)C] |
| 2-Chloro-N-[3-(5-{[(1S)-2-methyl-1-(methylcarbamoyl)propyl]carbamoyl}-2-furyl)benzyl]pyrimidine-4-carboxamide | 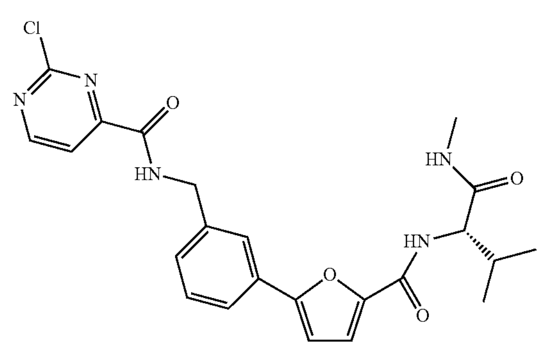 [SMILES: CNC(=O)[C@@H](NC(=O)c1ccc(-c2cccc(CNC(=O)c3ccnc(Cl)n3)c2)o1)C(C)C] |
| 5-Bromo-1-methyl-1H-pyrazole-3-carboxylic acid 3-[5-((S)-2-methyl-1-methylcarbamoyl-propylcarbamoyl)-furan-2-yl]-benzylamide | 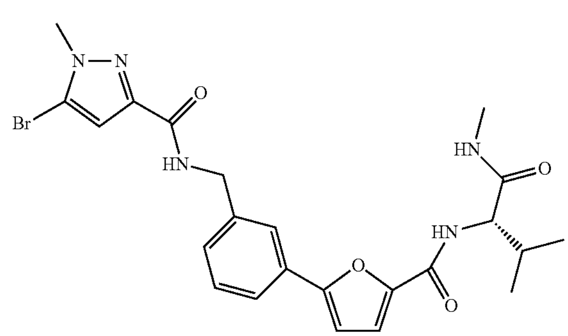 [SMILES: CNC(=O)[C@@H](NC(=O)c1ccc(-c2cccc(CNC(=O)c3cc(Br)n(C)n3)c2)o1)C(C)C] |

TABLE I-continued

| Name | Structure |
|---|---|
| 1-Difluoromethyl-1H-pyrazole-3-carboxylic acid 3-[5-((S)-2-methyl-1-methylcarbamoyl-propylcarbamoyl)-furan-2-yl]-benzylamide | 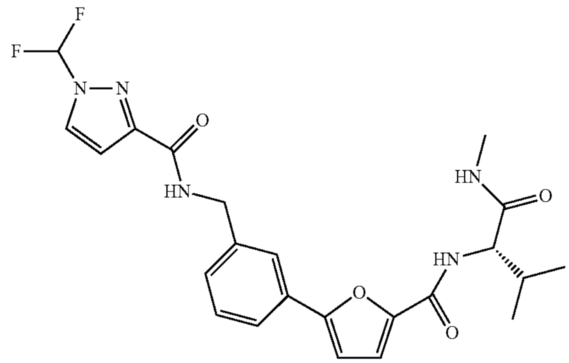 [SMILES: CNC(=O)[C@@H](NC(=O)c1ccc(-c2cccc(CNC(=O)c3ccn(C(F)F)n3)c2)o1)C(C)C] |
| 6-Bromo-N-[3-(5-{[(1S)-1-cyclopropyl-2-(methylamino)-2-oxoethyl]carbamoyl}-2-furyl)benzyl]pyridine-2-carboxamide | 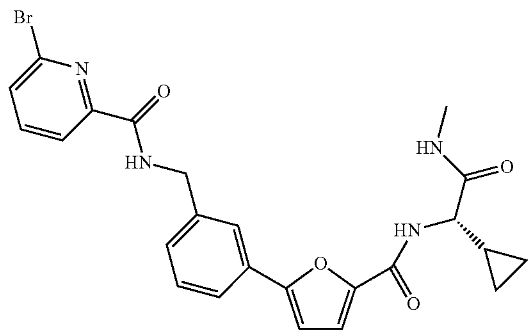 [SMILES: CNC(=O)[C@@H](NC(=O)c1ccc(-c2cccc(CNC(=O)c3cccc(Br)n3)c2)o1)C1CC1] |
| N-[3-(5-{[(1S)-1-cyclopropyl-2-(methylamino)-2-oxoethyl]carbamoyl}-2-furyl)benzyl]-6-(trifluoromethyl)pyridine-2-carboxamide | 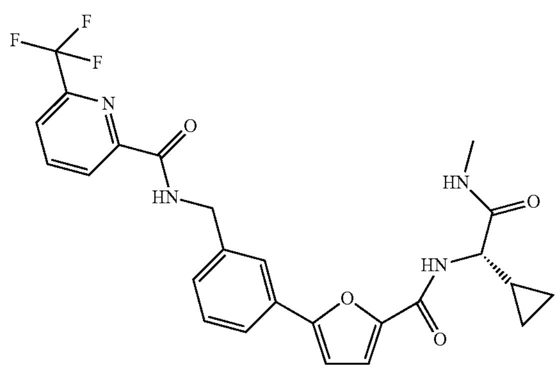 [SMILES: CNC(=O)[C@@H](NC(=O)c1ccc(-c2cccc(CNC(=O)c3cccc(C(F)(F)F)n3)c2)o1)C1CC1] |
| N-[3-(5-{[(1S)-2-methyl-1-(methylcarbamoyl)propyl]carbamoyl}-2-furyl)benzyl]pyrazine-2-carboxamide | 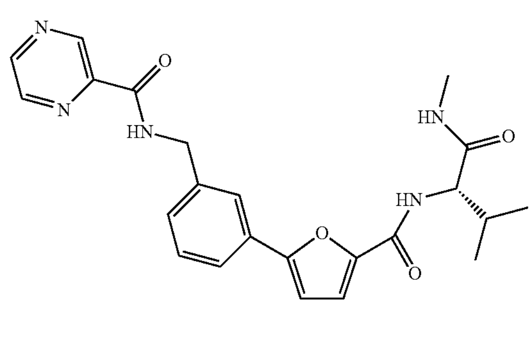 [SMILES: CNC(=O)[C@@H](NC(=O)c1ccc(-c2cccc(CNC(=O)c3cnccn3)c2)o1)C(C)C] |

TABLE I-continued

| Name | Structure |
|---|---|
| N-[3-(5-{[(1S)-2-methyl-1-(methylcarbamoyl)propyl]carbamoyl}-2-furyl)benzyl]-1H-benzimidazole-2-carboxamide | 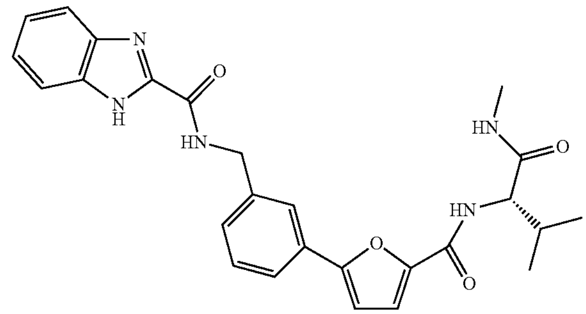 [SMILES: CNC(=O)[C@@H](NC(=O)c1ccc(-c2cccc(CNC(=O)c3nc4ccccc4[nH]3)c2)o1)C(C)C] |
| 1-Methyl-5-trifluoromethyl-1H-pyrazole-3-carboxylic acid 3-[5-((S)-2-methyl-1-methylcarbamoyl-propylcarbamoyl)-furan-2-yl]-benzylamide | 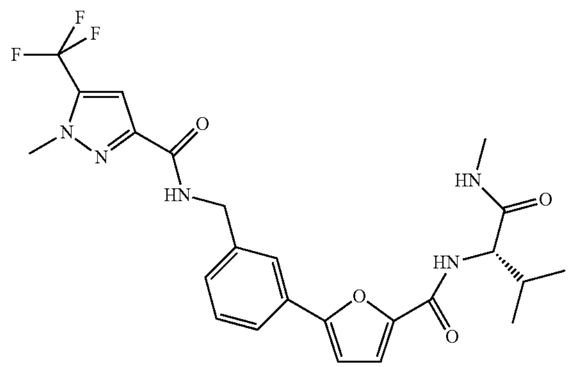 [SMILES: CNC(=O)[C@@H](NC(=O)c1ccc(-c2cccc(CNC(=O)c3cc(C(F)(F)F)n(C)n3)c2)o1)C(C)C] |
| 5-{3-[(3-Trifluoromethyl-benzoylamino)-methyl]-phenyl}-furan-2-carboxylic acid ((S)-2-methyl-1-methylcarbamoyl-propyl)-amide | 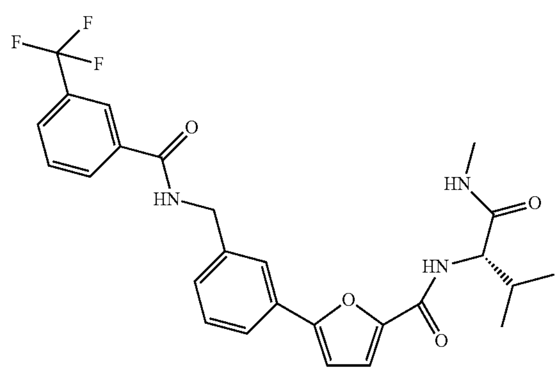 [SMILES: CNC(=O)[C@@H](NC(=O)c1ccc(-c2cccc(CNC(=O)c3cccc(C(F)(F)F)c3)c2)o1)C(C)C] |
| N-[3-(5-{[(1S)-2-methyl-1-(methylcarbamoyl)propyl]carbamoyl}-2-furyl)benzyl]tetrahydro-2H-pyran-2-carboxamide | 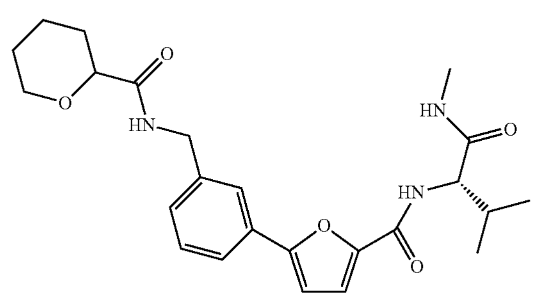 [SMILES: CNC(=O)[C@@H](NC(=O)c1ccc(-c2cccc(CNC(=O)C3CCCCO3)c2)o1)C(C)C] |

TABLE I-continued

| Name | Structure |
|---|---|
| 5-{3-[(4-Dimethylamino-benzoylamino)-methyl]-phenyl}-furan-2-carboxylic acid ((S)-2-methyl-1-methylcarbamoyl-propyl)-amide | 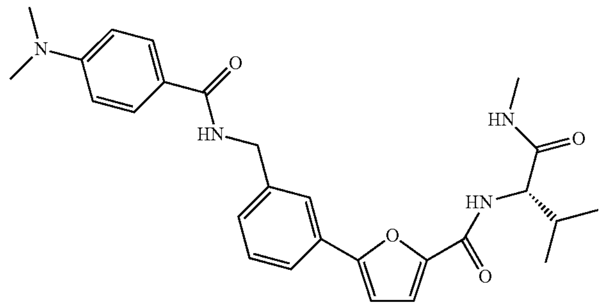 |
| 5-{3-[(3-Methyl-benzoylamino)-methyl]-phenyl}-furan-2-carboxylic acid ((S)-2-methyl-1-methylcarbamoyl-propyl)-amide | 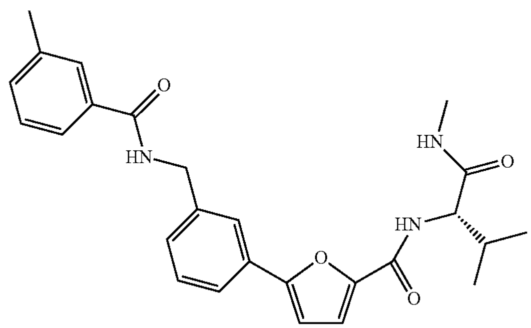 [SMILES: CNC(=O)[C@@H](NC(=O)c1ccc(-c2cccc(CNC(=O)c3cccc(C)c3)c2)o1)C(C)C] |
| 5-{3-[(4-Methoxy-benzoylamino)-methyl]-phenyl}-furan-2-carboxylic acid ((S)-2-methyl-1-methylcarbamoyl-propyl)-amide | 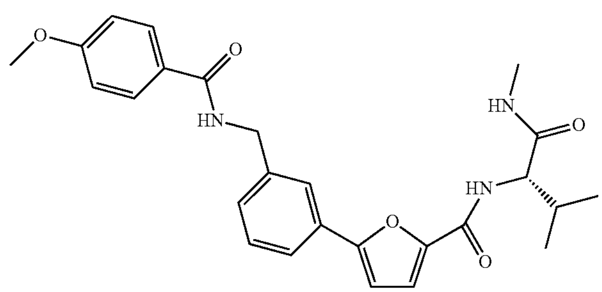 [SMILES: CNC(=O)[C@@H](NC(=O)c1ccc(-c2cccc(CNC(=O)c3ccc(OC)cc3)c2)o1)C(C)C] |
| 5-{3-[(3,4-Dimethyl-benzoylamino)-methyl]-phenyl}-furan-2-carboxylic acid ((S)-2-methyl-1-methylcarbamoyl-propyl)-amide | 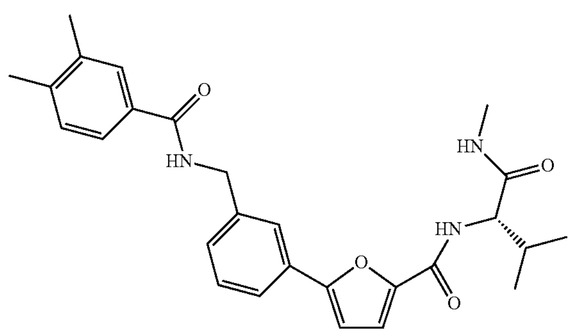 [SMILES: CNC(=O)[C@@H](NC(=O)c1ccc(-c2cccc(CNC(=O)c3ccc(C)c(C)c3)c2)o1)C(C)C] |

TABLE I-continued

| Name | Structure |
|---|---|
| 5-{3-[(3-Cyano-benzoylamino)-methyl]-phenyl}-furan-2-carboxylic acid ((S)-2-methyl-1-methylcarbamoyl-propyl)-amide | 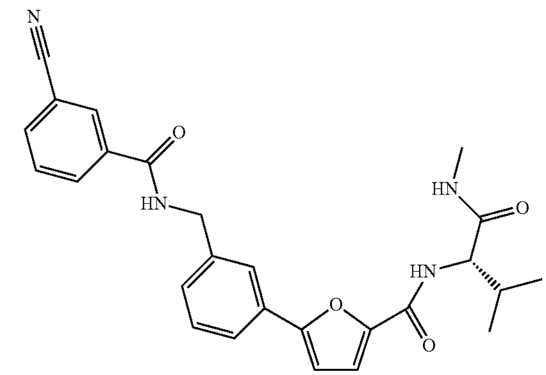 [SMILES: CNC(=O)[C@@H](NC(=O)c1ccc(-c2cccc(CNC(=O)c3cccc(C#N)c3)c2)o1)C(C)C] |
| 5-Trifluoromethyl-2H-pyrazole-3-carboxylic acid 3-[5-((S)-2-methyl-1-methylcarbamoyl-propylcarbamoyl)-furan-2-yl]-benzylamide | 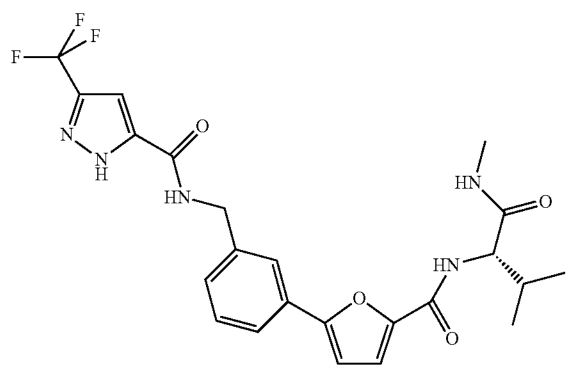 [SMILES: CNC(=O)[C@@H](NC(=O)c1ccc(-c2cccc(CNC(=O)c3cc(C(F)(F)F)n[nH]3)c2)o1)C(C)C] |
| 5-{3-[(3-Isopropyl-benzoylamino)-methyl]-phenyl}-furan-2-carboxylic acid ((S)-2-methyl-1-methylcarbamoyl-propyl)-amide | 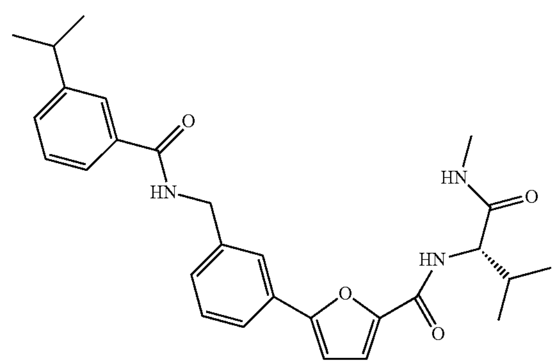 [SMILES: CNC(=O)[C@@H](NC(=O)c1ccc(-c2cccc(CNC(=O)c3cccc(C(C)C)c3)c2)o1)C(C)C] |
| 5-{3-[(3-Methoxy-benzoylamino)-methyl]-phenyl}-furan-2-carboxylic acid ((S)-2-methyl-1-methylcarbamoyl-propyl)-amide | 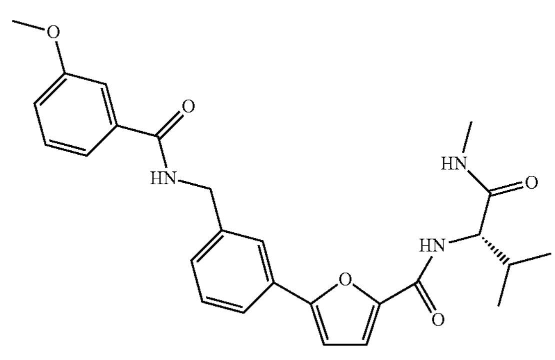 [SMILES: CNC(=O)[C@@H](NC(=O)c1ccc(-c2cccc(CNC(=O)c3cccc(OC)c3)c2)o1)C(C)C] |

TABLE I-continued

| Name | Structure |
|---|---|
| 5-{3-[(Cyclohexanecarbonyl-amino)-methyl]-phenyl}-furan-2-carboxylic acid ((S)-2-methyl-1-methylcarbamoyl-propyl)-amide | 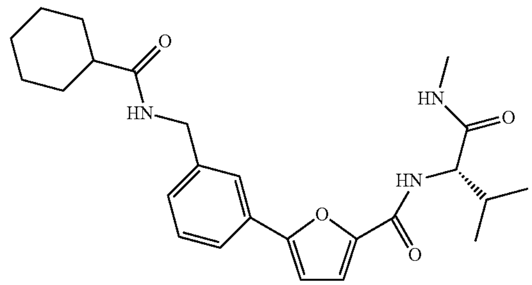 [SMILES: CNC(=O)[C@@H](NC(=O)c1ccc(-c2cccc(CNC(=O)C3CCCCC3)c2)o1)C(C)C] |
| 5-{3-[(4-Methyl-benzoylamino)-methyl]-phenyl}-furan-2-carboxylic acid ((S)-2-methyl-1-methylcarbamoyl-propyl)-amide | 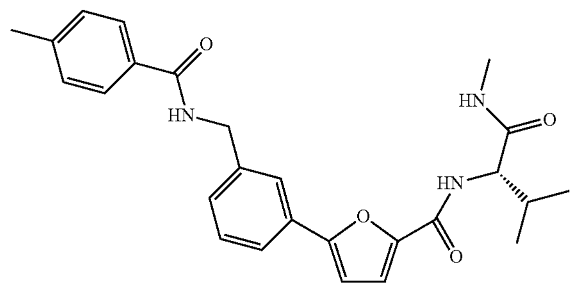 [SMILES: CNC(=O)[C@@H](NC(=O)c1ccc(-c2cccc(CNC(=O)c3ccc(C)cc3)c2)o1)C(C)C] |
| N-[3-(5-{[(1S)-2-methyl-1-(methylcarbamoyl)propyl]carbamoyl}-2-furyl)benzyl]pyridazine-4-carboxamide | 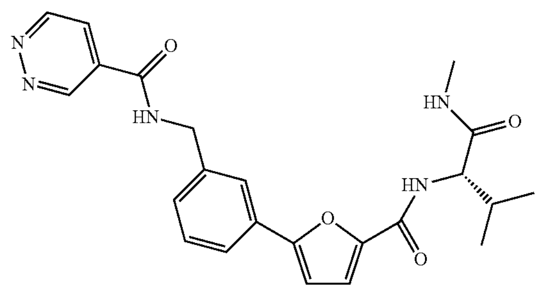 [SMILES: CNC(=O)[C@@H](NC(=O)c1ccc(-c2cccc(CNC(=O)c3ccnnc3)c2)o1)C(C)C] |
| 5-{3-[(4-Cyano-benzoylamino)-methyl]-phenyl}-furan-2-carboxylic acid ((S)-2-methyl-1-methylcarbamoyl-propyl)-amide | 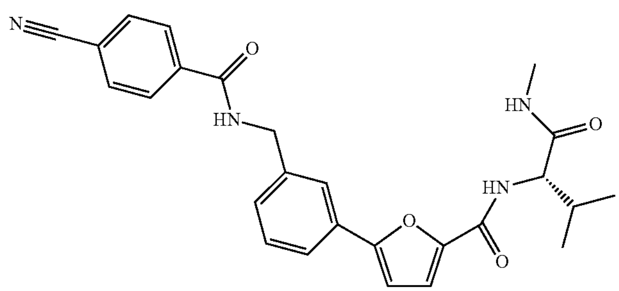 [SMILES: CNC(=O)[C@@H](NC(=O)c1ccc(-c2cccc(CNC(=O)c3ccc(C#N)cc3)c2)o1)C(C)C] |
| 5-[3-(Benzoylamino-methyl)-phenyl]-furan-2-carboxylic acid ((S)-2-methyl-1-methylcarbamoyl-propyl)-amide | 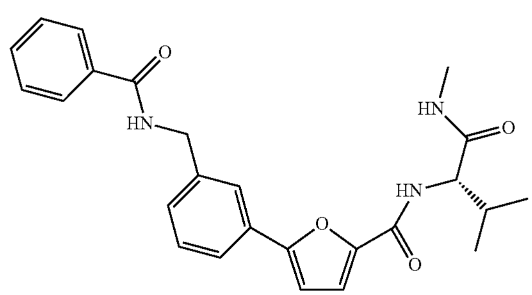 [SMILES: CNC(=O)[C@@H](NC(=O)c1ccc(-c2cccc(CNC(=O)c3ccccc3)c2)o1)C(C)C] |

TABLE I-continued

| Name | Structure |
|---|---|
| 5-{3-[(3-Dimethylamino-benzoylamino)-methyl]-phenyl}-furan-2-carboxylic acid ((S)-2-methyl-1-methylcarbamoyl-propyl)-amide | 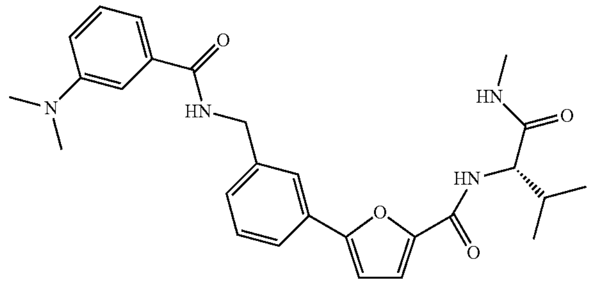 [SMILES: CNC(=O)[C@@H](NC(=O)c1ccc(-c2cccc(CNC(=O)c3cccc(N(C)C)c3)c2)o1)C(C)C] |
| 1-Methyl-N-[3-(5-{[(1S)-2-methyl-1-(methylcarbamoyl)propyl]carbamoyl}-2-furyl)benzyl]piperidine-3-carboxamide | 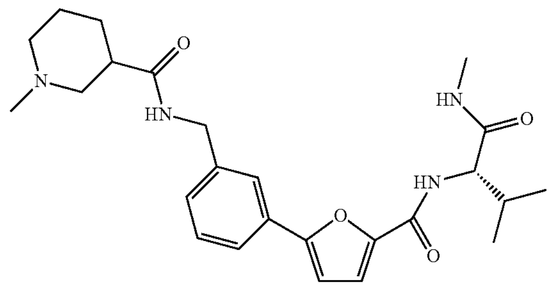 [SMILES: CNC(=O)[C@@H](NC(=O)c1ccc(-c2cccc(CNC(=O)C3CCCN(C)C3)c2)o1)C(C)C] |
| 5-{3-[(3-Trifluoromethyl-4-fluoro-benzoylamino)-methyl]-phenyl}-furan-2-carboxylic acid ((S)-2-methyl-1-methylcarbamoyl-propyl)-amide | 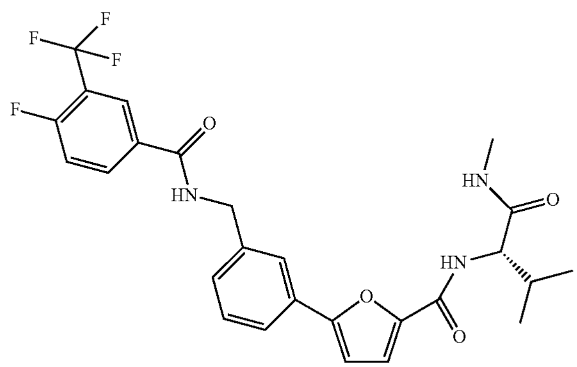 [SMILES: CNC(=O)[C@@H](NC(=O)c1ccc(-c2cccc(CNC(=O)c3ccc(F)c(C(F)(F)F)c3)c2)o1)C(C)C] |
| 5-{3-[(4-Isopropyl-benzoylamino)-methyl]-phenyl}-furan-2-carboxylic acid ((S)-2-methyl-1-methylcarbamoyl-propyl)-amide | 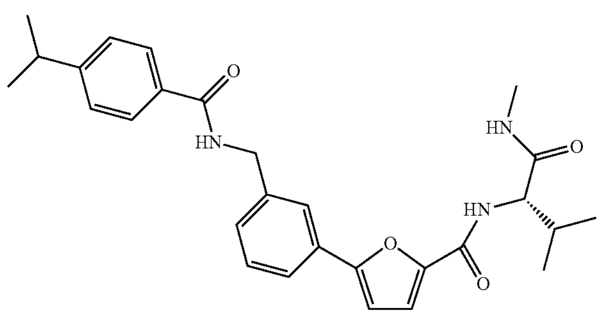 [SMILES: CNC(=O)[C@@H](NC(=O)c1ccc(-c2cccc(CNC(=O)c3ccc(C(C)C)cc3)c2)o1)C(C)C] |
| N-[3-(5-{[(1S)-2-methyl-1-(methylcarbamoyl)propyl]carbamoyl}-2-furyl)benzyl]piperidine-2-carboxamide | 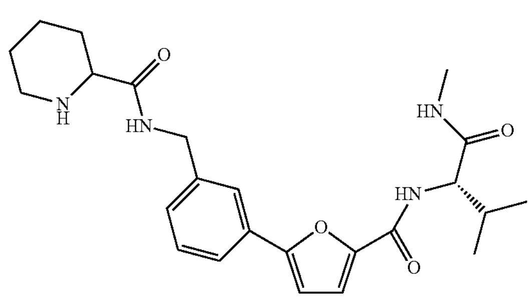 [SMILES: CNC(=O)[C@@H](NC(=O)c1ccc(-c2cccc(CNC(=O)C3CCCCN3)c2)o1)C(C)C] |

TABLE I-continued

| Name | Structure |
|---|---|
| 3-Methyl-isoxazole-5-carboxylic acid 3-[5-((S)-2-methyl-1-methylcarbamoyl-propylcarbamoyl)-furan-2-yl]-benzylamide | 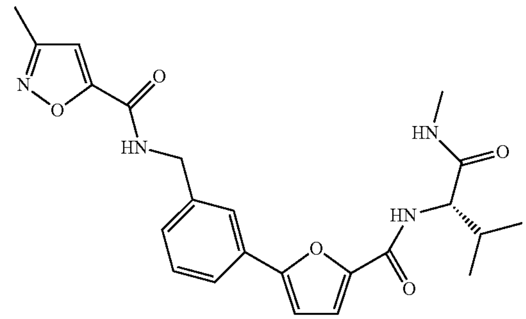 [SMILES: CNC(=O)[C@@H](NC(=O)c1ccc(-c2cccc(CNC(=O)c3cc(C)no3)c2)o1)C(C)C] |
| 1-Methyl-N-[3-(5-{[(1S)-2-methyl-1-(methylcarbamoyl)propyl]carbamoyl}-2-furyl)benzyl]piperidine-2-carboxamide | 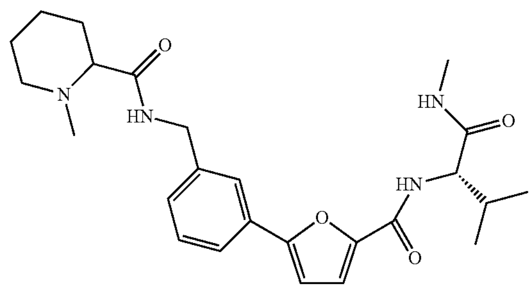 [SMILES: CNC(=O)[C@@H](NC(=O)c1ccc(-c2cccc(CNC(=O)C3CCCCN3C)c2)o1)C(C)C] |
| N-[3-(5-{[(1S)-2-methyl-1-(methylcarbamoy)propyl]carbamoyl}-2-furyl)benzyl]prolinamide | 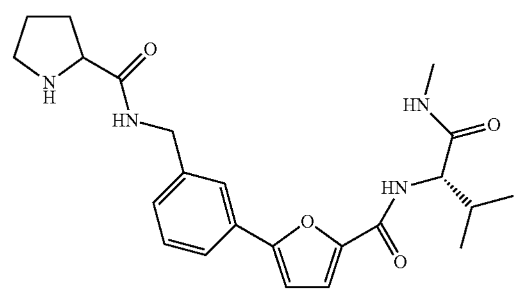 [SMILES: CNC(=O)[C@@H](NC(=O)c1ccc(-c2cccc(CNC(=O)C3CCCN3)c2)o1)C(C)C] |
| N-[3-(5-{[(1S)-2-methyl-1-(methylcarbamoyl)propyl]carbamoyl}-2-furyl)benzyl]tetrahydro-2H-pyran-4-carboxamide | 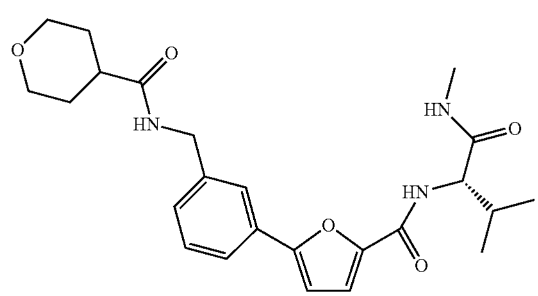 [SMILES: CNC(=O)[C@@H](NC(=O)c1ccc(-c2cccc(CNC(=O)C3CCOCC3)c2)o1)C(C)C] |
| N-[3-(5-{[(1S)-2-methyl-1-(methylcarbamoyl)propyl]carbamoyl}-2-furyl)benzyl]nicotinamide | 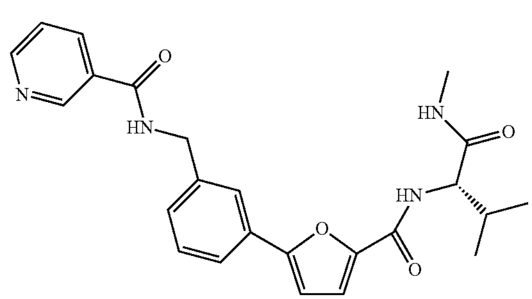 |

TABLE I-continued

| Name | Structure |
|---|---|
| N-[3-(5-{[(1S)-2-methyl-1-(methylcarbamoyl)propyl]carbamoyl}-2-furyl)benzyl]morpholine-2-carboxamide | 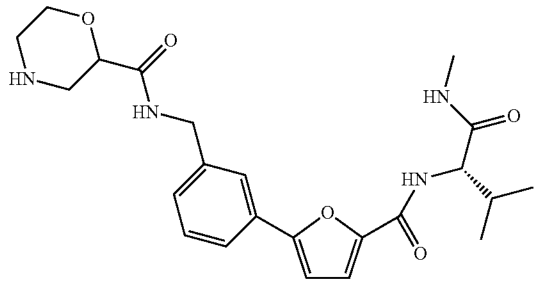 |
| 1-methyl-N-[3-(5-{[(1S)-2-methyl-1-(methylcarbamoyl)propyl]carbamoyl}-2-furyl)benzyl]-L-prolinamide | 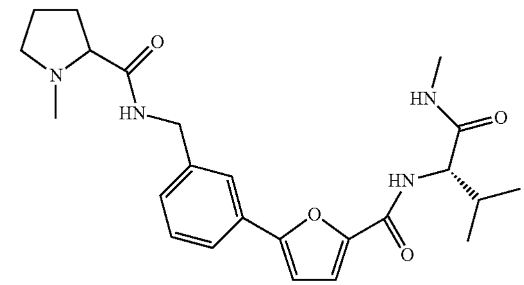 [SMILES: CNC(=O)[C@@H](NC(=O)c1ccc(-c2cccc(CNC(=O)C3CCCN3C)c2)o1)C(C)C] |
| 5-[3-(Aminomethyl)phenyl]-N-[(1S)-2-(methylamino)-2-oxo-1-(tetrahydro-2H-pyran-4-yl)ethyl]-2-furamide | 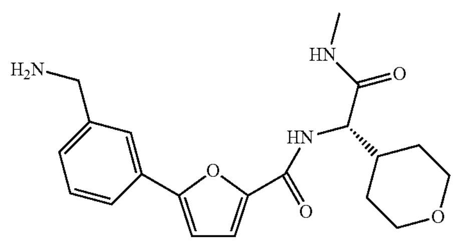 [SMILES: CNC(=O)[C@@H](NC(=O)c1ccc(-c2cccc(CN)c2)o1)C1CCOCC1] |
| N-[3-(5-{[(1S)-2-methyl-1-(methylcarbamoyl)propyl]carbamoyl}-2-furyl)benzyl]pyridazine-3-carboxamide | 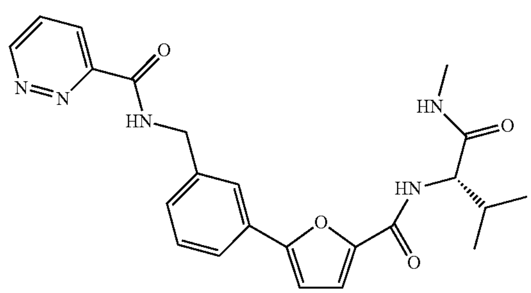 [SMILES: CNC(=O)[C@@H](NC(=O)c1ccc(-c2cccc(CNC(=O)c3cccnn3)c2)o1)C(C)C] |
| N-[3-(5-{[(1S)-2-methyl-1-(methylcarbamoyl)propyl]carbamoyl}-2-furyl)benzyl]piperidine-3-carboxamide | 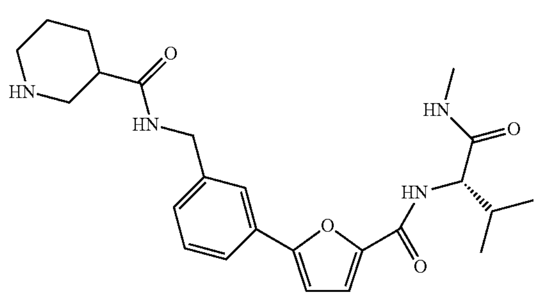 [SMILES: CNC(=O)[C@@H](NC(=O)c1ccc(-c2cccc(CNC(=O)C3CCCNC3)c2)o1)C(C)C] |

TABLE I-continued

| Name | Structure |
|---|---|
| N-Methyl-N~2~-(5-{3-[({[1-methyl-3-(trifluoromethyl)-1H-pyrazol-5-yl]carbonyl}amino)methyl]phenyl}-2-furoyl)-L-valinamide | 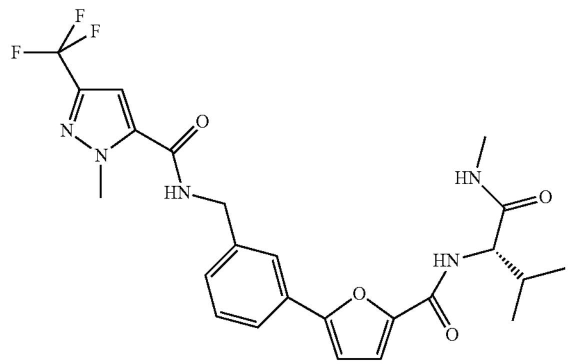 [SMILES: CNC(=O)[C@@H](NC(=O)c1ccc(-c2cccc(CNC(=O)c3cc(C(F)(F)F)nn3C)c2)o1)C(C)C] |
| N-[3-(5-{[(1S)-2-methyl-1-(methylcarbamoyl)propyl]carbamoyl}-2-furyl)benzyl]morpholine-3-carboxamide | 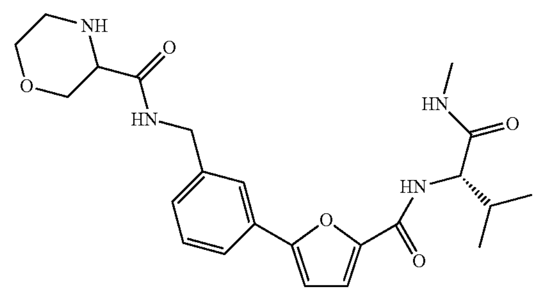 [SMILES: CNC(=O)[C@@H](NC(=O)c1ccc(-c2cccc(CNC(=O)C3COCCN3)c2)o1)C(C)C] |
| 5-[5-(4-Fluoro-phenyl)-pyridin-2-yl]-furan-2-carboxylic acid ((S)-2-methyl-1-methylcarbamoyl-propyl)-amide | 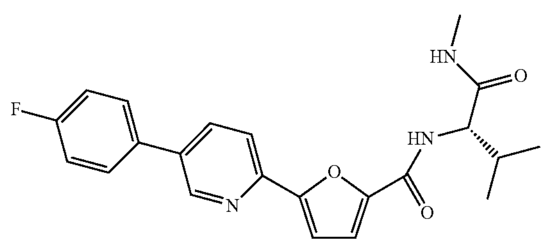 [SMILES: CNC(=O)[C@@H](NC(=O)c1ccc(-c2ccc(-c3ccc(F)cc3)cn2)o1)C(C)C] |
| 5-[5-(4-Methyl-phenyl)-pyridin-2-yl]-furan-2-carboxylic acid ((S)-2-methyl-1-methylcarbamoyl-propyl)-amide | 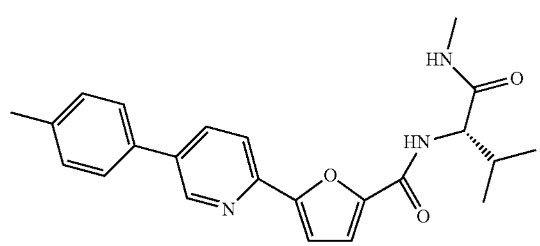 [SMILES: CNC(=O)[C@@H](NC(=O)c1ccc(-c2ccc(-c3ccc(C)cc3)cn2)o1)C(C)C] |
| 5-[5-(4-Cyano-phenyl)-pyridin-2-yl]-furan-2-carboxylic acid ((S)-2-methyl-1-methylcarbamoyl-propyl)-amide | 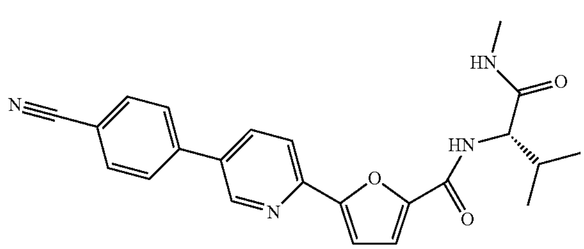 [SMILES: CNC(=O)[C@@H](NC(=O)c1ccc(-c2ccc(-c3ccc(C#N)cc3)cn2)o1)C(C)C] |

TABLE I-continued

| Name | Structure |
|---|---|
| 5-[5-(1H-Indol-5-yl)-pyridin-2-yl]-furan-2-carboxylic acid ((S)-2-methyl-1-methylcarbamoyl-propyl)-amide | 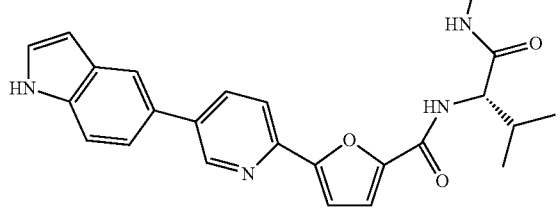 |
| 5-[5-(4-Ethoxy-phenyl)-pyridin-2-yl]-furan-2-carboxylic acid ((S)-2-methyl-1-methylcarbamoyl-propyl)-amide | 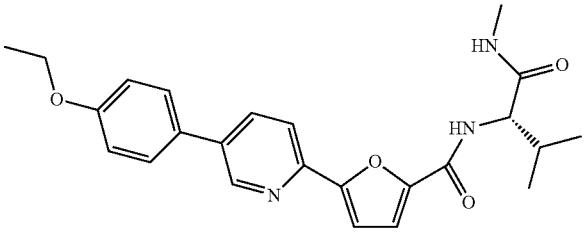 [SMILES: CCOc1ccc(-c2ccc(-c3ccc(C(=O)N[C@H](C(=O)NC)C(C)C)o3)nc2)cc1] |
| 5-[5-(4-Isopropoxy-phenyl)-pyridin-2-yl]-furan-2-carboxylic acid ((S)-2-methyl-1-methylcarbamoyl-propyl)-amide | 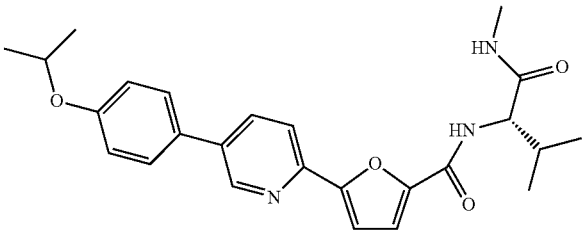 [SMILES: CNC(=O)[C@@H](NC(=O)c1ccc(-c2ccc(-c3ccc(OC(C)C)cc3)cn2)o1)C(C)C] |
| 5-[5-(3-Fluoro-phenyl)-pyridin-2-yl]-furan-2-carboxylic acid ((S)-2-methyl-1-methylcarbamoyl-propyl)-amide | 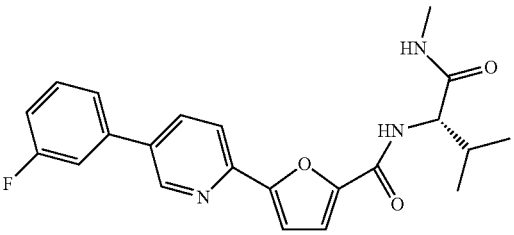 [SMILES: CNC(=O)[C@@H](NC(=O)c1ccc(-c2ccc(-c3cccc(F)c3)cn2)o1)C(C)C] |
| 5-[5-(3,5-Difluoro-phenyl)-pyridin-2-yl]-furan-2-carboxylic acid ((S)-2-methyl-1-methylcarbamoyl-propyl)-amide | 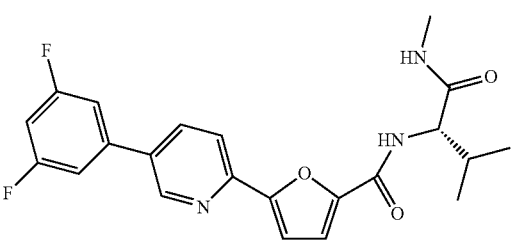 [SMILES: CNC(=O)[C@@H](NC(=O)c1ccc(-c2ccc(-c3cc(F)cc(F)c3)cn2)o1)C(C)C] |
| 5-[5-(1H-Indol-6-yl)-pyridin-2-yl]-furan-2-carboxylic acid ((S)-2-methyl-1-methylcarbamoyl-propyl)-amide | 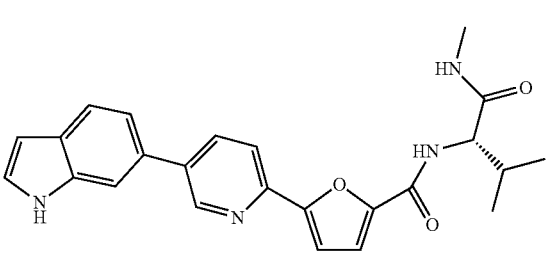 [SMILES: CNC(=O)[C@@H](NC(=O)c1ccc(-c2ccc(-c3ccc4cc[nH]c4c3)cn2)o1)C(C)C] |

TABLE I-continued

| Name | Structure |
|---|---|
| 5-[3,4']Bipyridinyl-6-yl-furan-2-carboxylic acid ((S)-2-methyl-1-methylcarbamoyl-propyl)-amide | 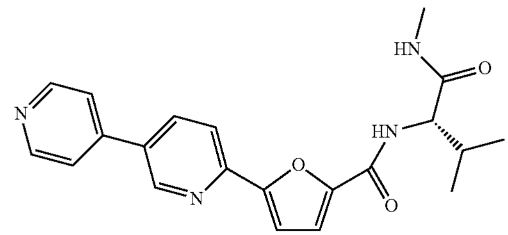 [SMILES: CNC(=O)[C@@H](NC(=O)c1ccc(-c2ccc(-c3ccncc3)cn2)o1)C(C)C] |
| 5-[3,3']Bipyridinyl-6-yl-furan-2-carboxylic acid ((S)-2-methyl-1-methylcarbamoyl-propyl)-amide | 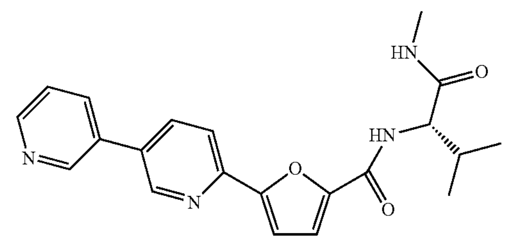 [SMILES: CNC(=O)[C@@H](NC(=O)c1ccc(-c2ccc(-c3cccnc3)cn2)o1)C(C)C] |
| 5-(2'-Methyl-[3,4']bipyridinyl-6-yl)-furan-2-carboxylic acid ((S)-2-methyl-1-methylcarbamoyl-propyl)-amide | 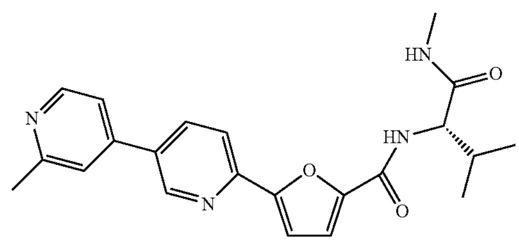 [SMILES: CNC(=O)[C@@H](NC(=O)c1ccc(-c2ccc(-c3ccnc(C)c3)cn2)o1)C(C)C] |
| 5-[5-(2-Amino-pyrimidin-5-yl)-pyridin-2-yl]-furan-2-carboxylic acid ((S)-2-methyl-1-methylcarbamoyl-propyl)-amide | 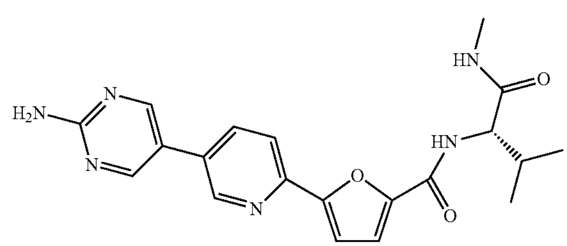 [SMILES: CNC(=O)[C@@H](NC(=O)c1ccc(-c2ccc(-c3cnc(N)nc3)cn2)o1)C(C)C] |
| 5-[3,4']Bipyridinyl-6-yl-furan-2-carboxylic acid ((S)-cyclohexyl-methylcarbamoyl-methyl)-amide | 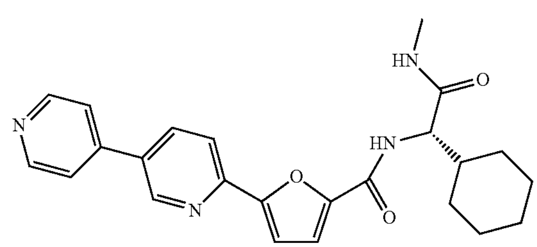 [SMILES: CNC(=O)[C@@H](NC(=O)c1ccc(-c2ccc(-c3ccncc3)cn2)o1)C1CCCCC1] |
| 5-(4'-Trifluoromethyl-biphenyl-4-yl)-furan-2-carboxylic acid ((S)-cyclohexyl-methylcarbamoyl-methyl)-amide | 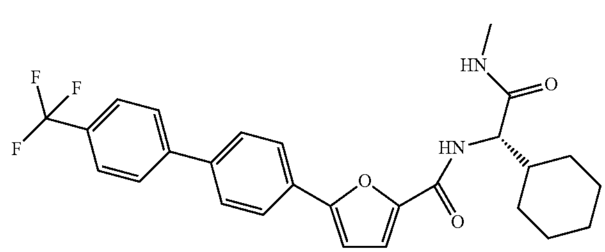 [SMILES: CNC(=O)[C@@H](NC(=O)c1ccc(-c2ccc(-c3ccc(C(F)(F)F)cc3)cc2)o1)C1CCCCC1] |

TABLE I-continued

| Name | Structure |
|---|---|
| 5-(5-Phenyl-pyridin-2-yl)-furan-2-carboxylic acid ((S)-2-methyl-1-methylcarbamoyl-propyl)-amide | 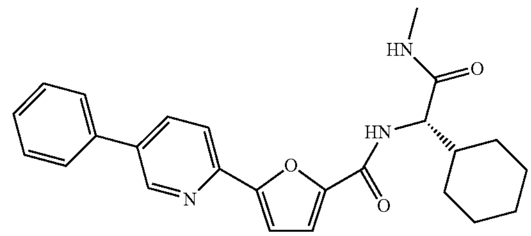 [SMILES: CNC(=O)[C@@H](NC(=O)c1ccc(-c2ccc(-c3ccccc3)cn2)o1)C1CCCCC1] |
| 6-(2,5-Dihydro-pyrrole-1-carbonyl)-imidazo[1,2-a]pyridine-2-carboxylic acid 3-{5-[((S)-cyclopropyl-methylcarbamoyl-methyl)-carbamoyl]-furan-2-yl}-benzylamide | 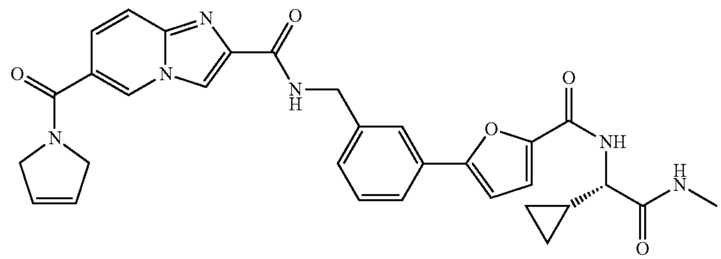 [SMILES: CNC(=O)[C@@H](NC(=O)c1ccc(-c2cccc(CNC(=O)c3cn4cc(C(=O)N5CC=CC5)ccc4n3)c2)o1)C1CC1] |
| 2-(3-{5-[((S)-Cyclopropyl-methylcarbamoyl-methyl)-carbamoyl]-furan-2-yl}-benzylcarbamoyl)-imidazo[1,2-a]pyridine-6-carboxylic acid | 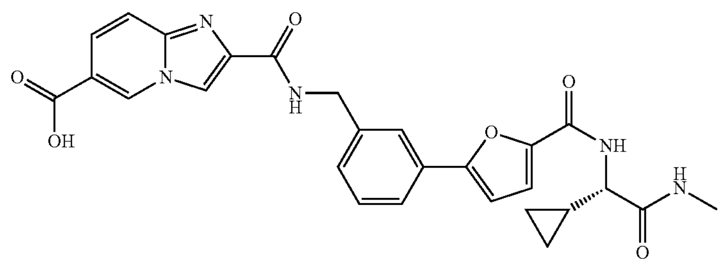 [SMILES: CNC(=O)[C@@H](NC(=O)c1ccc(-c2cccc(CNC(=O)c3cn4cc(C(=O)O)ccc4n3)c2)o1)C1CC1] |
| 2-(3-{5-[((S)-Cyclopropyl-methylcarbamoyl-methyl)-carbamoyl]-furan-2-yl}-benzylcarbamoyl)-imidazo[1,2-a]pyridine-6-carboxylic acid benzyl ester | | or a pharmaceutically acceptable salt thereof.

The following compounds in Table II are preferred MMP-13 inhibitors:

TABLE II

| Name | MMP-13 IC$_{50}$ (nM) |
|---|---|
| N-[(1S)-1-cyclohexyl-2-(methylamino)-2-oxoethyl]-5-{5-[(2-methylpyridin-4-yl)methoxy]pyridin-2-yl}furan-2-carboxamide | 1 |
| N-[(1S)-1-cyclohexyl-2-(methylamino)-2-oxoethyl]-5-[5-(pyridin-4-ylmethoxy)pyridin-2-yl]furan-2-carboxamide | 1 |
| N-[(1S)-1-cyclohexyl-2-(methylamino)-2-oxoethyl]-5-{5-[(1,3-dimethyl-1H-pyrazol-5-yl)methoxy]pyridin-2-yl}furan-2-carboxamide | 2 |
| N-[(1S)-1-cyclohexyl-2-(methylamino)-2-oxoethyl]-5-[5-(pyridin-3-ylmethoxy)pyridin-2-yl]furan-2-carboxamide | 2 |
| N-[(1S)-1-cyclohexyl-2-(methylamino)-2-oxoethyl]-5-{5-[(2,6-dimethylpyridin-4-yl)methoxy]pyridin-2-yl}furan-2-carboxamide | 2 |
| N-[3-(5-{[(1S)-2-(methylamino)-2-oxo-1-(tetrahydro-2H-pyran-4-yl)ethyl]carbamoyl}-2-furyl)benzyl]-6-(trifluoromethyl)pyridine-2-carboxamide | 2 |

TABLE II-continued

| Name | MMP-13 IC$_{50}$ (nM) |
|---|---|
| N-[3-(5-{[(1S)-2-(methylamino)-2-oxo-1-(tetrahydro-2H-pyran-4-yl)ethyl]carbamoyl}-2-furyl)benzyl]-2-(trifluoromethyl)pyrimidine-4-carboxamide | 2 |
| 6-Chloro-N-[3-(5-{[(1S)-2-methyl-1-(methylcarbamoyl)propyl]carbamoyl}-2-furyl)benzyl]pyridine-2-carboxamide | 2 |
| 6-Fluoro-N-[3-(5-{[(1S)-2-methyl-1-(methylcarbamoyl)propyl]carbamoyl}-2-furyl)benzyl]pyridine-2-carboxamide | 2 |
| N-[(1S)-1-cyclohexyl-2-(methylamino)-2-oxoethyl]-5-{5-[(3-methyl-1H-pyrazol-5-yl)methoxy]pyridin-2-yl}furan-2-carboxamide | 3 |
| N-[(1S)-1-cyclohexyl-2-(methylamino)-2-oxoethyl]-5-{5-[(3-methylpyridin-4-yl)methoxy]pyridin-2-yl}furan-2-carboxamide | 3 |
| 5-[5-(Benzyloxy)pyridin-2-yl]-N-[(1S)-2-(methylamino)-2-oxo-1-(tetrahydro-2H-pyran-4-yl)ethyl]furan-2-carboxamide | 3 |
| N-[(1S)-1-cyclohexyl-2-(methylamino)-2-oxoethyl]-5-{5-[(1R)-1-(pyridin-4-yl)ethoxy]pyridin-2-yl}furan-2-carboxamide | 3 |
| N-[(1S)-1-cyclohexyl-2-(methylamino)-2-oxoethyl]-5-{5-[(1,5-dimethyl-1H-pyrazol-3-yl)methoxy]pyridin-2-yl}furan-2-carboxamide | 4 |
| N-[3-(5-{[(1S)-1-cyclohexyl-2-(methylamino)-2-oxoethyl]carbamoyl}furan-2-yl)benzyl]-6-methylpyridine-2-carboxamide | 4 |
| N-[3-(5-{[(1S)-2-hydroxy-2-methyl-1-(methylcarbamoyl)propyl]carbamoyl}-2-furyl)benzyl]-2-(trifluoromethyl)pyrimidine-4-carboxamide | 5 |
| N-[(1S)-1-cyclohexyl-2-(methylamino)-2-oxoethyl]-5-[5-(1H-pyrazol-5-ylmethoxy)pyridin-2-yl]furan-2-carboxamide | 6 |
| 5-[5-(1-Benzofuran-2-ylmethoxy)pyridin-2-yl]-N-[(1S)-1-cyclohexyl-2-(methylamino)-2-oxoethyl]furan-2-carboxamide | 6 |
| N-[(1S)-1-cyclohexyl-2-(methylamino)-2-oxoethyl]-5-{5-[(1-methyl-1H-pyrazol-5-yl)methoxy]pyridin-2-yl}furan-2-carboxamide | 6 |
| 4-Trifluoromethyl-thiazole-2-carboxylic acid 3-[5-((S)-2-methyl-1-methylcarbamoyl-propylcarbamoyl)-furan-2-yl]-benzylamide | 6 |
| 5-[4-(2,5-Dimethyl-2H-pyrazol-3-ylmethoxy)-phenyl]-furan-2-carboxylic acid ((S)-cyclohexyl-methylcarbamoyl-methyl)-amide | 6 |
| N-[6-(5-{[(1S)-1-cyclohexyl-2-(methylamino)-2-oxoethyl]carbamoyl}furan-2-yl)pyridin-3-yl]-6-methylpyridine-2-carboxamide | 7 |
| N-[3-(5-{[(1S)-1-cyclohexyl-2-(methylamino)-2-oxoethyl]carbamoyl}furan-2-yl)benzyl]-2-(trifluoromethyl)pyrimidine-4-carboxamide | 7 |
| N-[3-(5-{[(1S)-2-methyl-1-(methylcarbamoyl)propyl]carbamoyl}-2-furyl)benzyl]-1-benzofuran-2-carboxamide | 8 |
| N-[(1S)-1-cyclohexyl-2-(methylamino)-2-oxoethyl]-5-{5-[(4-methylpyridin-2-yl)methoxy]pyridin-2-yl}furan-2-carboxamide | 8 |
| 2-Chloro-N-[3-(5-{[(1S)-2-methyl-1-(methylcarbamoyl)propyl]carbamoyl}-2-furyl)benzyl]pyrimidine-4-carboxamide | 9 |
| N-[3-(5-{[(1S)-1-cyclohexyl-2-(methylamino)-2-oxoethyl]carbamoyl}furan-2-yl)benzyl]pyridine-2-carboxamide | 9 |
| 5-[5-(Benzyloxy)pyridin-2-yl]-N-[(1S)-1-cyclohexyl-2-(methylamino)-2-oxoethyl]furan-2-carboxamide | 10 |
| N-[3-(5-{[(1S)-1-cyclohexyl-2-(methylamino)-2-oxoethyl]carbamoyl}furan-2-yl)benzyl]-5-methylfuran-2-carboxamide | 10 |
| N-[3-(5-{[(1S)-1-cyclohexyl-2-(methylamino)-2-oxoethyl]carbamoyl}furan-2-yl)benzyl]-1-benzofuran-2-carboxamide | 11 |
| 5-Bromo-1-methyl-1H-pyrazole-3-carboxylic acid 3-[5-((S)-2-methyl-1-methylcarbamoyl-propylcarbamoyl)-furan-2-yl]-benzylamide | 13 |
| 1-Difluoromethyl-1H-pyrazole-3-carboxylic acid 3-[5-((S)-2-methyl-1-methylcarbamoyl-propylcarbamoyl)-furan-2-yl]-benzylamide | 14 |
| 6-Methyl-N-[4-(5-{[(2S)-3-methyl-1-(methylamino)-1-oxobutan-2-yl]carbamoyl}furan-2-yl)phenyl]pyridine-2-carboxamide | 14 |
| N-[4-(5-{[(1S)-1-cyclohexyl-2-(methylamino)-2-oxoethyl]carbamoyl}furan-2-yl)phenyl]-6-methylpyridine-2-carboxamide | 17 |
| 5-[5-(Benzyloxy)pyridin-2-yl]-N-[(1S)-1-cyclohexyl-2-(ethylamino)-2-oxoethyl]furan-2-carboxamide | 17 |

TABLE II-continued

| Name | MMP-13 IC$_{50}$ (nM) |
|---|---|
| N-[(1S)-1-cyclohexyl-2-(methylamino)-2-oxoethyl]-5-{5-[(1-methyl-1H-imidazol-5-yl)methoxy]pyridin-2-yl}furan-2-carboxamide | 18 |
| 5-(5-Benzyloxy-pyridin-2-yl)-furan-2-carboxylic acid ((S)-2-methyl-1-methylcarbamoyl-propyl)-amide | 18 |
| 5-(5-Benzyloxy-pyridin-2-yl)-furan-2-carboxylic acid ((S)-2-hydroxy-2-methyl-1-methylcarbamoyl-propyl)-amide | 18 |
| N-[(1S)-1-cyclohexyl-2-(methylamino)-2-oxoethyl]-5-[5-(1H-imidazol-5-ylmethoxy)pyridin-2-yl]furan-2-carboxamide | 19 |
| N-[(1S)-1-cyclohexyl-2-(methylamino)-2-oxoethyl]-5-[5-(pyridin-2-ylmethoxy)pyridin-2-yl]furan-2-carboxamide | 21 |
| N-[4-(5-{[(1S)-1-cyclohexyl-2-{[(2R)-2-hydroxypropyl]amino}-2-oxoethyl]carbamoyl}furan-2-yl)phenyl]-6-methylpyridine-2-carboxamide | 22 |
| 5-[5-(4-Cyano-phenyl)-pyridin-2-yl]-furan-2-carboxylic acid ((S)-2-methyl-1-methylcarbamoyl-propyl)-amide | 22 |
| 5-[3,4']Bipyridinyl-6-yl-furan-2-carboxylic acid ((S)-cyclohexyl-methylcarbamoyl-methyl)-amide | 23 |
| 5-(3,4'-Bipyridin-6-yl)-N-[(1S)-1-cyclohexyl-2-(methylamino)-2-oxoethyl]furan-2-carboxamide | 23 |
| N-[4-(5-{[(1S)-1-cyclohexyl-2-{[(2S)-2-hydroxypropyl]amino}-2-oxoethyl]carbamoyl}furan-2-yl)phenyl]-6-methylpyridine-2-carboxamide | 23 |
| N-[3-(5-{[(1S)-1-cyclohexyl-2-(methylamino)-2-oxoethyl]carbamoyl}furan-2-yl)benzyl]-1-methyl-1H-pyrazole-3-carboxamide | 24 |
| N-[4-(5-{[(1S)-1-cyclohexyl-2-(methylamino)-2-oxoethyl]carbamoyl}furan-2-yl)phenyl]imidazo[1,2-a]pyridine-2,6-dicarboxamide | 24 |
| N-[(1S)-1-cyclohexyl-2-(methylamino)-2-oxoethyl]-5-{5-[(1-methyl-1H-pyrazol-3-yl)methoxy]pyridin-2-yl}furan-2-carboxamide | 25 |
| N-[(1S)-1-cyclohexyl-2-(methylamino)-2-oxoethyl]-5-[4-(1-methyl-1H-pyrazol-4-yl)phenyl]furan-2-carboxamide | 25 |
| 5-[4-(5-Methyl-3H-imidazol-4-ylmethoxy)-phenyl]-furan-2-carboxylic acid [(S)-methylcarbamoyl-(tetrahydro-pyran-4-yl)-methyl]-amide | 27 |
| 6-Bromo-N-[3-(5-{[(1S)-1-cyclopropyl-2-(methylamino)-2-oxoethyl]carbamoyl}-2-furyl)benzyl]pyridine-2-carboxamide | 27 |
| N-[3-(5-{[(1S)-1-cyclopropyl-2-(methylamino)-2-oxoethyl]carbamoyl}-2-furyl)benzyl]-6-(trifluoromethyl)pyridine-2-carboxamide | 29 |
| 5-[5-(5-Methyl-3H-imidazol-4-ylmethoxy)-pyridin-2-yl]-furan-2-carboxylic acid ((S)-2-methyl-1-methylcarbamoyl-propyl)-amide | 29 |
| 5-[5-(4-Isopropoxy-phenyl)-pyridin-2-yl]-furan-2-carboxylic acid ((S)-2-methyl-1-methylcarbamoyl-propyl)-amide | 29 |
| N-[3-(5-{[(1S)-1-cyclohexyl-2-(methylamino)-2-oxoethyl]carbamoyl}furan-2-yl)benzyl]-5-methylpyridine-3-carboxamide | 30 |
| N-[6-(5-{[(1S)-1-cyclohexyl-2-(methylamino)-2-oxoethyl]carbamoyl}furan-2-yl)pyridin-3-yl]-1-benzofuran-2-carboxamide | 30 |
| N-[4-(5-{[(1S)-1-cyclohexyl-2-(methylamino)-2-oxoethyl]carbamoyl}furan-2-yl)phenyl]-1-methyl-1H-pyrazole-3-carboxamide | 31 |
| N-[4-(5-{[(1S)-1-cyclohexyl-2-{[(2S)-1-methoxypropan-2-yl]amino}-2-oxoethyl]carbamoyl}furan-2-yl)phenyl]-6-methylpyridine-2-carboxamide | 32 |
| N-[(1S)-1-cyclohexyl-2-(methylamino)-2-oxoethyl]-5-(5-ethoxypyridin-2-yl)furan-2-carboxamide | 32 |
| N-[3-(5-{[(1S)-2-methyl-1-(methylcarbamoyl)propyl]carbamoyl}-2-furyl)benzyl]pyrazine-2-carboxamide | 32 |
| N-[3-(5-{[(1S)-2-methyl-1-(methylcarbamoyl)propyl]carbamoyl}-2-furyl)benzyl]-1H-benzimidazole-2-carboxamide | 33 |
| N-[(1S)-1-cyclohexyl-2-(methylamino)-2-oxoethyl]-5-{5-[(3-methylbenzyl)oxy]pyridin-2-yl}furan-2-carboxamide | 36 |
| N-[3-(5-{[(1S)-1-cyclohexyl-2-(methylamino)-2-oxoethyl]carbamoyl}furan-2-yl)benzyl]-4-ethylpyridine-2-carboxamide | 38 |
| N-[(1S)-1-cyclohexyl-2-(methylamino)-2-oxoethyl]-5-{5-[(6-methylpyridin-2-yl)methoxy]pyridin-2-yl}furan-2-carboxamide | 39 |
| 1-Methyl-5-trifluoromethyl-1H-pyrazole-3-carboxylic acid 3-[5-((S)-2-methyl-1-methylcarbamoyl-propylcarbamoyl)-furan-2-yl]-benzylamide | 39 |

TABLE II-continued

| Name | MMP-13 IC$_{50}$ (nM) |
|---|---|
| N-[(1S)-1-cyclohexyl-2-(methylamino)-2-oxoethyl]-5-{5-[(1R)-1-phenylethoxy]pyridin-2-yl}furan-2-carboxamide | 41 |
| 5-[5-(4-Ethoxy-phenyl)-pyridin-2-yl]-furan-2-carboxylic acid ((S)-2-methyl-1-methylcarbamoyl-propyl)-amide | 47 |
| 5-{3-[(3-Trifluoromethyl-benzoylamino)-methyl]-phenyl}-furan-2-carboxylic acid ((S)-2-methyl-1-methylcarbamoyl-propyl)-amide | 49 |
| N-[(1S)-1-cyclohexyl-2-(methylamino)-2-oxoethyl]-5-[3-({[(4,5-dimethylthiophen-2-yl)carbonyl]amino}methyl)phenyl]furan-2-carboxamide | 50 |
| N-[4-(5-{[(1S)-1-cyclohexyl-2-(methylamino)-2-oxoethyl]carbamoyl}furan-2-yl)phenyl]-5-methylfuran-2-carboxamide | 57 |
| 5-[3,4']Bipyridinyl-6-yl-furan-2-carboxylic acid ((S)-2-methyl-1-methylcarbamoyl-propyl)-amide | 62 |
| N-[4-(5-{[(1S)-1-cyclohexyl-2-(methylamino)-2-oxoethyl]carbamoyl}furan-2-yl)phenyl]-4,5-dimethylfuran-2-carboxamide | 63 |
| N-[4-(5-{[(1S)-1-cyclopropyl-2-(methylamino)-2-oxoethyl]carbamoyl}furan-2-yl)phenyl]-6-methylpyridine-2-carboxamide | 69 |
| 5-(5-Cyanopyridin-2-yl)-N-[(1S)-1-cyclohexyl-2-(methylamino)-2-oxoethyl]furan-2-carboxamide | 69 |
| N-[3-(5-{[(1S)-1-cyclohexyl-2-(methylamino)-2-oxoethyl]carbamoyl}furan-2-yl)benzyl]-1,5-dimethyl-1H-pyrazole-3-carboxamide | 72 |
| N-[(1S)-1-cyclohexyl-2-(methylamino)-2-oxoethyl]-5-{5-[(1R)-1-phenylethoxy]pyridin-2-yl}furan-2-carboxamide | 73 |
| N-[(1S)-1-cyclohexyl-2-(methylamino)-2-oxoethyl]-5-(5-nitropyridin-2-yl)furan-2-carboxamide | 74 |
| 5-(4-Cyanophenyl)-N-{(1S)-1-cyclohexyl-2-[(2-methoxyethyl)amino]-2-oxoethyl}furan-2-carboxamide | 74 |
| N-[(1S)-1-cyclohexyl-2-(methylamino)-2-oxoethyl]-5-(3-{[(furan-2-ylcarbonyl)amino]methyl}phenyl)furan-2-carboxamide | 75 |
| 5-[5-(4-Fluoro-phenyl)-pyridin-2-yl]-furan-2-carboxylic acid ((S)-2-methyl-1-methylcarbamoyl-propyl)-amide | 78 |
| 5-[(5-Phenyl)-pyridin-2-yl]-furan-2-carboxylic acid ((S)-2-methyl-1-methylcarbamoyl-propyl)-amide | 79 |
| 5-[5-(1,5-Dimethyl-1H-pyrazol-3-ylmethoxy)-pyridin-2-yl]-furan-2-carboxylic acid ((S)-2-methyl-1-methylcarbamoyl-propyl)-amide | 80 |
| N-[4-(5-{[(1S)-1-cyclohexyl-2-(methylamino)-2-oxoethyl]carbamoyl}furan-2-yl)phenyl]-5-methyl-1H-pyrazole-3-carboxamide | 87 |
| 5-(4-Cyanophenyl)-N-[(1S)-2-(methylamino)-2-oxo-1-(tetrahydro-2H-pyran-4-yl)ethyl]furan-2-carboxamide | 90 |
| 5-[5-(1H-Indol-6-yl)-pyridin-2-yl]-furan-2-carboxylic acid ((S)-2-methyl-1-methylcarbamoyl-propyl)-amide | 91 |
| N-[4-(5-{[(1S)-1-cyclohexyl-2-(methylamino)-2-oxoethyl]carbamoyl}furan-2-yl)phenyl]-3-methylfuran-2-carboxamide | 93 |
| N-[4-(5-{[(1S)-1-cyclohexyl-2-(methylamino)-2-oxoethyl]carbamoyl}furan-2-yl)phenyl]-1-methyl-1H-pyrazole-5-carboxamide | 99 |
| N-[4-(5-{[(1S)-1-cyclohexyl-2-(methylamino)-2-oxoethyl]carbamoyl}furan-2-yl)phenyl]-8-methylimidazo[1,2-a]pyridine-2-carboxamide | 99 |
| 5-(4-Cyanophenyl)-N-{(1S)-1-cyclohexyl-2-[(2-hydroxyethyl)amino]-2-oxoethyl}furan-2-carboxamide | 100 |
| N-[3-(5-{[(1S)-2-methyl-1-(methylcarbamoyl)propyl]carbamoyl}-2-furyl)benzyl]tetrahydro-2H-pyran-2-carboxamide | 101 |
| N-[3-(5-{[(1S)-1-cyclohexyl-2-(methylamino)-2-oxoethyl]carbamoyl}furan-2-yl)benzyl]imidazo[1,2-a]pyridine-2-carboxamide | 102 |
| N-[3-(5-{[(1S)-1-cyclohexyl-2-(methylamino)-2-oxoethyl]carbamoyl}furan-2-yl)benzyl]-3-methylpyridine-2-carboxamide | 103 |
| 5-Cyano-N-[4-(5-{[(1S)-1-cyclohexyl-2-(methylamino)-2-oxoethyl]carbamoyl}furan-2-yl)phenyl]imidazo[1,2-a]pyridine-2-carboxamide | 103 |
| 5-(3-{[(tert-butylcarbamoyl)amino]methyl}phenyl)-N-[(1S)-1-cyclohexyl-2-(methylamino)-2-oxoethyl]furan-2-carboxamide | 105 |
| N-[4-(5-{[(1S)-1-cyclohexyl-2-(methylamino)-2-oxoethyl]carbamoyl}furan-2-yl)phenyl]imidazo[1,2-a]pyridine-2-carboxamide | 109 |

TABLE II-continued

| Name | MMP-13 IC$_{50}$ (nM) |
|---|---|
| N-[3-(5-{[(1S)-1-cyclohexyl-2-(methylamino)-2-oxoethyl]carbamoyl}furan-2-yl)benzyl]-5-methylimidazo[1,2-a]pyridine-2-carboxamide | 110 |
| 5-(2'-Methyl-[3,4']bipyridinyl-6-yl)-furan-2-carboxylic acid ((S)-2-methyl-1-methylcarbamoyl-propyl)-amide | 110 |
| 5-{3-[(4-Dimethylamino-benzoylamino)-methyl]-phenyl}-furan-2-carboxylic acid ((S)-2-methyl-1-methylcarbamoyl-propyl)-amide | 110 |
| N-[(1S)-1-cyclohexyl-2-(methylamino)-2-oxoethyl]-5-{5-[(3,5-dimethylbenzyl)oxy]pyridin-2-yl}furan-2-carboxamide | 115 |
| N-[(1S)-1-cyclohexyl-2-(methylamino)-2-oxoethyl]-5-{5-[(1-methyl-1H-imidazol-4-yl)methoxy]pyridin-2-yl}furan-2-carboxamide | 119 |
| N-[3-(5-{[(1S)-1-cyclohexyl-2-(methylamino)-2-oxoethyl]carbamoyl}furan-2-yl)benzyl]-3-methyl-1H-pyrazole-5-carboxamide | 123 |
| 5-{3-[(3-Methyl-benzoylamino)-methyl]-phenyl}-furan-2-carboxylic acid ((S)-2-methyl-1-methylcarbamoyl-propyl)-amide | 132 |
| N-[3-(5-{[(1S)-1-cyclohexyl-2-(methylamino)-2-oxoethyl]carbamoyl}furan-2-yl)benzyl]-1-methyl-1H-pyrazole-4-carboxamide | 137 |
| N-[3-(5-{[(1S)-1-cyclohexyl-2-(methylamino)-2-oxoethyl]carbamoyl}furan-2-yl)benzyl]-7-methylimidazo[1,2-a]pyridine-2-carboxamide | 137 |
| N-[4-(5-{[(1S)-1-cyclohexyl-2-(methylamino)-2-oxoethyl]carbamoyl}furan-2-yl)phenyl]-1-methyl-1H-imidazole-4-carboxamide | 140 |
| 5-[3,3']Bipyridinyl-6-yl-furan-2-carboxylic acid ((S)-2-methyl-1-methylcarbamoyl-propyl)-amide | 140 |
| N-[3-(5-{[(1S)-1-cyclohexyl-2-(methylamino)-2-oxoethyl]carbamoyl}furan-2-yl)benzyl]-1-methyl-1H-pyrazole-5-carboxamide | 143 |
| N-[4-(5-{[(1S)-1-cyclohexyl-2-(methylamino)-2-oxoethyl]carbamoyl}furan-2-yl)phenyl]-5-methylpyridine-3-carboxamide | 150 |
| N-[4-(5-{[(1S)-1-cyclohexyl-2-(methylamino)-2-oxoethyl]carbamoyl}furan-2-yl)phenyl]-5-methylimidazo[1,2-a]pyridine-2-carboxamide | 150 |
| 5-{3-[(4-Methoxy-benzoylamino)-methyl]-phenyl}-furan-2-carboxylic acid ((S)-2-methyl-1-methylcarbamoyl-propyl)-amide | 155 |
| 5-{3-[(3,4-Dimethyl-benzoylamino)-methyl]-phenyl}-furan-2-carboxylic acid ((S)-2-methyl-1-methylcarbamoyl-propyl)-amide | 156 |
| N-[(1S)-1-cyclohexyl-2-(methylamino)-2-oxoethyl]-5-(3-{[(2-methylpropanoyl)amino]methyl}phenyl)furan-2-carboxamide | 157 |
| 5-{3-[(3-Cyano-benzoylamino)-methyl]-phenyl}-furan-2-carboxylic acid ((S)-2-methyl-1-methylcarbamoyl-propyl)-amide | 160 |
| 5-Trifluoromethyl-2H-pyrazole-3-carboxylic acid 3-[5-((S)-2-methyl-1-methylcarbamoyl-propylcarbamoyl)-furan-2-yl]-benzylamide | 160 |
| 5-{3-[(3-Isopropyl-benzoylamino)-methyl]-phenyl}-furan-2-carboxylic acid ((S)-2-methyl-1-methylcarbamoyl-propyl)-amide | 160 |
| 5-{3-[(3-Methoxy-benzoylamino)-methyl]-phenyl}-furan-2-carboxylic acid ((S)-2-methyl-1-methylcarbamoyl-propyl)-amide | 163 |
| N-[(1S)-2-(methylamino)-2-oxo-1-(piperidin-4-yl)ethyl]-5-{5-[(1-methyl-1H-imidazol-4-yl)methoxy]pyridin-2-yl}furan-2-carboxamide | 163 |
| 5-{3-[(Cyclohexanecarbonyl-amino)-methyl]-phenyl}-furan-2-carboxylic acid ((S)-2-methyl-1-methylcarbamoyl-propyl)-amide | 165 |
| 5-(4-cyanophenyl)-N-{(1S)-1-cyclohexyl-2-[(2-hydroxypropyl)amino]-2-oxoethyl}furan-2-carboxamide | 170 |
| N-[(1S)-1-cyclohexyl-2-(methylamino)-2-oxoethyl]-5-[4-(methylsulfanyl)phenyl]furan-2-carboxamide | 175 |
| 5-(4-Cyanophenyl)-N-[(1S)-1-cyclohexyl-2-(methylamino)-2-oxoethyl]furan-2-carboxamide | 175 |
| 5-{3-[(4-Methyl-benzoylamino)-methyl]-phenyl}-furan-2-carboxylic acid ((S)-2-methyl-1-methylcarbamoyl-propyl)-amide | 175 |
| N-[3-(5-{[(1S)-2-methyl-1-(methylcarbamoyl)propyl]carbamoyl}-2-furyl)benzyl]pyridazine-4-carboxamide | 180 |
| N-[4-(5-{[(1S)-1-cyclohexyl-2-(methylamino)-2-oxoethyl]carbamoyl}furan-2-yl)phenyl]-1-methyl-1H-pyrazole-4-carboxamide | 180 |
| N-[3-(5-{[(1S)-1-cyclohexyl-2-(methylamino)-2-oxoethyl]carbamoyl}furan-2-yl)benzyl]-3-methylfuran-2-carboxamide | 180 |
| 5-[5-(4-Methyl-phenyl)-pyridin-2-yl]-furan-2-carboxylic acid ((S)-2-methyl-1-methylcarbamoyl-propyl)-amide | 180 |

TABLE II-continued

| Name | MMP-13 IC$_{50}$ (nM) |
|---|---|
| 5-{3-[(4-Cyano-benzoylamino)-methyl]-phenyl}-furan-2-carboxylic acid ((S)-2-methyl-1-methylcarbamoyl-propyl)-amide | 185 |
| 5-(4-Cyanophenyl)-N-[(1S)-1-cyclohexyl-2-{[(2S)-1-hydroxypropan-2-yl]amino}-2-oxoethyl]furan-2-carboxamide | 195 |
| 5-(4-Cyanophenyl)-N-[(1S)-1-cyclohexyl-2-{[(2S)-1-methoxypropan-2-yl]amino}-2-oxoethyl]furan-2-carboxamide | 195 |
| N-[(1S)-1-cyclohexyl-2-(methylamino)-2-oxoethyl]-5-(3-{[(propan-2-ylcarbamoyl)amino]methyl}phenyl)furan-2-carboxamide | 205 |
| 5-[(3-Benzoylamino-methyl)-phenyl]-furan-2-carboxylic acid ((S)-2-methyl-1-methylcarbamoyl-propyl)-amide | 205 |
| 5-{3-[(3-Dimethylamino-benzoylamino)-methyl]-phenyl}-furan-2-carboxylic acid ((S)-2-methyl-1-methylcarbamoyl-propyl)-amide | 213 |
| 1-Methyl-N-[3-(5-{[(1S)-2-methyl-1-(methylcarbamoyl)propyl]carbamoyl}-2-furyl)benzyl]piperidine-3-carboxamide | 215 |
| 5-{3-[(4-Fluoro-3-trifluoromethyl-benzoylamino)-methyl]-phenyl}-furan-2-carboxylic acid ((S)-2-methyl-1-methylcarbamoyl-propyl)-amide | 215 |
| N-[(1S)-1-cyclohexyl-2-(methylamino)-2-oxoethyl]-5-(4-methoxyphenyl)furan-2-carboxamide | 215 |
| Methyl [4-(5-{[(1S)-1-cyclohexyl-2-(methylamino)-2-oxoethyl]carbamoyl}furan-2-yl)phenyl]carbamate | 225 |
| 5-{3-[(4-Isopropyl-benzoylamino)-methyl]-phenyl}-furan-2-carboxylic acid ((S)-2-methyl-1-methylcarbamoyl-propyl)-amide | 225 |
| 2-Methylpropyl [3-(5-{[(1S)-1-cyclohexyl-2-(methylamino)-2-oxoethyl]carbamoyl}furan-2-yl)benzyl]carbamate | 240 |
| 5-(5-Chloropyridin-2-yl)-N-[(1S)-1-cyclohexyl-2-(methylamino)-2-oxoethyl]furan-2-carboxamide | 245 |
| 5-[5-(1H-Indol-5-yl)-pyridin-2-yl]-furan-2-carboxylic acid ((S)-2-methyl-1-methylcarbamoyl-propyl)-amide | 260 |
| N-[(1S)-1-cyclohexyl-2-(methylamino)-2-oxoethyl]-5-(4-ethoxyphenyl)furan-2-carboxamide | 270 |
| N-[3-(5-{[(1S)-2-methyl-1-(methylcarbamoyl)propyl]carbamoyl}-2-furyl)benzyl]piperidine-2-carboxamide | 270 |
| 3-Methyl-isoxazole-5-carboxylic acid 3-[5-((S)-2-methyl-1-methylcarbamoyl-propylcarbamoyl)-furan-2-yl]-benzylamide | 280 |
| 5-{4-[(Acetylamino)methyl]phenyl}-N-[(1S)-1-cyclohexyl-2-(methylamino)-2-oxoethyl]furan-2-carboxamide | 285 |
| N-[(1S)-1-cyclohexyl-2-(methylamino)-2-oxoethyl]-5-(4-methylphenyl)furan-2-carboxamide | 290 |
| 5-(4-Cyanophenyl)-N-[(1S)-1-cyclohexyl-2-(ethylamino)-2-oxoethyl]furan-2-carboxamide | 295 |
| N-[(1S)-1-cyclohexyl-2-(methylamino)-2-oxoethyl]-5-{5-[(1S)-1-phenylethoxy]pyridin-2-yl}furan-2-carboxamide | 295 |
| 5-(4-Chloro-phenyl)-furan-2-carboxylic acid ((1S,2S)-2-methyl-1-methylcarbamoyl-butyl)-amide | 300 |
| 1-Methyl-N-[3-(5-{[(1S)-2-methyl-1-(methylcarbamoyl)propyl]carbamoyl}-2-furyl)benzyl]piperidine-2-carboxamide | 300 |
| N-[3-(5-{[(1S)-2-methyl-1-(methylcarbamoyl)propyl]carbamoyl}-2-furyl)benzyl]prolinamide | 305 |
| N-[3-(5-{[(1S)-1-cyclohexyl-2-(methylamino)-2-oxoethyl]carbamoyl}furan-2-yl)benzyl]-1-methyl-1H-imidazole-2-carboxamide | 313 |
| N-[(1S)-1-cyclohexyl-2-(methylamino)-2-oxoethyl]-5-(4-ethylphenyl)furan-2-carboxamide | 315 |
| N-[(1S)-2-{[2-(2-amino-2-oxoethoxy)ethyl]amino}-1-cyclohexyl-2-oxoethyl]-5-(4-chlorophenyl)furan-2-carboxamide | 325 |
| 5-[5-(3-Fluoro-phenyl)-pyridin-2-yl]-furan-2-carboxylic acid ((S)-2-methyl-1-methylcarbamoyl-propyl)-amide | 325 |
| N-[(1S)-1-cyclohexyl-2-(methylamino)-2-oxoethyl]-5-[3-({[(2-methylfuran-3-yl)carbonyl]amino}methyl)phenyl]furan-2-carboxamide | 330 |
| N-[3-(5-{[(1S)-2-methyl-1-(methylcarbamoyl)propyl]carbamoyl}-2-furyl)benzyl]tetrahydro-2H-pyran-4-carboxamide | 337 |
| N-[3-(5-{[(1S)-2-methyl-1-(methylcarbamoyl)propyl]carbamoyl}-2-furyl)benzyl]nicotinamide | 355 |
| N-{4-[5-({(1S)-1-cyclohexyl-2-[(1-methoxypropan-2-yl)amino]-2-oxoethyl}carbamoyl)furan-2-yl]phenyl}-1-benzofuran-2-carboxamide | 355 |

TABLE II-continued

| Name | MMP-13 IC$_{50}$ (nM) |
|---|---|
| 5-[5-(3,5-Difluoro-phenyl)-pyridin-2-yl]-furan-2-carboxylic acid ((S)-2-methyl-1-methylcarbamoyl-propyl)-amide | 370 |
| N-[3-(5-{[(1S)-2-methyl-1-(methylcarbamoyl)propyl]carbamoyl}-2-furyl)benzyl]morpholine-2-carboxamide | 370 |
| 5-(4'-Trifluoromethyl-biphenyl-4-yl)-furan-2-carboxylic acid (cyclohexyl-methylcarbamoyl-methyl)-amide | 373 |
| 1-Methyl-N-[3-(5-{[(1S)-2-methyl-1-(methylcarbamoyl)propyl]carbamoyl}-2-furyl)benzyl]-L-prolinamide | 380 |
| 5-[5-(2-Amino-pyrimidin-5-yl)-pyridin-2-yl]-furan-2-carboxylic acid ((S)-2-methyl-1-methylcarbamoyl-propyl)-amide | 380 |
| 2-(4-Chloro-phenyl)-thiazole-4-carboxylic acid ((1S,2S)-2-methyl-1-methylcarbamoyl-butyl)-amide | 380 |
| 5-(4-bromophenyl)-N-[(1S)-1-cyclohexyl-2-(methylamino)-2-oxoethyl]furan-2-carboxamide | 395 |
| N-[(1S)-1-cyclohexyl-2-(methylamino)-2-oxoethyl]-5-(3-{[(cyclopropylcarbonyl)amino]methyl}phenyl)furan-2-carboxamide | 397 |
| 2-methoxyethyl [3-(5-{[(1S)-1-cyclohexyl-2-(methylamino)-2-oxoethyl]carbamoyl}furan-2-yl)benzyl]carbamate | 397 |
| 5-[5-(5-Methyl-3H-imidazol-4-ylmethoxy)-pyridin-2-yl]-furan-2-carboxylic acid [(S)-methylcarbamoyl-(tetrahydro-pyran-4-yl)-methyl]-amide | 415 |
| 5-[3-(Aminomethyl)phenyl]-N-[(1S)-2-(methylamino)-2-oxo-1-(tetrahydro-2H-pyran-4-yl)ethyl]-2-furamide | 415 |
| N-[3-(5-{[(1S)-2-methyl-1-(methylcarbamoyl)propyl]carbamoyl}-2-furyl)benzyl]pyridazine-3-carboxamide | 420 |
| N-[(1S)-1-cyclohexyl-2-(methylamino)-2-oxoethyl]-5-(4-{[(cyclopropylcarbonyl)amino]methyl}phenyl)furan-2-carboxamide | 423 |
| 5-(4-Chlorophenyl)-N-[(1S)-2-(methylamino)-2-oxo-1-(piperidin-4-yl)ethyl]furan-2-carboxamide | 430 |
| N-[3-(5-{[(1S)-2-methyl-1-(methylcarbamoyl)propyl]carbamoyl}-2-furyl)benzyl]piperidine-3-carboxamide | 430 |
| N-[(1S)-1-cyclohexyl-2-(methylamino)-2-oxoethyl]-5-{4-[(methylsulfonyl)amino]phenyl}furan-2-carboxamide | 455 |
| 5-(4-Chlorophenyl)-N-[(1S)-1-cyclopentyl-2-(methylamino)-2-oxoethyl]furan-2-carboxamide | 465 |
| N-[(1S)-1-cyclohexyl-2-(methylamino)-2-oxoethyl]-5-(4-nitrophenyl)furan-2-carboxamide | 470 |
| 2-(4-Chlorophenyl)-N-[(1S)-1-cyclohexyl-2-(methylamino)-2-oxoethyl]-1,3-thiazole-4-carboxamide | 470 |
| 5-(4-Chlorophenyl)-N-[(1S)-1-cyclohexyl-2-(methylamino)-2-oxoethyl]furan-2-carboxamide | 475 |
| N-[(1S)-1-cyclohexyl-2-(methylamino)-2-oxoethyl]-5-[4-(methylsulfamoyl)phenyl]furan-2-carboxamide | 480 |
| N-[4-(5-{[(1S)-1-cyclohexyl-2-(methylamino)-2-oxoethyl]carbamoyl}furan-2-yl)phenyl]-1-benzofuran-2-carboxamide | 496 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example azatidinyl, furanyl, pyranyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, tetrazolyl, pyrrolyl, pyrrolidinyl, pyrrolidinone, imidazolyl, thienyl, thiadiazolyl, oxadiazolyl, thiomorpholinyl, 1,1-dioxo-1$\lambda^6$-thiomorpholinyl, morpholinyl, pyridinyl, pyridinone, 1-oxy-pyridinyl, pyrimidinyl, pyridazinyl, pyrazinyl, triazinyl, pyrrolidinyl, piperidinyl, piperazinyl, purinyl, quinolinyl, dihydro-2H-quinolinyl, tetrahydroquinolinyl, isoquinolinyl, quinazolinyl, indazolyl, indolyl, indolinone, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" (or acyl) refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

Each alkyl (or any term using an "alk" or "alkyl" prefix), carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—(C1-C4 alkyl)-4+ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

GENERAL SYNTHETIC METHODS

The invention also provides processes for making compounds of Formula (I). In all Schemes, unless specified otherwise, $R^1$, $R^2$, $R^3$, $R^4$, Ar and X in the formulas below shall have the meaning of $R^1$, $R^2$, $R^3$, $R^4$, Ar and X in Formula (I) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The appropriately substituted starting materials and intermediates used in the preparation of compounds of the invention are either commercially available or readily prepared by methods known in the literature to those skilled in the art, and are illustrated in the synthetic examples below.

Compounds of Formula (I) may be synthesized by methods outlined in Schemes 1-4.

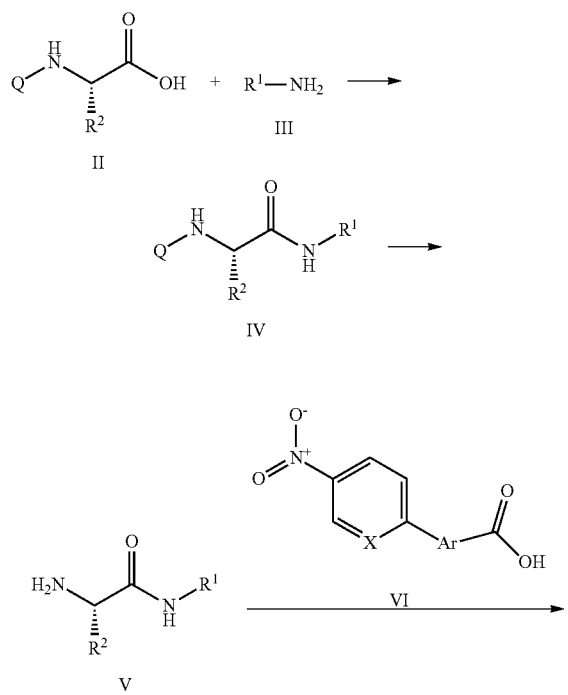

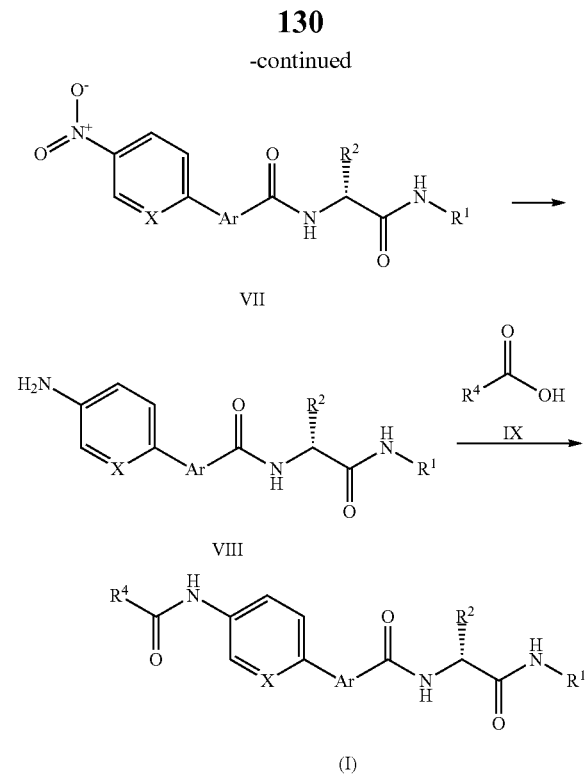

$R^3 = -C(O)-NH-$

As shown in scheme 1, reaction of an amino acid of formula (II), wherein Q is an amine protecting group such as BOC, with an amine of formula (III), under standard amide coupling conditions, provides an amide of formula (IV). Deprotection of the intermediate (IV), under standard conditions, provides a free amine of formula (V). Coupling the amine of formula (V) with an acid of formula (VI), under standard conditions, provides the corresponding coupled product of formula (VII). Reducing the nitro group, in a suitable solvent, under standard conditions, provides an amine of formula (VIII). Coupling the amine of formula (VIII) with an acid of formula (IX), under standard amide coupling conditions, provides a compound of formula (I), wherein $R^3 = -C(O)-NH-$.

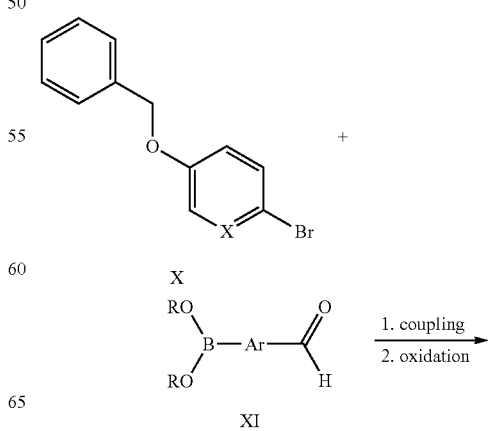

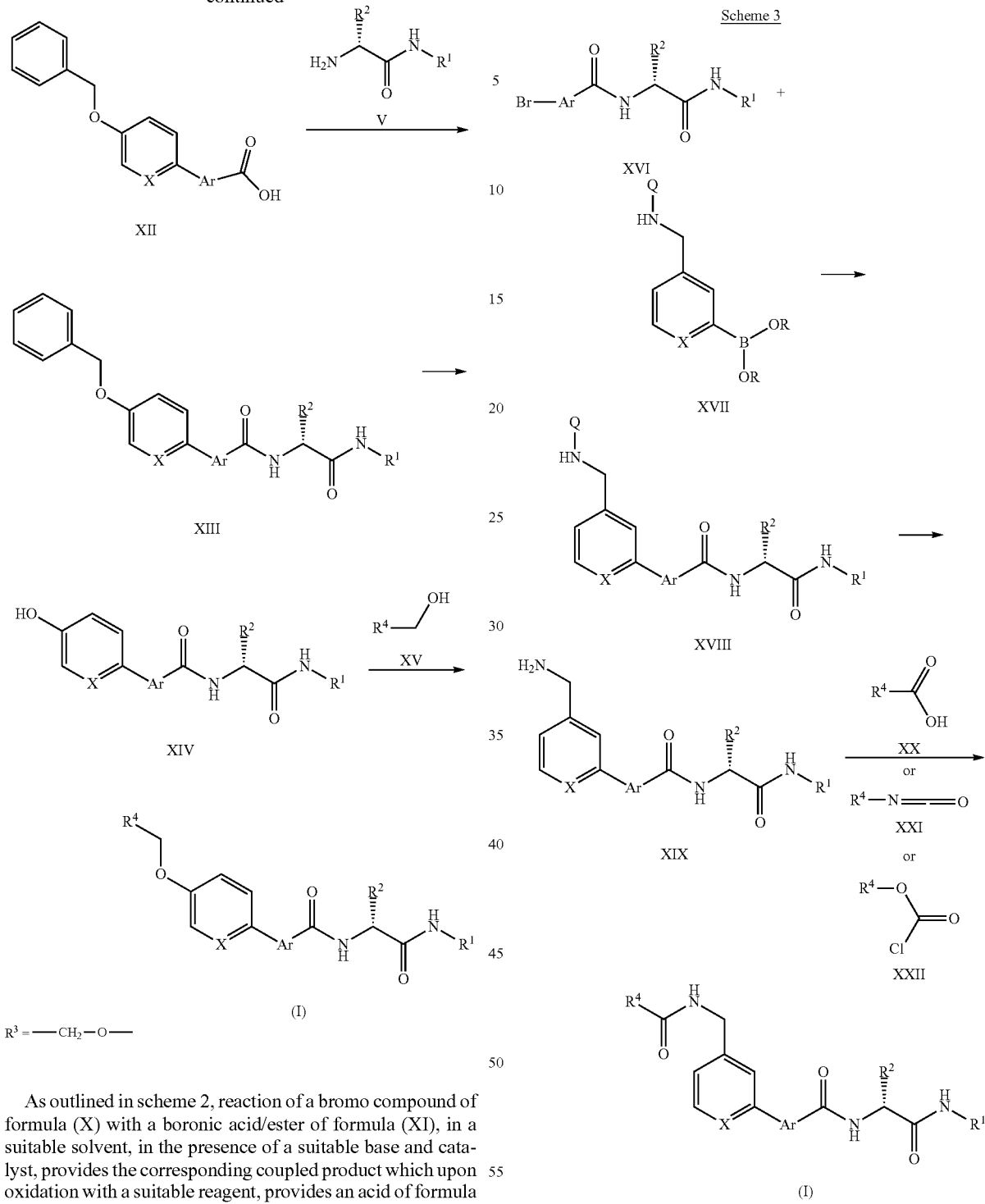

$R^3 = -CH_2-O-$

As outlined in scheme 2, reaction of a bromo compound of formula (X) with a boronic acid/ester of formula (XI), in a suitable solvent, in the presence of a suitable base and catalyst, provides the corresponding coupled product which upon oxidation with a suitable reagent, provides an acid of formula (XII). Reaction of the acid of formula (XII) with an amine of formula (V) under standard amide coupling reaction conditions, provides a compound of formula (XIII). Removal of the benzyloxy group from compound (XIII), in a suitable solvent, in the presence of a suitable catalyst, provides the hydroxyl compound of formula (XIV). Reaction of the hydroxyl compound of formula (XIV) with an alcohol of formula (XV), in a suitable solvent, in the presence of a reagent such as diisopropyl azodicarboxylate (DIAD) and triphenylphosphine, provides a compound of Formula (I), wherein $R^3 = -CH_2-O-$ $R^3 = -C(O)-NH-CH_2-$ As shown in scheme 3, reaction of a bromo compound of formula (XVI) with a boronic acid/ester of formula (XVII), wherein Q is an amine protecting group such as BOC, in a suitable solvent, in the presence of a suitable base and catalyst, provides the corresponding coupled product of formula (XVIII). Deprotection of the amine protecting group, under standard conditions, provides the free amine of formula (XIX). Reaction of the amine of formula (XIX) with an acid of formula (XX), under standard amide coupling reaction conditions, provides a compound of Formula (I), wherein $R^3$=—C(O)—NH—CH$_2$—. Reaction of the amine of formula (XIX) with an isocyanate of formula (XXI), under standard urea forming reaction conditions, provides a compound of Formula (I), wherein $R^3$=—N—C(O)—NH—CH$_2$—. Reaction of the amine of formula (XIX) with a chloroformate of formula (XXII), under standard carbamate formation reaction conditions, provides a compound of Formula (I), wherein $R^3$=—O—C(O)—NH—CH$_2$—.

Scheme 4

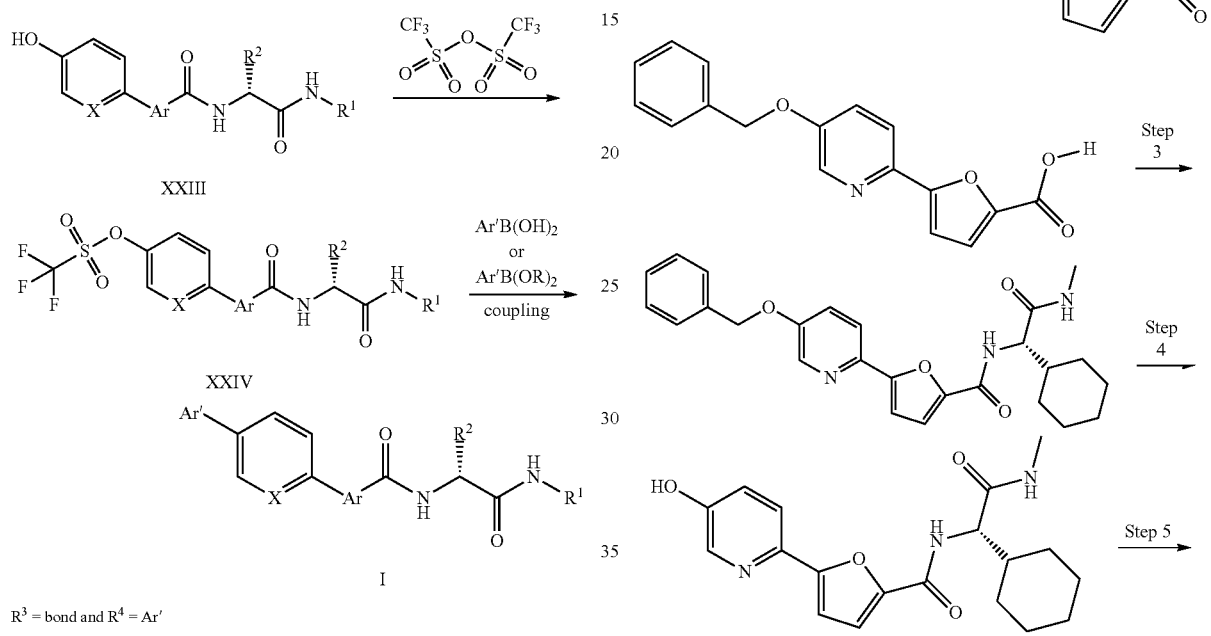

As outlined in scheme 4, reaction of hydroxy compound of formula (XXI) with trifluormethanesulfonic anhydride under standard protection conditions provides a compound of formula (XXII). Reaction of the triflate (XXII) with a boronic acid/ester in a suitable solvent, in the presence of a suitable base and catalyst, provides a compound of Formula (I), wherein $R^3$=bond and $R^4$=Ar'.

Further modification of the initial product of Formula (I) by methods known in the art and illustrated in the Examples below, may be used to prepare additional compounds of this invention.

EXAMPLE 1

5-[5-(Pyridin-3-ylmethoxy)-pyridin-2-yl]-furan-2-carboxylic acid ((S)-cyclohexyl-methylcarbamoyl-methyl)-amide

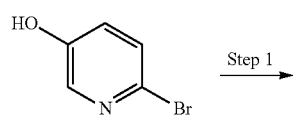

Step 1:
To a solution of 2-Bromo 5-hydroxypyridine (5 g, 29 mmol) in acetone (100 mL), is added K$_2$CO$_3$ (7.9 g, 58 mmol.) followed by benzyl bromide (5.1 mL, 43 mmol). The resulting suspension is heated at 70° C. for 2 hours. The solution is then diluted with water, and the acetone removed in vacuo. The aqueous phase is extracted with ethyl acetate, and the combined organic extracts are washed with brine, dried over Na$_2$SO$_4$ and concentrated in vacuo. The resulting residue is purified on silica with hexanes/ethyl acetate as the eluent, 6.4 g, 85%, LC/MS ESI m/z (M+H)+=266.3.
Step 2:
2-furaldehyde 4-boronic acid (10.2 g, 73 mmol), palladiumtetrakistriphenylphosphine (2.9 g, 2 4 mmol) and 5-benzyloxy-2-bromo-pyridine (6.4 g, 24 mmol) are diluted with an aqueous sodium carbonate solution (30 mL, 61 mmol), 1,2-dimethyoxethane (120 mL) and then degassed with argon over 5 minutes. The solution is heated to reflux (94° C.) overnight under argon. Upon cooling, the reaction mixture is diluted with ethyl acetate and water, and the aqueous phase is extracted with copious amounts of ethyl acetate. The combined organic extracts are washed with brine and concentrated in vacuo. The resulting residue is purified on silica with hexanes/ethyl acetate as the eluent to give an yellow solid, 3.1 g, 46%, LC/MS ESI m/z (M+H)$^+$=280.4.

Step 3:

To a solution of 5-(5-benzyloxy-pyridin-2-yl)-furan-2-carbaldehyde (4.4 g, 14 mmol) in 1,4-dioxane (160 mL) is added sodium phosphate (monobasic, 7.7 g, 56 mmol) in water (30 mL), followed by sulfamic acid (2.1 g, 22 mmol). The reaction mixture is cooled to 0° C., and sodium chlorite (3.27 g, 80%, 29 mmol) in water (30 mL) is added over a 10 minute period at 0° C. The ice bath is removed and the solution stirred for 30 minutes. Excess sodium sulfite is added and resulting suspension is stirred for 30 minutes. The reaction mixture is acidified with 2 N HCl (pH=4) and extracted with ethyl acetate (2×100 mL). The combined organic layers are washed with brine, dried over MgSO$_4$, filtered, and the solvent is evaporated in vacuo. The product is obtained as a dark yellow-brown solid, and used without further purification, 4.0 g, 94%, LC/MS ESI m/z (M+H)$^+$=296.6.

Step 4:

5-(5-Benzyloxy-pyridin-2-yl)-furan-2-carboxylate (4.4 g, 15 mmol) is dissolved in DMF (150 mL) and TBTU (9.7 g, 30 mmol), diisopropylethylamine (16 mL, 91 mmol), and (S)-2-Amino-2-cyclohexyl-N-methyl-acetamide (6.4 g, 22 mmol) are added. The reaction is capped and stirred at room temperature for 5 hours. The reaction is quenched with excess water, and the product extracted into ethyl acetate. The combined organic layers are washed with water, dried (sodium sulfate), filtered, and evaporated in vacuo to give an oil. The crude material is purified on silica gel with methanol/dichloromethane as the eluent to yield brown solid, 4.3 g, 64%, LC/MS ESI m/z (M+H)$^+$=448.7.

Step 5:

To a solution of 5-(5-benzyloxy-pyridin-2-yl)-furan-2-carboxylic acid ((S)-cyclohexyl-methylcarbamoyl-methyl)-amide (1.43 g, 2.8 mmol) in ethyl acetate (26 mL) and methanol (26 mL) is added 10% Pd/C (277 mg, 0.26 mmol). The reaction is purged with argon, and 1,4-cyclohexadiene (2.4 mL, 26 mmol) is added via syringe. The reaction mixture is heated to reflux for 2 hours, cooled to room temperature, filtered through a pad of celite, and the pad rinsed with ethyl acetate. The resulting filtrate is evaporated in vacuo to give light yellow solid that is used without further purification, 1.06 g, 95%, LC/MS ESI m/z (M+H)+=358.4.

Step 6.

To a solution of 5-(5-hydroxy-pyridin-2-yl)-furan-2-carboxylic acid ((S)-cyclohexyl-methylcarbamoyl-methyl)-amide (170 mg, 0.47 mmol.), 2-pyridine methanol (103 mg, 0.95 mmol) and PPh$_3$ (supported on polystyrene resin, 320 mg 0.95 mmol) in THF (2 mL) is added DIAD (0.18 mL, 0.95 mmol) dropwise at 0° C. under argon. The mixture is allowed to warm to room temperature, stirred for 19 hours, diluted with THF, and filtered through celite. The filtrate is evaporated in vacuo, and the crude material is purified on reverse phase HPLC to yield a white solid 72 mg, 34%, LC/MS ESI m/z (M+H)$^+$=449.7.

The following compounds in Table III are made in an analogous manner:

TABLE III

| Name | Structure | LC/MS (M + H) |
|---|---|---|
| 5-(5-Benzyloxy-pyridin-2-yl)-furan-2-carboxylic acid ((S)-2-hydroxy-2-methyl-1-methylcarbamoyl-propyl)-amide | 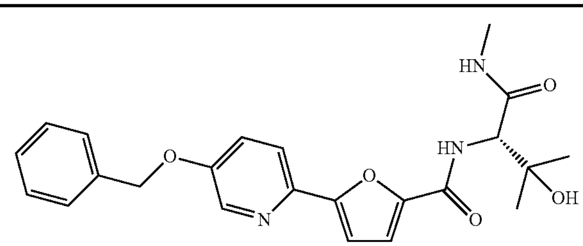 | 424.4 |
| 5-[5-(Benzyloxy)pyridin-2-yl]-N-[(1S)-2-(methylamino)-2-oxo-1-(tetrahydro-2H-pyran-4-yl)ethyl]furan-2-carboxamide | 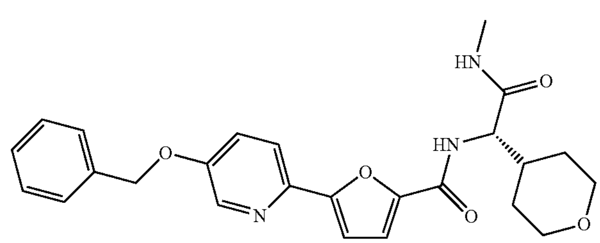 [SMILES: CNC(=O)[C@@H](NC(=O)c1ccc(-c2ccc(OCc3ccccc3)cn2)o1)C1CCOCC1] | 450.44 |
| 5-[5-(Benzyloxy)pyridin-2-yl]-N-[(1S)-1-cyclohexyl-2-(methylamino)-2-oxoethyl]furan-2-carboxamide | 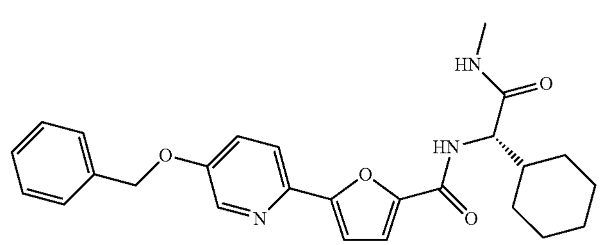 [SMILES: CNC(=O)[C@@H](NC(=O)c1ccc(-c2ccc(OCc3ccccc3)cn2)o1)C1CCCCC1] | 448.47 |

TABLE III-continued

| Name | Structure | LC/MS (M + H) |
|---|---|---|
| N-[(1S)-1-cyclohexyl-2-(methylamino)-2-oxoethyl]-5-[5-(pyridin-2-ylmethoxy)pyridin-2-yl]furan-2-carboxamide | 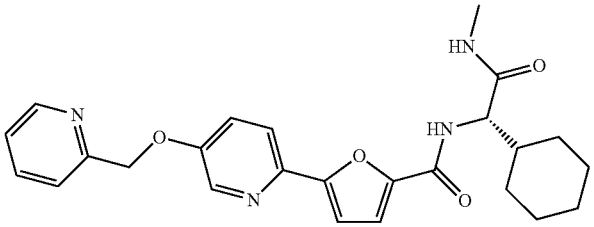 | 449.53 |
| 5-[5-(1-Benzofuran-2-ylmethoxy)pyridin-2-yl]-N-[(1S)-1-cyclohexyl-2-(methylamino)-2-oxoethyl]furan-2-carboxamide | 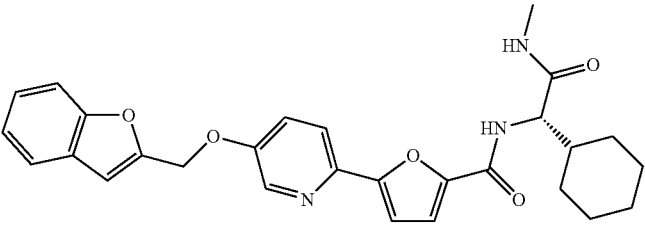 [SMILES: CNC(=O)[C@@H](NC(=O)c1ccc(-c2ccc(OCc3cc4ccccc4o3)cn2)o1)C1CCCCC1] | 488.48 |
| N-[(1S)-1-cyclohexyl-2-(methylamino)-2-oxoethyl]-5-[5-(pyridin-4-ylmethoxy)pyridin-2-yl]furan-2-carboxamide | 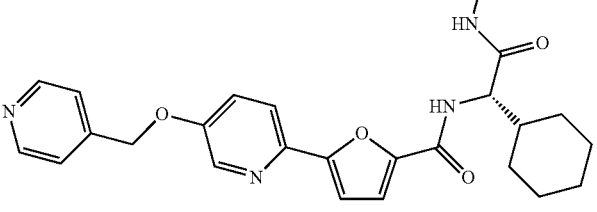 | 449.46 |
| N-[(1S)-1-cyclohexyl-2-(methylamino)-2-oxoethyl]-5-{5-[(1-methyl-1H-imidazol-4-yl)methoxy]pyridin-2-yl}furan-2-carboxamide | 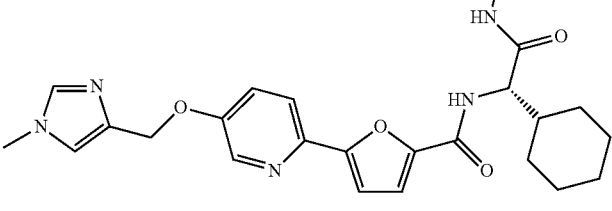 | 452.49 |
| N-[(1S)-1-cyclohexyl-2-(methylamino)-2-oxoethyl]-5-{5-[(6-methylpyridin-2-yl)methoxy]pyridin-2-yl}furan-2-carboxamide | 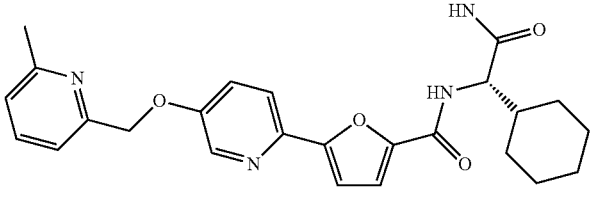 | 463.48 |
| N-[(1S)-1-cyclohexyl-2-(methylamino)-2-oxoethyl]-5-{5-[(1-methyl-1H-imidazol-5-yl)methoxy]pyridin-2-yl}furan-2-carboxamide | 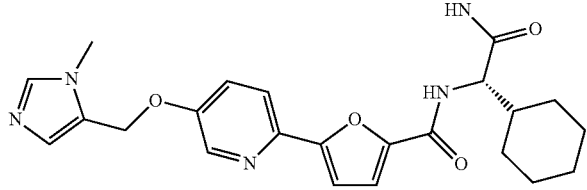 | 452.49 |

TABLE III-continued

| Name | Structure | LC/MS (M + H) |
|---|---|---|
| N-[(1S)-1-cyclohexyl-2-(methylamino)-2-oxoethyl]-5-{5-[(1,5-dimethyl-1H-pyrazol-3-yl)methoxy]pyridin-2-yl}furan-2-carboxamide | 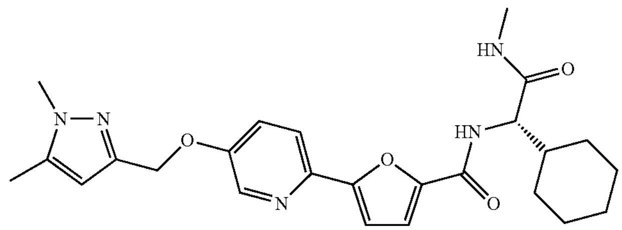 [SMILES: CNC(=O)[C@@H](NC(=O)c1ccc(-c2ccc(OCc3cc(C)n(C)n3)cn2)o1)C1CCCCC1] | 466.47 |
| 5-(5-Benzyloxy-pyridin-2-yl)-furan-2-carboxylic acid ((S)-cyclohexyl-methylcarbamoyl-methyl)-amide | 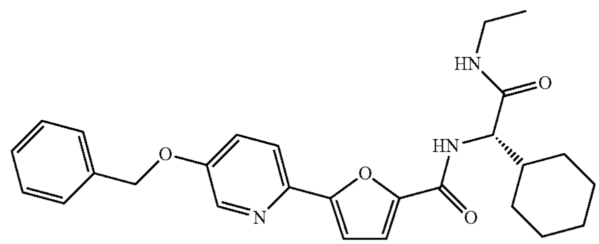 [SMILES: CCNC(=O)[C@@H](NC(=O)c1ccc(-c2ccc(OCc3ccccc3)cn2)o1)C1CCCCC1] | 462.46 |
| N-[(1S)-1-cyclohexyl-2-(methylamino)-2-oxoethyl]-5-{5-[(1-methyl-1H-pyrazol-3-yl)methoxy]pyridin-2-yl}furan-2-carboxamide | 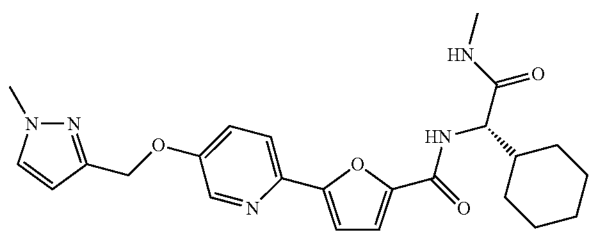 [SMILES: CNC(=O)[C@@H](NC(=O)c1ccc(-c2ccc(OCc3ccn(C)n3)cn2)o1)C1CCCCC1] | 452.47 |
| N-[(1S)-1-cyclohexyl-2-(methylamino)-2-oxoethyl]-5-{5-[(3-methylbenzyl)oxy]pyridin-2-yl}furan-2-carboxamide | 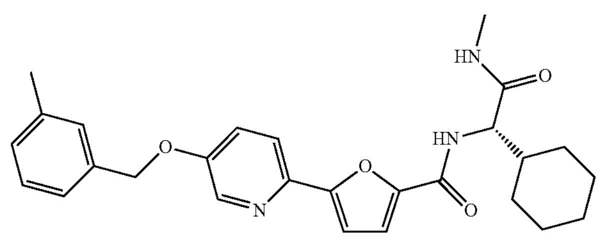 [SMILES: CNC(=O)[C@@H](NC(=O)c1ccc(-c2ccc(OCc3cccc(C)c3)cn2)o1)C1CCCCC1] | 462.48 |
| N-[(1S)-1-cyclohexyl-2-(methylamino)-2-oxoethyl]-5-{5-[(3,5-dimethylbenzyl)oxy]pyridin-2-yl}furan-2-carboxamide | 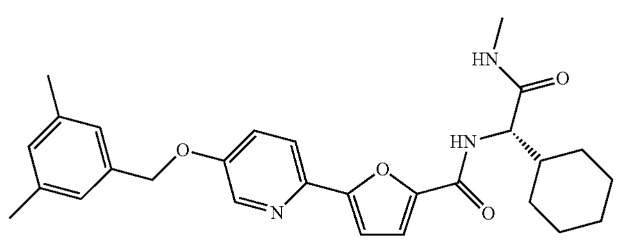 [SMILES: CNC(=O)[C@@H](NC(=O)c1ccc(-c2ccc(OCc3cc(C)cc(C)c3)cn2)o1)C1CCCCC1] | 476.5 |
| N-[(1S)-1-cyclohexyl-2-(methylamino)-2-oxoethyl]-5-{5-[(1S)-1-phenylethoxy]pyridin-2-yl}furan-2-carboxamide | 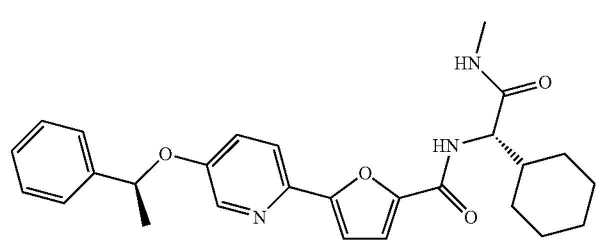 [SMILES: CNC(=O)[C@@H](NC(=O)c1ccc(-c2ccc(O[C@@H](C)c3ccccc3)cn2)o1)C1CCCCC1] | 462.74 |

TABLE III-continued

| Name | Structure | LC/MS (M + H) |
|---|---|---|
| N-[(1S)-1-cyclohexyl-2-(methylamino)-2-oxoethyl]-5-{5-[(1R)-1-phenylethoxy]pyridin-2-yl}furan-2-carboxamide | 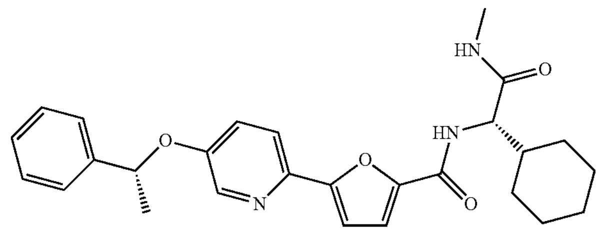 [SMILES: CNC(=O)[C@@H](NC(=O)c1ccc(-c2ccc(O[C@H](C)c3ccccc3)cn2)o1)C1CCCCC1] | 462.74 |
| N-[(1S)-1-cyclohexyl-2-(methylamino)-2-oxoethyl]-5-{5-[(1-methyl-1H-imidazol-2-yl)methoxy]pyridin-2-yl}furan-2-carboxamide | 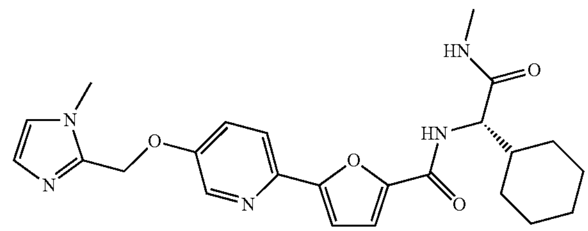 [SMILES: CNC(=O)[C@@H](NC(=O)c1ccc(-c2ccc(OCc3nccn3C)cn2)o1)C1CCCCC1] | 452.48 |
| N-[(1S)-1-cyclohexyl-2-(methylamino)-2-oxoethyl]-5-{5-[(4-methylpyridin-2-yl)methoxy]pyridin-2-yl}furan-2-carboxamide | 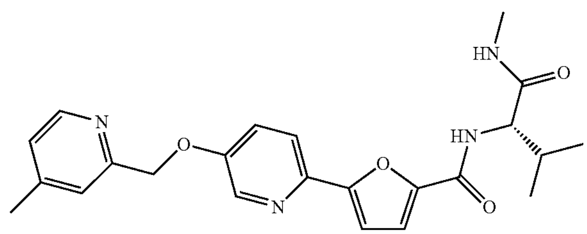 [SMILES: CNC(=O)[C@@H](NC(=O)c1ccc(-c2ccc(OCc3cc(C)ccn3)cn2)o1)C(C)C] | 463.47 |
| N-[(1S)-1-cyclohexyl-2-(methylamino)-2-oxoethyl]-5-[5-(1H-pyrazol-5-ylmethoxy)pyridin-2-yl]furan-2-carboxamide | 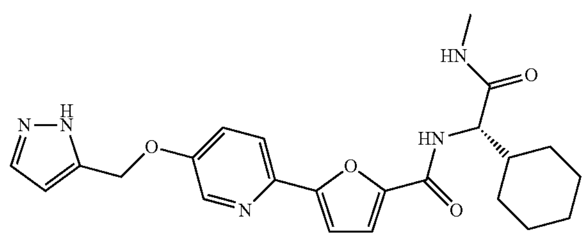 [SMILES: CNC(=O)[C@@H](NC(=O)c1ccc(-c2ccc(OCc3ccn[nH]3)cn2)o1)C1CCCCC1] | 438.74 |
| 5-(5-Benzyloxy-pyridin-2-yl)-furan-2-carboxylic acid ((S)-2-methyl-1-methylcarbamoyl-propyl)-amide | 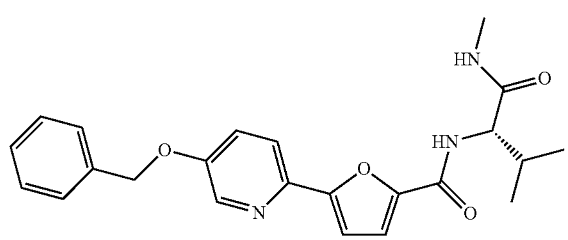 [SMILES: CNC(=O)[C@@H](NC(=O)c1ccc(-c2ccc(OCc3ccccc3)cn2)o1)C(C)C] | 408.43 |
| N-[(1S)-1-cyclohexyl-2-(methylamino)-2-oxoethyl]-5-{5-[(3-methyl-1H-pyrazol-5-yl)methoxy]pyridin-2-yl}furan-2-carboxamide | 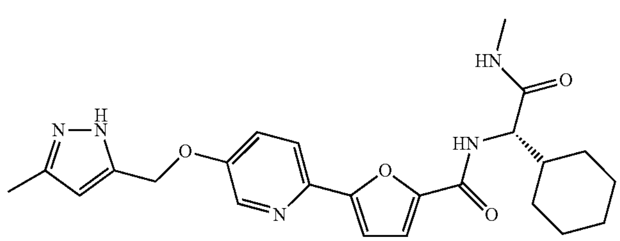 [SMILES: CNC(=O)[C@@H](NC(=O)c1ccc(-c2ccc(OCc3cc(C)n[nH]3)cn2)o1)C1CCCCC1] | 452.5 |

TABLE III-continued

| Name | Structure | LC/MS (M + H) |
|---|---|---|
| N-[(1S)-1-cyclohexyl-2-(methylamino)-2-oxoethyl]-5-[5-(pyridin-3-ylmethoxy)pyridin-2-yl]furan-2-carboxamide | 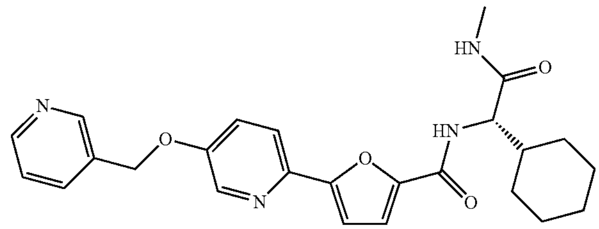 [SMILES: CNC(=O)[C@@H](NC(=O)c1ccc(-c2ccc(OCc3cccnc3)cn2)o1)C1CCCCC1] | 449.66 |
| 5-[5-(5-Methyl-3H-imidazol-4-ylmethoxy)-pyridin-2-yl]-furan-2-carboxylic acid ((S)-2-methyl-1-methylcarbamoyl-propyl)-amide | 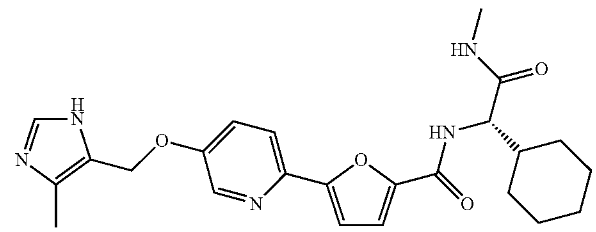 [SMILES: CNC(=O)[C@@H](NC(=O)c1ccc(-c2ccc(OCc3[nH]cnc3C)cn2)o1)C1CCCCC1] | 452.51 |
| 5-[5-(2,5-Dimethyl-2H-pyrazol-3-ylmethoxy)-pyridin-2-yl]-furan-2-carboxylic acid ((S)-cyclohexyl-methylcarbamoyl-methyl)-amide | 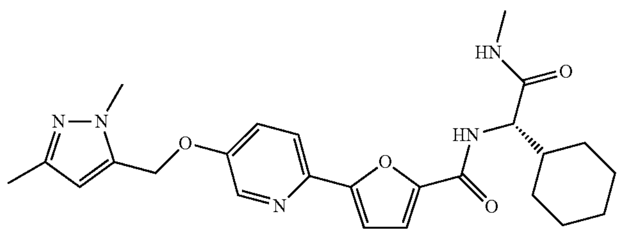 | 466.68 |
| 5-[4-(2,5-Dimethyl-2H-pyrazol-3-ylmethoxy)-phenyl]-furan-2-carboxylic acid ((S)-cyclohexyl-methylcarbamoyl-methyl)-amide | 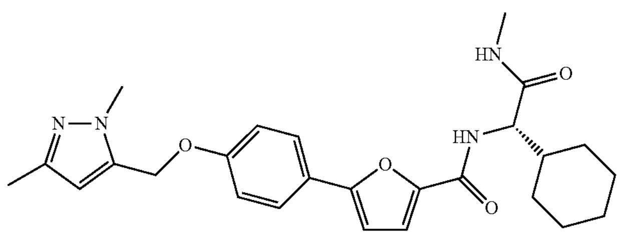 [SMILES: CNC(=O)[C@@H](NC(=O)c1ccc(-c2ccc(OCc3cc(C)nn3C)cc2)o1)C1CCCCC1] | 465.53 |
| N-[(1S)-1-cyclohexyl-2-(methylamino)-2-oxoethyl]-5-{5-[(1-methyl-1H-pyrazol-5-yl)methoxy]pyridin-2-yl}furan-2-carboxamide | 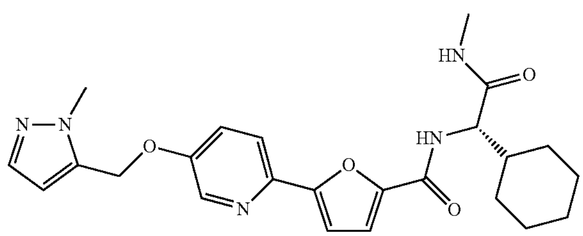 [SMILES: CNC(=O)[C@@H](NC(=O)c1ccc(-c2ccc(OCc3ccnn3C)cn2)o1)C1CCCCC1] | 452.68 |
| N-[(1S)-1-cyclohexyl-2-(methylamino)-2-oxoethyl]-5-{5-[(2-methylpyridin-4-yl)methoxy]pyridin-2-yl}furan-2-carboxamide | 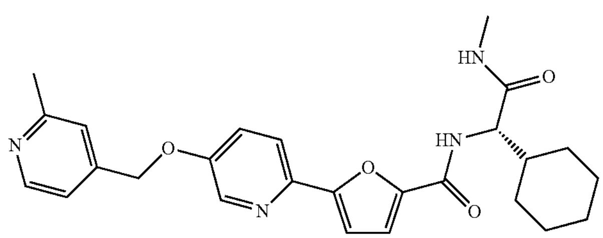 [SMILES: CNC(=O)[C@@H](NC(=O)c1ccc(-c2ccc(OCc3ccnc(C)c3)cn2)o1)C1CCCCC1] | 463.48 |

TABLE III-continued

| Name | Structure | LC/MS (M + H) |
|---|---|---|
| N-[(1S)-1-cyclohexyl-2-(methylamino)-2-oxoethyl]-5-{5-[(3-methylpyridin-4-yl)methoxy]pyridin-2-yl}furan-2-carboxamide | 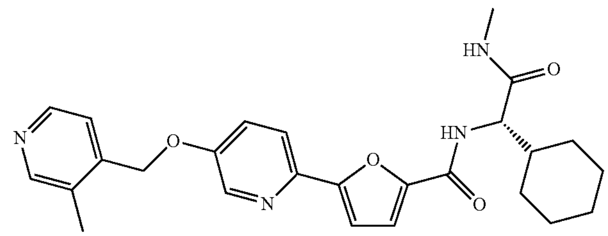 [SMILES: CNC(=O)[C@@H](NC(=O)c1ccc(-c2ccc(OCc3ccncc3C)cn2)o1)C1CCCCC1] | 463.71 |
| 5-[5-(1,5-Dimethyl-1H-pyrazol-3-ylmethoxy)-pyridin-2-yl]-furan-2-carboxylic acid ((S)-2-methyl-1-methyl-carbamoyl-propyl)-amide | 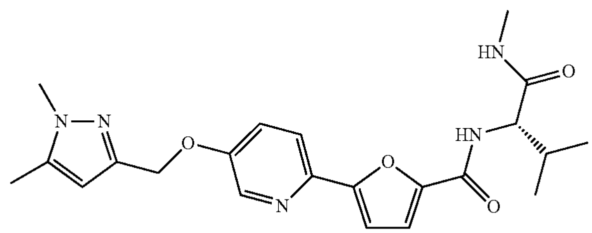 [SMILES: CNC(=O)[C@@H](NC(=O)c1ccc(-c2ccc(OCc3cc(C)n(C)n3)cn2)o1)C(C)C] | 426.47 |
| N-[(1S)-1-cyclohexyl-2-(methylamino)-2-oxoethyl]-5-{5-[(2,6-dimethylpyridin-4-yl)methoxy]pyridin-2-yl}furan-2-carboxamide | 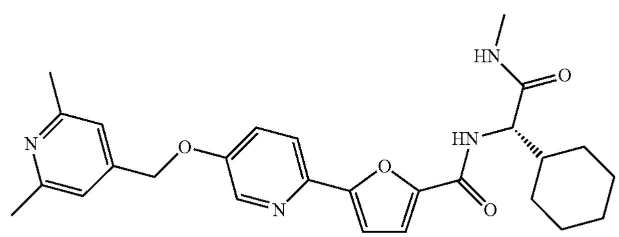 | 477.55 |
| N-[(1S)-1-cyclohexyl-2-(methylamino)-2-oxoethyl]-5-[5-(1H-imidazol-5-ylmethoxy)pyridin-2-yl]furan-2-carboxamide | 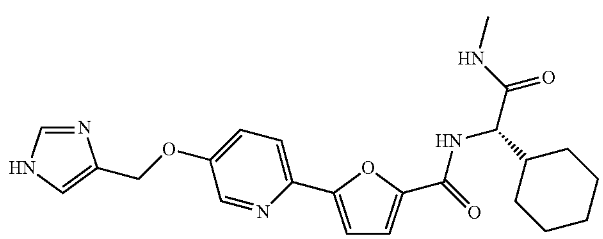 [SMILES: CNC(=O)[C@@H](NC(=O)c1ccc(-c2ccc(OCc3c[nH]cn3)cn2)o1)C1CCCCC1] | 438.49 |
| N-[(1S)-2-(methylamino)-2-oxo-1-(piperidin-4-yl)ethyl]-5-{5-[(1-methyl-1H-imidazol-4-yl)methoxy]pyridin-2-yl}furan-2-carboxamide | 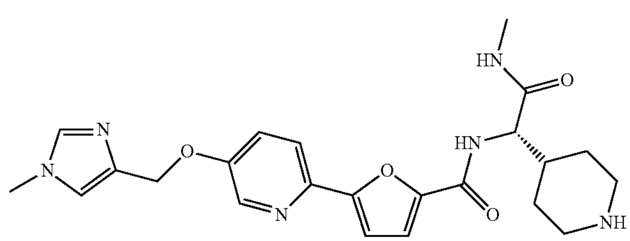 [SMILES: CNC(=O)[C@@H](NC(=O)c1ccc(-c2ccc(OCc3cn(C)cn3)cn2)o1)C1CCNCC1] | 453.48 |
| 5-{5-[(1,5-dimethyl-1H-pyrazol-3-yl)methoxy]pyridin-2-yl}-N-[(1S)-2-methyl-1-(4-methyl-1H-imidazol-2-yl)propyl]furan-2-carboxamide | 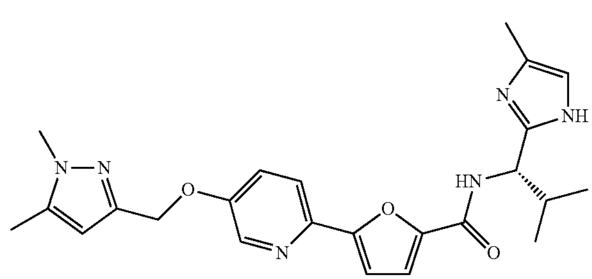 [SMILES: Cc1c[nH]c([C@@H](NC(=O)c2ccc(-c3ccc(OCc4cc(C)n(C)n4)cn3)o2)C(C)C)n1] | 449.67 |

TABLE III-continued

| Name | Structure | LC/MS (M + H) |
|---|---|---|
| N-[(1S)-1-cyclohexyl-2-(methylamino)-2-oxoethyl]-5-{5-[(1R)-1-(pyridin-4-yl)ethoxy]pyridin-2-yl}furan-2-carboxamide | 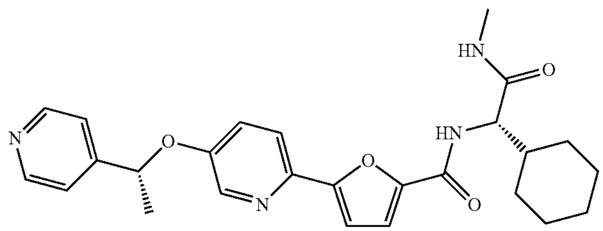 [SMILES: CNC(=O)[C@@H](NC(=O)c1ccc(-c2ccc(O[C@H](C)c3ccncc3)cn2)o1)C1CCCCC1] | 463.54 |
| 5-[5-((R)-1-Phenyl-ethoxy)-pyridin-2-yl]-furan-2-carboxylic acid ((S)-2-methyl-1-methylcarbamoyl-propyl)-amide | 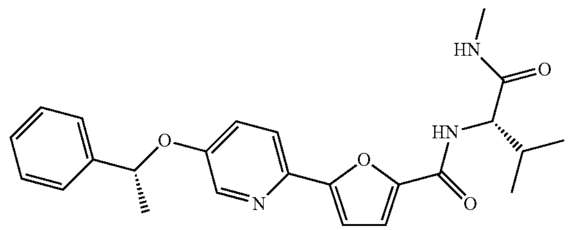 [SMILES: CNC(=O)[C@@H](NC(=O)c1ccc(-c2ccc(O[C@H](C)c3ccccc3)cn2)o1)C(C)C] | 422.48 |
| N-[(1S)-1-cyclohexyl-2-(methylamino)-2-oxoethyl]-5-{5-[(1S)-1-(pyridin-2-yl)ethoxy]pyridin-2-yl}furan-2-carboxamide | 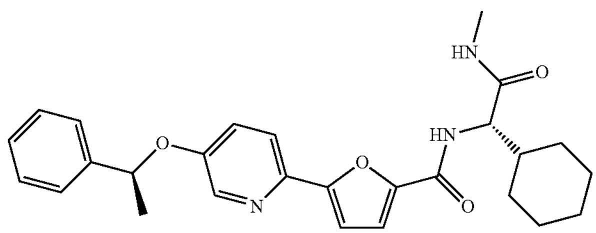 [SMILES: CNC(=O)[C@@H](NC(=O)c1ccc(-c2ccc(O[C@@H](C)c3ccccc3)cn2)o1)C1CCCCC1] | 463.51 |
| 5-[5-((S)-1-Phenyl-ethoxy)-pyridin-2-yl]-furan-2-carboxylic acid ((S)-2-methyl-1-methylcarbamoyl-propyl)-amide | 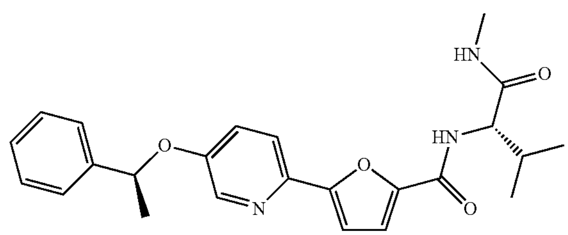 [SMILES: CNC(=O)[C@@H](NC(=O)c1ccc(-c2ccc(O[C@@H](C)c3ccccc3)cn2)o1)C(C)C] | 422.48 |
| N-[(1S)-1-cyclohexyl-2-(methylamino)-2-oxoethyl]-5-{5-[(1S)-1-(pyridin-4-yl)ethoxy]pyridin-2-yl}furan-2-carboxamide | 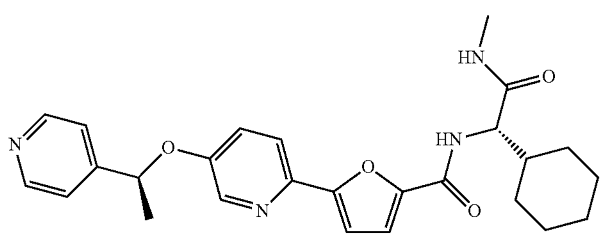 [SMILES: CNC(=O)[C@@H](NC(=O)c1ccc(-c2ccc(O[C@@H](C)c3ccncc3)cn2)o1)C1CCCCC1] | 463.52 |
| N-[(1S)-1-cyclohexyl-2-(methylamino)-2-oxoethyl]-5-{5-[(1R)-1-(pyridin-2-yl)ethoxy]pyridin-2-yl}furan-2-carboxamide | 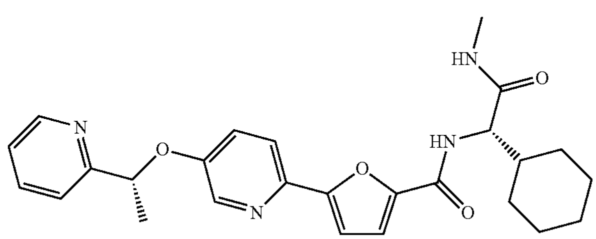 [SMILES: CNC(=O)[C@@H](NC(=O)c1ccc(-c2ccc(O[C@H](C)c3ccccn3)cn2)o1)C1CCCCC1] | 463.5 |

TABLE III-continued

| Name | Structure | LC/MS (M + H) |
|---|---|---|
| N-[(1S)-1-cyclohexyl-2-(methylamino)-2-oxoethyl]-5-{5-[1-(pyridin-3-yl)ethoxy]pyridin-2-yl}furan-2-carboxamide | 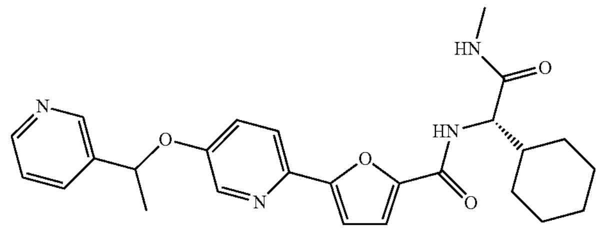 [SMILES: CNC(=O)[C@@H](NC(=O)c1ccc(-c2ccc(OC(C)c3cccnc3)cn2)o1)C1CCCCC1] | 463.74 |
| 5-[5-(5-Methyl-3H-imidazol-4-ylmethoxy)-pyridin-2-yl]-furan-2-carboxylic acid ((S)-2-methyl-1-methylcarbamoyl-propyl)-amide | 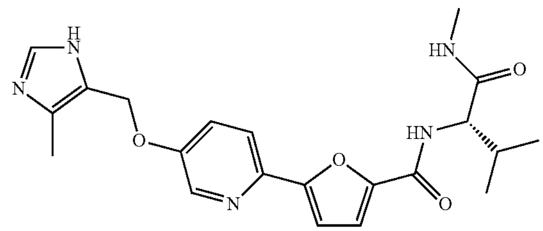 [SMILES: CNC(=O)[C@@H](NC(=O)c1ccc(-c2ccc(OCc3[nH]cnc3C)cn2)o1)C(C)C] | 412.5 |
| 5-[5-(5-Methyl-3H-imidazol-4-ylmethoxy)-pyridin-2-yl]-furan-2-carboxylic acid [(S)-methylcarbamoyl-(tetrahydro-pyran-4-yl)-methyl]-amide | 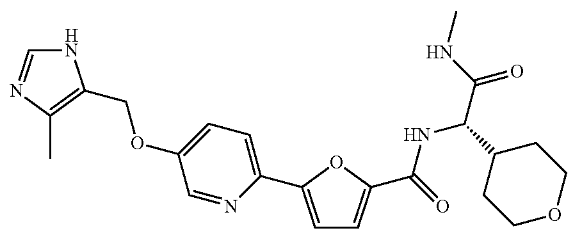 [SMILES: CNC(=O)[C@@H](NC(=O)c1ccc(-c2ccc(OCc3[nH]cnc3C)cn2)o1)C1CCOCC1] | 454.57 |
| 5-[4-(5-Methyl-3H-imidazol-4-ylmethoxy)-phenyl]-furan-2-carboxylic acid [(S)-methylcarbamoyl-(tetrahydro-pyran-4-yl)-methyl]-amide | 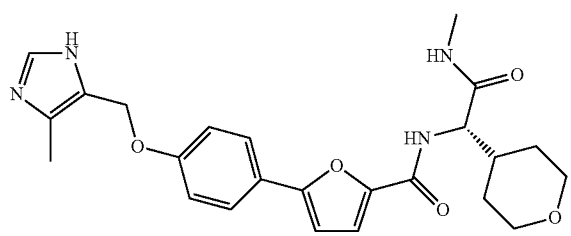 [SMILES: CNC(=O)[C@@H](NC(=O)c1ccc(-c2ccc(OCc3[nH]cnc3C)cc2)o1)C1CCOCC1] | 435.5 |

EXAMPLE 2

N-[4-(5-{[(1S)-1-cyclohexyl-2-(methylamino)-2-oxoethyl]carbamoyl}furan-2-yl)phenyl]-5-methylfuran-2-carboxamide

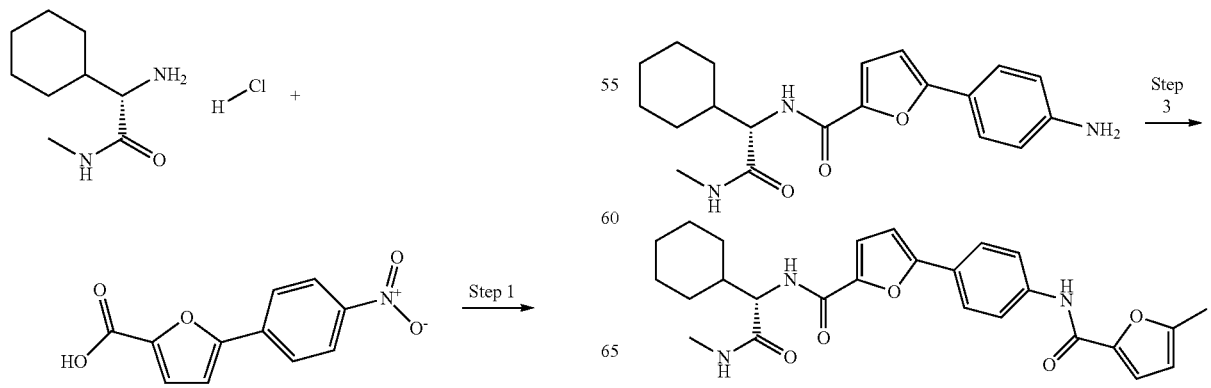

Step 1:
(S)-2-Amino-2-cyclohexyl-N-methyl-acetamide hydrochloride (0.75 g, 3.6 mmol) is taken up in dichloromethane (5 mL) and DIEA (1.87 mL, 10.7 mmol) is added to the solution. 5-(4-Nitro-phenyl)-furan-2-carboxylic acid (0.92 g, 3.9 mmol) EDC (1.37 g, 7.2 mmol) and HOBT (0.97 g, 7.2 mmol) are added and the reaction is stirred at room temperature overnight. The reaction is diluted with DCM and washed with 10% citric acid. The combined organic layer is washed with saturated sodium bicarbonate, brine and dried over anhydrous magnesium sulfate. The solution is filtered and concentrated in vacuo to give a solid that is purified on silica gel (hexanes/ethyl acetate) to provide 0.96 g of the title compound 63% LC/MS ESI m/z (M+H)$^+$=383.3.

Step 2:
5-(4-Nitro-phenyl)-furan-2-carboxylic acid ((S)-cyclohexyl-methylcarbamoyl-methyl)-amide (760 mg, 1.96 mmol), acetic acid 15 mL and zinc (1.2 g, 19 mmol) are combined and stirred at room temperature for 30 minutes. The crude reaction mixture is filtered through celite, washed with acetonitrile and the combined washings concentrated in vacuo. The crude material is taken up in 10% methanol in DCM and washed with saturated aqueous sodium bicarbonate. The organic layer is dried, filtered and evaporated in vacuo to yield the title compound that is used without further purification, 660 mg, 94%, LC/MS ESI m/z (M+H)+=356.2.

Step 3:

5-(4-Amino-phenyl)-furan-2-carboxylic acid ((S)-1-cyclohexyl-2-methylamino-allyl)-amide (35 mg, 0.1 mmol) is dissolved in DMF (1 mL) and 4-methylmorpholine is added (43 uL, 0.4 mmol). HATU (57 mg, 0.15 mmol) in 1 mL of DMF is added to 5-methylfurancarboxylate (14 mg, 0.11 mmol), and this mixture is added to the amine mixture and the resulting solution stirred overnight. After 16 hours the solvents are evaporated in vacuo and the residue purified by reverse phase LC to give the title compound 20 mg, 43%, LC/MS ESI m/z (M+H)+ 464.2.

The following compounds in Table IV are made in an analogous manner:

TABLE IV

| Name | Structure | LC/MS (M + H) |
|---|---|---|
| N-{4-[5-({(1S)-1-cyclohexyl-2-[(1-methoxypropan-2-yl)amino]-2-oxoethyl}carbamoyl)furan-2-yl]phenyl}-1-benzofuran-2-carboxamide | 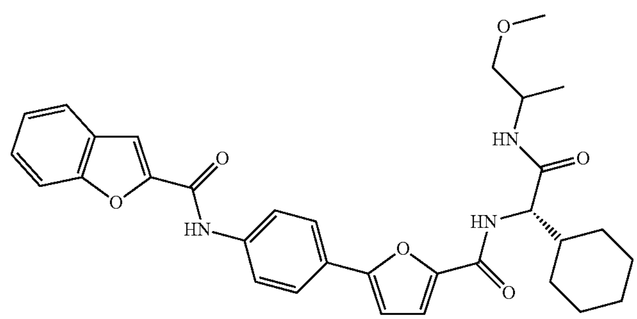 [SMILES: COCC(C)NC(=O)[C@@H](NC(=O)c1ccc(-c2ccc(NC(=O)c3cc4ccccc4o3)cc2)o1)C1CCCCC1] | 558.49 |
| N-[4-(5-{[(1S)-1-cyclopropyl-2-(methylamino)-2-oxoethyl]carbamoyl}furan-2-yl)phenyl]-6-methylpyridine-2-carboxamide | 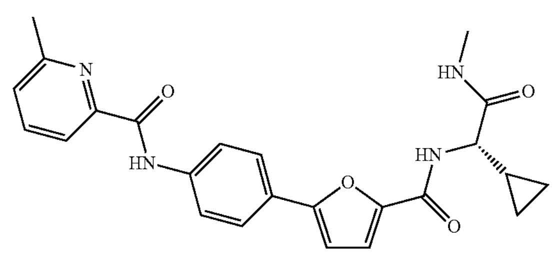 [SMILES: CNC(=O)[C@@H](NC(=O)c1ccc(-c2ccc(NC(=O)c3cccc(C)n3)cc2)o1)C1CC1] | 433.67 |
| 6-Methyl-N-[4-(5-{[(2S)-3-methyl-1-(methylamino)-1-oxobutan-2-yl]carbamoyl}furan-2-yl)phenyl]pyridine-2-carboxamide | 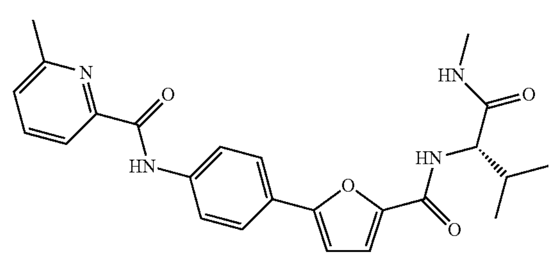 [SMILES: CNC(=O)[C@@H](NC(=O)c1ccc(-c2ccc(NC(=O)c3cccc(C)n3)cc2)o1)C(C)C] | 435.64 |

TABLE IV-continued

| Name | Structure | LC/MS (M + H) |
|---|---|---|
| N-[4-(5-{[(1S)-1-cyclohexyl-2-{[(2S)-1-methoxypropan-2-yl]amino]-2-oxoethyl]carbamoyl}furan-2-yl)phenyl]-6-methylpyridine-2-carboxamide | | 533.54 |
| N-[4-(5-{[(1S)-1-cyclohexyl-2-{[(2S)-2-hydroxypropyl]amino}-2-oxoethyl]carbamoyl}furan-2-yl)phenyl]-6-methyl-pyridine-2-carboxamide | 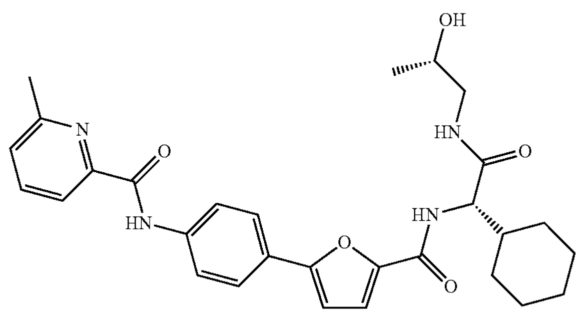 [SMILES: Cc1cccc(C(=O)Nc2ccc(-c3ccc(C(=O)N[C@H](C(=O)NC[C@H](C)O)C4CCCCC4)o3)cc2)n1] | 519.53 |
| N-[4-(5-{[(1S)-1-cyclohexyl-2-{[(2R)-2-hydroxypropyl]amino}-2-oxoethyl]carbamoyl}furan-2-yl)phenyl]-6-methyl-pyridine-2-carboxamide | 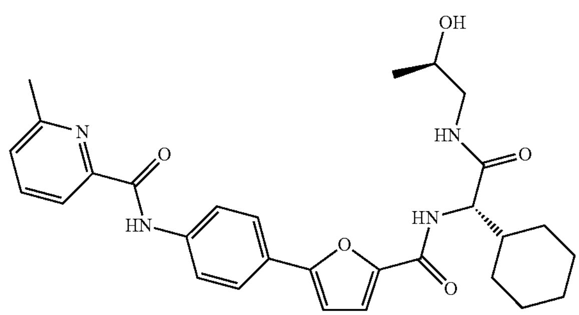 [SMILES: Cc1cccc(C(=O)Nc2ccc(-c3ccc(C(=O)N[C@H](C(=O)NC[C@@H](C)O)C4CCCCC4)o3)cc2)n1] | 519.53 |
| N-[6-(5-{[(1S)-1-cyclohexyl-2-(methylamino)-2-oxoethyl]carbamoyl}furan-2-yl)pyridin-3-yl]-1-benzofuran-2-carboxamide | 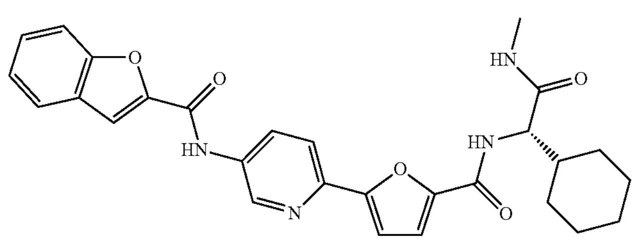 | 501.47 |
| N-[6-(5-{[(1S)-1-cyclohexyl-2-(methylamino)-2-oxoethyl]carbamoyl}furan-2-yl)pyridin-3-yl]-6-methylpyridine-2-carboxamide | 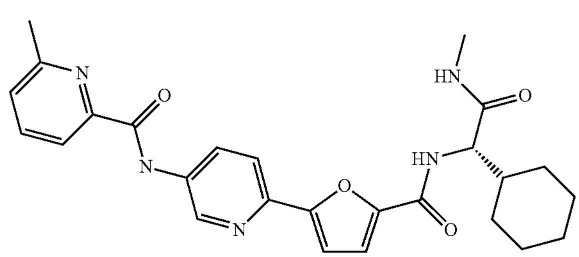 [SMILES: CNC(=O)[C@@H](NC(=O)c1ccc(-c2ccc(NC(=O)c3cccc(C)n3)cn2)o1)C1CCCCC1] | 476.47 |

TABLE IV-continued

| Name | Structure | LC/MS (M + H) |
|---|---|---|
| N-[4-(5-{[(1S)-1-cyclohexyl-2-(methylamino)-2-oxoethyl]carbamoyl}furan-2-yl)phenyl]-4,5-dimethylfuran-2-carboxamide | 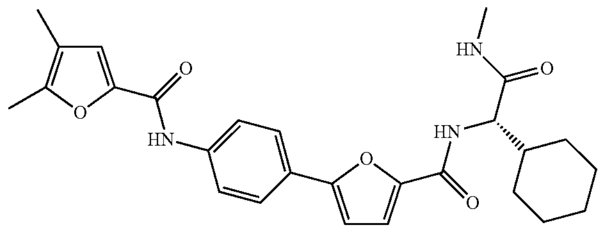 [SMILES: CNC(=O)[C@@H](NC(=O)c1ccc(-c2ccc(NC(=O)c3cc(C)c(C)o3)cc2)o1)C1CCCCC1] | 478.2 |
| N-[4-(5-{[(1S)-1-cyclohexyl-2-(methylamino)-2-oxoethyl]carbamoyl}furan-2-yl)phenyl]-1-methyl-1H-imidazole-4-carboxamide | 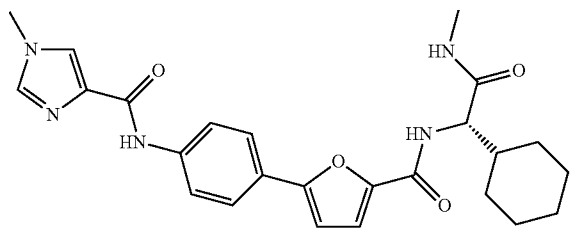 [SMILES: CNC(=O)[C@@H](NC(=O)c1ccc(-c2ccc(NC(=O)c3cn(C)cn3)cc2)o1)C1CCCCC1] | 464.2 |
| N-[4-(5-{[(1S)-1-cyclohexyl-2-(methylamino)-2-oxoethyl]carbamoyl}furan-2-yl)phenyl]-1-methyl-1H-imidazole-5-carboxamide | 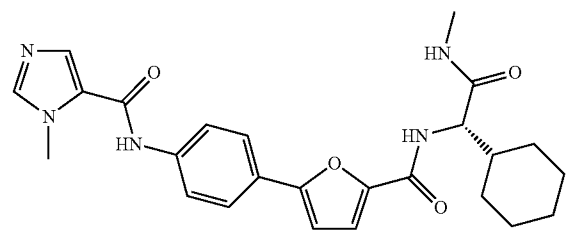 [SMILES: CNC(=O)[C@@H](NC(=O)c1ccc(-c2ccc(NC(=O)c3cncn3C)cc2)o1)C1CCCCC1] | 464.2 |
| N-[4-(5-{[(1S)-1-cyclohexyl-2-(methylamino)-2-oxoethyl]carbamoyl}furan-2-yl)phenyl]-6-methylpyridine-2-carboxamide | 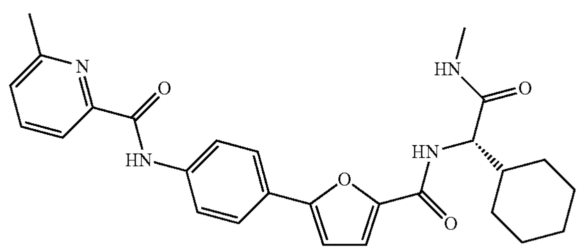 [SMILES: CNC(=O)[C@@H](NC(=O)c1ccc(-c2ccc(NC(=O)c3cccc(C)n3)cc2)o1)C1CCCCC1] | 475.2 |
| N-[4-(5-{[(1S)-1-cyclohexyl-2-(methylamino)-2-oxoethyl]carbamoyl}furan-2-yl)phenyl]-5-methylpyridine-3-carboxamide | 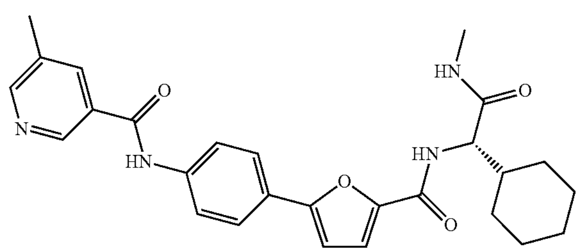 [SMILES: CNC(=O)[C@@H](NC(=O)c1ccc(-c2ccc(NC(=O)c3cncc(C)c3)cc2)o1)C1CCCCC1] | 475.2 |
| N-[4-(5-{[(1S)-1-cyclohexyl-2-(methylamino)-2-oxoethyl]carbamoyl}furan-2-yl)phenyl]-1-methyl-1H-pyrazole-5-carboxamide | 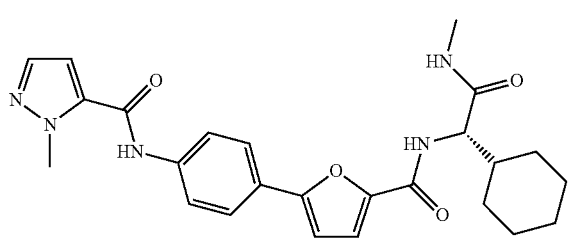 [SMILES: CNC(=O)[C@@H](NC(=O)c1ccc(-c2ccc(NC(=O)c3ccnn3C)cc2)o1)C1CCCCC1] | 464.2 |

TABLE IV-continued

| Name | Structure | LC/MS (M + H) |
|---|---|---|
| N-[4-(5-{[(1S)-1-cyclohexyl-2-(methylamino)-2-oxoethyl]carbamoyl}furan-2-yl)phenyl]-3-methylfuran-2-carboxamide | 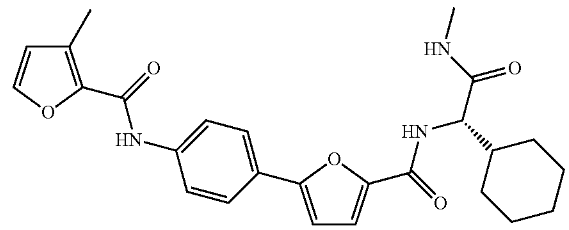 [SMILES: CNC(=O)[C@@H](NC(=O)c1ccc(-c2ccc(NC(=O)c3occc3C)cc2)o1)C1CCCCC1] | 464.1 |
| N-[(1S)-1-cyclohexyl-2-(methylamino)-2-oxoethyl]-5-(4-{[(2-methylfuran-3-yl)carbonyl]amino}phenyl)furan-2-carboxamide | 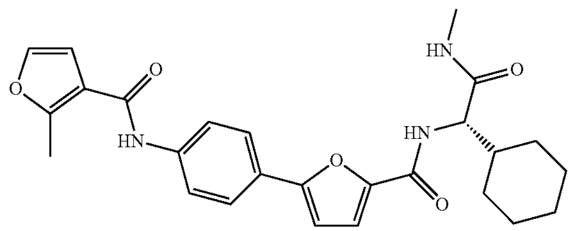 [SMILES: CNC(=O)[C@@H](NC(=O)c1ccc(-c2ccc(NC(=O)c3ccoc3C)cc2)o1)C1CCCCC1] | 464.1 |
| N-[4-(5-{[(1S)-1-cyclohexyl-2-(methylamino)-2-oxoethyl]carbamoyl}furan-2-yl)phenyl]-5-methylfuran-2-carboxamide | 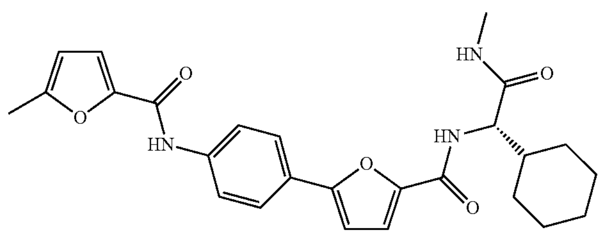 [SMILES: CNC(=O)[C@@H](NC(=O)c1ccc(-c2ccc(NC(=O)c3ccc(C)o3)cc2)o1)C1CCCCC1] | 464.2 |
| N-[4-(5-{[(1S)-1-cyclohexyl-2-(methylamino)-2-oxoethyl]carbamoyl}furan-2-yl)phenyl]-5-methyl-1H-pyrazole-3-carboxamide | 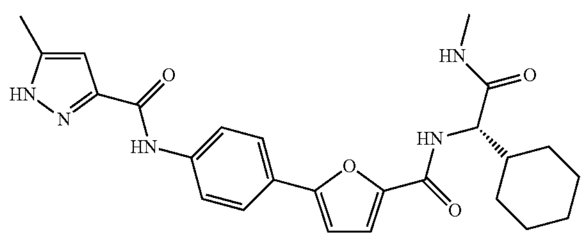 [SMILES: CNC(=O)[C@@H](NC(=O)c1ccc(-c2ccc(NC(=O)c3cc(C)[nH]n3)cc2)o1)C1CCCCC1] | 464.2 |
| N-[4-(5-{[(1S)-1-cyclohexyl-2-(methylamino)-2-oxoethyl]carbamoyl}furan-2-yl)phenyl]-1-methyl-1H-pyrazole-3-carboxamide | 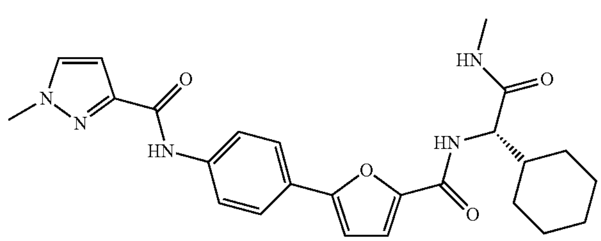 [SMILES: CNC(=O)[C@@H](NC(=O)c1ccc(-c2ccc(NC(=O)c3ccn(C)n3)cc2)o1)C1CCCCC1] | 464.2 |
| N-[4-(5-{[(1S)-1-cyclohexyl-2-(methylamino)-2-oxoethyl]carbamoyl}furan-2-yl)phenyl]-1-methyl-1H-pyrazole-4-carboxamide | 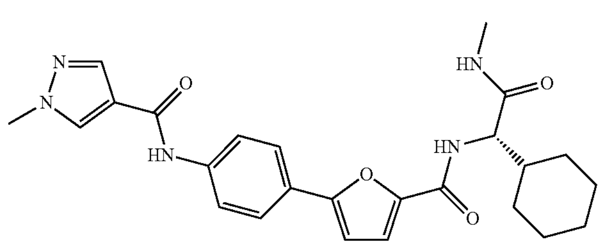 [SMILES: CNC(=O)[C@@H](NC(=O)c1ccc(-c2ccc(NC(=O)c3cnn(C)c3)cc2)o1)C1CCCCC1] | 464.2 |

TABLE IV-continued

| Name | Structure | LC/MS (M + H) |
|---|---|---|
| N-[4-(5-{[(1S)-1-cyclohexyl-2-(methylamino)-2-oxoethyl]carbamoyl}furan-2-yl)phenyl]imidazo[1,2-a]pyridine-2-carboxamide | | 500.2 |
| N-[4-(5-{[(1S)-1-cyclohexyl-2-(methylamino)-2-oxoethyl]carbamoyl}furan-2-yl)phenyl]-8-methyl-imidazo[1,2-a]pyridine-2-carboxamide | 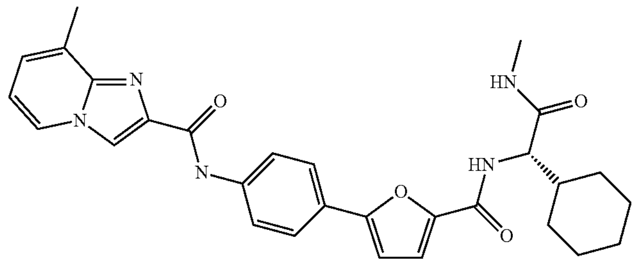 [SMILES: CNC(=O)[C@@H](NC(=O)c1ccc(-c2ccc(NC(=O)c3cn4cccc(C)c4n3)cc2)o1)C1CCCCC1] | 514.2 |
| N-[4-(5-{[(1S)-1-cyclohexyl-2-(methylamino)-2-oxoethyl]carbamoyl}furan-2-yl)phenyl]-7-methylimidazo[1,2-a]pyridine-2-carboxamide | 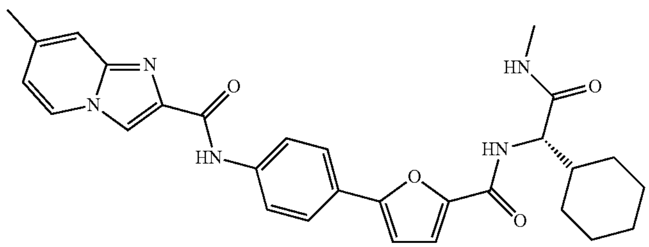 [SMILES: CNC(=O)[C@@H](NC(=O)c1ccc(-c2ccc(NC(=O)c3cn4ccc(C)cc4n3)cc2)o1)C1CCCCC1] | 514.2 |
| N-[4-(5-{[(1S)-1-cyclohexyl-2-(methylamino)-2-oxoethyl]carbamoyl}furan-2-yl)phenyl]-5-methylimidazo[1,2-a]pyridine-2-carboxamide | 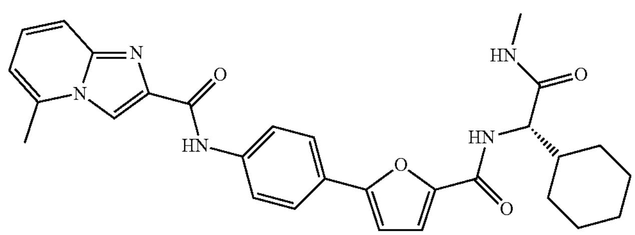 [SMILES: CNC(=O)[C@@H](NC(=O)c1ccc(-c2ccc(NC(=O)c3cn4c(C)cccc4n3)cc2)o1)C1CCCCC1] | 514.2 |
| 5-Cyano-N-[4-(5-{[(1S)-1-cyclohexyl-2-(methylamino)-2-oxoethyl]carbamoyl}furan-2-yl)phenyl]imidazo[1,2-a]pyridine-2-carboxamide | 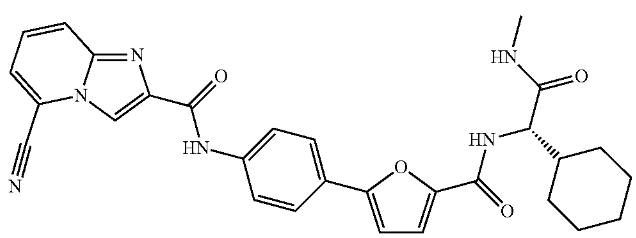 [SMILES: CNC(=O)[C@@H](NC(=O)c1ccc(-c2ccc(NC(=O)c3cn4c(C#N)cccc4n3)cc2)o1)C1CCCCC1] | 523.2 |
| Imidazo[1,2-a]pyridine-2,6-dicarboxylic acid 6-amide 2-[(4-{5-[((S)-cyclohexyl-methylcarbamoyl-methyl)-carbamoyl]-furan-2-yl}-phenyl)-amide] | 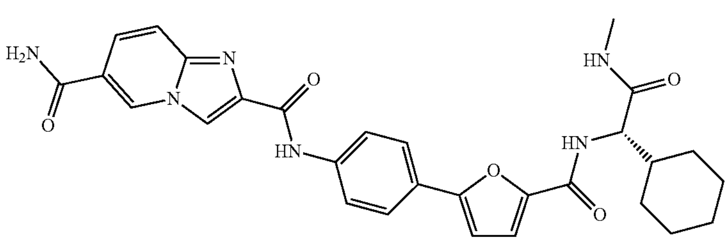 [SMILES: CNC(=O)[C@@H](NC(=O)c1ccc(-c2ccc(NC(=O)c3cn4cc(C(N)=O)ccc4n3)cc2)o1)C1CCCCC1] | 543.2 |

| Name | Structure | LC/MS (M + H) |
|---|---|---|
| N-[4-(5-{[(1S)-1-cyclohexyl-2-(methylamino)-2-oxoethyl]carbamoyl}furan-2-yl)phenyl]-1-benzofuran-2-carboxamide | 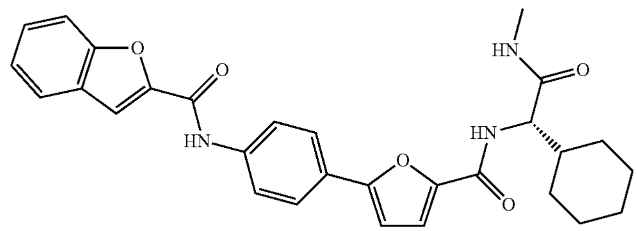 [SMILES: CNC(=O)[C@@H](NC(=O)c1ccc(-c2ccc(NC(=O)c3cc4ccccc4o3)cc2)o1)C1CCCCC1] | 500.1 |

EXAMPLE 3

N-(3-{5-[((S)-Cyclohexyl-methylcarbamoyl-methyl)-carbamoyl]-furan-2-yl}-benzyl)-2-fluoro-isonicotinamide

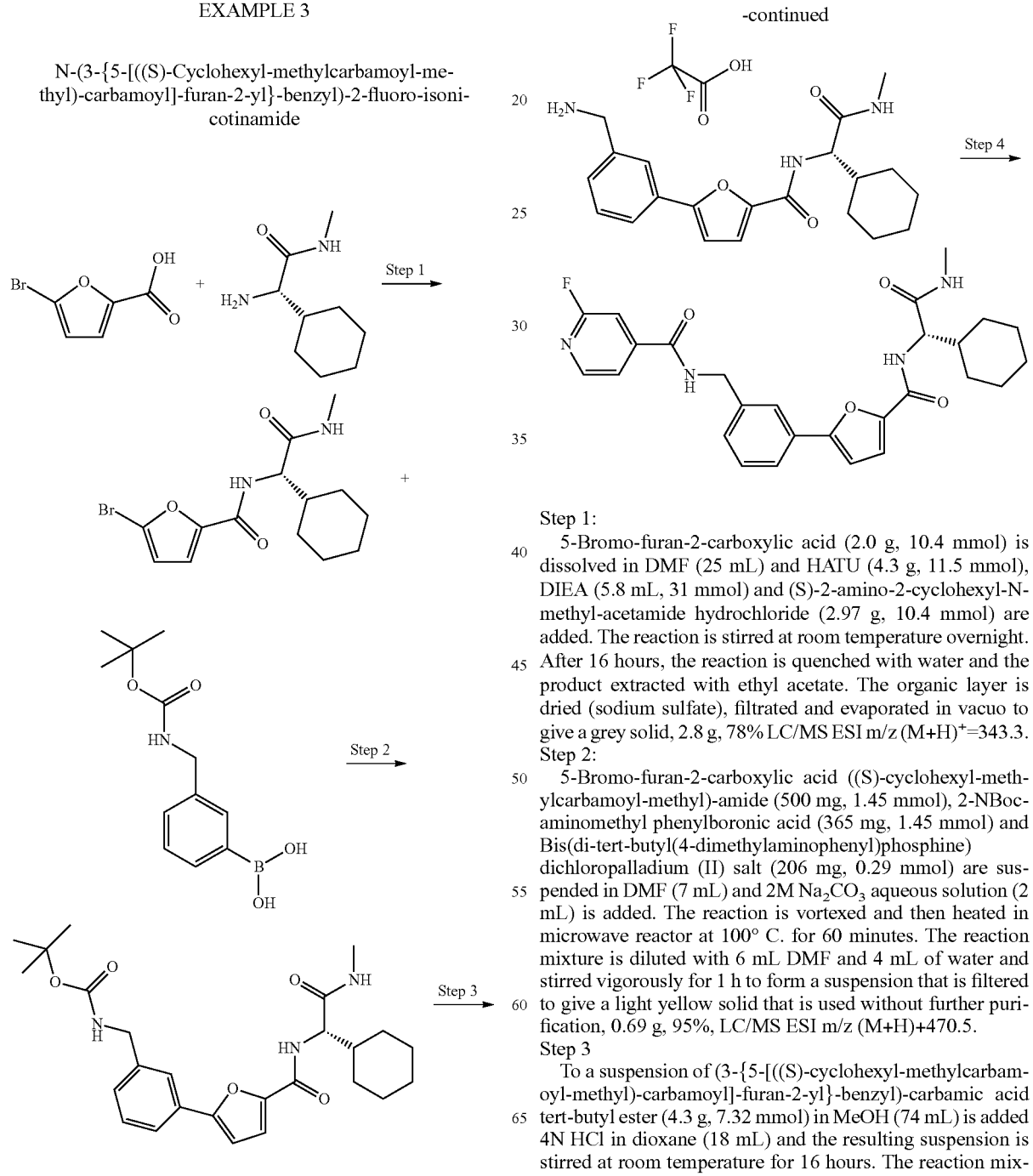

Step 1:

5-Bromo-furan-2-carboxylic acid (2.0 g, 10.4 mmol) is dissolved in DMF (25 mL) and HATU (4.3 g, 11.5 mmol), DIEA (5.8 mL, 31 mmol) and (S)-2-amino-2-cyclohexyl-N-methyl-acetamide hydrochloride (2.97 g, 10.4 mmol) are added. The reaction is stirred at room temperature overnight. After 16 hours, the reaction is quenched with water and the product extracted with ethyl acetate. The organic layer is dried (sodium sulfate), filtrated and evaporated in vacuo to give a grey solid, 2.8 g, 78% LC/MS ESI m/z (M+H)$^+$=343.3.

Step 2:

5-Bromo-furan-2-carboxylic acid ((S)-cyclohexyl-methylcarbamoyl-methyl)-amide (500 mg, 1.45 mmol), 2-NBoc-aminomethyl phenylboronic acid (365 mg, 1.45 mmol) and Bis(di-tert-butyl(4-dimethylaminophenyl)phosphine) dichloropalladium (II) salt (206 mg, 0.29 mmol) are suspended in DMF (7 mL) and 2M Na$_2$CO$_3$ aqueous solution (2 mL) is added. The reaction is vortexed and then heated in microwave reactor at 100° C. for 60 minutes. The reaction mixture is diluted with 6 mL DMF and 4 mL of water and stirred vigorously for 1 h to form a suspension that is filtered to give a light yellow solid that is used without further purification, 0.69 g, 95%, LC/MS ESI m/z (M+H)+470.5.

Step 3

To a suspension of (3-{5-[((S)-cyclohexyl-methylcarbamoyl-methyl)-carbamoyl]-furan-2-yl}-benzyl)-carbamic acid tert-butyl ester (4.3 g, 7.32 mmol) in MeOH (74 mL) is added 4N HCl in dioxane (18 mL) and the resulting suspension is stirred at room temperature for 16 hours. The reaction mixture is diluted with ethyl acetate and basified to pH 10 with saturated NaHCO₃ aqueous solution. The water layer is extracted with a copious amount of ethyl acetate. The combined organics are washed with water, brine, dried over MgSO₄, and concentrated in vacuo to give a bright yellow solid which is purified on silica to give the title compound as a off-white solid, 1.37 g, 50%, LC/MS ESI m/z (M+H)+ 370.5.

Step 4:

To a solution of 2-fluoro-isonicotinic acid (22 mg, 0.16 mmol) in DMF (1 mL) is added HATU (61 mg, 0.16 mmol) and Et₃N (0.044 mL, 0.3 mmol). After stirring at room temperature for 30 minutes, a solution of 5-(3-aminomethyl-phenyl)-furan-2-carboxylic acid ((S)-cyclohexyl-methylcarbamoyl-methyl)-amide trifluoroacetate salt (50 mg, 0.12 mmol) in DMF (1 mL) is added. The reaction is stirred for 2 hours, diluted with ethyl acetate and the organic layer washed with water and brine. The organic layer is evaporated in vacuo, and the resulting oil is purified by reverse phase HPLC to give the title compound as a solid, 21 mg, 41%, LC/MS ESI m/z (M+H)+493.5.

EXAMPLE 4

N-[(1S)-1-cyclohexyl-2-(methylamino)-2-oxoethyl]-5-(3-{[(propan-2-ylcarbamoyl)amino]methyl}phenyl)furan-2-carboxamide

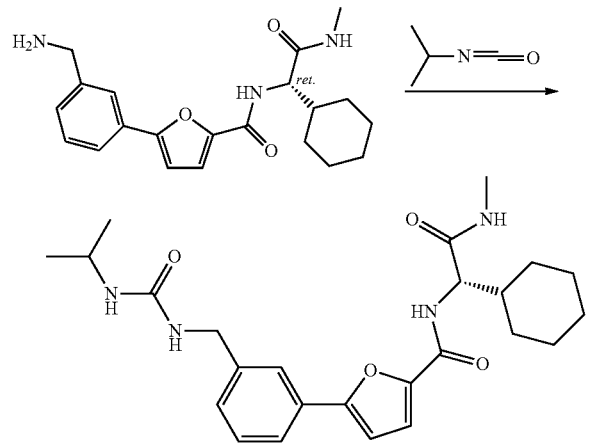

To a solution of 5-(3-aminomethyl-phenyl)-furan-2-carboxylic acid ((S)-cyclohexyl-methylcarbamoyl-methyl)-amide (20 mg, 0.05 mmol) in DMF (0.5 mL) is added 2-isocyanato-propane (5.8 µL, 0.06 mmol). After 2 h stirring at room temperature, the mixture evaporated in vacuo and purified on reverse phase HPLC. The product is obtained as a pale yellow solid, 16 mg, 63%, LC/MS ESI m/z (M+H)+=455.5.

EXAMPLE 5

2-methylpropyl [3-(5-{[(1S)-1-cyclohexyl-2-(methylamino)-2-oxoethyl]carbamoyl}furan-2-yl)benzyl]carbamate

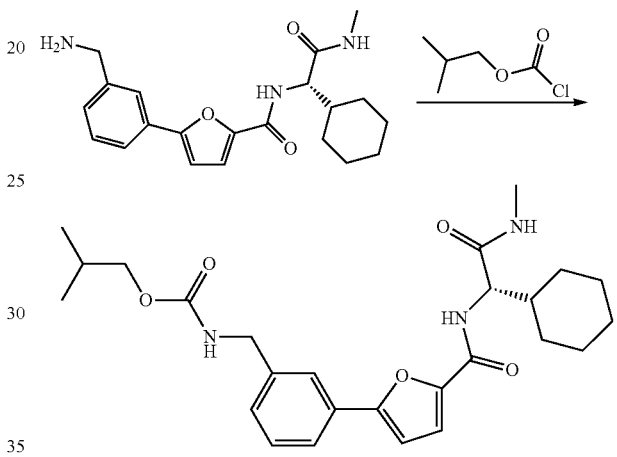

To a solution of 5-(3-aminomethyl-phenyl)-furan-2-carboxylic acid ((S)-cyclohexyl-methylcarbamoyl-methyl)-amide (37 mg, 0.10 mmol) in DMF (2.0 mL) is added 4-methylmorpholine (44 µL, 0.40 mmol) followed by isobutyl chloroformate (21 mg, 0.15 mmol). After stirring at room temperature for 12 hours, the mixture is evaporated in vacuo and the resulting oil purified on reverse phase HPLC to obtain a white solid, 26 mg, 54%, LC/MS ESI m/z (M+H)+=470.4.

The following compounds in Table V are made in an analogous manner to examples 3, 4, and 5:

TABLE V

| Name | Structure | LC/MS (M + H) |
|---|---|---|
| 5-{4-[(acetylamino)methyl]phenyl}-N-[(1S)-1-cyclohexyl-2-(methylamino)-2-oxoethyl]furan-2-carboxamide | 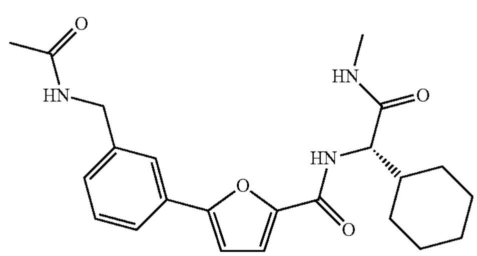 [SMILES: CNC(=O)[C@@H](NC(=O)c1ccc(-c2cccc(CNC(C)=O)c2)o1)C1CCCCC1] | 412.44 |

TABLE V-continued

| Name | Structure | LC/MS (M + H) |
|---|---|---|
| N-[3-(5-{[(1S)-1-cyclohexyl-2-(methylamino)-2-oxoethyl]carbamoyl}furan-2-yl)benzyl]-1-benzofuran-2-carboxamide | 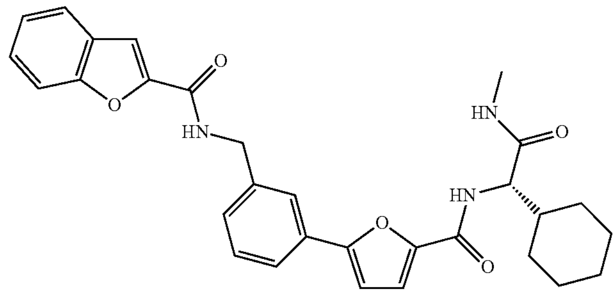 [SMILES: CNC(=O)[C@@H](NC(=O)c1ccc(-c2cccc(CNC(=O)c3cc4ccccc4o3)c2)o1)C1CCCCC1] | 514.47 |
| N-[3-(5-{[(1S)-1-cyclohexyl-2-(methylamino)-2-oxoethyl]carbamoyl}furan-2-yl)benzyl]imidazo[1,2-a]pyridine-2-carboxamide | 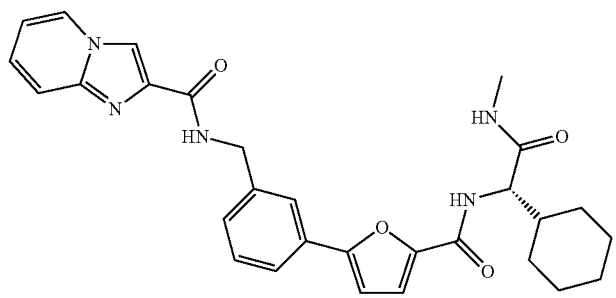 [SMILES: CNC(=O)[C@@H](NC(=O)c1ccc(-c2cccc(CNC(=O)c3cn4ccccc4n3)c2)o1)C1CCCCC1] | 514.48 |
| N-{[2-(5-{[(2S)-3-methyl-1-(methylamino)-l-oxobutan-2-yl]carbamoyl}furan-2-yl)pyridin-4-yl]methyl}-2-(trifluoromethyl)pyrimidine-4-carboxamide | 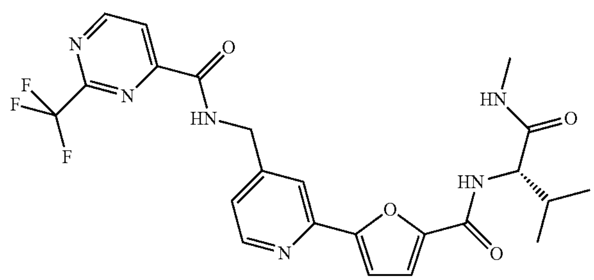 | 505.44 |
| N-{[2-(5-{[(1S)-1-cyclohexyl-2-(methylamino)-2-oxoethyl]carbamoyl}furan-2-yl)pyridin-4-yl]methyl}-6-methylpyridine-2-carboxamide | 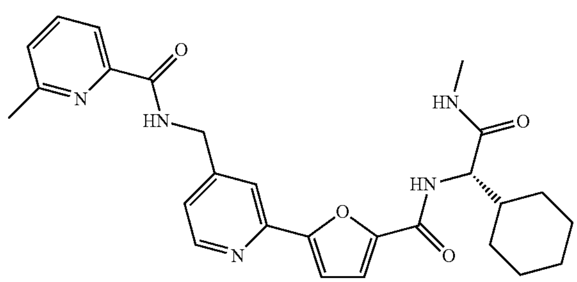 [SMILES: CNC(=O)[C@@H](NC(=O)c1ccc(-c2cc(CNC(=O)c3cccc(C)n3)ccn2)o1)C1CCCCC1] | 490.51 |
| N-{[2-(5-{[(1S)-1-cyclohexyl-2-(methylamino)-2-oxoethyl]carbamoyl}furan-2-yl)pyridin-4-yl]methyl}pyridine-2-carboxamide | 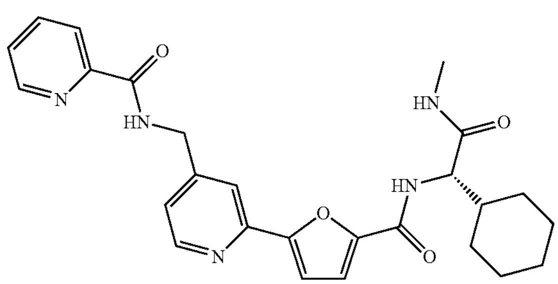 [SMILES: CNC(=O)[C@@H](NC(=O)c1ccc(-c2cc(CNC(=O)c3ccccn3)ccn2)o1)C1CCCCC1] | 476.49 |

TABLE V-continued

| Name | Structure | LC/MS (M + H) |
|---|---|---|
| N-{[2-(5-{[(1S)-1-cyclohexyl-2-(methylamino)-2-oxoethyl]carbamoyl}furan-2-yl)pyridin-4-yl]methyl}-6-fluoropyridine-2-carboxamide | 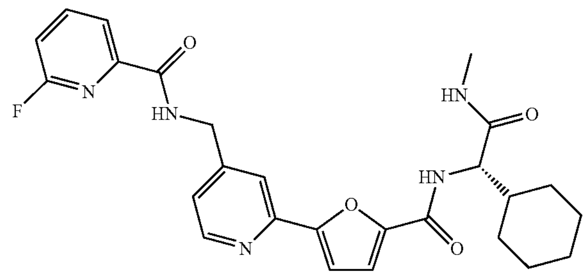 [SMILES: CNC(=O)[C@@H](NC(=O)c1ccc(-c2cc(CNC(=O)c3cccc(F)n3)ccn2)o1)C1CCCCC1] | 494.49 |
| N-{[2-(5-{[(1S)-1-cyclohexyl-2-(methylamino)-2-oxoethyl]carbamoyl}furan-2-yl)pyridin-4-yl]methyl}-1,5-dimethyl-1H-pyrazole-3-carboxamide | 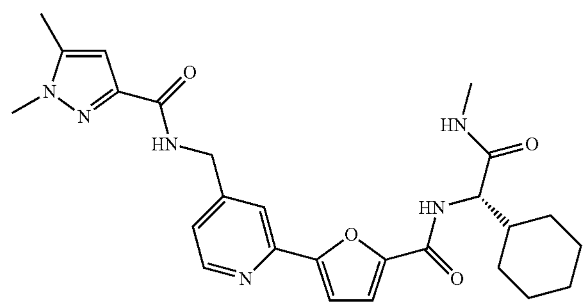 [SMILES: CNC(=O)[C@@H](NC(=O)c1ccc(-c2cc(CNC(=O)c3cc(C)n(C)n3)ccn2)o1)C1CCCCC1] | 493.52 |
| N-{[2-(5-{[(1S)-1-cyclohexyl-2-(methylamino)-2-oxoethyl]carbamoyl}furan-2-yl)pyridin-4-yl]methyl}-5-methylpyridine-3-carboxamide | 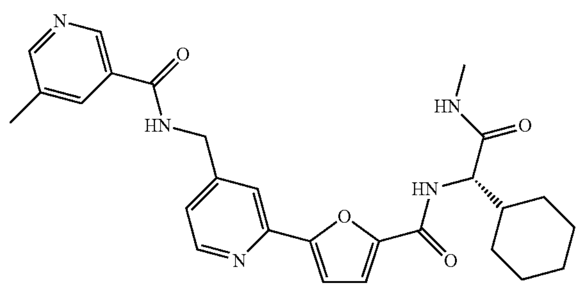 [SMILES: CNC(=O)[C@@H](NC(=O)c1ccc(-c2cc(CNC(=O)c3cncc(C)c3)ccn2)o1)C1CCCCC1] | 490.49 |
| N-{[2-(5-{[(1S)-1-cyclohexyl-2-(methylamino)-2-oxoethyl]carbamoyl}furan-2-yl)pyridin-4-yl]methyl}-4,5-dimethylfuran-2-carboxamide | 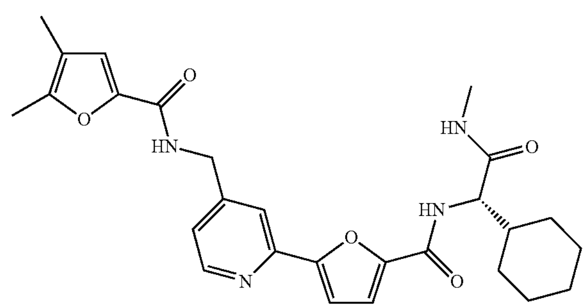 [SMILES: CNC(=O)[C@@H](NC(=O)c1ccc(-c2cc(CNC(=O)c3cc(C)c(C)o3)ccn2)o1)C1CCCCC1] | 493.51 |
| N-{[2-(5-{[(1S)-1-cyclohexyl-2-(methylamino)-2-oxoethyl]carbamoyl}furan-2-yl)pyridin-4-yl]methyl}-5-ethylfuran-2-carboxamide | 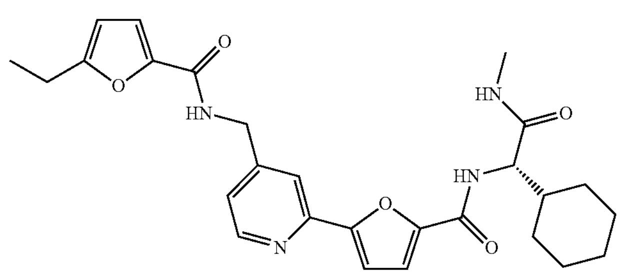 [SMILES: CCc1ccc(C(=O)NCc2ccnc(-c3ccc(C(=O)N[C@H](C(=O)NC)C4CCCCC4)o3)c2)o1] | 493.51 |

TABLE V-continued

| Name | Structure | LC/MS (M + H) |
|---|---|---|
| N-{[2-(5-{[(1S)-1-cyclohexyl-2-(methylamino)-2-oxoethyl]carbamoyl}furan-2-yl)pyridin-4-yl]methyl}-1-benzofuran-2-carboxamide | 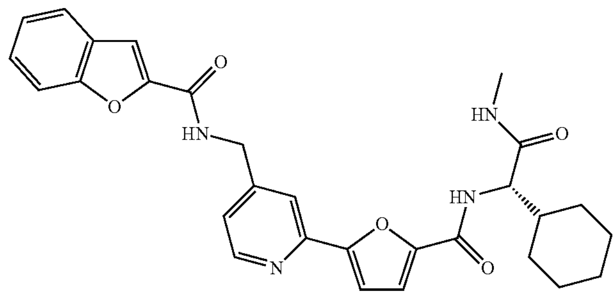 [SMILES: CNC(=O)[C@@H](NC(=O)c1ccc(-c2cc(CNC(=O)c3cc4ccccc4o3)ccn2)o1)C1CCCCC1] | 515.49 |
| 6-Methyl-N-{[2-(5-{[(2S)-3-methyl-1-(methylamino)-1-oxobutan-2-yl]carbamoyl}furan-2-yl)pyridin-4-yl]methyl}pyridine-2-carboxamide | 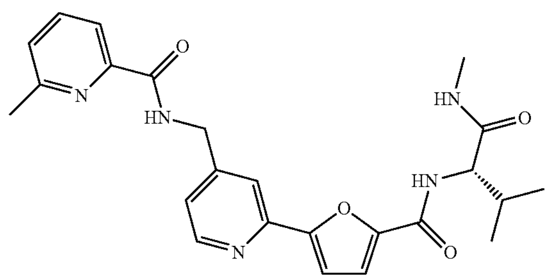 [SMILES: CNC(=O)[C@@H](NC(=O)c1ccc(-c2cc(CNC(=O)c3cccc(C)n3)ccn2)o1)C(C)C] | 450.47 |
| N-{[2-(5-{[(2S)-3-methyl-1-(methylamino)-1-oxobutan-2-yl]carbamoyl}furan-2-yl)pyridin-4-yl]methyl}pyridine-2-carboxamide | 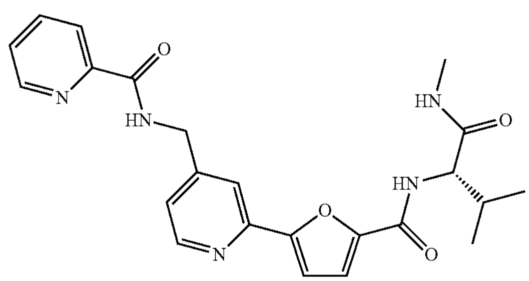 [SMILES: CNC(=O)[C@@H](NC(=O)c1ccc(-c2cc(CNC(=O)c3ccccn3)ccn2)o1)C(C)C] | 436.45 |
| 6-Fluoro-N-{[2-(5-{[(2S)-3-methyl-1-(methylamino)-1-oxobutan-2-yl]carbamoyl}furan-2-yl)pyridin-4-yl]methyl}pyridine-2-carboxamide | 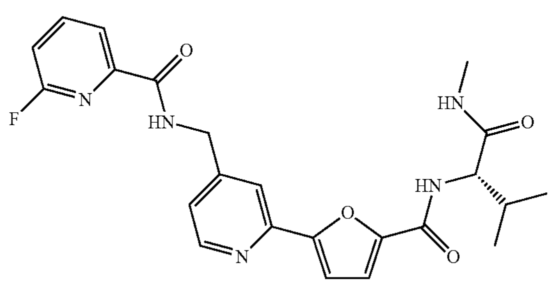 [SMILES: CNC(=O)[C@@H](NC(=O)c1ccc(-c2cc(CNC(=O)c3cccc(F)n3)ccn2)o1)C(C)C] | 454.51 |
| 5-Methyl-N-{[2-(5-{[(2S)-3-methyl-1-(methylamino)-1-oxobutan-2-yl]carbamoyl}furan-2-yl)pyridin-4-yl]methyl}pyridine-3-carboxamide | 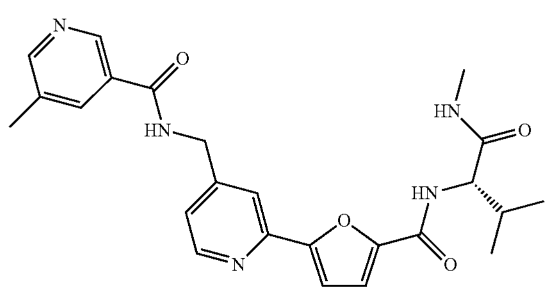 [SMILES: CNC(=O)[C@@H](NC(=O)c1ccc(-c2cc(CNC(=O)c3cncc(C)c3)ccn2)o1)C(C)C] | 450.52 |

TABLE V-continued

| Name | Structure | LC/MS (M + H) |
|---|---|---|
| N-{[2-(5-{[(1S)-1-cyclohexyl-2-(methylamino)-2-oxoethyl]carbamoyl}furan-2-yl)pyridin-4-yl]methyl}-2-(trifluoromethyl)pyrimidine-4-carboxamide | 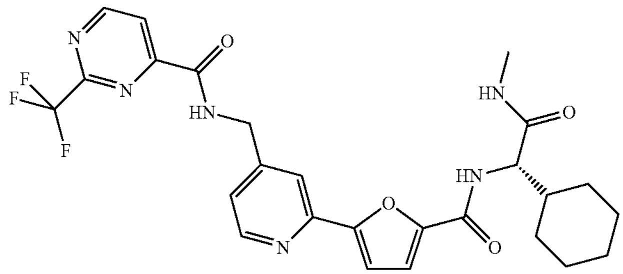 [SMILES: CNC(=O)[C@@H](NC(=O)c1ccc(-c2cc(CNC(=O)c3ccnc(C(F)(F)F)n3)ccn2)o1)C1CCCCC1] | 545.53 |
| 1,5-Dimethyl-1H-pyrazole-3-carboxylic acid {2-[5-((S)-2-methyl-1-methylcarbamoyl-propylcarbamoyl)-furan-2-yl]-pyridin-4-ylmethyl}-amide | 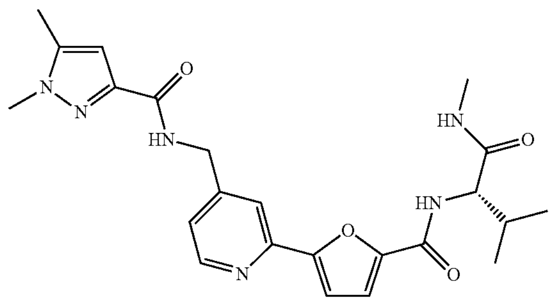 [SMILES: CNC(=O)[C@@H](NC(=O)c1ccc(-c2cc(CNC(=O)c3cc(C)n(C)n3)ccn2)o1)C(C)C] | 453.57 |
| 4,5-Dimethyl-furan-2-carboxylic acid {2-[5-((S)-2-methyl-1-methylcarbamoyl-propylcarbamoyl)-furan-2-yl]-pyridin-4-ylmethyl}-amide | 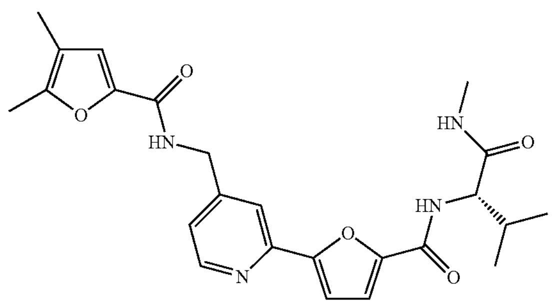 [SMILES: CNC(=O)[C@@H](NC(=O)c1ccc(-c2cc(CNC(=O)c3cc(C)c(C)o3)ccn2)o1)C(C)C] | 453.56 |
| 5-Ethyl-furan-2-carboxylic acid {2-[5-((S)-2-methyl-1-methylcarbamoyl-propylcarbamoyl)-furan-2-yl]-pyridin-4-ylmethyl}-amide | 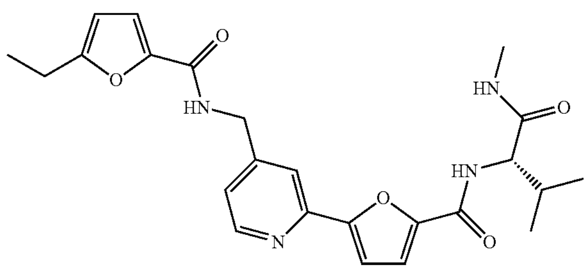 [SMILES: CCc1ccc(C(=O)NCc2ccnc(-c3ccc(C(=O)N[C@H](C(=O)NC)C(C)C)o3)c2)o1] | 453.55 |
| N-[3-(5-{[(1S)-1-cyclohexyl-2-(methylamino)-2-oxoethyl]carbamoyl}furan-2-yl)benzyl]pyrimidine-4-carboxamide | 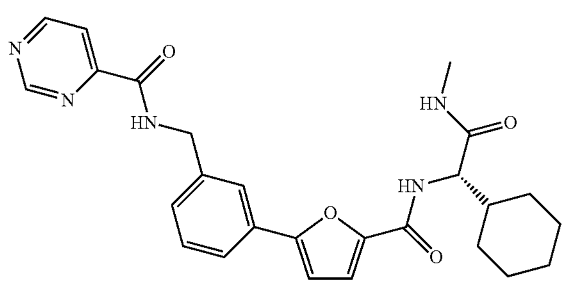 | 476.52 |

TABLE V-continued

| Name | Structure | LC/MS (M + H) |
|---|---|---|
| N-{[2-(5-{[(1S)-2-(methylamino)-2-oxo-1-(tetrahydro-2H-pyran-4-yl)ethyl]carbamoyl}furan-2-yl)pyridin-4-yl]methyl}-2-(trifluoromethyl)pyrimidine-4-carboxamide | 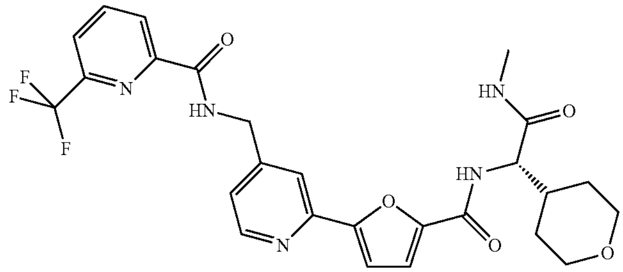 [SMILES: CNC(=O)[C@@H](NC(=O)c1ccc(-c2cc(CNC(=O)c3cccc(C(F)(F)F)n3)ccn2)o1)C1CCOCC1] | 547.52 |
| N-{[2-(5-{[(1S)-1-cyclohexyl-2-(methylamino)-2-oxoethyl]carbamoyl}furan-2-yl)pyridin-4-yl]methyl}-6-(trifluoromethyl)pyridine-2-carboxamide | 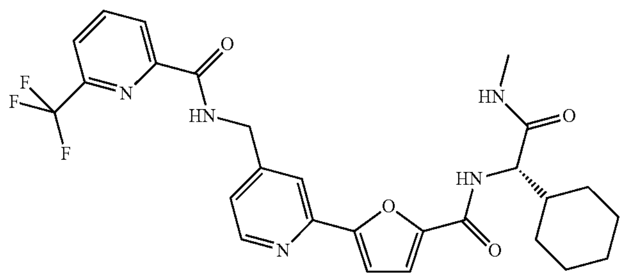 [SMILES: CNC(=O)[C@@H](NC(=O)c1ccc(-c2cc(CNC(=O)c3cccc(C(F)(F)F)n3)ccn2)o1)C1CCCCC1] | 544.56 |
| N-{[2-(5-{[(2S)-3-methyl-1-(methylamino)-1-oxobutan-2-yl]carbamoyl}furan-2-yl)pyridin-4-yl]methyl}-6-(trifluoromethyl)pyridine-2-carboxamide | 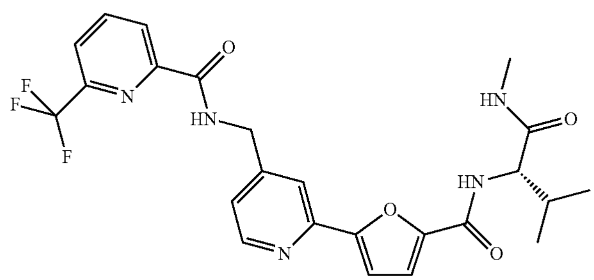 [SMILES: CNC(=O)[C@@H](NC(=O)c1ccc(-c2cc(CNC(=O)c3cccc(C(F)(F)F)n3)ccn2)o1)C(C)C] | 504.51 |
| N-[3-(5-{[(1S)-1-cyclohexyl-2-(methylamino)-2-oxoethyl]carbamoyl}furan-2-yl)benzyl]-6-(trifluoromethyl)pyridine-2-carboxamide | 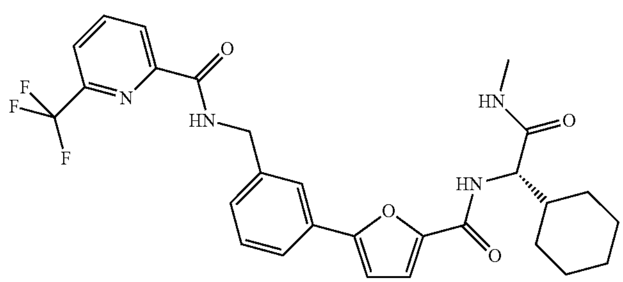 [SMILES: CNC(=O)[C@@H](NC(=O)c1ccc(-c2cccc(CNC(=O)c3cccc(C(F)(F)F)n3)c2)o1)C1CCCCC1] | 543.54 |
| 2-Chloro-N-[3-(5-{[(1S)-1-cyclohexyl-2-(methylamino)-2-oxoethyl]carbamoyl}furan-2-yl)benzyl]pyrimidine-4-carboxamide | 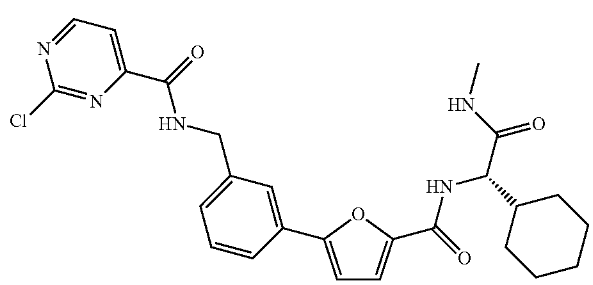 [SMILES: CNC(=O)[C@@H](NC(=O)c1ccc(-c2cccc(CNC(=O)c3ccnc(Cl)n3)c2)o1)C1CCCCC1] | 510.49 |

TABLE V-continued

| Name | Structure | LC/MS (M + H) |
|---|---|---|
| 2-Chloro-N-[3-(5-{[(1S)-1-cyclohexyl-2-(methylamino)-2-oxoethyl]carbamoyl}furan-2-yl)benzyl]pyridine-4-carboxamide | 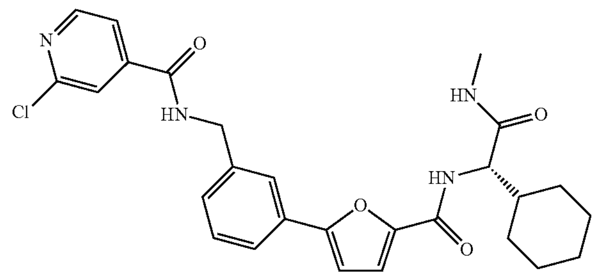 [SMILES: CNC(=O)[C@@H](NC(=O)c1ccc(-c2cccc(CNC(=O)c3ccnc(Cl)c3)c2)o1)C1CCCCC1] | 509.49 |
| 5-(3-{[(tert-Butylcarbamoyl)amino]methyl}phenyl)-N-[(1S)-1-cyclohexyl-2-(methylamino)-2-oxoethyl]furan-2-carboxamide | 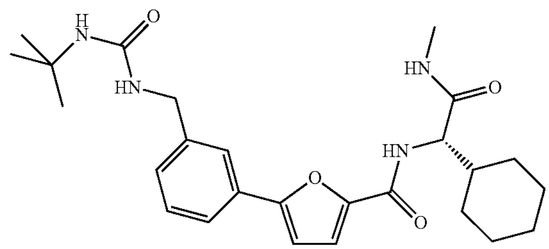 [SMILES: CNC(=O)[C@@H](NC(=O)c1ccc(-c2cccc(CNC(=O)NC(C)(C)C)c2)o1)C1CCCCC1] | 469.53 |
| N-[(1S)-1-cyclohexyl-2-(methylamino)-2-oxoethyl]-5-{4-[(pyridin-4-ylmethyl)carbamoyl]phenyl}furan-2-carboxamide | 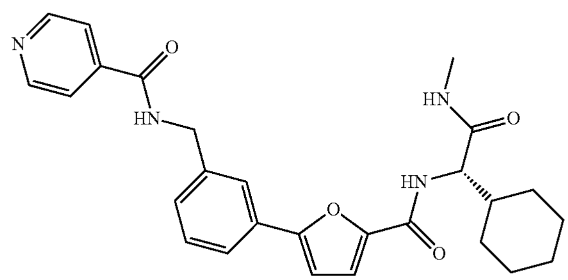 [SMILES: CNC(=O)[C@@H](NC(=O)c1ccc(-c2cccc(CNC(=O)c3ccncc3)c2)o1)C1CCCCC1] | 475.48 |
| N-[3-(5-{[(1S)-1-cyclohexyl-2-(methylamino)-2-oxoethyl]carbamoyl}furan-2-yl)benzyl]-N'-methylpyrimidine-4,6-dicarboxamide | 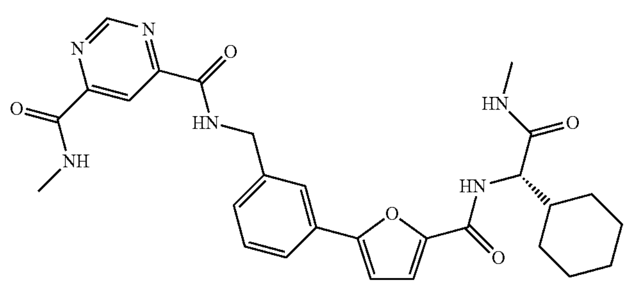 [SMILES: CNC(=O)c1cc(C(=O)NCc2cccc(-c3ccc(C(=O)N[C@H](C(=O)NC)C4CCCCC4)o3)c2)ncn1] | 533.6 |
| N-[3-(5-{[(1S)-1-cyclohexyl-2-(methylamino)-2-oxoethyl]carbamoyl}furan-2-yl)benzyl]-1-methyl-1H-imidazole-5-carboxamide | 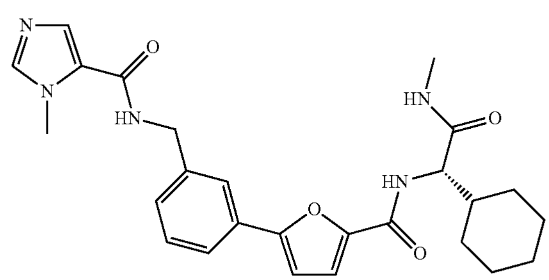 [SMILES: CNC(=O)[C@@H](NC(=O)c1ccc(-c2cccc(CNC(=O)c3cncn3C)c2)o1)C1CCCCC1] | 478.36 |

TABLE V-continued

| Name | Structure | LC/MS (M + H) |
|---|---|---|
| N-[3-(5-{[(1S)-1-cyclohexyl-2-(methylamino)-2-oxoethyl]carbamoyl}furan-2-yl)benzyl]-6-methylpyridine-2-carboxamide | 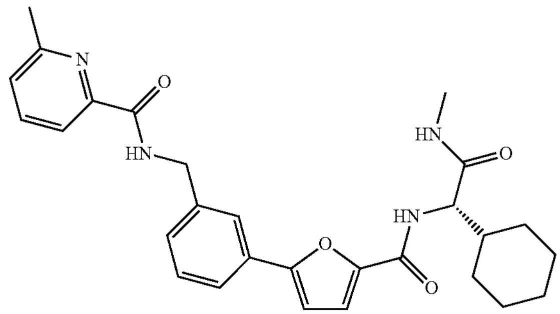 [SMILES: CNC(=O)[C@@H](NC(=O)c1ccc(-c2cccc(CNC(=O)c3cccc(C)n3)c2)o1)C1CCCCC1] | 489.35 |
| N-[3-(5-{[(1S)-1-cyclohexyl-2-(methylamino)-2-oxoethyl]carbamoyl}furan-2-yl)benzyl]-5-methylpyridine-3-carboxamide | 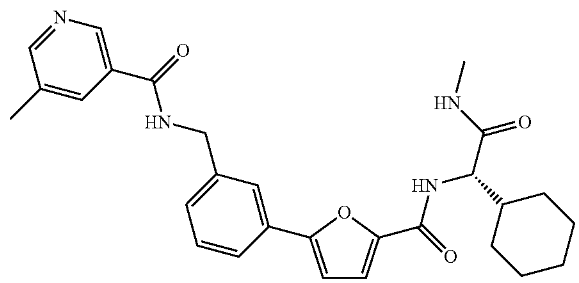 [SMILES: CNC(=O)[C@@H](NC(=O)c1ccc(-c2cccc(CNC(=O)c3cncc(C)c3)c2)o1)C1CCCCC1] | 489.37 |
| N-[3-(5-{[(1S)-1-cyclohexyl-2-(methylamino)-2-oxoethyl]carbamoyl}furan-2-yl)benzyl]-1-methyl-1H-pyrazole-5-carboxamide | 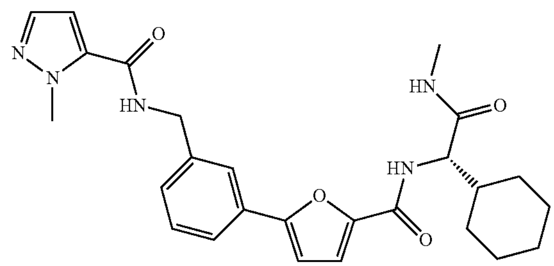 [SMILES: CNC(=O)[C@@H](NC(=O)c1ccc(-c2cccc(CNC(=O)c3ccnn3C)c2)o1)C1CCCCC1] | 478.34 |
| N-[3-(5-{[(1S)-1-cyclohexyl-2-(methylamino)-2-oxoethyl]carbamoyl}furan-2-yl)benzyl]-3-methylfuran-2-carboxamide | 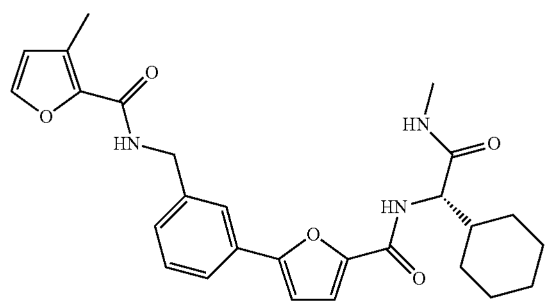 [SMILES: CNC(=O)[C@@H](NC(=O)c1ccc(-c2cccc(CNC(=O)c3occc3C)c2)o1)C1CCCCC1] | 478.33 |
| N-[(1S)-1-cyclohexyl-2-(methylamino)-2-oxoethyl]-5-[3-({[(2-methylfuran-3-yl)carbonyl]amino}methyl)phenyl]furan-2-carboxamide | 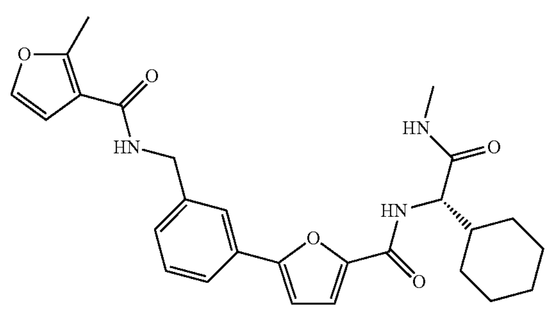 [SMILES: CNC(=O)[C@@H](NC(=O)c1ccc(-c2cccc(CNC(=O)c3ccoc3C)c2)o1)C1CCCCC1] | 478.31 |

TABLE V-continued

| Name | Structure | LC/MS (M + H) |
|---|---|---|
| N-[3-(5-{[(1S)-1-cyclohexyl-2-(methylamino)-2-oxoethyl]carbamoyl}furan-2-yl)benzyl]-5-methylfuran-2-carboxamide | 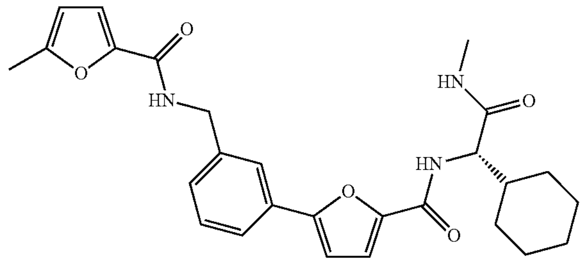 [SMILES: CNC(=O)[C@@H](NC(=O)c1ccc(-c2cccc(CNC(=O)c3ccc(C)o3)c2)o1)C1CCCCC1] | 478.31 |
| N-[3-(5-{[(1S)-1-cyclohexyl-2-(methylamino)-2-oxoethyl]carbamoyl}furan-2-yl)benzyl]-3-methyl-1H-pyrazole-5-carboxamide | 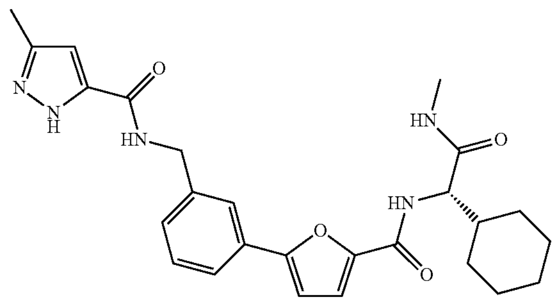 [SMILES: CNC(=O)[C@@H](NC(=O)c1ccc(-c2cccc(CNC(=O)c3cc(C)n[nH]3)c2)o1)C1CCCCC1] | 478.34 |
| N-[3-(5-{[(1S)-1-cyclohexyl-2-(methylamino)-2-oxoethyl]carbamoyl}furan-2-yl)benzyl]-1-methyl-1H-pyrazole-3-carboxamide | 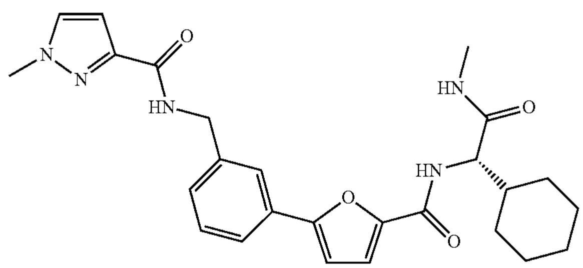 [SMILES: CNC(=O)[C@@H](NC(=O)c1ccc(-c2cccc(CNC(=O)c3ccn(C)n3)c2)o1)C1CCCCC1] | 478.33 |
| N-[3-(5-{[(1S)-1-cyclohexyl-2-(methylamino)-2-oxoethyl]carbamoyl}furan-2-yl)benzyl]-1-methyl-1H-pyrazole-4-carboxamide | 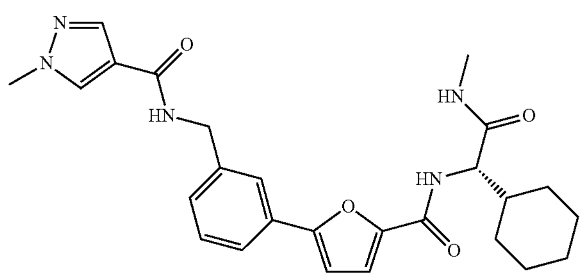 [SMILES: CNC(=O)[C@@H](NC(=O)c1ccc(-c2cccc(CNC(=O)c3cnn(C)c3)c2)o1)C1CCCCC1] | 478.33 |
| N-[(1S)-1-cyclohexyl-2-(methylamino)-2-oxoethyl]-5-{3-[(propanoylamino)methyl]phenyl}furan-2-carboxamide | 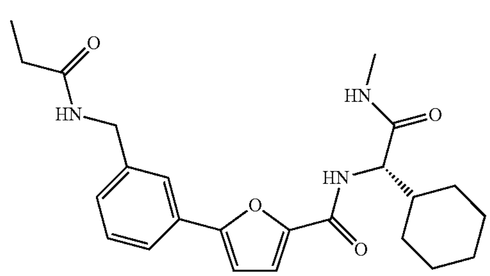 [SMILES: CCC(=O)NCc1cccc(-c2ccc(C(=O)N[C@H](C(=O)NC)C3CCCCC3)o2)c1] | 426.28 |

TABLE V-continued

| Name | Structure | LC/MS (M + H) |
|---|---|---|
| N-[(1S)-1-cyclohexyl-2-(methylamino)-2-oxoethyl]-5-(3-{[(2-methylpropanoyl)amino]methyl}phenyl)furan-2-carboxamide | 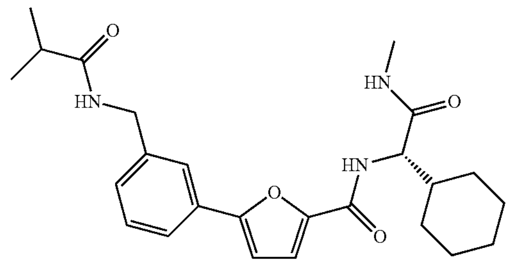 [SMILES: CNC(=O)[C@@H](NC(=O)c1ccc(-c2cccc(CNC(=O)C(C)C)c2)o1)C1CCCCC1] | 440.31 |
| N-[(1S)-1-cyclohexyl-2-(methylamino)-2-oxoethyl]-5-(3-{[(cyclopropylcarbonyl)amino]methyl}phenyl)furan-2-carboxamide | 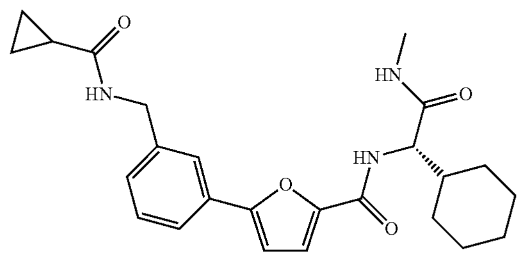 [SMILES: CNC(=O)[C@@H](NC(=O)c1ccc(-c2cccc(CNC(=O)C3CC3)c2)o1)C1CCCCC1] | 438.28 |
| N-[3-(5-{[(1S)-1-cyclohexyl-2-(methylamino)-2-oxoethyl]carbamoyl}furan-2-yl)benzyl]pyridine-2-carboxamide | 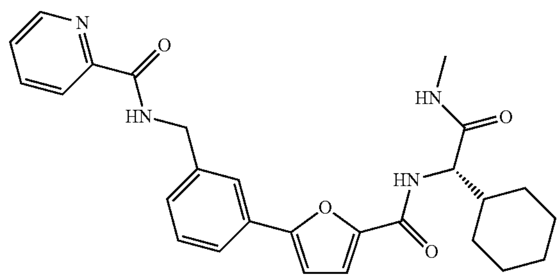 [SMILES: CNC(=O)[C@@H](NC(=O)c1ccc(-c2cccc(CNC(=O)c3ccccn3)c2)o1)C1CCCCC1] | 475.33 |
| N-[3-(5-{[(1S)-1-cyclohexyl-2-(methylamino)-2-oxoethyl]carbamoyl}furan-2-yl)benzyl]-3-methylpyridine-2-carboxamide | 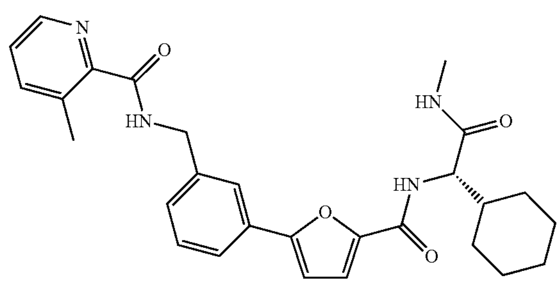 [SMILES: CNC(=O)[C@@H](NC(=O)c1ccc(-c2cccc(CNC(=O)c3ncccc3C)c2)o1)C1CCCCC1] | 489.38 |
| N-[3-(5-{[(1S)-1-cyclohexyl-2-(methylamino)-2-oxoethyl]carbamoyl}furan-2-yl)benzyl]-4-ethylpyridine-2-carboxamide | 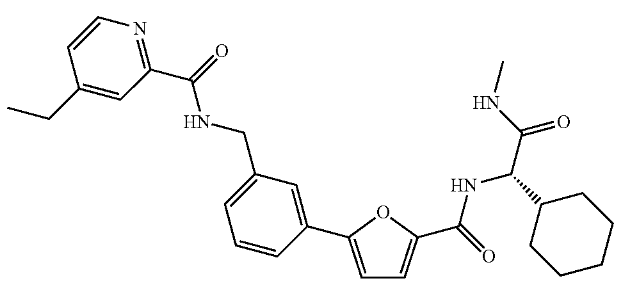 [SMILES: CCc1ccnc(C(=O)NCc2cccc(-c3ccc(C(=O)N[C@H](C(=O)NC)C4CCCCC4)o3)c2)c1] | 503.42 |

TABLE V-continued

| Name | Structure | LC/MS (M + H) |
|---|---|---|
| N-[(1S)-1-cyclohexyl-2-(methylamino)-2-oxoethyl]-5-(3-{[(furan-2-ylcarbonyl)amino]methyl}phenyl)furan-2-carboxamide | 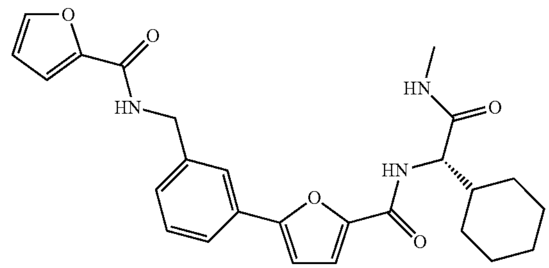 [SMILES: CNC(=O)[C@@H](NC(=O)c1ccc(-c2cccc(CNC(=O)c3ccco3)c2)o1)C1CCCCC1] | 464.27 |
| N-[3-(5-{[(1S)-1-cyclohexyl-2-(methylamino)-2-oxoethyl]carbamoyl}furan-2-yl)benzyl]-1-methyl-1H-imidazole-2-carboxamide | 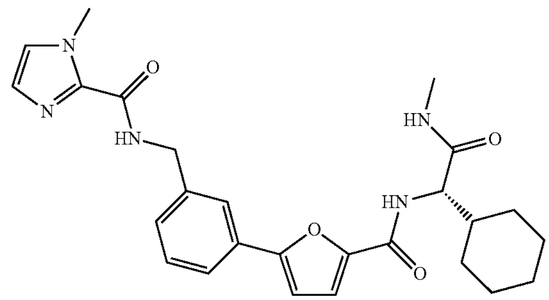 [SMILES: CNC(=O)[C@@H](NC(=O)c1ccc(-c2cccc(CNC(=O)c3nccn3C)c2)o1)C1CCCCC1] | 478.37 |
| N-[3-(5-{[(1S)-1-cyclohexyl-2-(methylamino)-2-oxoethyl]carbamoyl}furan-2-yl)benzyl]-2-(trifluoromethyl)pyrimidine-4-carboxamide | 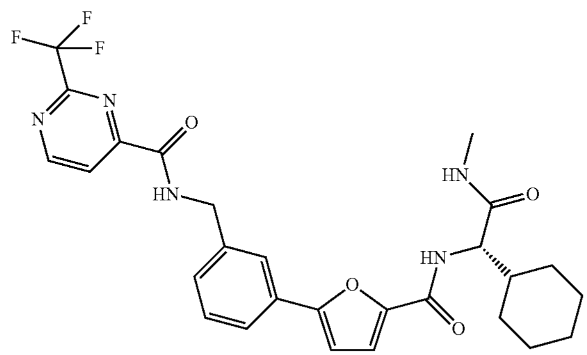 | 544.29 |
| N-[3-(5-{[(1S)-1-cyclohexyl-2-(methylamino)-2-oxoethyl]carbamoyl}furan-2-yl)benzyl]-7-methylimidazo[1,2-a]pyridine-2-carboxamide | 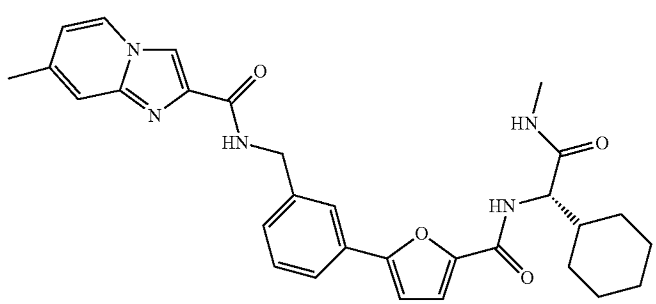 [SMILES: CNC(=O)[C@@H](NC(=O)c1ccc(-c2cccc(CNC(=O)c3cn4ccc(C)cc4n3)c2)o1)C1CCCCC1] | 528.38 |
| N-[3-(5-{[(1S)-1-cyclohexyl-2-(methylamino)-2-oxoethyl]carbamoyl}furan-2-yl)benzyl]-5-methylimidazo[1,2-a]pyridine-2-carboxamide | 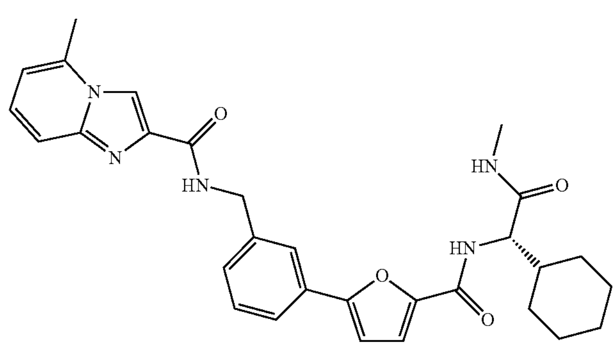 [SMILES: CNC(=O)[C@@H](NC(=O)c1ccc(-c2cccc(CNC(=O)c3cn4c(C)cccc4n3)c2)o1)C1CCCCC1] | 528.23 |

TABLE V-continued

| Name | Structure | LC/MS (M + H) |
|---|---|---|
| N-[(1S)-1-cyclohexyl-2-(methylamino)-2-oxoethyl]-5-[3-({[(4,5-dimethylthiophen-2-yl)carbonyl]amino}methyl)phenyl]furan-2-carboxamide | 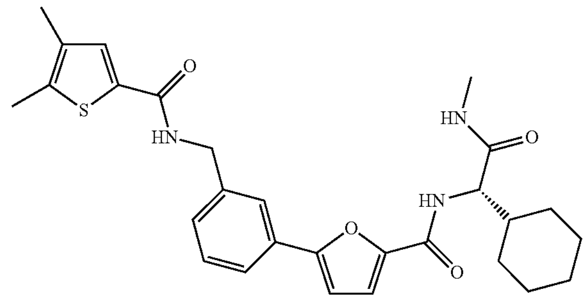 [SMILES: CNC(=O)[C@@H](NC(=O)c1ccc(-c2cccc(CNC(=O)c3cc(C)c(C)s3)c2)o1)C1CCCCC1] | 508.32 |
| N-[3-(5-{[(1S)-1-cyclohexyl-2-(methylamino)-2-oxoethyl]carbamoyl}furan-2-yl)benzyl]-1,5-dimethyl-1H-pyrazole-3-carboxamide | 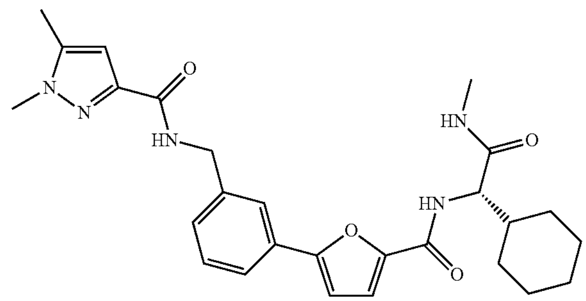 [SMILES: CNC(=O)[C@@H](NC(=O)c1ccc(-c2cccc(CNC(=O)c3cc(C)n(C)n3)c2)o1)C1CCCCC1] | 492.38 |
| 2-Methoxyethyl [3-(5-{[(1S)-1-cyclohexyl-2-(methylamino)-2-oxoethyl]carbamoyl}furan-2-yl)benzyl]carbamate | 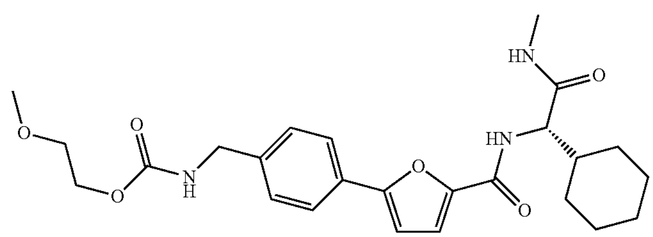 [SMILES: CNC(=O)[C@@H](NC(=O)c1ccc(-c2ccc(CNC(=O)OCCOC)cc2)o1)C1CCCCC1] | 472.31 |
| Benzyl [3-(5-{[(1S)-1-cyclohexyl-2-(methylamino)-2-oxoethyl]carbamoyl}furan-2-yl)benzyl]carbamate | 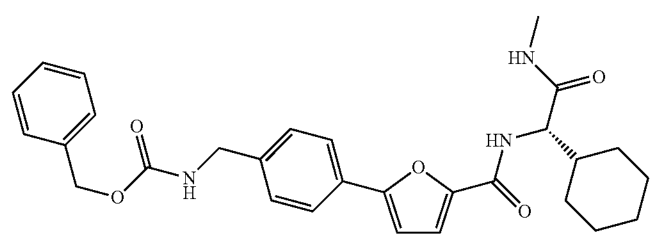 [SMILES: CNC(=O)[C@@H](NC(=O)c1ccc(-c2ccc(CNC(=O)OCc3ccccc3)cc2)o1)C1CCCCC1] | 504.37 |
| N-[4-(5-{[(1S)-1-cyclohexyl-2-(methylamino)-2-oxoethyl]carbamoyl}furan-2-yl)benzyl]-4,5-dimethylfuran-2-carboxamide | 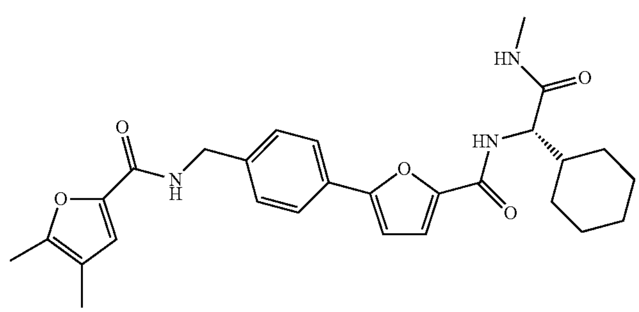 [SMILES: CNC(=O)[C@@H](NC(=O)c1ccc(-c2ccc(CNC(=O)c3cc(C)c(C)o3)cc2)o1)C1CCCCC1] | 492.32 |

TABLE V-continued

| Name | Structure | LC/MS (M + H) |
|---|---|---|
| N-[4-(5-{[(1S)-1-cyclohexyl-2-(methylamino)-2-oxoethyl]carbamoyl}furan-2-yl)benzyl]-1-methyl-1H-imidazole-5-carboxamide | 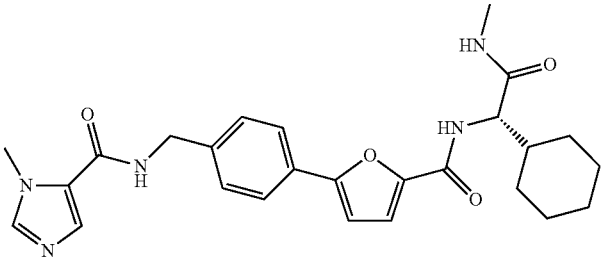 [SMILES: CNC(=O)[C@@H](NC(=O)c1ccc(-c2ccc(CNC(=O)c3cncn3C)cc2)o1)C1CCCCC1] | 478.34 |
| N-[4-(5-{[(1S)-1-cyclohexyl-2-(methylamino)-2-oxoethyl]carbamoyl}furan-2-yl)benzyl]-6-methylpyridine-2-carboxamide | 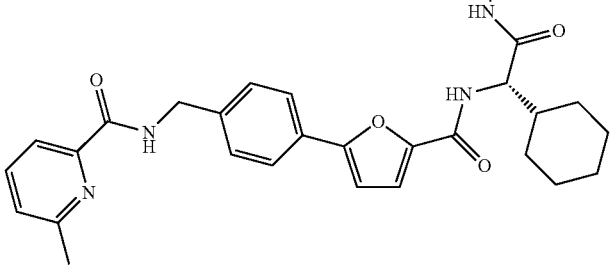 | 489.37 |
| N-[4-(5-{[(1S)-1-cyclohexyl-2-(methylamino)-2-oxoethyl]carbamoyl}furan-2-yl)benzyl]-5-methylpyridine-3-carboxamide | 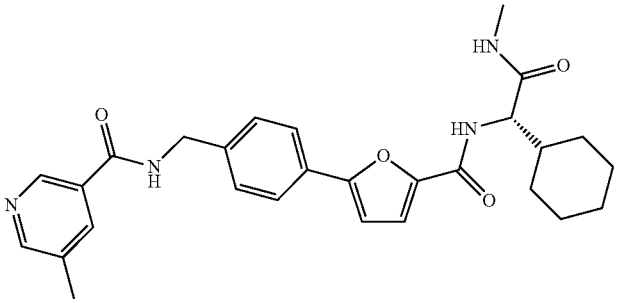 [SMILES: CNC(=O)[C@@H](NC(=O)c1ccc(-c2ccc(CNC(=O)c3cncc(C)c3)cc2)o1)C1CCCCC1] | 489.37 |
| N-[4-(5-{[(1S)-1-cyclohexyl-2-(methylamino)-2-oxoethyl]carbamoyl}furan-2-yl)benzyl]-1-methyl-1H-pyrazole-5-carboxamide | 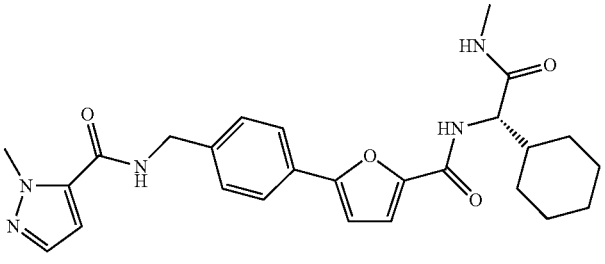 [SMILES: CNC(=O)[C@@H](NC(=O)c1ccc(-c2ccc(CNC(=O)c3ccnn3C)cc2)o1)C1CCCCC1] | 478.34 |
| N-[4-(5-{[(1S)-1-cyclohexyl-2-(methylamino)-2-oxoethyl]carbamoyl}furan-2-yl)benzyl]-3-methylfuran-2-carboxamide | 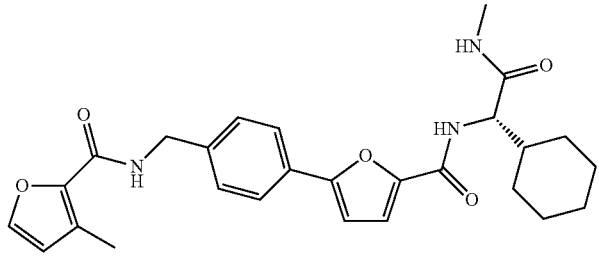 [SMILES: CNC(=O)[C@@H](NC(=O)c1ccc(-c2ccc(CNC(=O)c3occc3C)cc2)o1)C1CCCCC1] | 478.3 |

TABLE V-continued

| Name | Structure | LC/MS (M + H) |
|---|---|---|
| N-[(1S)-1-cyclohexyl-2-(methylamino)-2-oxoethyl]-5-[4-({[(2-methylfuran-3-yl)carbonyl]amino}methyl)phenyl]furan-2-carboxamide | 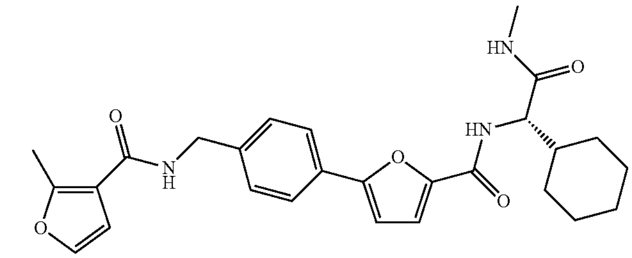 [SMILES: CNC(=O)[C@@H](NC(=O)c1ccc(-c2ccc(CNC(=O)c3ccoc3C)cc2)o1)C1CCCCC1] | 478.32 |
| N-[4-(5-{[(1S)-1-cyclohexyl-2-(methylamino)-2-oxoethyl]carbamoyl}furan-2-yl)benzyl]-5-methylfuran-2-carboxamide | 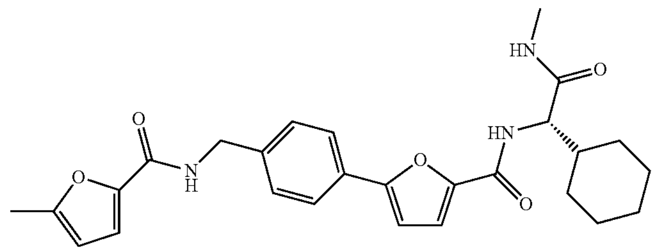 [SMILES: CNC(=O)[C@@H](NC(=O)c1ccc(-c2ccc(CNC(=O)c3ccc(C)o3)cc2)o1)C1CCCCC1] | 478.29 |
| N-[4-(5-{[(1S)-1-cyclohexyl-2-(methylamino)-2-oxoethyl]carbamoyl}furan-2-yl)benzyl]-1-methyl-1H-pyrazole-3-carboxamide | 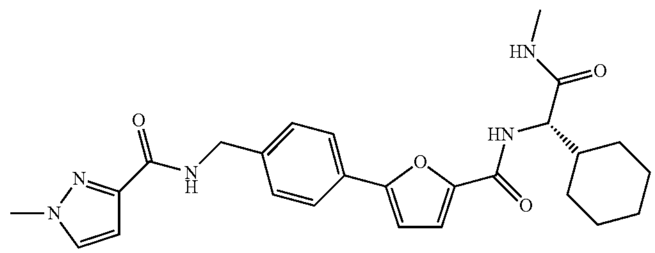 [SMILES: CNC(=O)[C@@H](NC(=O)c1ccc(-c2ccc(CNC(=O)c3ccn(C)n3)cc2)o1)C1CCCCC1] | 478.32 |
| N-[4-(5-{[(1S)-1-cyclohexyl-2-(methylamino)-2-oxoethyl]carbamoyl}furan-2-yl)benzyl]-1-methyl-1H-pyrazole-4-carboxamide | 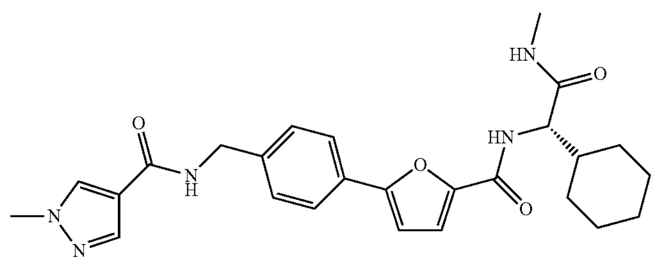 [SMILES: CNC(=O)[C@@H](NC(=O)c1ccc(-c2ccc(CNC(=O)c3cnn(C)c3)cc2)o1)C1CCCCC1] | 478.32 |
| N-[(1S)-1-cyclohexyl-2-(methylamino)-2-oxoethyl]-5-{4-[(propanoylamino)methyl]phenyl}furan-2-carboxamide | 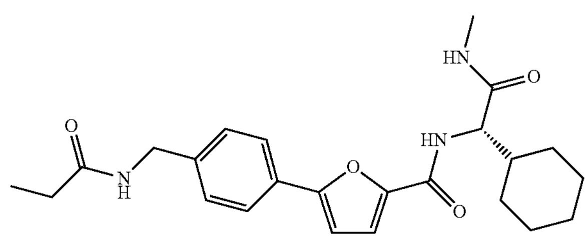 [SMILES: CCC(=O)NCc1ccc(-c2ccc(C(=O)N[C@H](C(=O)NC)C3CCCCC3)o2)cc1] | 426.27 |
| N-[(1S)-1-cyclohexyl-2-(methylamino)-2-oxoethyl]-5-(4-{[(2-methylpropanoyl)amino]methyl}phenyl)furan-2-carboxamide | 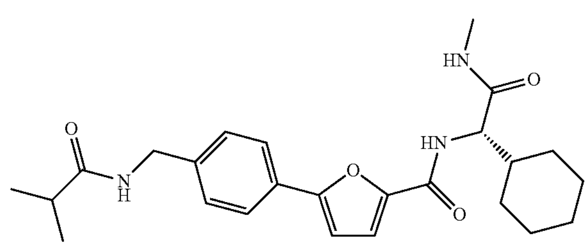 [SMILES: CNC(=O)[C@@H](NC(=O)c1ccc(-c2ccc(CNC(=O)C(C)C)cc2)o1)C1CCCCC1] | 440.33 |

TABLE V-continued

| Name | Structure | LC/MS (M + H) |
|---|---|---|
| N-[(1S)-1-cyclohexyl-2-(methylamino)-2-oxoethyl]-5-(4-{[(cyclopropylcarbonyl)amino]methyl}phenyl)furan-2-carboxamide | 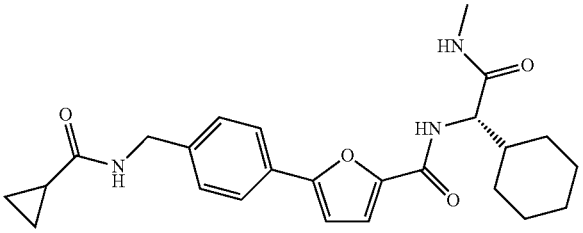 [SMILES: CNC(=O)[C@@H](NC(=O)c1ccc(-c2ccc(CNC(=O)C3CC3)cc2)o1)C1CCCCC1] | 438.28 |
| N-[4-(5-{[(1S)-1-cyclohexyl-2-(methylamino)-2-oxoethyl]carbamoyl}furan-2-yl)benzyl]pyridine-2-carboxamide | 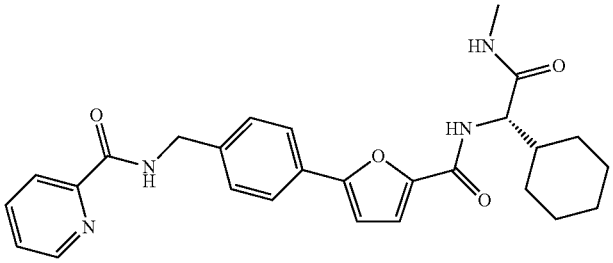 [SMILES: CNC(=O)[C@@H](NC(=O)c1ccc(-c2ccc(CNC(=O)c3ccccn3)cc2)o1)C1CCCCC1] | 475.32 |
| N-[4-(5-{[(1S)-1-cyclohexyl-2-(methylamino)-2-oxoethyl]carbamoyl}furan-2-yl)benzyl]-3-methylpyridine-2-carboxamide | 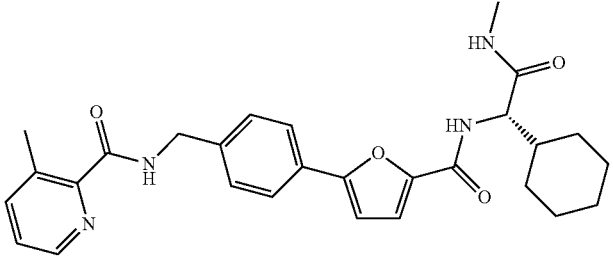 [SMILES: CNC(=O)[C@@H](NC(=O)c1ccc(-c2ccc(CNC(=O)c3ncccc3C)cc2)o1)C1CCCCC1] | 489.34 |
| N-[4-(5-{[(1S)-1-cyclohexyl-2-(methylamino)-2-oxoethyl]carbamoyl}furan-2-yl)benzyl]-4-ethylpyridine-2-carboxamide | 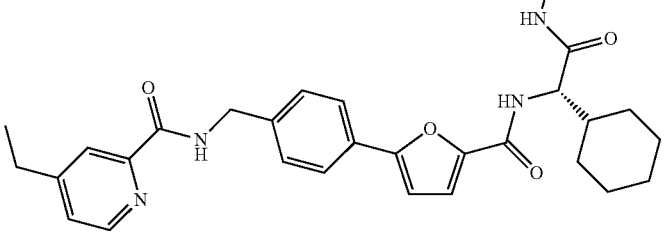 | 503.39 |
| N-[(1S)-1-cyclohexyl-2-(methylamino)-2-oxoethyl]-5-(4-{[(furan-2-ylcarbonyl)amino]methyl}phenyl)furan-2-carboxamide | 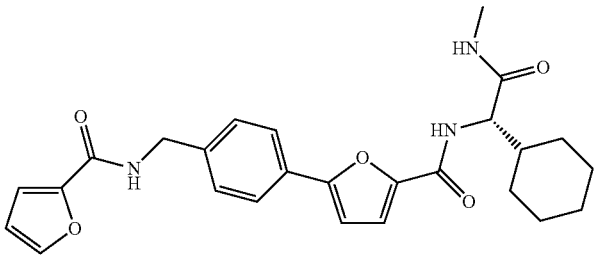 [SMILES: CNC(=O)[C@@H](NC(=O)c1ccc(-c2ccc(CNC(=O)c3ccco3)cc2)o1)C1CCCCC1] | 464.28 |

TABLE V-continued

| Name | Structure | LC/MS (M + H) |
|---|---|---|
| N-[4-(5-{[(1S)-1-cyclohexyl-2-(methylamino)-2-oxoethyl]carbamoyl}furan-2-yl)benzyl]-2-(trifluoromethyl)pyrimidine-4-carboxamide | 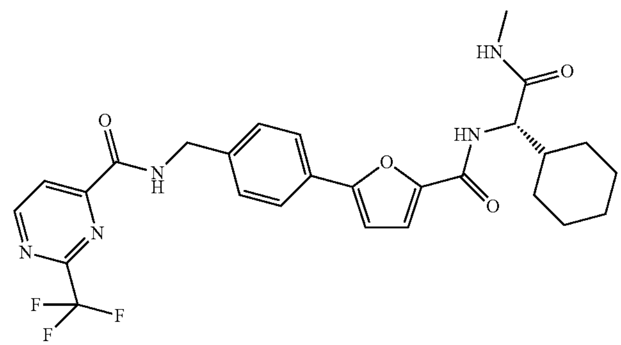 [SMILES: CNC(=O)[C@@H](NC(=O)c1ccc(-c2ccc(CNC(=O)c3ccnc(C(F)(F)F)n3)cc2)o1)C1CCCCC1] | 544.29 |
| N-[4-(5-{[(1S)-1-cyclohexyl-2-(methylamino)-2-oxoethyl]carbamoyl}furan-2-yl)benzyl]-1-methyl-1H-imidazole-4-carboxamide | 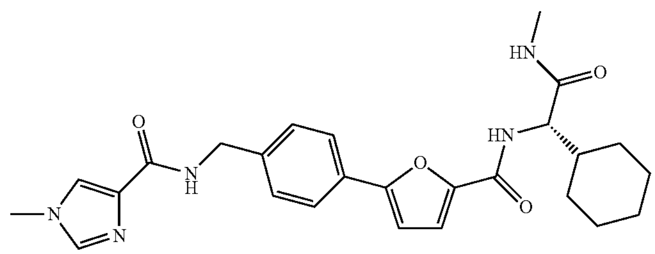 [SMILES: CNC(=O)[C@@H](NC(=O)c1ccc(-c2ccc(CNC(=O)c3cn(C)cn3)cc2)o1)C1CCCCC1] | 478.35 |
| N-[4-(5-{[(1S)-1-cyclohexyl-2-(methylamino)-2-oxoethyl]carbamoyl}furan-2-yl)benzyl]-1-benzofuran-2-carboxamide | 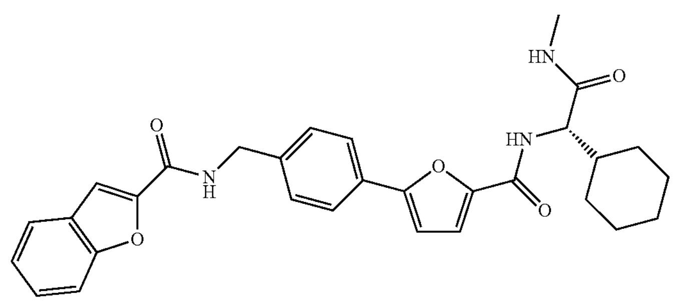 [SMILES: CNC(=O)[C@@H](NC(=O)c1ccc(-c2ccc(CNC(=O)c3cc4ccccc4o3)cc2)o1)C1CCCCC1] | 514.3 |
| N-[3-(5-{[(1S)-2-(methylamino)-2-oxo-1-(tetrahydro-2H-pyran-4-yl)ethyl]carbamoyl}-2-furyl)benzyl]-6-(trifluoromethyl)pyridine-2-carboxamide | 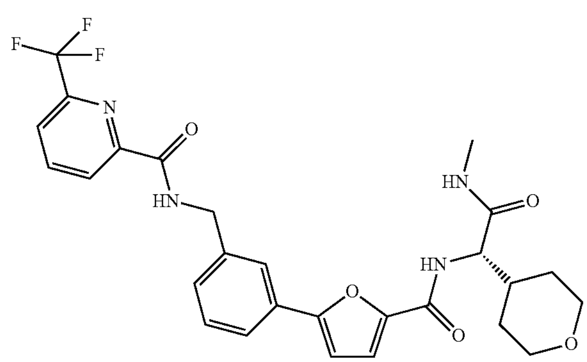 [SMILES: CNC(=O)[C@@H](NC(=O)c1ccc(-c2cccc(CNC(=O)c3cccc(C(F)(F)F)n3)c2)o1)C1CCOCC1] | 545.54 |

TABLE V-continued

| Name | Structure | LC/MS (M + H) |
|---|---|---|
| N-[3-(5-{[(1S)-2-(methylamino)-2-oxo-1-(tetrahydro-2H-pyran-4-yl)ethyl]carbamoyl}-2-furyl)benzyl]-2-(trifluoromethyl)pyrimidine-4-carboxamide | 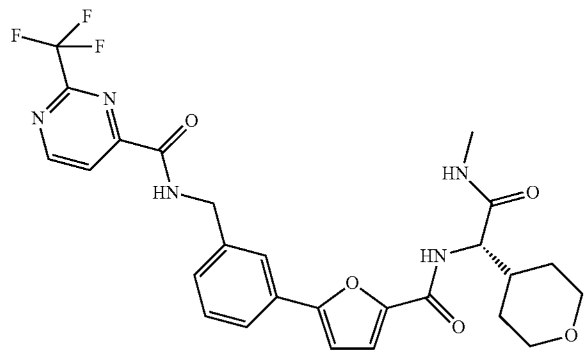 [SMILES: CNC(=O)[C@@H](NC(=O)c1ccc(-c2cccc(CNC(=O)c3ccnc(C(F)(F)F)n3)c2)o1)C1CCOCC1] | 546.49 |
| 6-Chloro-N-[3-(5-{[(1S)-2-methyl-1-(methylcarbamoyl)propyl]carbamoyl}-2-furyl)benzyl]pyridine-2-carboxamide | 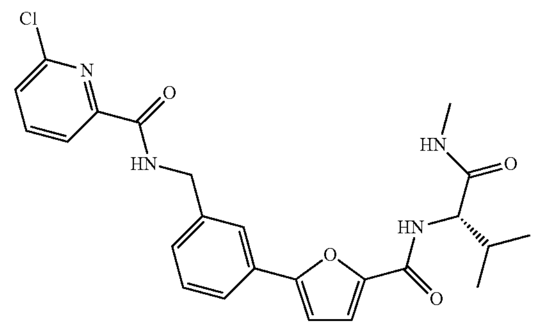 [SMILES: CNC(=O)[C@@H](NC(=O)c1ccc(-c2cccc(CNC(=O)c3cccc(Cl)n3)c2)o1)C(C)C] | 469.61 |
| 6-Fluoro-N-[3-(5-{[(1S)-2-methyl-1-(methylcarbamoyl)propyl]carbamoyl}-2-furyl)benzyl]pyridine-2-carboxamide | 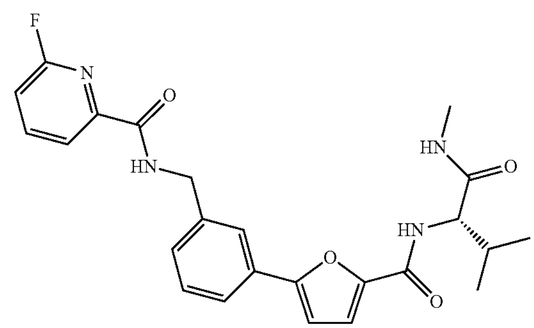 [SMILES: CNC(=O)[C@@H](NC(=O)c1ccc(-c2cccc(CNC(=O)c3cccc(F)n3)c2)o1)C(C)C] | 453.5 |
| N-[3-(5-{[(1S)-2-hydroxy-2-methyl-1-(methylcarbamoyl)propyl]carbamoyl}-2-furyl)benzyl]-2-(trifluoromethyl)pyrimidine-4-carboxamide | 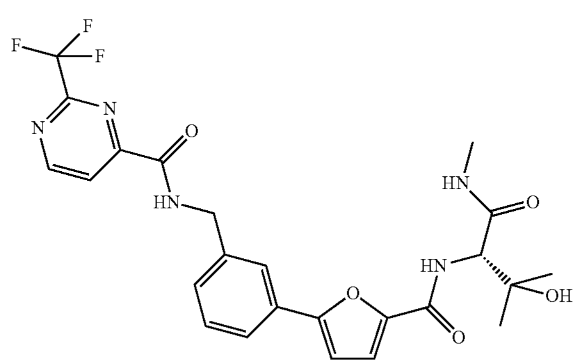 [SMILES: CNC(=O)[C@@H](NC(=O)c1ccc(-c2cccc(CNC(=O)c3ccnc(C(F)(F)F)n3)c2)o1)C(C)(C)O] | 520.47 |

TABLE V-continued

| Name | Structure | LC/MS (M + H) |
|---|---|---|
| 4-Trifluoromethyl-thiazole-2-carboxylic acid 3-[5-((S)-2-methyl-1-methylcarbamoyl-propylcarbamoyl)-furan-2-yl]-benzylamide | 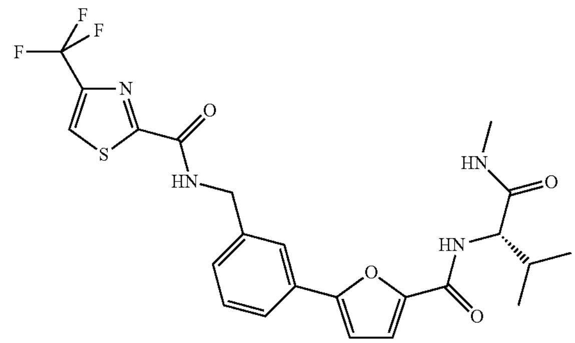 [SMILES: CNC(=O)[C@@H](NC(=O)c1ccc(-c2cccc(CNC(=O)c3nc(C(F)(F)F)cs3)c2)o1)C(C)C] | 509.48 |
| N-[3-(5-{[(1S)-2-methyl-1-(methylcarbamoyl)propyl]carbamoyl}-2-furyl)benzyl]-1-benzofuran-2-carboxamide | 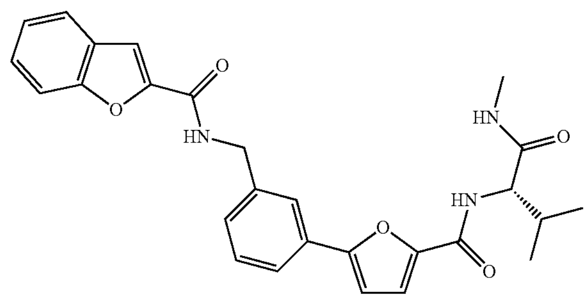 [SMILES: CNC(=O)[C@@H](NC(=O)c1ccc(-c2cccc(CNC(=O)c3cc4ccccc4o3)c2)o1)C(C)C] | 474.51 |
| 2-Chloro-N-[3-(5-{[(1S)-2-methyl-1-(methylcarbamoyl)propyl]carbamoyl}-2-furyl)benzyl]pyrimidine-4-carboxamide | 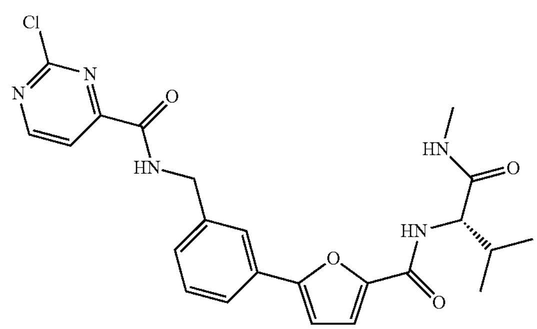 [SMILES: CNC(=O)[C@@H](NC(=O)c1ccc(-c2cccc(CNC(=O)c3ccnc(Cl)n3)c2)o1)C(C)C] | 470.49 |
| 5-Bromo-1-methyl-1H-pyrazole-3-carboxylic acid 3-[5-((S)-2-methyl-1-methylcarbamoyl-propylcarbamoyl)-furan-2-yl]-benzylamide | 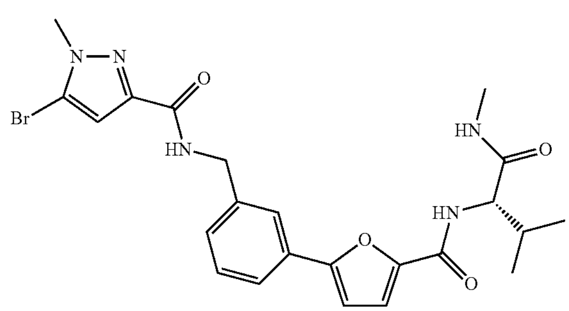 [SMILES: CNC(=O)[C@@H](NC(=O)c1ccc(-c2cccc(CNC(=O)c3cc(Br)n(C)n3)c2)o1)C(C)C] | 516.43 |

TABLE V-continued

| Name | Structure | LC/MS (M + H) |
|---|---|---|
| 1-Difluoromethyl-1H-pyrazole-3-carboxylic acid 3-[5-((S)-2-methyl-1-methylcarbamoyl-propylcarbamoyl)-furan-2-yl]-benzylamide | 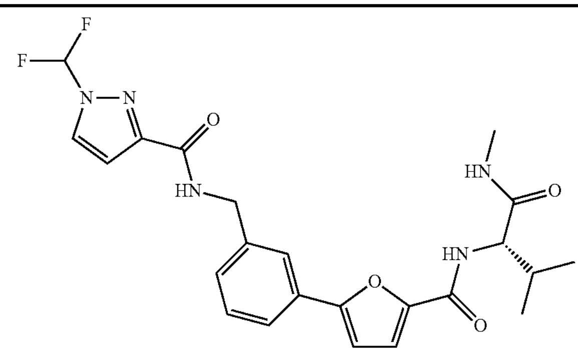 | 474.54 |
| 6-Bromo-N-[3-(5-{[(1S)-1-cyclopropyl-2-(methylamino)-2-oxoethyl]carbamoyl}-2-furyl)benzyl]pyridine-2-carboxamide | 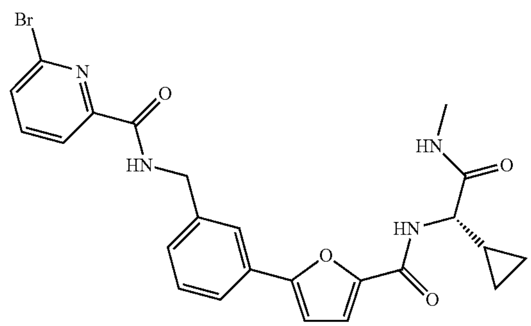 [SMILES: CNC(=O)[C@@H](NC(=O)c1ccc(-c2cccc(CNC(=O)c3cccc(Br)n3)c2)o1)C1CC1] | 511.44 |
| N-[3-(5-{[(1S)-1-cyclopropyl-2-(methylamino)-2-oxoethyl]carbamoyl}-2-furyl)benzyl]-6-(trifluoromethyl)pyridine-2-carboxamide | 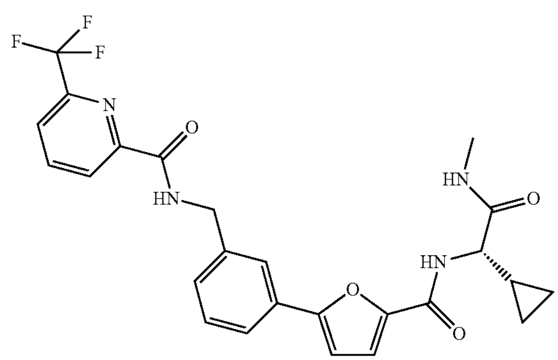 [SMILES: CNC(=O)[C@@H](NC(=O)c1ccc(-c2cccc(CNC(=O)c3cccc(C(F)(F)F)n3)c2)o1)C1CC1] | 501.52 |
| N-[3-(5-{[(1S)-2-methyl-1-(methylcarbamoyl)propyl]carbamoyl}-2-furyl)benzyl]pyrazine-2-carboxamide | 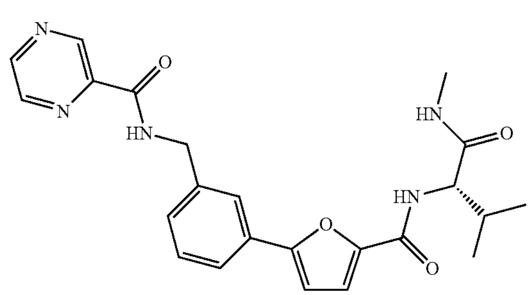 [SMILES: CNC(=O)[C@@H](NC(=O)c1ccc(-c2cccc(CNC(=O)c3cnccn3)c2)o1)C(C)C] | 436.3 |

TABLE V-continued

| Name | Structure | LC/MS (M + H) |
|---|---|---|
| N-[3-(5-{[(1S)-2-methyl-1-(methylcarbamoyl)propyl]carbamoyl}-2-furyl)benzyl]-1H-benzimidazole-2-carboxamide | 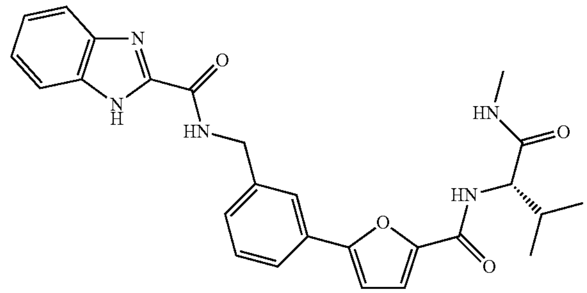 [SMILES: CNC(=O)[C@@H](NC(=O)c1ccc(-c2cccc(CNC(=O)c3nc4ccccc4[nH]3)c2)o1)C(C)C] | 474.56 |
| 1-Methyl-5-trifluoromethyl-2H-pyrazole-3-carboxylic acid 3-[5-((S)-2-methyl-1-methylcarbamoyl-propylcarbamoyl)-furan-2-yl]-benzylamide | 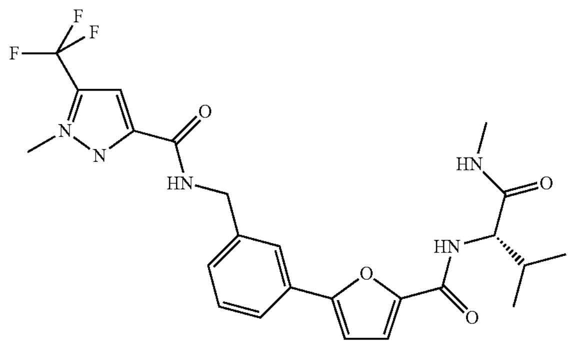 | 506.3 |
| 5-{3-[(3-Trifluoromethyl-benzoylamino)-methyl]-phenyl}-furan-2-carboxylic acid ((S)-2-methyl-1-methylcarbamoyl-propyl)-amide | 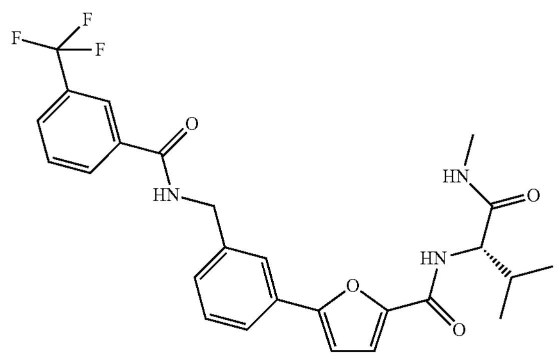 [SMILES: CNC(=O)[C@@H](NC(=O)c1ccc(-c2cccc(CNC(=O)c3cccc(C(F)(F)F)c3)c2)o1)C(C)C] | 502.48 |
| N-[3-(5-{[(1S)-2-methyl-1-(methylcarbamoyl)propyl]carbamoyl}-2-furyl)benzyl]tetrahydro-2H-pyran-2-carboxamide | 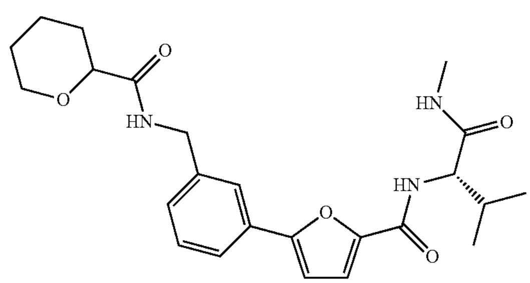 [SMILES: CNC(=O)[C@@H](NC(=O)c1ccc(-c2cccc(CNC(=O)C3CCCCO3)c2)o1)C(C)C] | 442.3 |
| 5-{3-[(4-Dimethylamino-benzoylamino)-methyl]-phenyl}-furan-2-carboxylic acid ((S)-2-methyl-1-methylcarbamoyl-propyl)-amide | 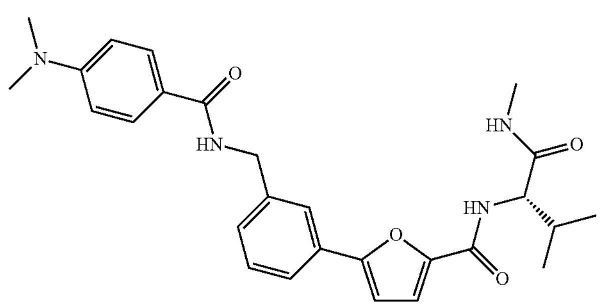 | 477.4 |

TABLE V-continued

| Name | Structure | LC/MS (M + H) |
|---|---|---|
| 5-{3-[(3-Methyl-benzoylamino)-methyl]-phenyl}-furan-2-carboxylic acid ((S)-2-methyl-1-methylcarbamoyl-propyl)-amide | 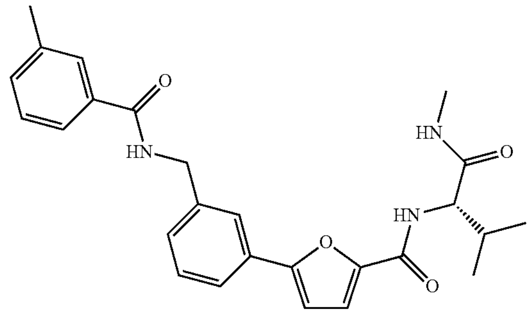 [SMILES: CNC(=O)[C@@H](NC(=O)c1ccc(-c2cccc(CNC(=O)c3cccc(C)c3)c2)o1)C(C)C] | 448.3 |
| 5-{3-[(4-Methoxy-benzoylamino)-methyl]-phenyl}-furan-2-carboxylic acid ((S)-2-methyl-1-methylcarbamoyl-propyl)-amide | 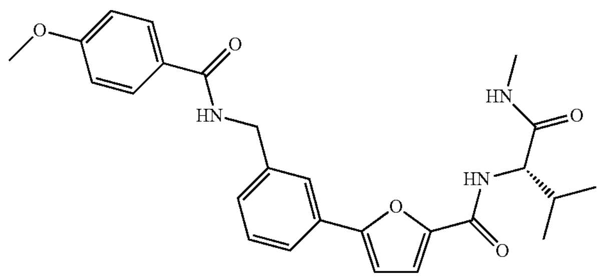 [SMILES: CNC(=O)[C@@H](NC(=O)c1ccc(-c2cccc(CNC(=O)c3ccc(OC)cc3)c2)o1)C(C)C] | 464.3 |
| 5-{3-[(3,4-Dimethyl-benzoylamino)-methyl]-phenyl}-furan-2-carboxylic acid ((S)-2-methyl-1-methylcarbamoyl-propyl)-amide | 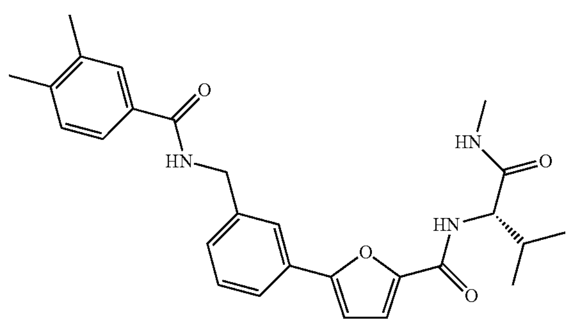 [SMILES: CNC(=O)[C@@H](NC(=O)c1ccc(-c2cccc(CNC(=O)c3ccc(C)c(C)c3)c2)o1)C(C)C] | 462.3 |
| 5-{3-[(3-Cyano-benzoylamino)-methyl]-phenyl}-furan-2-carboxylic acid ((S)-2-methyl-1-methylcarbamoyl-propyl)-amide | 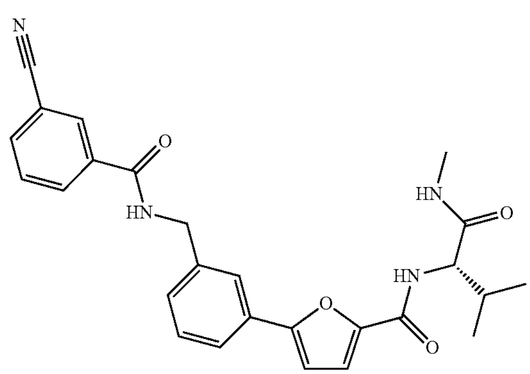 [SMILES: CNC(=O)[C@@H](NC(=O)c1ccc(-c2cccc(CNC(=O)c3cccc(C#N)c3)c2)o1)C(C)C] | 459.3 |

TABLE V-continued

| Name | Structure | LC/MS (M + H) |
|---|---|---|
| 5-Trifluoromethyl-2H-pyrazole-3-carboxylic acid 3-[5-((S)-2-methyl-1-methylcarbamoyl-propylcarbamoyl)-furan-2-yl]-benzylamide | 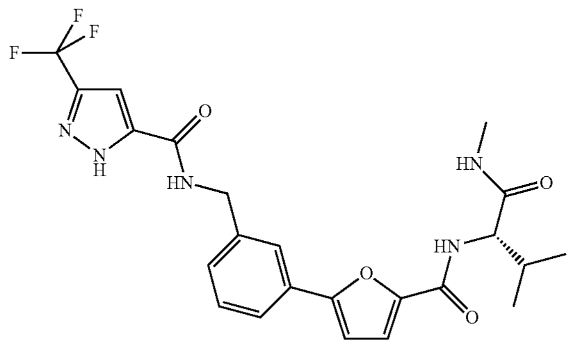 [SMILES: CNC(=O)[C@@H](NC(=O)c1ccc(-c2cccc(CNC(=O)c3cc(C(F)(F)F)n[nH]3)c2)o1)C(C)C] | 492.3 |
| 5-{3-[(3-Isopropyl-benzoylamino)-methyl]-phenyl}-furan-2-carboxylic acid ((S)-2-methyl-1-methylcarbamoyl-propyl)-amide | 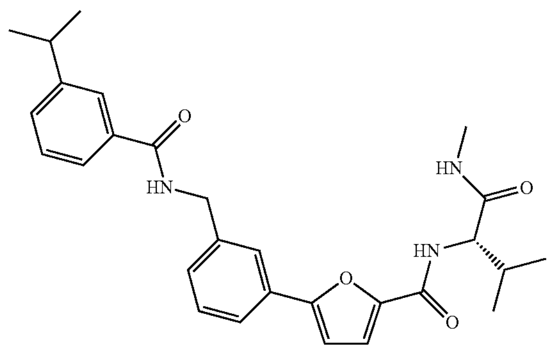 [SMILES: CNC(=O)[C@@H](NC(=O)c1ccc(-c2cccc(CNC(=O)c3cccc(C(C)C)c3)c2)o1)C(C)C] | 476.4 |
| 5-{3-[(3-Methoxy-benzoylamino)-methyl]-phenyl}-furan-2-carboxylic acid ((S)-2-methyl-1-methylcarbamoyl-propyl)-amide | 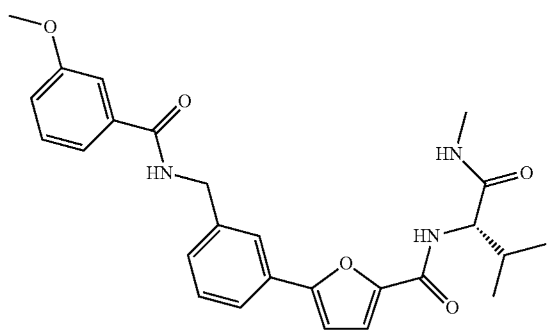 [SMILES: CNC(=O)[C@@H](NC(=O)c1ccc(-c2cccc(CNC(=O)c3cccc(OC)c3)c2)o1)C(C)C] | 464.3 |
| 5-{3-[(Cyclohexanecarbonyl-amino)-methyl]-phenyl}-furan-2-carboxylic acid ((S)-2-methyl-1-methylcarbamoyl-propyl)-amide | 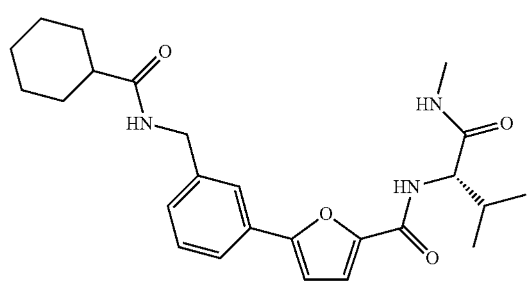 [SMILES: CNC(=O)[C@@H](NC(=O)c1ccc(-c2cccc(CNC(=O)C3CCCCC3)c2)o1)C(C)C] | 440.3 |
| 5-{3-[(4-methyl-benzoylamino)-methyl]-phenyl}-furan-2-carboxylic acid ((S)-2-methyl-1-methylcarbamoyl-propyl)-amide | 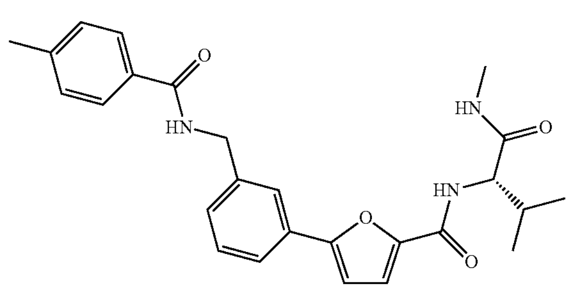 [SMILES: CNC(=O)[C@@H](NC(=O)c1ccc(-c2cccc(CNC(=O)c3ccc(C)cc3)c2)o1)C(C)C] | 448.3 |

TABLE V-continued

| Name | Structure | LC/MS (M + H) |
|---|---|---|
| N-[3-(5-{[(1S)-2-methyl-1-(methylcarbamoyl)propyl]carbamoyl}-2-furyl)benzyl]pyridazine-4-carboxamide | 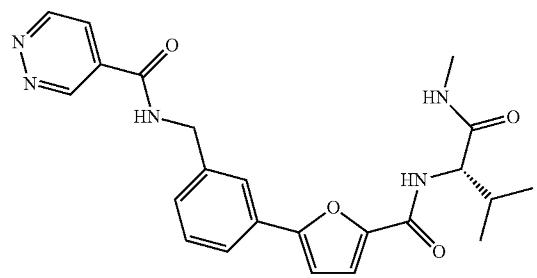 [SMILES: CNC(=O)[C@@H](NC(=O)c1ccc(-c2cccc(CNC(=O)c3ccnnc3)c2)o1)C(C)C] | 436.3 |
| 5-{3-[(4-Cyano-benzoylamino)-methyl]-phenyl}-furan-2-carboxylic acid ((S)-2-methyl-1-methylcarbamoyl-propyl)-amide | 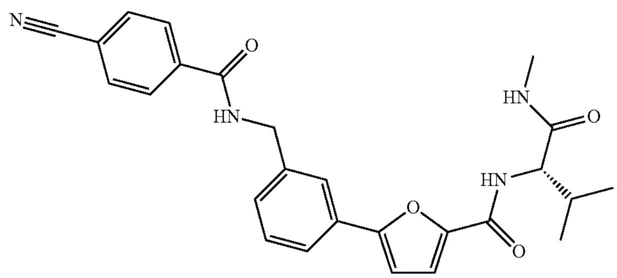 [SMILES: CNC(=O)[C@@H](NC(=O)c1ccc(-c2cccc(CNC(=O)c3ccc(C#N)cc3)c2)o1)C(C)C] | 459.3 |
| 5-[3-(Benzoylamino-methyl)-phenyl]-furan-2-carboxylic acid ((S)-2-methyl-1-methylcarbamoyl-propyl)-amide | 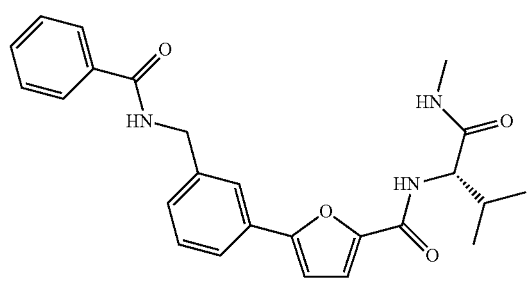 [SMILES: CNC(=O)[C@@H](NC(=O)c1ccc(-c2cccc(CNC(=O)c3ccccc3)c2)o1)C(C)C] | 434.3 |
| 5-{3-[(3-Dimethylamino-benzoylamino)-methyl]-phenyl}-furan-2-carboxylic acid ((S)-2-methyl-1-methylcarbamoyl-propyl)-amide | 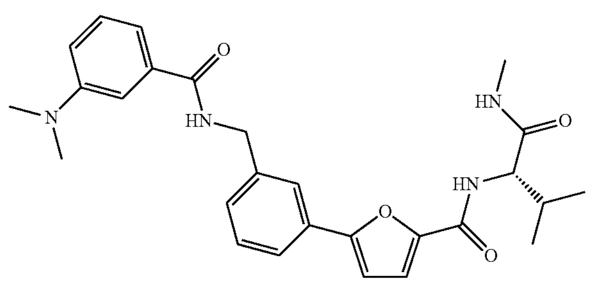 [SMILES: CNC(=O)[C@@H](NC(=O)c1ccc(-c2cccc(CNC(=O)c3cccc(N(C)C)c3)c2)o1)C(C)C] | 477.2 |
| 1-Methyl-N-[3-(5-{[(1S)-2-methyl-1-(methylcarbamoyl)propyl]carbamoyl}-2-furyl)benzyl]piperidine-3-carboxamide | 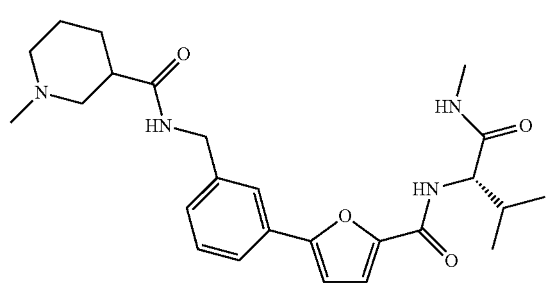 [SMILES: CNC(=O)[C@@H](NC(=O)c1ccc(-c2cccc(CNC(=O)C3CCCN(C)C3)c2)o1)C(C)C] | 455.4 |

TABLE V-continued

| Name | Structure | LC/MS (M + H) |
|---|---|---|
| 5-{3-[(3-Trifluoromethyl-4-fluoro-benzoylamino)-methyl]-phenyl}-furan-2-carboxylic acid ((S)-2-methyl-1-methylcarbamoyl-propyl)-amide | 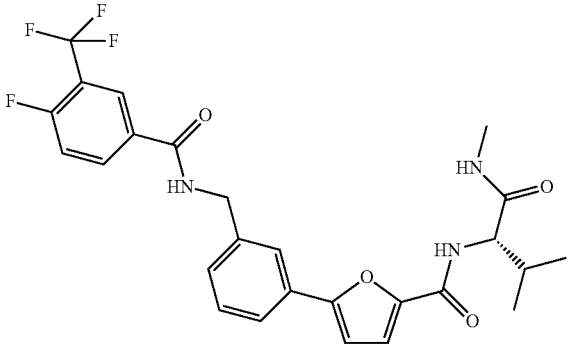 [SMILES: CNC(=O)[C@@H](NC(=O)c1ccc(-c2cccc(CNC(=O)c3ccc(F)c(C(F)(F)F)c3)c2)o1)C(C)C] | 520.3 |
| 5-{3-[(4-Isopropyl-benzoylamino)-methyl]-phenyl}-furan-2-carboxylic acid ((S)-2-methyl-1-methylcarbamoyl-propyl)-amide | 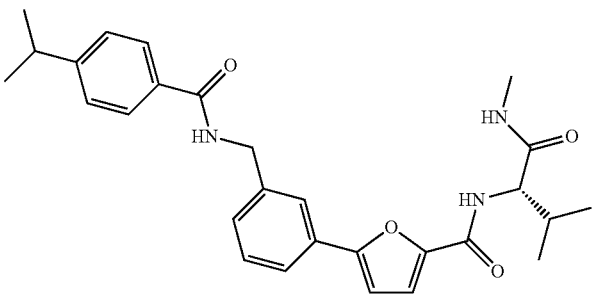 [SMILES: CNC(=O)[C@@H](NC(=O)c1ccc(-c2cccc(CNC(=O)c3ccc(C(C)C)cc3)c2)o1)C(C)C] | 476.4 |
| N-[3-(5-{[(1S)-2-methyl-1-(methylcarbamoyl)propyl]carbamoyl}-2-furyl)benzyl]piperidine-2-carboxamide | 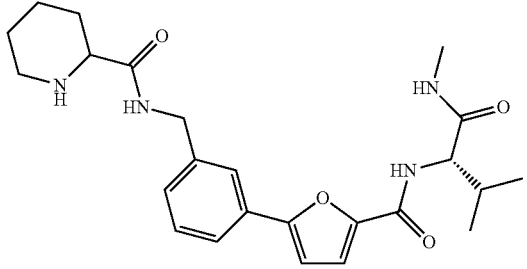 | 441.2 |
| 3-Methyl-isoxazole-5-carboxylic acid 3-[5-((S)-2-methyl-1-methylcarbamoyl-propylcarbamoyl)-furan-2-yl]-benzylamide | 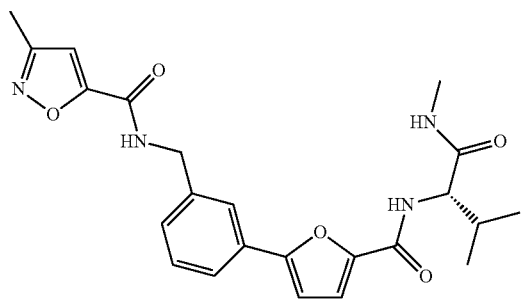 [SMILES: CNC(=O)[C@@H](NC(=O)c1ccc(-c2cccc(CNC(=O)c3cc(C)no3)c2)o1)C(C)C] | 439.3 |
| 1-Methyl-N-[3-(5-{[(1S)-2-methyl-1-(methylcarbamoyl)propyl]carbamoyl}-2-furyl)benzyl]piperidine-2-carboxamide | 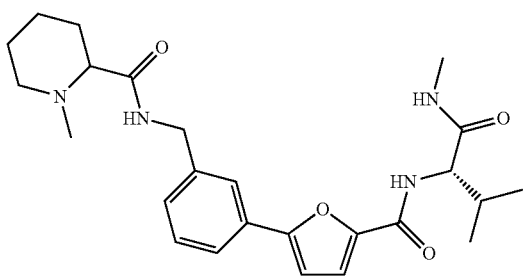 [SMILES: CNC(=O)[C@@H](NC(=O)c1ccc(-c2cccc(CNC(=O)C3CCCCN3C)c2)o1)C(C)C] | 455.4 |

TABLE V-continued

| Name | Structure | LC/MS (M + H) |
|---|---|---|
| N-[3-(5-{[(1S)-2-methyl-1-(methylcarbamoyl)propyl]carbamoyl}-2-furyl)benzyl]prolinamide | 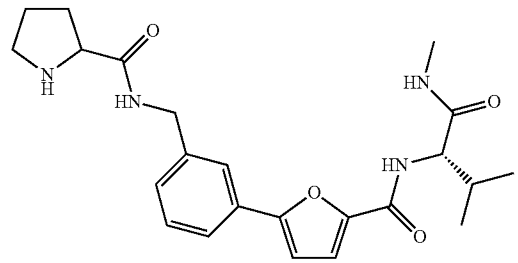 [SMILES: CNC(=O)[C@@H](NC(=O)c1ccc(-c2cccc(CNC(=O)C3CCCN3)c2)o1)C(C)C] | 427.1 |
| N-[3-(5-{[(1S)-2-methyl-1-(methylcarbamoyl)propyl]carbamoyl}-2-furyl)benzyl]tetrahydro-2H-pyran-4-carboxamide | 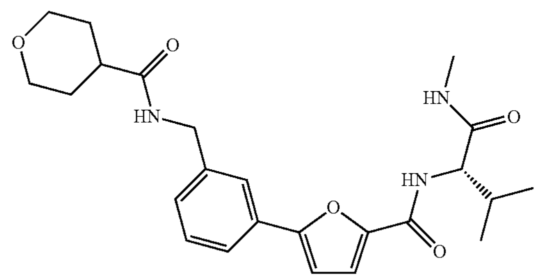 [SMILES: CNC(=O)[C@@H](NC(=O)c1ccc(-c2cccc(CNC(=O)C3CCOCC3)c2)o1)C(C)C] | 442.3 |
| N-[3-(5-{[(1S)-2-methyl-1-(methylcarbamoyl)propyl]carbamoyl}-2-furyl)benzyl]nicotinamide | 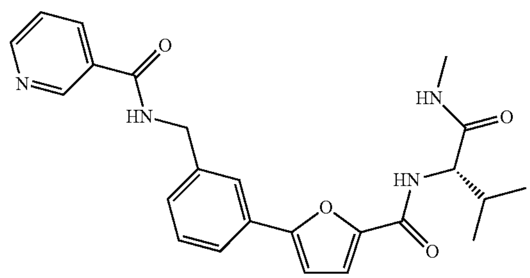 | 435.2 |
| N-[3-(5-{[(1S)-2-methyl-1-(methylcarbamoyl)propyl]carbamoyl}-2-furyl)benzyl]morpholine-2-carboxamide | 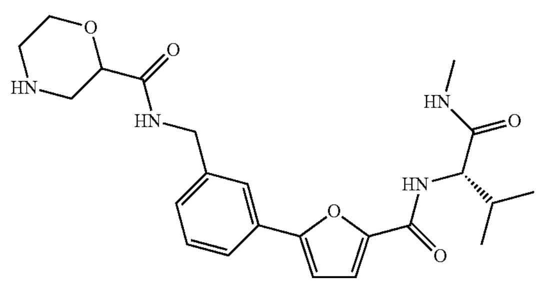 [SMILES: CNC(=O)[C@@H](NC(=O)c1ccc(-c2cccc(CNC(=O)C3CNCCO3)c2)o1)C(C)C] | 443.2 |
| 1-Methyl-N-[3-(5-{[(1S)-2-methyl-1-(methylcarbamoyl)propyl]carbamoyl}-2-furyl)benzyl]-L-prolinamide | 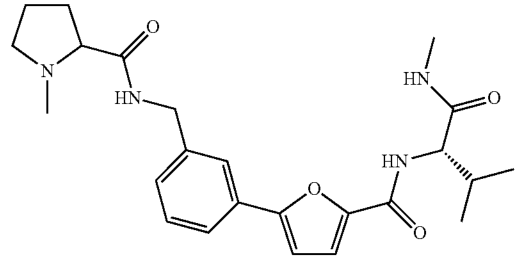 [SMILES: CNC(=O)[C@@H](NC(=O)c1ccc(-c2cccc(CNC(=O)C3CCCN3C)c2)o1)C(C)C] | 441.2 |

TABLE V-continued

| Name | Structure | LC/MS (M + H) |
|---|---|---|
| 5-[3-(Aminomethyl)phenyl]-N-[(1S)-2-(methylamino)-2-oxo-1-(tetrahydro-2H-pyran-4-yl)ethyl]-2-furamide | 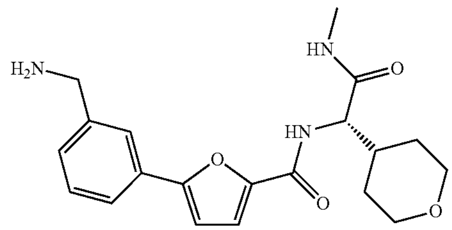 [SMILES: CNC(=O)[C@@H](NC(=O)c1ccc(-c2cccc(CN)c2)o1)C1CCOCC1] | 372.47 |
| N-[3-(5-{[(1S)-2-methyl-1-(methylcarbamoyl)propyl]carbamoyl}-2-furyl)benzyl]pyridazine-3-carboxamide | 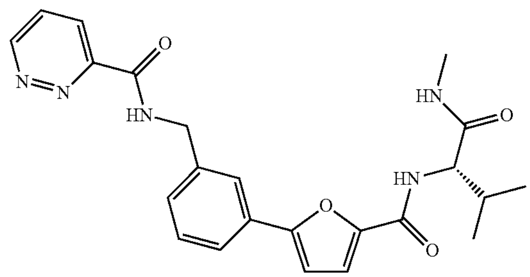 [SMILES: CNC(=O)[C@@H](NC(=O)c1ccc(-c2cccc(CNC(=O)c3cccnn3)c2)o1)C(C)C] | 436.3 |
| N-[3-(5-{[(1S)-2-methyl-1-(methylcarbamoyl)propyl]carbamoyl}-2-furyl)benzyl]piperidine-3-carboxamide | 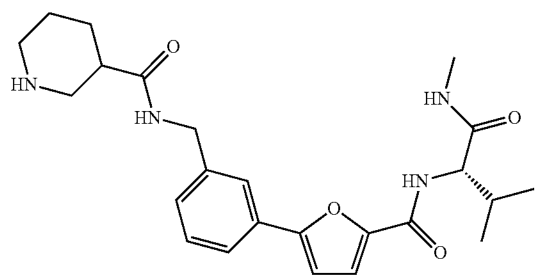 [SMILES: CNC(=O)[C@@H](NC(=O)c1ccc(-c2cccc(CNC(=O)C3CCCNC3)c2)o1)C(C)C] | 441.2 |
| N-Methyl-N~2~-(5-{3-[({[1-methyl-3-(trifluoromethyl)-1H-pyrazol-5-yl]carbonyl}amino)methyl]phenyl}-2-furoyl)-L-valinamide | 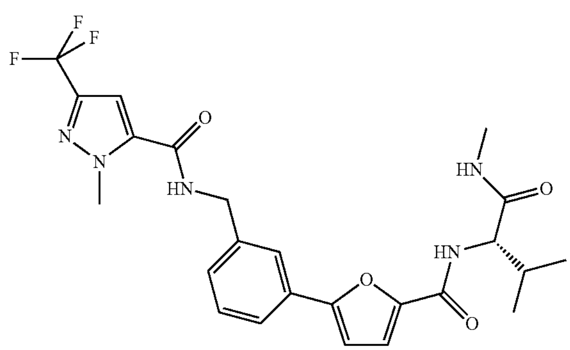 [SMILES: CNC(=O)[C@@H](NC(=O)c1ccc(-c2cccc(CNC(=O)c3cc(C(F)(F)F)nn3C)c2)o1)C(C)C] | 506.3 |
| N-[3-(5-{[(1S)-2-methyl-1-(methylcarbamoyl)propyl]carbamoyl}-2-furyl)benzyl]morpholine-3-carboxamide | 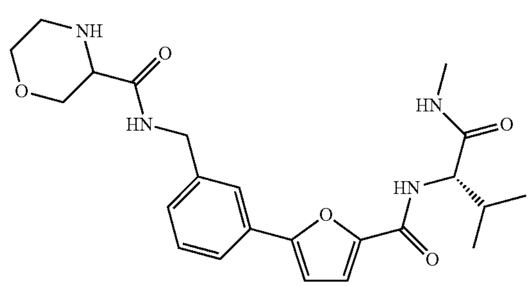 [SMILES: CNC(=O)[C@@H](NC(=O)c1ccc(-c2cccc(CNC(=O)C3COCCN3)c2)o1)C(C)C] | 443.1 |

TABLE V-continued

| Name | Structure | LC/MS (M + H) |
|---|---|---|
| 6-(2,5-Dihydro-pyrrole-1-carbonyl)-imidazol[1,2-a]pyridine-2-carboxylic acid 3-{5-[((S)-cyclopropyl-methylcarbamoyl-methyl)-carbamoyl]-furan-2-yl}-benzylamide | 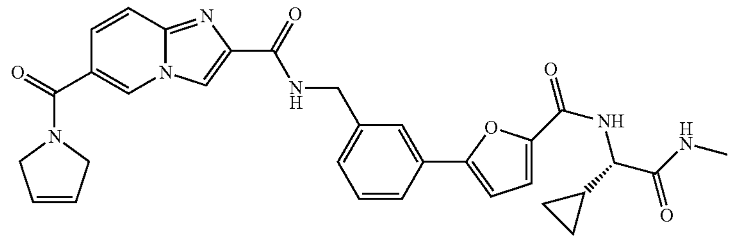 [SMILES: CNC(=O)[C@@H](NC(=O)c1ccc(-c2cccc(CNC(=O)c3cn4cc(C(=O)N5CC=CC5)ccc4n3)c2)o1)C1CC1] | |
| 2-(3-{5-[((S)-Cyclopropyl-methylcarbamoyl-methyl)-carbamoyl]-furan-2-yl}-benzylcarbamoyl)-imidazo[1,2-a]pyridine-6-carboxylic acid | 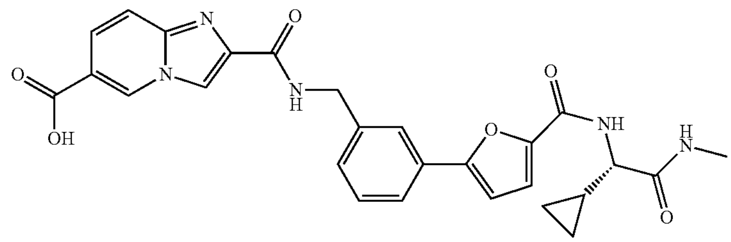 [SMILES: CNC(=O)[C@@H](NC(=O)c1ccc(-c2cccc(CNC(=O)c3cn4cc(C(=O)O)ccc4n3)c2)o1)C1CC1] | |
| 2-(3-{5-[((S)-Cyclopropyl-methylcarbamoyl-methyl)-carbamoyl]-furan-2-yl}-benzylcarbamoyl)-imidazol[1,2-a]pyridine-6-carboxylic acid benzyl ester | 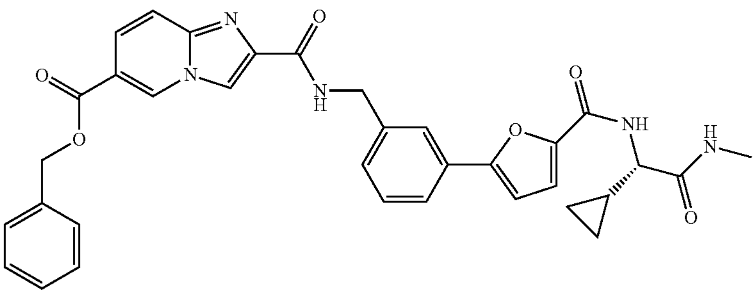 [SMILES: CNC(=O)[C@@H](NC(=O)c1ccc(-c2cccc(CNC(=O)c3cn4cc(C(=O)OCc5ccccc5)ccc4n3)c2)o1)C1CC1] | |

EXAMPLE 6

5-(5-Phenyl-pyridin-2-yl)-furan-2-carboxylic acid ((S)-2-methyl-1-methylcarbamoyl-propyl)-amide

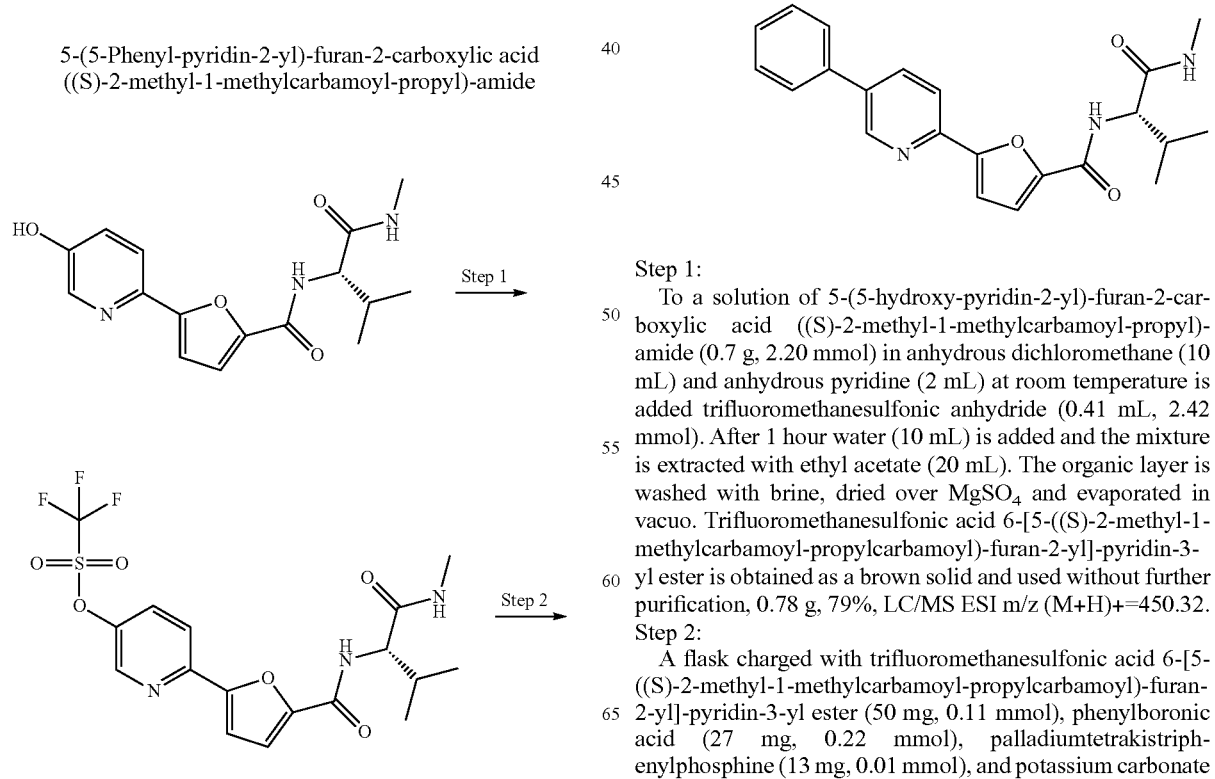

Step 1:

To a solution of 5-(5-hydroxy-pyridin-2-yl)-furan-2-carboxylic acid ((S)-2-methyl-1-methylcarbamoyl-propyl)-amide (0.7 g, 2.20 mmol) in anhydrous dichloromethane (10 mL) and anhydrous pyridine (2 mL) at room temperature is added trifluoromethanesulfonic anhydride (0.41 mL, 2.42 mmol). After 1 hour water (10 mL) is added and the mixture is extracted with ethyl acetate (20 mL). The organic layer is washed with brine, dried over MgSO₄ and evaporated in vacuo. Trifluoromethanesulfonic acid 6-[5-((S)-2-methyl-1-methylcarbamoyl-propylcarbamoyl)-furan-2-yl]-pyridin-3-yl ester is obtained as a brown solid and used without further purification, 0.78 g, 79%, LC/MS ESI m/z (M+H)+=450.32.

Step 2:

A flask charged with trifluoromethanesulfonic acid 6-[5-((S)-2-methyl-1-methylcarbamoyl-propylcarbamoyl)-furan-2-yl]-pyridin-3-yl ester (50 mg, 0.11 mmol), phenylboronic acid (27 mg, 0.22 mmol), palladiumtetrakistriphenylphosphine (13 mg, 0.01 mmol), and potassium carbonate (61 mg, 0.44 mmol) is flushed with argon. Toluene (2 mL), ethanol (0.5 mL), and water (1 mL) are added and the reaction is stirred at 100° C. for 2 hours. The reaction is cooled to room temperature, ethyl acetate (10 mL), is added and the mixture washed with water (10 mL), brine (10 mL), and dried over MgSO$_4$. The solution is filtered and evaporated in vacuo to give an oil that is purified by preparative HPLC. 5-(5-Phenyl-pyridin-2-yl)-furan-2-carboxylic acid ((S)-2-methyl-1-methylcarbamoyl-propyl)-amide is obtained as a white solid, 16 mg, 38%, LC/MS ESI m/z (M+H)+=377.43.

The following compounds in Table VI are made in an analogous manner:

TABLE VI

| Name | Structure | LC/MS (M + H) |
|---|---|---|
| 5-[5-(4-Fluoro-phenyl)-pyridin-2-yl]-furan-2-carboxylic acid ((S)-2-methyl-1-methylcarbamoyl-propyl)-amide | 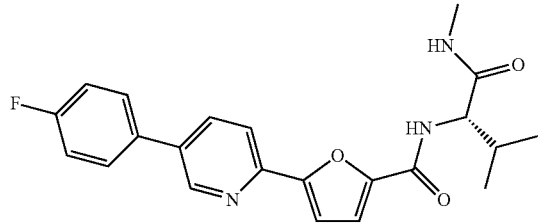 [SMILES: CNC(=O)[C@@H](NC(=O)c1ccc(-c2ccc(-c3ccc(F)cc3)cn2)o1)C(C)C] | 396.27 |
| 5-[5-(4-Methyl-phenyl)-pyridin-2-yl]-furan-2-carboxylic acid ((S)-2-methyl-1-methylcarbamoyl-propyl)-amide | 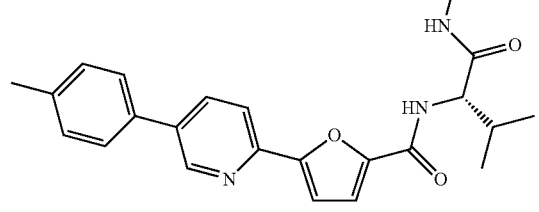 | 393.44 |
| 5-[5-(4-Cyano-phenyl)-pyridin-2-yl]-furan-2-carboxylic acid ((S)-2-methyl-1-methylcarbamoyl-propyl)-amide | 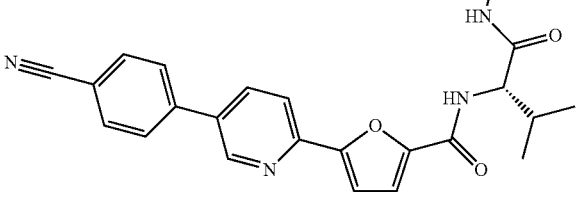 | 403.38 |
| 5-[5-(1H-Indol-5-yl)-pyridin-2-yl]-furan-2-carboxylic acid ((S)-2-methyl-1-methylcarbamoyl-propyl)-amide | 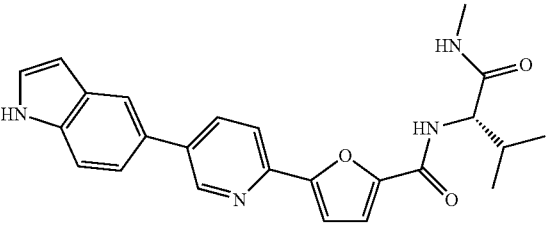 [SMILES: CNC(=O)[C@@H](NC(=O)c1ccc(-c2ccc(-c3ccc4[nH]ccc4c3)cn2)o1)C(C)C] | 417.38 |
| 5-[5-(4-Ethoxy-phenyl)-pyridin-2-yl]-furan-2-carboxylic acid ((S)-2-methyl-1-methylcarbamoyl-propyl)-amide | 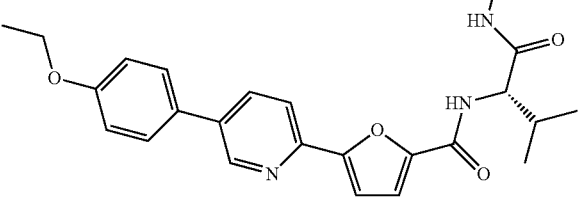 | 422.44 |
| 5-[5-(4-Isopropoxy-phenyl)-pyridin-2-yl]-furan-2-carboxylic acid ((S)-2-methyl-1-methylcarbamoyl-propyl)-amide | 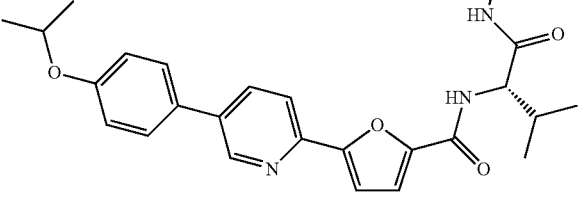 | 436.45 |

TABLE VI-continued

| Name | Structure | LC/MS (M + H) |
|------|-----------|---------------|
| 5-[5-(3-Fluoro-phenyl)-pyridin-2-yl]-furan-2-carboxylic acid ((S)-2-methyl-1-methylcarbamoyl-propyl)-amide | 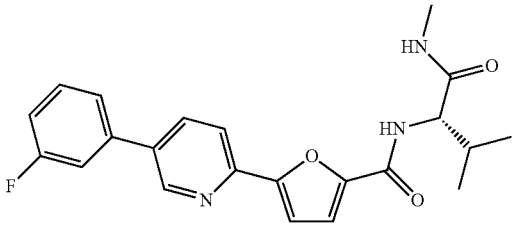 [SMILES: CNC(=O)[C@@H](NC(=O)c1ccc(-c2ccc(-c3cccc(F)c3)cn2)o1)C(C)C] | 396.37 |
| 5-[5-(3,5-Difluoro-phenyl)-pyridin-2-yl]-furan-2-carboxylic acid ((S)-2-methyl-1-methylcarbamoyl-propyl)-amide | 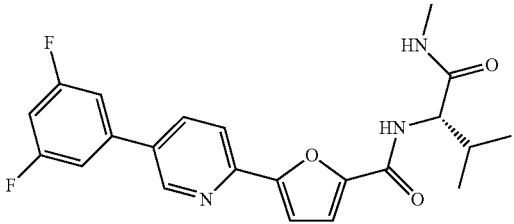 [SMILES: CNC(=O)[C@@H](NC(=O)c1ccc(-c2ccc(-c3cc(F)cc(F)c3)cn2)o1)C(C)C] | 414.37 |
| 5-[5-(1H-Indol-6-yl)-pyridin-2-yl]-furan-2-carboxylic acid ((S)-2-methyl-1-methylcarbamoyl-propyl)-amide | 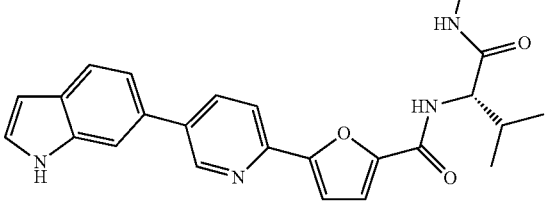 | 417.42 |
| 5-[3,4']Bipyridinyl-6-yl-furan-2-carboxylic acid ((S)-2-methyl-1-methylcarbamoyl-propyl)-amide | 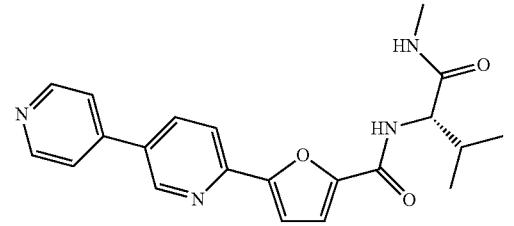 [SMILES: CNC(=O)[C@@H](NC(=O)c1ccc(-c2ccc(-c3ccncc3)cn2)o1)C(C)C] | 379.37 |
| 5-[3,3']Bipyridinyl-6-yl-furan-2-carboxylic acid ((S)-2-methyl-1-methylcarbamoyl-propyl)-amide | 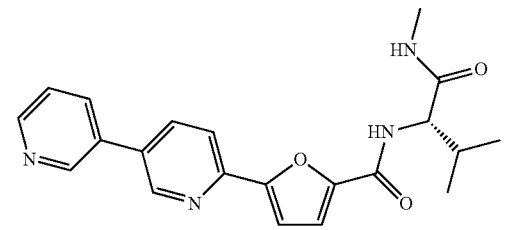 [SMILES: CNC(=O)[C@@H](NC(=O)c1ccc(-c2ccc(-c3cccnc3)cn2)o1)C(C)C] | 379.37 |
| 5-(2'-Methyl-[3,4']bipyridinyl-6-yl)-furan-2-carboxylic acid ((S)-2-methyl-1-methylcarbamoyl-propyl)-amide | 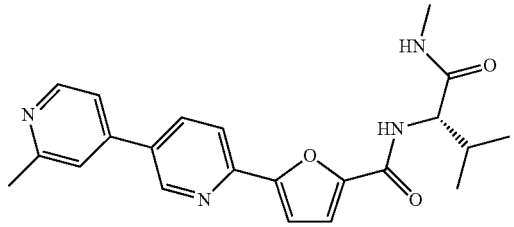 [SMILES: CNC(=O)[C@@H](NC(=O)c1ccc(-c2ccc(-c3ccnc(C)c3)cn2)o1)C(C)C] | 393.38 |

TABLE VI-continued

| Name | Structure | LC/MS (M + H) |
|---|---|---|
| 5-[5-(2-Amino-pyrimidin-5-yl)-pyridin-2-yl]-furan-2-carboxylic acid ((S)-2-methyl-1-methylcarbamoyl-propyl)-amide | 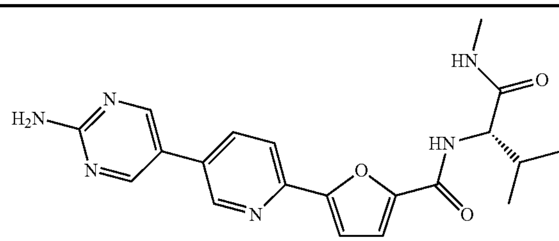 | 395.37 |
| 5-[3,4']Bipyridinyl-6-yl-furan-2-carboxylic acid ((S)-cyclohexyl-methylcarbamoyl-methyl)-amide | 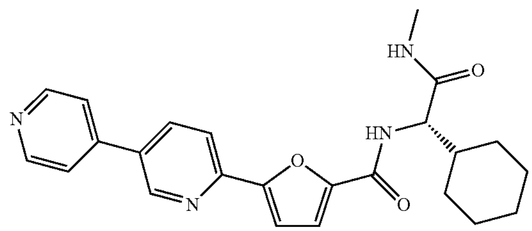 [SMILES: CNC(=O)[C@@H](NC(=O)c1ccc(-c2ccc(-c3ccncc3)cn2)o1)C1CCCCC1] | 419.49 |
| 5-(4'-Trifluoromethyl-biphenyl-4-yl)-furan-2-carboxylic acid ((S)-cyclohexyl-methylcarbamoyl-methyl)-amide | 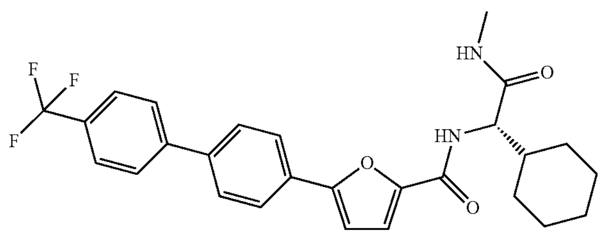 [SMILES: CNC(=O)[C@@H](NC(=O)c1ccc(-c2ccc(-c3ccc(C(F)(F)F)cc3)cc2)o1)C1CCCCC1] | 484.5 |

Assessment of Biological Properties

The biological properties of the compounds of the formula I can be assessed using the assays described below in addition to other art recognized assays.

The EnzoLyte™ 520 Generic MMP Assay Kit (AnaSpec Inc.) can detect the activity of several MMPs including MMP-1, 2, 3, 7, 8, 9, 13, and 14. This kit uses a 5-FAM/QXL™520 fluorescence resonance energy transfer (FRET) peptide as an MMP substrate. In the intact FRET peptide, the fluorescence of 5-FAM is quenched by QXL™520. Upon cleavage into two separate fragments by MMPs, the fluorescence of 5-FAM is recovered, and can be monitored at excitation/emission wavelengths=490 nm/520 nm The assays are performed in a convenient 96-well or 384-well microplate format.

Preferred compounds will have an IC50 of <500 nM.

Therapeutic Use

As can be demonstrated by the assays described above, the compounds of the invention are useful in inhibiting MMP-13. Compounds of formula 1 are therefore useful in the treatment of diseases including rheumatoid arthritis, osteoarthritis, osteoporosis, peridontitis, atherosclerosis, congestive heart failure, multiple sclerosis and tumor metastasis. They can be used in patients as drugs, particularly in the form of pharmaceutical compositions as set forth herein. As mentioned previously, MMP-13 are thought to play a major role on extracellular matrix degradation and cellular processes such as proliferation, migration (adhesion/dispersion), differentiation, angiogenesis, apoptosis and host defense, compounds of formula I are therefore also useful in the treatment of the following diseases:

contact dermatitis, bone resorption diseases, reperfusion injury, asthma, Guillain-Barre syndrome, Crohn's disease, ulcerative colitis, psoriasis, graft versus host disease, systemic lupus erythematosus and insulin-dependent diabetes mellitus, toxic shock syndrome, Alzheimer's disease, diabetes, inflammatory bowel diseases, acute and chronic pain as well as symptoms of inflammation and cardiovascular disease, stroke, myocardial infarction, alone or following thrombolytic therapy, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, complications including restenosis following percutaneous transluminal coronary angioplasty, traumatic arthritis, sepsis, chronic obstructive pulmonary disease and congestive heart failure.

As disclosed in the Background of the Invention, the compounds of the invention will be useful for treating tumor metastasis. These diseases include but are not limited to solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma and mesothelioma.

Examples of brain cancers include, but are not limited to brain stem, optic and hypophtalmic glioma, cerebella and cerebral astrocytoma, medulloblastoma, ependymoma, as well as pituitary, neuroectodermal and pineal tumor.

Examples of peripheral nervous system tumors include, but are not limited to neuroblastoma, ganglioneuroblastoma, and peripheral nerve sheath tumors.

Examples of tumors of the endocrine and exocrine system include, but are not limited to thyroid carcinoma, adrenocortical carcinoma, pheochromocytoma, and carcinoid tumors.

Tumors of the male reproductive organs include, but are not limited to prostate and testicular cancer.

Tumors of the female reproductive organs include, but are not limited to endometrial, cervical, ovarian, vaginal, and vulvar cancer, as well as sarcoma of the uterus.

Tumors of the digestive tract include, but are not limited to anal, colon, colorectal, esophageal, gallblader, gastric, pancreatic, rectal, small-intestine, and salivary gland cancers.

Tumors of the urinary tract include, but are not limited to bladder, penile, kidney, renal pelvis, ureter, and urethral cancers.

Eye cancers include, but are not limited to intraocular melanoma and retinoblastoma.

Examples of liver cancers include, but are not limited to hepatocellular carcinoma (liver cell carcinomas with or without fibrolamellar variant), hepatoblastoma, cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal/hypopharyngeal/nasopharyngeal/oropharyngeal cancer, and lip and oral cavity cancer.

Lymphomas include, but are not limited to AIDS-related lymphoma, non-Hodgkin's lymphoma, Hodgkins lymphoma, cutaneous T-cell lymphoma, and lymphoma of the central nervous system.

Sarcomas include, but are not limited to sarcoma of the soft tissue, osteosarcoma, Ewings sarcoma, malignant fibrous histiocytoma, lymphosarcoma, angiosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia.

Plasma cell dyscrasias include, but are not limited to multiple myeloma, and Waldenstrom's macroglobulinemia.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:

1. A compound of the formula (I):

(I)

wherein:
$R^1$ is $C_1$-$C_5$ alkyl optionally substituted with 1-3 substituents chosen from hydroxyl, $C_1$-$C_5$ alkoxy which is optionally substituted with a carboxamido group, $C_3$-$C_6$ carbocyclyl, amino, alkylamino, dialkylamino and aryl;

$R^2$ is $C_1$-$C_5$ alkyl, carbocycle, or aryl, each optionally independently substituted with 1-2 substituents chosen from amino, hydroxyl, $C_1$-$C_5$ alkoxy, oxo, aryl, $C_3$-$C_6$ carbocyclyl and carboxyl;

$R^3$ is a bond, hydrogen, $CH_2$, —C(O)—NH—, —NH—C(O)—, —CHR$_a$—O—, —O—CH$_2$—, —C(O)—NH—CH$_2$—, —CH$_2$—NH—C(O), S(O)$_{0-2}$—, SO$_2$—NH— or —NH—SO$_2$—; wherein $R_a$ is $C_1$-$C_5$ alkyl;

R⁴ is pyridinyl optionally independently substituted with 1-3 substituents chosen from $C_1$-$C_5$ alkyl, $C_1$-$C_5$ acyl, amino, aryl, halogen, hydroxyl, oxo, trihaloalkyl, carboxamide and $C_1$-$C_5$ alkoxy;
X is CH and
Ar is furanyl optionally substituted with 1-2 substituents chosen from $C_1$-$C_5$ alkyl, halogen, amino and oxo;
or a pharmaceutically acceptable salt thereof.

2. The compound according to claim 1, and wherein
$R^1$ is $C_1$-$C_5$ alkyl optionally substituted with 1-3 substituents chosen from hydroxyl, $C_1$-$C_5$ alkoxy which is optionally substituted with a carboxamido group, $C_3$-$C_6$ carbocyclyl, amino, alkylamino and dialkylamino;
$R^2$ is $C_1$-$C_5$ alkyl, cyclopropyl, cyclobutyl, cyclopentyl, cyclohexyl, cycloheptyl, phenyl or naphthyl, each optionally independently substituted with 1-2 substituents chosen from hydroxyl, $C_1$-$C_5$ alkoxy, $C_3$-$C_6$ carbocyclyl, phenyl and carboxyl;
$R^3$ is a bond, hydrogen, —C(O)—NH—, —NH—C(O)—, —CHR$_a$—O—, —O—CH$_2$—, —C(O)—NH—CH$_2$—, —CH$_2$—NH—C(O), SO$_2$—NH— or —NH—SO$_2$—;
$R^4$ is pyridinyl, optionally independently substituted with 1-3 substituents chosen from $C_1$-$C_5$ alkyl, $C_1$-$C_5$ acyl, amino, phenyl, halogen, hydroxyl, oxo, trifluoromethyl, carboxamide and $C_1$-$C_5$ alkoxy; and
Ar is furanyl optionally substituted with 1-2 substituents chosen from $C_1$-$C_5$ alkyl, halogen, amino and oxo.

3. The compound according to claim 2, and wherein
$R^1$ is $C_1$-$C_5$ alkyl optionally substituted with 1-3 substituents chosen from hydroxyl, $C_1$-$C_5$ alkoxy optionally substituted with a carboxamido group and $C_3$-$C_6$ cycloalkyl;
$R^2$ is $C_1$-$C_5$ alkyl, cyclopropyl, cyclopentyl or cyclohexyl, each optionally independently substituted with 1-2 substituents chosen from hydroxyl, $C_1$-$C_5$ alkoxy and phenyl;
$R^3$ is a bond, —C(O)—NH—, —NH—C(O)—, —CHR$_a$—O—, —O—CH$_2$—, —C(O)—NH—CH$_2$—, —CH$_2$—NH—C(O), SO$_2$—NH— or —NH—SO$_2$—;
$R^4$ is pyridinyl, optionally independently substituted with 1-3 substituents chosen from $C_1$-$C_5$ alkyl, amino, halogen, trifluoromethyl and $C_1$-$C_5$ alkoxy; and
Ar is furanyl.

4. The compound according to claim 3,
$R^1$ is $C_1$-$C_5$ alkyl optionally substituted with 1-2 substituents chosen from hydroxyl and methoxy;
$R^2$ is $C_1$-$C_3$ alkyl or cyclohexyl, wherein the alkyl group is optionally substituted with a hydroxyl;
$R^3$ is a bond, —C(O)—NH—, —NH—C(O)—, —CHR$_a$—O—, —O—CH$_2$—, —C(O)—NH—CH$_2$—, or —CH$_2$—NH—C(O);
$R^4$ is pyridinyl, optionally independently substituted with 1-3 substituents chosen from $C_1$-$C_3$ alkyl and trifluoromethyl; and
Ar is furanyl.

5. The compound according to claim 4, and wherein
$R^1$ is methyl;
$R^3$ is —O—CH$_2$—.

6. The compound according to claim 4, and wherein
$R^1$ is methyl;
$R^3$ is —NH—C(O)—.

7. The compound according to claim 4, and wherein
$R^1$ is methyl;
$R^3$ is —CH$_2$—NH—C(O)—.

8. A compound chosen from

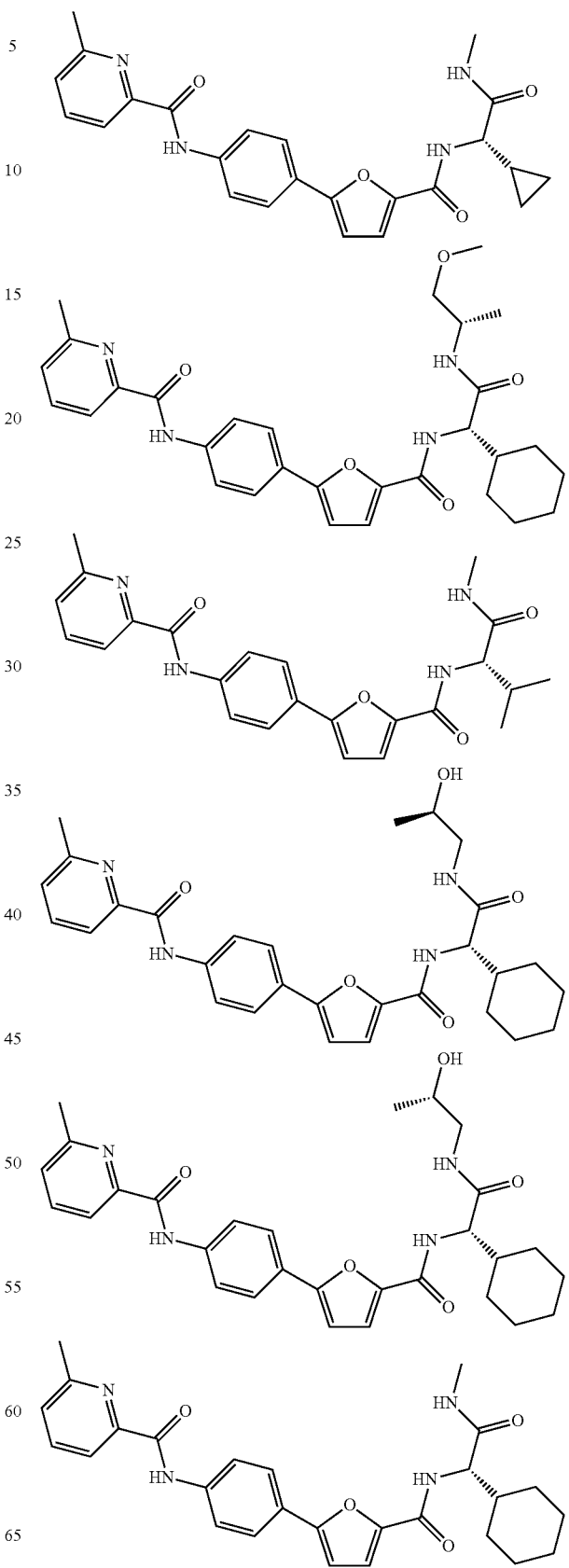

227
-continued
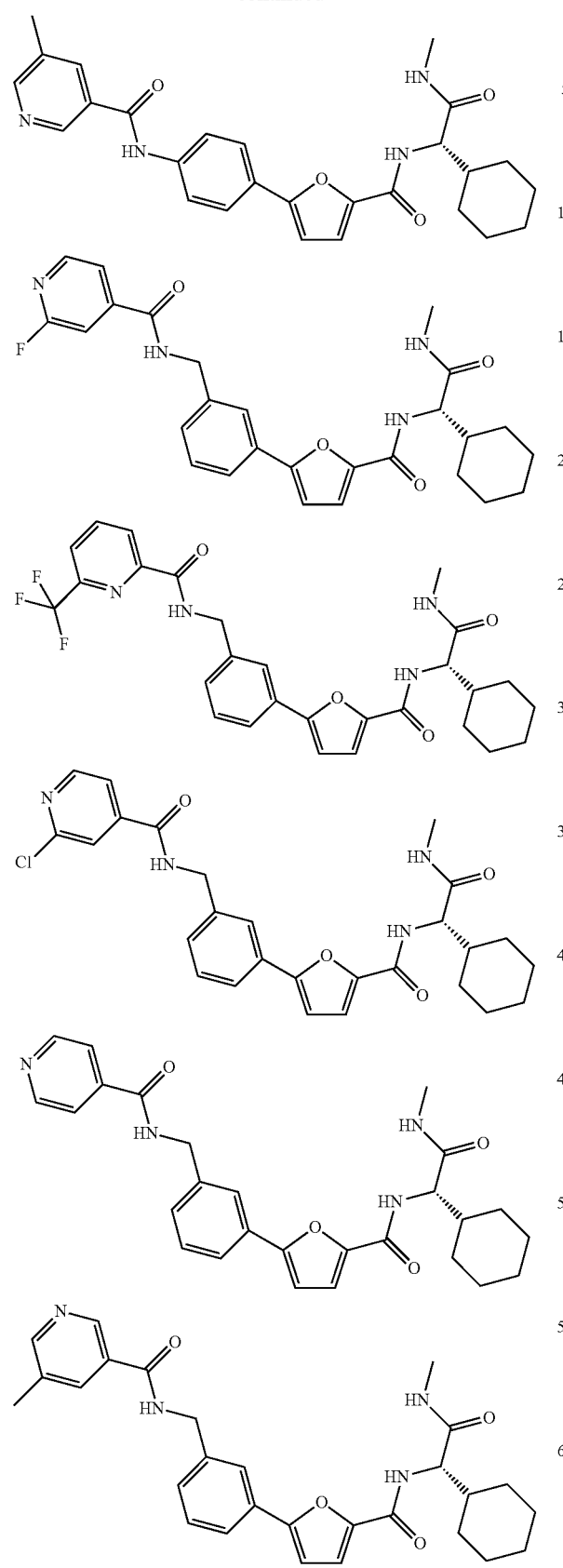
228
-continued
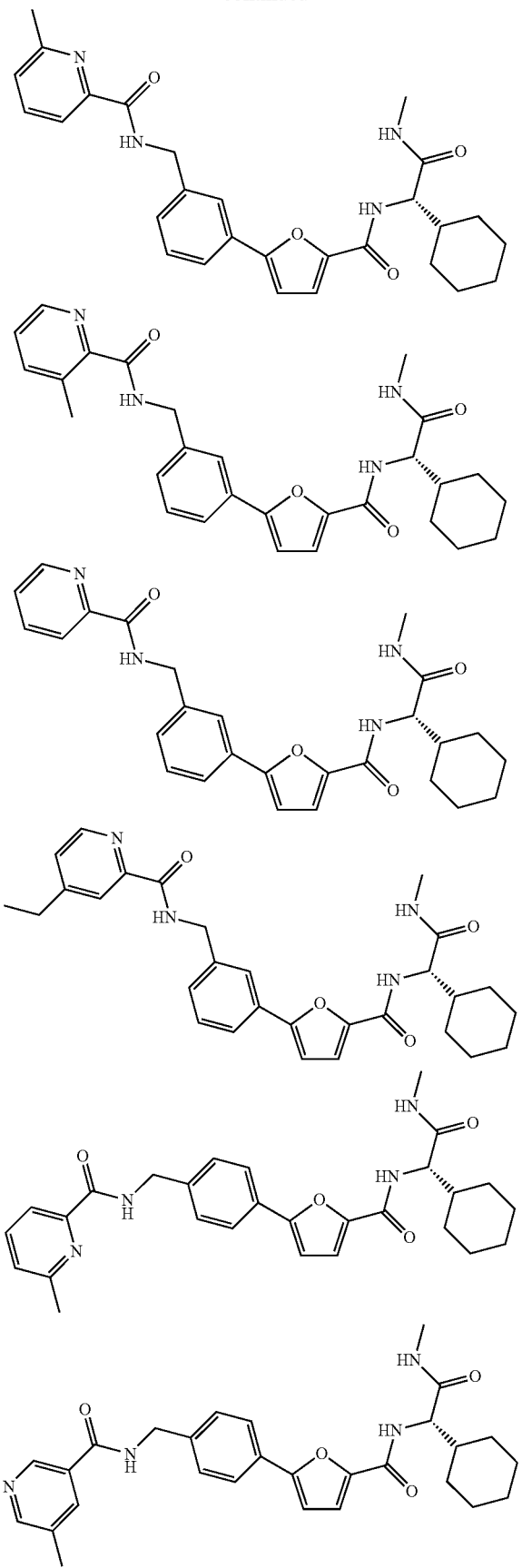

-continued
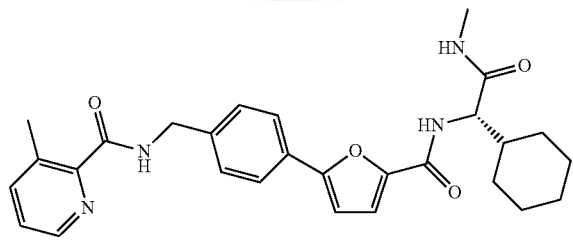
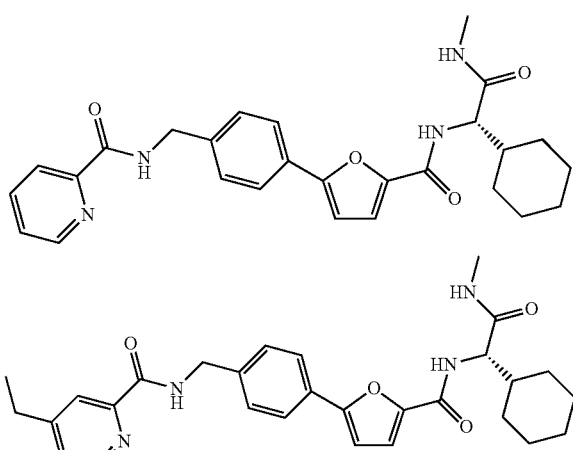
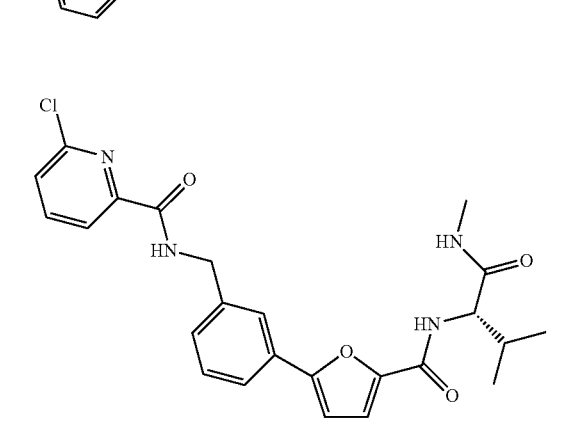
-continued
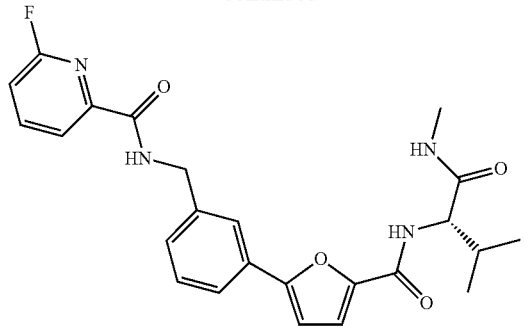
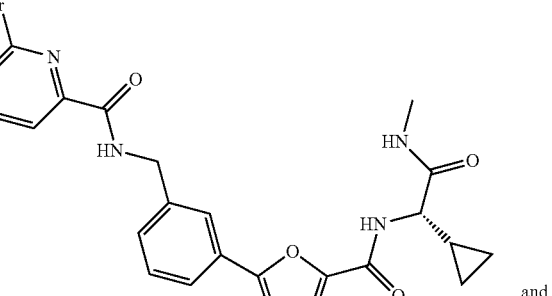
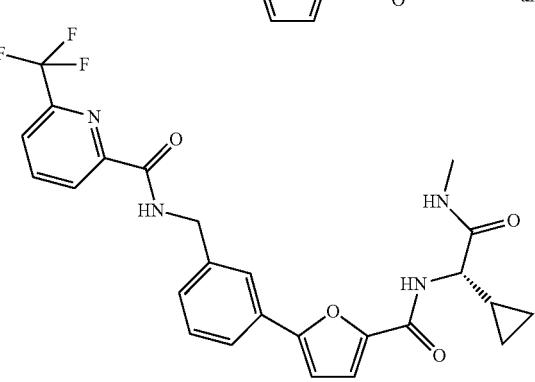
and
or a pharmaceutically acceptable salt thereof.
9. A pharmaceutical composition comprising a therapeutically effective amount of a compound according to claim 1 and one or more pharmaceutically acceptable carriers and/or adjuvants.
* * * * *

UNITED STATES PATENT AND TRADEMARK OFFICE
CERTIFICATE OF CORRECTION

PATENT NO. : 8,637,550 B2  Page 1 of 1
APPLICATION NO. : 13/127256
DATED : January 28, 2014
INVENTOR(S) : Farrow et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 198 days.

Signed and Sealed this
Twenty-second Day of September, 2015

Michelle K. Lee
*Director of the United States Patent and Trademark Office*